(12) United States Patent
Kassick et al.

(10) Patent No.: US 9,388,162 B2
(45) Date of Patent: *Jul. 12, 2016

(54) SUBSTITUTED MORPHINANS AND THE USE THEREOF

(71) Applicant: Purdue Pharma L.P., Stamford, CT (US)

(72) Inventors: Andrew Kassick, Scotch Plains, NJ (US); Jeffrey Lockman, Princeton Junction, NJ (US); Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/576,718

(22) Filed: Dec. 19, 2014

(65) Prior Publication Data

US 2015/0175571 A1    Jun. 25, 2015

Related U.S. Application Data

(63) Continuation of application No. 14/138,691, filed on Dec. 23, 2013, now Pat. No. 8,946,255.

(60) Provisional application No. 61/746,878, filed on Dec. 28, 2012.

(51) Int. Cl.
| | |
|---|---|
| *C07D 401/06* | (2006.01) |
| *C07D 215/20* | (2006.01) |
| *C07D 215/14* | (2006.01) |
| *C07D 471/08* | (2006.01) |

(52) U.S. Cl.
CPC ............ *C07D 401/06* (2013.01); *C07D 215/14* (2013.01); *C07D 215/20* (2013.01); *C07D 471/08* (2013.01)

(58) Field of Classification Search
None
See application file for complete search history.

(56) References Cited

U.S. PATENT DOCUMENTS

| | | | |
|---|---|---|---|
| 2,178,010 | A | 10/1939 | Small et al. |
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,230,712 | A | 10/1980 | Kotick et al. |
| 4,242,514 | A | 12/1980 | Leland |
| 4,272,541 | A | 6/1981 | Kotick et al. |
| 4,362,733 | A | 12/1982 | Ghosh et al. |
| 4,370,333 | A | 1/1983 | Ghosh et al. |
| 4,423,221 | A | 12/1983 | Razdan et al. |
| 4,912,114 | A | 3/1990 | Revesz |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,698,155 | A | 12/1997 | Grosswald et al. |
| 5,733,566 | A | 3/1998 | Lewis |
| 5,952,495 | A | 9/1999 | Huang et al. |
| 7,655,671 | B2 | 2/2010 | Schmidhammer et al. |
| 8,067,596 | B2 | 11/2011 | Wang et al. |
| 8,426,594 | B2 | 4/2013 | Kyle |
| 8,937,084 | B2 | 1/2015 | Park et al. |
| 2007/0105884 | A1 | 5/2007 | Welsh et al. |
| 2008/0312411 | A1 | 12/2008 | Wolf et al. |
| 2009/0156818 | A1 | 6/2009 | Wang et al. |
| 2009/0156820 | A1 | 6/2009 | Wang et al. |
| 2012/0010412 | A1 | 1/2012 | Duncan |
| 2013/0231485 | A1 | 9/2013 | Tamura et al. |

FOREIGN PATENT DOCUMENTS

| | | |
|---|---|---|
| CN | 101878214 A | 11/2010 |
| CN | 101210016 B | 7/2011 |
| EP | 0 829 481 A1 | 3/1998 |
| EP | 1 974 731 A1 | 10/2008 |
| EP | 2 196 206 A1 | 6/2010 |
| GB | 1031364 | 6/1966 |
| JP | 2008-179554 | 8/2008 |
| WO | WO 97/25331 A1 | 7/1997 |
| WO | WO 98/02033 A1 | 1/1998 |
| WO | WO 01/12197 A1 | 2/2001 |

(Continued)

OTHER PUBLICATIONS

Aceto, M., et al., "Dependence Studies of New Compounds in the Rhesus Monkey, Rat, and Mouse 1987," *NIDA Research Monograph Series, Problems of Drug Dependence 1987* 81: 485-542, Department of Health and Human Services, United States (1988).

(Continued)

*Primary Examiner* — Timothy R Rozof
(74) *Attorney, Agent, or Firm* — Sterne, Kessler, Goldstein & Fox P.L.L.C.

(57) ABSTRACT

The application is directed to compounds of Formula I:

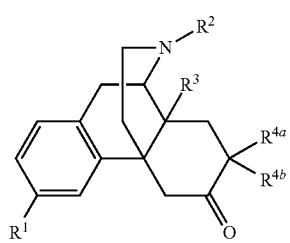

and pharmaceutically acceptable salts and solvates thereof, wherein $R^1$, $R^2$, $R^3$, $R^{4a}$, and $R^{4b}$ are defined as set forth in the specification. The invention is also directed to use of compounds of Formula I to treat disorders responsive to the modulation of one or more opioid receptors, or as synthetic intermediates. Certain compounds of the present invention are especially useful for treating pain.

20 Claims, No Drawings

(56) References Cited

FOREIGN PATENT DOCUMENTS

| WO | WO 2004/005294 A2 | 1/2004 |
|---|---|---|
| WO | WO 2005/033073 A2 | 4/2005 |
| WO | WO 2006/035195 A1 | 4/2006 |
| WO | WO 2008/070462 A2 | 6/2008 |
| WO | WO 2008/144394 A2 | 11/2008 |
| WO | WO 2009/059048 A2 | 5/2009 |
| WO | WO 2009/067275 A1 | 5/2009 |
| WO | WO 2011/009015 A1 | 1/2011 |
| WO | WO 2012/063933 A1 | 5/2012 |
| WO | WO 2012/088494 A1 | 6/2012 |
| WO | WO 2013/029762 A1 | 3/2013 |
| WO | WO 2013/035833 A1 | 3/2013 |

OTHER PUBLICATIONS

Alexander, G.J. and Chatterjie, N., "Naloxone-6α-Spirohydantoin: A Long-Acting Opiate Antagonist," *Neurochemical Research 14* (12): 1229-1234, Plenum Publishing Corporation, United States (1989).

Alexander, G.J., et al., "Prolonged Enhancement of Passive Avoidance in Rats by a Hydantoin Derivative of Naloxone," *Research Communications in Substances of Abuse 12* (1-2): 41-50, PJD Publications Ltd., United States (1991).

Alexander, G.J., et al., "A Spirohydantoin Derivative of Oxymorphone: An Agonist With Delayed Antagonist Activity," *Pharmacology Biochemistry & Behavior 32* (4): 939-943, Pergamon Press, United States (1989).

Ballini, R., et al., "1,3-Dioxolanes from Carbonyl Compounds over Zeolite HSZ-360 as a Reusable, Heterogeneous Catalyst," *Tetrahedron Letters 39*(12):1615-1618, Elsevier Science Ltd., England (1998).

Barthó, L., et al., "Involvement of capsaicin-sensitive neurones in hyperalgesia and enhanced opioid antinociception in inflammation," *Naunyn-Schmiedeberg's Arch. Pharmacol. 342*:666-670, Springer Verlag, Germany (1990).

Bingham, A.L., et al., "Over one hundred solvates of sulfathiazole," *Chem. Commun.*, 603-604, The Royal Society of Chemistry, England (2001).

Bolognesi, M., et al., "Opioid Antagonist Activity of Naltrexone-Derived Bivalent Ligands: Importance of a Properly Oriented Molecular Scaffold to Guide 'Address' Recognition at κ Opioid Receptors," *J. Med. Chem. 39* (9): 1816-1822, American Chemical Society, United States (1996).

Bös, M., et al., "6-aza und 7-Azacodeinone," *J. Heterocyclic Chem. 19*:1113-1115, Institut für Pharnazeutische Chemie, Austria (1982).

Buchwald, H., et al., "Long-term, continuous intravenous heparin administration by an implantable infusion pump in ambulatory patients with recurrent venous thrombosis," *Surgery 88*:507-516, The C.V. Mosby Co., United States (1980).

Caira, M.R., et al., "Preparation and Crystal Characterization of a Polymorph, a Monohydrate, and an Ethyl Acetate Solvate of the Antifungal Fluconazole," *Journal of Pharmaceutical Sciences 93*(3):601-611, Wiley-Liss, Inc., United States (2004).

Cas Reg. No. 88298-70-8, Chemical Abstracts Service, STN International, entered STN on Nov. 16, 1984, (accessed online on Apr. 24, 2014).

Chatterjie, N. and Alexander, G.J., "Stereochemical Results of the Bucherer-Bergs Reaction in the 14-Hydroxydihydromorphinone Series," *Research Communications in Substances of Abuse 12* (3): 132-143, PJD Publications Ltd., United States (1991).

Chatterjie, N., and Alexander, G.J., "Nalocone-6-Spirohydantoin: A New Non-Toxic Compound with Anticonvulsive Properties," *Neuropharmacology 22* (9): 1151-1153, Pergamon Press, Ltd., United Kingdom (1983).

Chatterjie, N. and Alexander, G.J., "Anticonvulsive spirohydantoin derivatives of opiate antagonists," *IRCS Medical Science 12* (1): 340-341, Elsevier Inc., United States (1984).

Chatterjie, N., et al., "Prevention of Hyperthermia-Induced Seizures in Immature Rats by a Hydantoin Derivative of Naloxone," *Life Sciences 45*: 857-862, Pergamon Press, United Kingdom (1989).

D'Amour, F.E. and Smith, D.L., "A Method for Determining Loss of Pain Sensation," *The Journal of Pharmacology and Experimental Therapeutics 72*:74-79, The American Society for Pharmacology and Experimental Therapeutics Incorporated, United States (1941).

During, M.J., et al., "Controlled Release of Dopamine from a Polymeric Brain Implant: In Vivo Characterization," *Annals of Neurology 25*(4): 351-356, Little, Brown and Company, United States (1989).

English machine abstract translation of the abstract from Chinese Patent Publication No. CN 101210016 B (listed as document FP1 on the accompanying form PTO/SB/08a).

English machine translation of Japanese Patent Publication No. JP 2008-179554 (listed as document FP6 on the accompanying form PTO/SB/08a).

Grupp, I.L., et al., "Protection against Hypoxia-reoxygenation in the Absence of Poly (ADP-ribose) Synthetase in Isolated Working Hearts," *J. Mol. Cell. Cardiol. 31*:297-303, Academic Press, United States (1999).

Hargreaves, K., et al., "A new and sensitive method for measuring thermal nociception in cutaneous hyperalgesia," *Pain 32*(1):77-88, Elsevier, Netherlands (1988).

Hernandez-Gallegos, Z. and Lehmann F., P.A., "A Free-Wilson/Fujita-Ban Analysis and Prediction of the Analgesic Potency of Some 3-Hydroxy- and 3-Methoxy-*N*-alklmorphinan-6-one Opioids," *J. Med. Chem. 33*:2813-2817, American Chemical Society (1990).

Hopkins, G.C., et al., "Alkylations of Heterocyclic Ambident Anions. II. Alkylation of 2-Pyridone Salts," *Journal of Organic Chemistry 32*: 4040-4044, American Chemical Society, United States (1967).

Howard III, M.A., et al., "Intracerebral drug delivery in rats with lesion-induced memory deficits," *J. Neurosurg. 71*(1):105-112, American Association of Neurological Surgeons, United States (1989).

Hupp, C.D. and Neumeyer, J.L., "Rapid access to morphinones: removal of 4,5-ether bridge with Pd-catalyzed triflate reduction," *Tetrahedron Letters 51*:2359-2361, Elsevier Ltd., England (2010).

Ida, Y., et al., "Synthesis of quinolinomorphinan-4-ol derivatives as δ opioid receptor agonists," *Bioorganic & Medicinal Chemistry 20*:949-961, Elsevier Ltd., England (2012) (available online Dec. 2011).

International Search Report and Written Opinion for International Patent Application No. PCT/IB2013/002883, mailed Mar. 18, 2014, European Patent Office, Rijswijk, Netherlands.

Kim, S.H. and Chung, J.M., "An experimental model for peripheral neuropathy produced by segmental spinal nerve ligation in the rat," *Pain 50*:355-363, Elsevier Science Publishers B.V., Netherlands (1992).

Kotick, M.P., "Analgesic Narcotic Antagonists. 6. 7β,8β-Methano- and 7β,8β-Epoxydihydrocodeinone," *J. Med. Chem. 24*(6):722-726, American Chemical Society (1981).

Langer, R. and Peppas, N., "Chemical and Physical Structure of Polymers as Carriers for Controlled Release of Bioactive Agents: A Review," *JMS-Rev. Macromol. Chem. Phys. C23*(1):61-126, Marcel Dekker, Inc., United States (1983).

Langer, R., "New Methods of Drug Delivery," *Science 249*(4976):1527-1533, American Association for the Advancement of Science, United States (1990).

Leland, D.L. and Kotick, M.P., "Analgesic Narcotic Antagonists. 4. 7-Methyl-*N*-(cycloalkylmethyl)-3-hydroxymorphinan-6-ones and -isomorphinan-6-ones," *J. Med. Chem. 23*:1427-1431, American Chemical Society (1980).

Levy, R.J., et al., "Inhibition of Calcification of Bioprosthetic Heart Valves by Local Controlled-Release Diphosphonate," *Science 228*(4696):190-192, American Association for the Advancement of Science, United States (1985).

Lopez-Berestein, G., "Treatment of Systematic Fungal Infections with Liposomal-Amphotericin B," in *Liposomes in the Therapy of Infectious Diseases and Cancer*, 317-327, Alan R. Liss, Inc., United States (1989).

Mavunkel, B.J., et al., "Synthesis and Characterization of Pseudopeptide Bradykinin B2 Receptor Antagonists Containing the 1,3,8-Triazaspiro[4.5]decan-4-one Ring System," *J. Med. Chem. 39*: 3169-3173, American Chemical Society, United States (1996).

(56) References Cited

OTHER PUBLICATIONS

Nagase, H., et al., "Design and synthesis of KNT-127, a δ-opiod receptor agonist effective by systemic administration," *Bioorganic & Medicinal Chemistry Letters 20*: 6302-6305, Elsevier Ltd., England (2010).

Negus, S.S., et al., "Effects of kappa opioids in an assay of pain-depressed intracranial self-stimulation in rats," *Pscyhopharmacology 210*:149-159, Springer-Verlag, Germany (2010).

Pande, A.C., et al., "Analgesic Efficacy of Enadoline Versus Placebo or Morphine in Postsurgical Pain," *Clin. Neuropharmacol. 19*(5):451-456, Lippincott-Raven Publishers, United States (1996).

Pande, A.C., et al., "Analgesic Efficacy of the κ-Receptor Agonist, Enadoline, in Dental Surgery Pain," *Clin. Neuropharmacol. 19*(1):92-97, Lippincott-Raven Publishers, United States (1996).

Polazzi, J.O., et al., "Analgesic Narcotic Antagonists. 2. 8-Alkymophinan-6-ones," *J. Med. Chem. 23*(2):174-179, American Chemical Society, United States (1980).

Saudek, C.D., et al., "A Preliminary Trial of the Programmable Implantable Medication System for Insulin Delivery," *The New England Journal of Medicine 321*(9): 574-579, Massachusetts Medical Society, United States (1989).

Sefton, M.V., "Implantable Pumps," *Critical Reviews™ in Biomedical Engineering 14*(3):201-240, CRC Press, Inc., United States (1987).

Seltzer, Z., et al., "A novel behavioral model of neuropathic pain disorders produced in rats by partial sciatic nerve injury," *Pain 43*:205-218, Elsevier Science Publishers B.V., Netherlands (1990).

Shibasaki, M., et al., "The Catalytic Asymmetric Strecker Reaction," *Organic Reactions 70*: 1-119, John Wiley & Sons, Inc., United States (2008).

Shütz, J., et al., "Synthesis of 6-Amino Acid Substituted Derivatives of the Highly Potent Analgesic 14-*O*-Methyloxymorphone," *Helvetica Chimica Acta 86*:2142-2148, Verlag Helvetica Chimica Acta AG, Switzerland (2003).

Stein, C., et al., "Unilateral Inflammation of the Hindpaw in Rats as a Model of Prolonged Noxious Stimulation: Alterations in Behavior and Nociceptive Thresholds," *Pharmacology Biochemistry & Behavior 31*:445-451, Pergamon Press PLC, United States (1988).

Streitwieser, A. and Heathcock, C.H., "Organische Chemie," *15.7.2*: 447-452, Verlag Chemie, Germany (1980).

Torbati, D., et al., "Effect of hypothermia on ventilation in anesthetized, spontaneously breathing rats: theoretical implications for mechanical ventilation," *Intensive Care Med. 26*:585-591, Springer-Verlag, Germany (2000).

Treat, J., et al., "Liposome Encapsulated Doxorubicin Preliminary Results of Phase I and Phase II Trials," in *Liposomes in the Therapy of Infectious Diseases and Cancer*, 353-365, Alan R. Liss, Inc., United States (1989).

Van Tonder, E.C., et al., "Preparation and Physicochemical Characterization of 5 Niclosamide Solvates and 1 Hemisolvate," *AAPS PharmSciTech 5*(1):1-10, Article 12, Springer Science + Business Media LLC, United States (2004).

Vanderah, T.W., et al., "FE200041 ($_D$—Phe—$_D$—Phe—$_D$—Nle—$_D$—Arg—$NH_2$): A Peripheral Efficacious κ Opioid Agonist with Unprecedented Selectivity," *The Journal of Pharmacology and Experimental Therapeutics 310*(1):326-333, The American Society for Pharmacology and Experimental Therapeutics, United States (2004).

Wadenberg, M-L.G., "A Review of the Properties of Spiradoline: A Potent and Selective κ-Opioid Receptor Agonist," *CNS Drug Review 9*(2):187-198, Neva Press, United States (2003).

Woods, J., et al., "Evaluation of New Compounds for Opioid Activity: 1987 Annual Report," *NIDA Research Monograph Series, Problems of Drug Dependence 1987 81*:543-590, Department of Health and Human Services, United States (1988).

Woolfe, G. and MacDonald, A.D., "The Evaluation of the Analgesic Action of Pethidine Hydrochloride (Demerol)," *The Journal of Pharmacology and Experimental Therapeutics 80-81*:300-307, The American Society for Pharmacology and Experimental Therapeutics Incorporated, United States (1944).

SUBSTITUTED MORPHINANS AND THE USE THEREOF

BACKGROUND OF THE INVENTION

1. Field of the Invention

This application is in the field of medicinal chemistry. The application relates to novel substituted morphinan derivatives, pharmaceutical compositions comprising any of these compounds, and their use.

2. Description of the Related Art

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone, oxymorphone, or buprenorphine).

Until recently, there was evidence of three major classes of opioid receptors in the central nervous system (CNS), with each class having subtype receptors. These receptor classes are known as $\mu$, $\delta$, and $\kappa$. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This more recently discovered receptor was classified as an opioid receptor based only on structural grounds, as the receptor did not exhibit pharmacological homology. It was initially demonstrated that non-selective ligands having a high affinity for $\mu$, $\delta$, and $\kappa$ receptors had low affinity for the ORL-1 receptor. This characteristic, along with the fact that an endogenous ligand had not yet been discovered, led to the ORL-1 receptor being designated as an "orphan receptor".

Kappa ($\kappa$) opioid receptor agonists have been evaluated as alternatives to existing analgesics for the treatment of pain. Centrally penetrating $\kappa$ agonists produce antinociceptive effects in conventional preclinical assays of basal, inflammatory and neuropathic pain (Vanderah et al., *J. Pharmacol. Exp. Ther.* 310:326-333 (2004); Negus et al., *Psychopharmacology (Berl)* 210:149-159 (2010)). However, centrally penetrating $\kappa$ agonists also produce undesirable side-effects, such as sedative and psychotomimetic effects (Pande et al., *Clin. Neuropharmacol.* 19:92-97 (1996); Pande el al., *Clin. Neuropharmacol.* 19:451-456 (1996); and Wadenberg, *CNS Drug Rev.* 9:187-198 (2003)).

Opioid receptor agonists that do not readily cross the blood-brain barrier are peripherically restricted and distribute poorly to the central nervous system after systemic administration. Such compounds would retain an ability to produce analgesia by acting on peripheral opioid receptors, such as peripheral $\kappa$-opioid receptors, but their potency to produce centrally mediated side-effects would be reduced.

There is a need for effective analgesics that work by acting on opioid receptors. There is also a need for analgesics that work by acting on peripheral opioid receptors. There is also a need for analgesics that work by acting on central opioid receptors. There is also a need for analgesics that work by acting on $\kappa$-opioid receptors. There is also a need for analgesics that work by acting on peripheral $\kappa$-opioid receptors.

BRIEF SUMMARY OF THE INVENTION

In one aspect, the present disclosure provides compounds represented by Formulae I-XIII, I-A-XIII-A, and XIV-XVI, below, and the pharmaceutically acceptable salts and solvates thereof, collectively referred to herein as "Compounds of the Invention" (each is individually referred to hereinafter as a "Compound of the Invention").

In another aspect, the present disclosure provides Compounds of the Invention for use as synthetic intermediates.

In another aspect, the present disclosure provides the use of Compounds of the Invention as modulators of one or more opioid receptors. Specifically, the present disclosure provides the use of Compounds of the Invention as modulators of $\mu$, $\delta$, $\kappa$, and/or ORL-1 opioid receptors, and especially modulators of $\mu$ and/or $\kappa$ opioid receptors.

In another aspect, the present disclosure provides a method of treating or preventing a disorder responsive to the modulation of one or more opioid receptors in a patient, comprising administering to the patient an effective amount of a Compound of the Invention.

In another aspect, the present disclosure provides a use of a Compound of the Invention as an analgesic to treat or prevent pain; or as an agent to treat or prevent withdrawal from alcohol or drug addiction; or as an agent to treat or prevent addictive disorders; or as an agent to treat a pruritic condition; or as an agent to treat or prevent constipation; or as an agent to treat or prevent diarrhea (each of pain, alcohol withdrawal, drug withdrawal, addictive disorders, pruritis, constipation, and diarrhea being a "Condition").

The present invention further provides methods of treating or preventing a Condition, comprising administering to a patient in need thereof a therapeutically effective amount of a Compound of the Invention. In certain embodiments, the Condition is pair (including acute pain, chronic pain (which includes but is not limited to, neuropathic pain, postoperative pain, and inflammatory pain), and surgical pain). The Compounds of the Invention are particularly useful for treating or preventing chronic pain.

In another aspect, the present disclosure provides a pharmaceutical composition comprising a therapeutically effective amount of a Compound of the Invention and one or more pharmaceutically acceptable carriers. Such compositions are useful for treating or preventing a Condition in a patient.

In another aspect, the present disclosure provides Compounds of the Invention for use in treatment or prevention of a disorder responsive to the modulation of one or more opioid receptors. Preferably, the disorder is responsive to modulation of the $\mu$-opioid receptor or the $\kappa$-opioid receptor, or to modulation of a combination thereof.

In another aspect, the present disclosure provides a method of modulating one or more opioid receptors in a patient in need of said modulation, comprising administering to the patient an opioid receptor modulating amount of a Compound of the Invention.

In another aspect, the present disclosure provides Compounds of the Invention for use in treatment or prevention of one or more Conditions in a patient in need of said treatment or prevention.

In another aspect, the present disclosure provides Compounds of the Invention for use in treatment or prevention of pain in a patient, such as acute pain, chronic pain (which includes but is not limited to, neuropathic pain, postoperative pain, and inflammatory pain), or surgical pain surgical.

In another aspect, the present disclosure provides Compounds of the Invention for use in modulation of one or more opioid receptors in a patient.

In another aspect, the present disclosure provides use of Compounds of the Invention in the manufacture of a medicament for treating or preventing a disorder responsive to the modulation of one or more opioid receptors.

In another aspect, the present disclosure provides use of Compounds of the Invention in the manufacture of a medicament for modulating of one or more opioid receptors in a patient. Preferably, the μ- or κ-opioid receptor is modulated, or both the μ- and κ-receptors are modulated.

In another aspect, the present disclosure provides Compounds of the Invention for use as a medicament.

In another aspect, the present disclosure provides use of a Compound of the Invention in the manufacture of a medicament for treating or preventing a Condition in a patient.

In another aspect, the present disclosure provides use of a Compound of the Invention in the manufacture of a medicament for treating or preventing pain in a patient, such as acute pain, chronic pain, or surgical pain.

In another aspect, the present disclosure provides a pharmaceutical composition, comprising a Compound of the Invention for treating or preventing a disorder responsive to the modulation of one or more opioid receptors.

The present invention further provides methods for preparing a pharmaceutical composition, comprising admixing a Compound of the Invention and a pharmaceutically acceptable carrier to form the pharmaceutical composition.

In another aspect, the present invention provides radiolabeled Compounds of the Invention, especially $^1$H, $^{11}$C, and $^{14}$C radiolabeled Compounds of the Invention, and the use of such compounds as radioligands to detect binding to an opioid receptor in screening assays.

In another aspect, the present invention provides a method for screening a candidate compound for the ability to bind to an opioid receptor, comprising a) introducing a fixed concentration of a radiolabeled Compound of the Invention to the receptor under conditions that permit binding of the radiolabeled compound to the receptor to form a complex; b) titrating the complex with a candidate compound; and c) determining the binding of the candidate compound to said receptor.

In a further aspect, the invention relates to a kit, comprising a sterile container containing an effective amount of a Compound of the Invention and instructions for therapeutic use.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

Certain Compounds of the Invention are useful for modulating a pharmacodynamic response from one or more opioid receptors, e.g., μ, δ, κ, or ORL-1, either centrally or peripherally, or both. The pharmacodynamic response may be attributed to the compound either stimulating (agonizing) or inhibiting (antagonizing) the one or more receptors. Certain Compounds of the Invention may antagonize one or more opioid receptors, and also agonize one or more other receptors. Compounds of the Invention having agonist activity may be either full or partial agonists. Certain Compounds of the Invention are also useful as synthesis intermediates.

In one embodiment, Compounds of the Invention are compounds represented by Formula I-A:

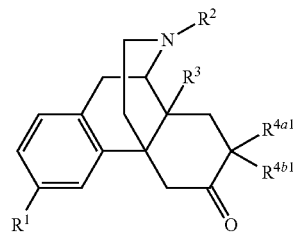

I-A and the pharmaceutically acceptable salts and solvates thereof, wherein:

$R^1$ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups; or —O—PG, wherein PG is a hydroxyl protecting group;

$R^2$ is:

(a) hydrogen or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^3$ is hydrogen, OH, or halo; or alkoxy, alkylamino, or dialkylamino, any of which is optionally substituted with 1, 2, or 3 substituents, each independently selected from the group consisting of hydroxyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^{4a1}$ is selected from the group consisting of $C_3$-$C_6$ alkyl, arylalkyl, (cycloalkyl)alkyl, $C_3$-$C_6$ alkoxy, aralkyloxy, —N(H)COR$^{4c}$, —CH$_2$C(=O)NR$^{4d}$R$^{4e}$, —N(H)SO$_2$R$^{4f}$,

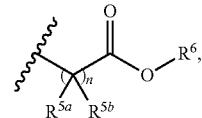

$R^{4a}$-I

-continued

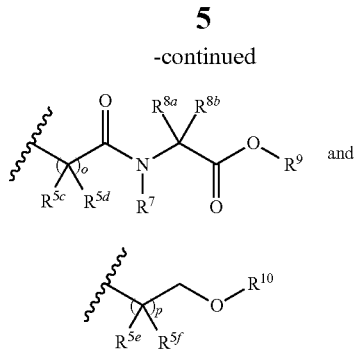

R$^{4a}$-II

R$^{4a}$-III

R$^{4b1}$ is selected from the group consisting of hydrogen and R$^{4a}$-I; or

R$^{4a1}$ and R$^{4b1}$ taken together form an alkenyl; e.g., =C(H)CH$_3$CH(CH$_3$);

R$^{4c}$ is alkyl, cycloalkyl, heterocyclo, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl and cycloalkyl are optionally substituted with 1, 2, or 3 independently selected R$^{11a}$ groups;

R$^{4d}$ is hydrogen; or alkyl, cycloalkyl, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected R$^{11a}$ groups;

R$^{4e}$ is hydrogen; or alkyl, optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl; or R$^{4d}$ and R$^{4e}$ taken together with the nitrogen atom to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, alkoxy, aminocarbonyl, arylalkyl, and aryl, wherein the alkyl, arylalkyl, and aryl are optionally substituted with 1, 2, or 3 independently selected R$^{11a}$ groups;

R$^{4f}$ is alkyl, cycloalkyl, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl and cycloalkyl are optionally substituted with 1, 2, or 3 independently selected R$^{11a}$ groups;

each R$^{5a}$, R$^{5b}$, R$^{5c}$, R$^{5d}$, R$^{5e}$, and R$^{5f}$ is independently selected from the group consisting of hydrogen and alkyl;

R$^6$ is hydrogen or alkyl;

R$^7$ is hydrogen or alkyl;

R$^{8a}$ is hydrogen, or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected R$^{11a}$ groups;

R$^{8b}$ is hydrogen or alkyl, wherein the alkyl is optionally substituted with 1, 2, or 3 substituents, each independently selected from the group consisting of alkyl, hydroxy, halo, haloalkyl, amino, alkylamino, dialkylamino, carboxy, alkoxy, alkoxycarbonyl, and aminocarbonyl; or R$^{8a}$ and R$^{8b}$ taken together with the carbon atom to which they are attached form a 3- to 8-membered cycloalkyl; or R$^7$ and R$^{8a}$ taken together with the atoms to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, carboxy, alkoxy, alkoxycarbonyl, and aminocarbonyl;

R$^9$ is hydrogen or alkyl;

R$^{10}$ is hydrogen, or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected R$^{11a}$ groups;

each R$^{11a}$ is independently selected from the group consisting of hydroxy, halo, alkyl, haloalkyl, cyano, nitro, amino, alkylamino, dialkylamino, carboxy, alkoxy, and alkoxycarbonyl;

n is 1, 2, or 3;

o is 1, 2, or 3; and p is 1, 2, or 3.

In another embodiment, Compounds of the Invention are compounds represented by Formula I:

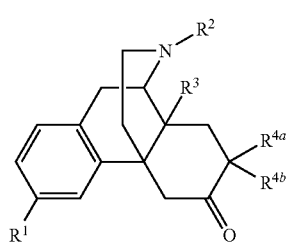

I and the pharmaceutically acceptable salts and solvates thereof, wherein:

R$^1$ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected R$^{11}$ groups; or —O—PG, wherein PG is a hydroxyl protecting group;

$R^2$ is:
(a) hydrogen or carboxamido; or
(b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, of 3 independently selected $R^{11}$ groups;

$R^3$ is hydrogen, OH, or halo; or alkoxy, alkylamino, or dialkylamino, any of which is optionally substituted with 1, 2, or 3 substituents, each independently selected from the group consisting of hydroxyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups;

$R^{4a}$ is selected from the group consisting of:

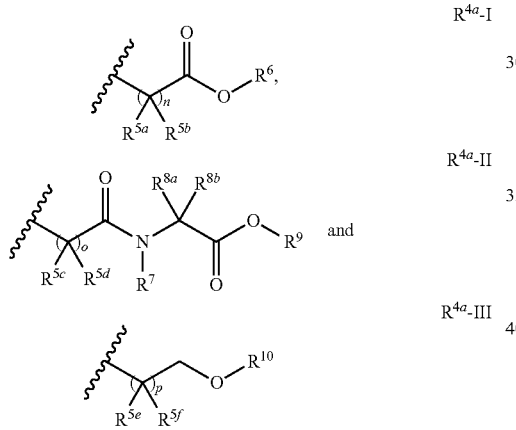

$R^{4b}$ is selected from the group consisting of hydrogen and $R^{4a}$-I;

each $R^{5a}$, $R^{5b}$, $R^{5c}$, $R^{5d}$, $R^{5e}$, and $R^{5f}$ is independently selected from the group consisting of hydrogen and alkyl;

$R^6$ is hydrogen or alkyl;

$R^7$ is hydrogen or alkyl;

$R^{8a}$ is hydrogen, or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups;

$R^{8b}$ is hydrogen or alkyl, wherein the alkyl is optionally substituted with 1, 2, or 3 substituents, each independently selected from the group consisting of alkyl, hydroxy, halo, haloalkyl, amino, alkylamino, dialkylamino, carboxy, alkoxy, alkoxycarbonyl, and aminocarbonyl; or $R^{8a}$ and $R^{8b}$ taken together with the carbon atom to which they are attached form a 3- to 8-membered cycloalkyl; or $R^7$ and $R^{8a}$ taken together with the atoms to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, carboxy, alkoxy, alkoxycarbonyl, and aminocarbonyl;

$R^9$ is hydrogen or alkyl;

$R^{10}$ is hydrogen, or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups;

each $R^{11}$ is independently selected from the group consisting of hydroxy, halo, alkyl, haloalkyl, nitro, amino, alkylamino, dialkylamino, carboxy, alkoxy, and alkoxycarbonyl;

n is 1, 2, or 3;

o is 1, 2, or 3; and p is 1, 2, or 3.

In another embodiment, Compounds of the Invention are compounds represented by Formula II-A:

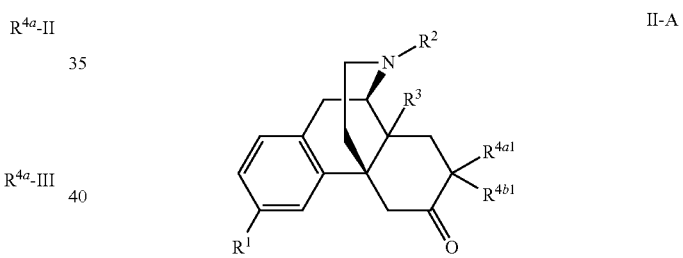

and the pharmaceutically acceptable salts and solvates thereof, wherein $R^1$, $R^2$, $R^3$, $R^{4a1}$ and $R^{4b1}$ are as defined above in connection with Formula I-A.

In another embodiment, Compounds of the Invention are compounds represented by Formula II:

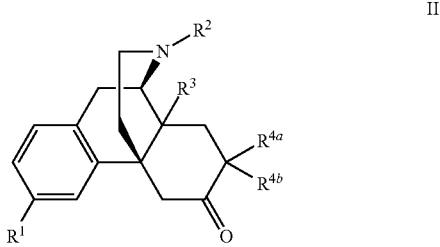

and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula III-A:

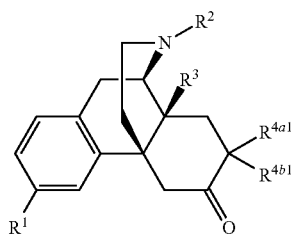

III-A and the pharmaceutically acceptable salts and solvates thereof, wherein $R^1$, $R^2$, $R_3$, $R^{4a1}$, and $R^{4b1}$ are as defined above in connection with Formula I-A.

In another embodiment, Compounds of the Invention are compounds represented by Formula III:

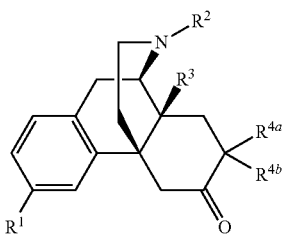

III and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula IV-A:

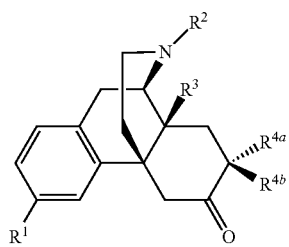

III and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula IV:

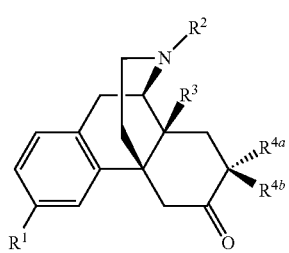

IV and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula V-A:

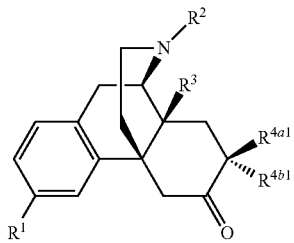

V-A and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula V:

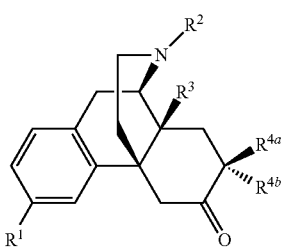

V and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula VI-A:

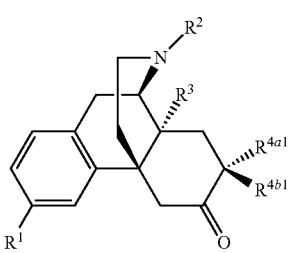

VI-A and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula VI:

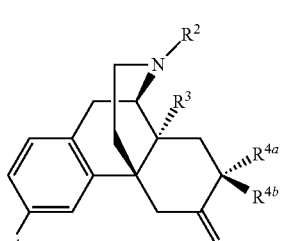

VI and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula VII-A:

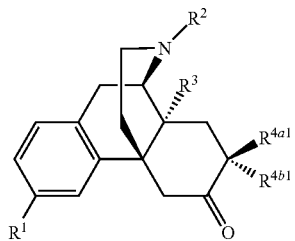

VII-A and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula VII:

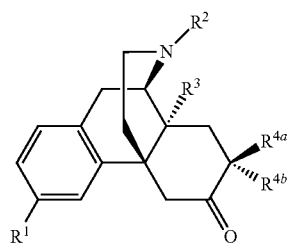

VII and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula VIII-A:

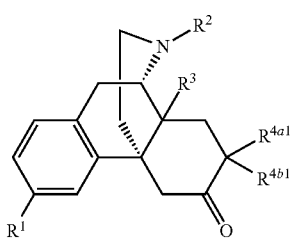

VIII-A and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula VIII:

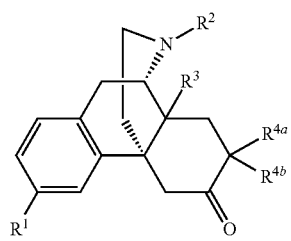

VIII and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula IX-A:

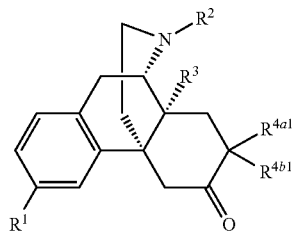

IX-A and the pharmaceutically acceptable salts and solvates thereof, wherein $R^1$, $R^2$, $R_3$, $R^{4a1}$, and $R^{4b1}$ are as defined above in connection with Formula I-A.

In another embodiment, Compounds of the Invention are compounds represented by Formula IX:

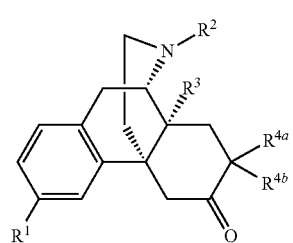

IX and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula X-A:

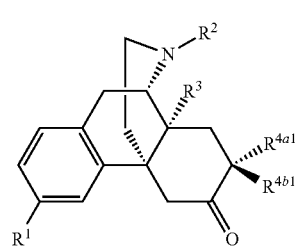

X-A and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula X:

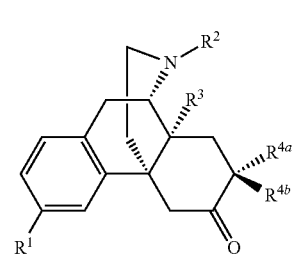

X and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula XI-A:

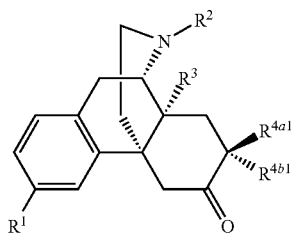

XI-A and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula XI:

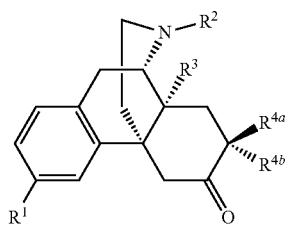

XI and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula XII-A:

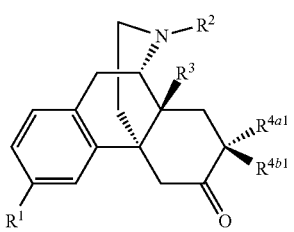

XII-A and the pharmaceutically acceptable salts and solvates thereof, wherein $R^1$, $R^2$, $R^3$, $R^{4a1}$, and $R^{4b1}$ are as defined above in connection with Formula I.

In another embodiment, Compounds of the Invention are compounds represented by Formula XII:

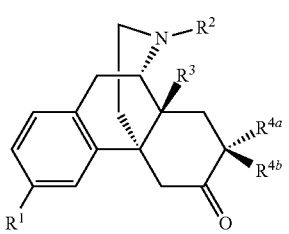

XII and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by Formula XIII-A:

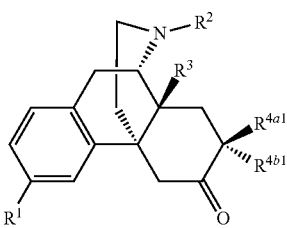

XIII-A and the pharmaceutically acceptable salts and solvates thereof, wherein $R^1$, $R^2$, $R^3$, $R^{4a1}$, and $R^{4b1}$ are as defined above in connection with Formula I-A.

In another embodiment, Compounds of the Invention are compounds represented by Formula XIII:

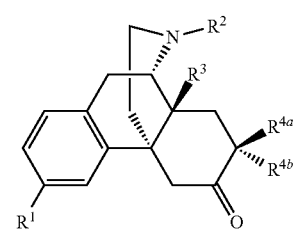

XIII and the pharmaceutically acceptable salts and solvates thereof, wherein $R^1$, $R^2$, $R^3$, $R^{4a}$, and $R^{4b}$ are as defined above in connection with Formula I.

In another embodiment, Compounds of the Invention are compounds represented by any one of Formula I-A, II-A, III-A, IV-A, V-A, VI-A, VII-A, VIII-A, IX-A, X-A, XI-A, XII-A, or XIII-A (referred to collectively as "Formulae I-A-XIII-A"), and the pharmaceutically acceptable salts and solvates thereof, wherein $R^{4b1}$ is hydrogen, and $R^1$, $R^2$, $R^3$, and $R^{4a1}$ are as defined above in connection with Formula I-A.

In another embodiment, Compounds of the Invention are compounds represented by any one of Formulae I-XIII, and the pharmaceutically acceptable salts and solvates thereof; wherein $R^{4b}$ is hydrogen, and $R^1$, $R^2$, $R^3$, and $R^{4a}$ are as defined above in connection with Formula I.

In another embodiment, Compounds of the Invention are compounds represented by any one of Formulae I-A-XIII-A, and the pharmaceutically acceptable salts and solvates thereof, wherein $R^1$ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups, and $R^2$, $R^3$, $R^{4a1}$, $R^{4b1}$, and $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^1$ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups, and $R^2$, $R^3$, $R^{4a}$, $R^{4b}$, and $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^1$ is OH or unsubstituted $C_{1-6}$ alkoxy, e.g., —$OCH_3$, and $R^2$, $R^3$, $R^{4a1}$, and $R^{4b1}$ are as defined above in connection with Formula I-A.

In another embodiment, Compounds of the Invention are compounds represented by any one of Formulae I-XIII, and the pharmaceutically acceptable salts and solvates thereof, wherein $R^1$ is OH or unsubstituted $C_{1-6}$ alkoxy, e.g., —$OCH_3$, and $R^2$, $R^3$, $R^{4a}$, and $R^{4b}$ are as defined above in connection with Formula I.

In another embodiment, Compounds of the Invention are compounds represented by any one of Formulae I-A-XIII-A, and the pharmaceutically acceptable salts and solvates thereof, wherein $R^2$ is hydrogen or carboxamido, and $R^1$, $R^3$, $R^{4a1}$, and $R^{4b1}$ are as defined above in connection with Formula I-A.

In another embodiment, Compounds of the Invention are compounds represented by any one of Formulae I-XIII, and the pharmaceutically acceptable salts and solvates thereof, wherein $R^2$ is hydrogen or carboxamido, and $R^1$, $R^3$, $R^{4a}$, and $R^{4b}$ are as defined above in connection with Formula I.

In another embodiment, Compounds of the Invention are compounds represented by any one of Formulae I-A-XIII-A, and the pharmaceutically acceptable salts and solvates thereof, wherein $R^2$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups, and $R^1$, $R^3$, $R^{4a1}$, $R^{4b1}$, and $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^2$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups, and $R^1$, $R^3$, $R^{4a}$, $R^{4b}$, and $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^2$ is $C_{3-7}$ (cycloalkyl)($C_{1-4}$)alkyl or $C_{3-7}$ (cycloalkenyl)($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and $R^3$, $R^{4a1}$, and $R^{4b1}$ are as defined above in connection with Formula I-A, In another embodiment, Compounds of the Invention are compounds represented by any one of Formulae I-XIII, and the pharmaceutically acceptable salts and solvates thereof, wherein $R^2$ is $C_{3-7}$ (cycloalkyl)($C_{1-4}$)alkyl or $C_{3-7}$ (cycloalkenyl)($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and $R^1$, $R^3$, $R^{4a}$, and $R^{4b}$ are as defined above in connection with Formula I.

In another embodiment, Compounds of the Invention are compounds represented by any one of Formulae I-A-XIII-A, and the pharmaceutically acceptable salts and solvates thereof, wherein $R^2$ is cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl, and $R^1$, $R^3$, $R^{4a1}$, and $R^{4b1}$ are as defined above in connection with Formula I-A.

In another embodiment, Compounds of the Invention are compounds represented by any one of Formulae I-XII, and the pharmaceutically acceptable salts and solvates thereof, wherein $R^2$ is cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, alkoxy, and alkoxycarbonyl, and $R^1$, $R^3$, $R^{4a}$, and $R^{4b}$ are as defined above in connection with Formula I.

In another embodiment, Compounds of the Invention are compounds represented by any one of Formulae I-A-XIII-A, and the pharmaceutically acceptable salts and solvates thereof, wherein $R^2$ is cyclopropylmethyl, cyclobutylmethyl, cyclopentylmethyl, or cyclohexylmethyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, alkoxy, and $C_{1-4}$ alkoxycarbonyl, and $R^1$, $R^3$, $R^{4a1}$, and $R^{4b1}$ are as defined above in connection with Formula I-A.

In another embodiment, Compounds of the Invention are compounds represented by any one of Formulae I-XIII, and the pharmaceutically acceptable salts and solvates thereof, wherein $R^2$ is cyclopropylmethyl, cyclobutylmethyl, cyclopentylmethyl, or cyclohexylmethyl, optionally substituted with 1, 2, or 3 substituents, each independently selected from the group consisting of hydroxy, $C_{1-4}$ alkyl, halo, halo($C_{1-4}$) alkyl, amino, $C_{1-4}$ alkylamino, di($C_{1-4}$)alkylamino, carboxy, $C_{1-4}$ alkoxy, and $C_{1-4}$ alkoxycarbonyl, and $R^1$, $R^3$, $R^{4a1}$, and $R^{4b1}$ are as defined above in connection with Formula I.

In another embodiment, Compounds of the Invention are compounds represented by any one of Formulae I-A-XIII-A, and the pharmaceutically acceptable salts and solvates thereof, wherein $R^3$ is hydrogen, and $R^1$, $R^2$, $R^{4a1}$, and $R^{4b1}$ are as defined above in connection with Formula I-A.

In another embodiment, Compounds of the Invention are compounds represented by any one of Formulae I-XIII, and the pharmaceutically acceptable salts and solvates thereof, wherein $R^3$ is hydrogen, and $R^1$, $R^2$, $R^{4a}$, and $R^{4b}$ are as defined above in connection with Formula I.

In another embodiment, Compounds of the Invention are compounds represented by any one of Formulae I-A-XIII-A, and the pharmaceutically acceptable salts and solvates thereof, wherein $R^3$ is hydroxy, and $R^1$, $R^2$, $R^{4a1}$, and $R^{4b1}$ are as defined above in connection with Formula I-A.

In another embodiment, Compounds of the Invention are compounds represented by any one of Formulae I-XIII, and the pharmaceutically acceptable salts and solvates thereof, wherein $R^3$ is hydroxy, and $R^1$, $R^2$, $R^{4a}$, and $R^{4b}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-I, i.e., $R^{4a1}$ is:

[structure showing group with O, $R^6$, $R^{5a}$, $R^{5b}$, n]

and $R^1$, $R^2$, $R^3$, $R^{4b1}$, $R^{5a}$, $R^{5b}$, n, and $R^6$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-I, i.e., $R^{4a}$ is:

[structure showing group with O, $R^6$, $R^{5a}$, $R^{5b}$, n]

and $R^1$, $R^2$, $R^3$, $R^{4b}$, $R^{5a}$, $R^{5b}$, n, and $R^6$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-I, $R^{5a}$ and $R^{5b}$ are each hydrogen, and $R^1$, $R^2$, $R^3$, $R^{4b1}$, n, and $R^6$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-I, $R^{5a}$ and $R^{5b}$ are each hydrogen, and $R^1$, $R^2$, $R^3$, $R^{4b}$, n, and $R^6$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-I and n is 1, and $R^1$, $R^2$, $R^3$, $R^{4b1}$, $R^{5a}$, $R^{5b}$, and $R^6$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-I and n is 1, and $R^1$, $R^2$, $R^3$, $R^{4b}$, $R^{5a}$, $R^{5b}$, and $R^6$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-I and $R^6$ is selected from the group consisting of hydrogen and $C_{1-4}$ alkyl, and $R^1$, $R^2$, $R^3$, $R^{4b1}$, $R^{5a}$, $R^{5b}$, and n are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-I and $R^6$ is selected from the group consisting of hydrogen and $C_{1-4}$ alkyl, and $R^1$, $R^2$, $R^3$, $R^{4b}$, $R^{5a}$, $R^{5b}$, and n are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-I and $R^6$ is hydrogen, and $R^1$, $R^2$, $R^3$, $R^{4b1}$, $R^{5a}$, $R^{5b}$, and n are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-I and $R^6$ is hydrogen, and $R^1$, $R^2$, $R^3$, $R^{4b}$, $R^{5a}$, $R^{5b}$, and n are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-I, $R^{5a}$ and $R^{5b}$ are each hydrogen, n is 1, and $R^6$ is hydrogen, and $R^1$, $R^2$, $R^3$, and $R^{4b1}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-I, $R^{5a}$ and $R^{5b}$ are each hydrogen, n is 1, and $R^6$ is hydrogen, and $R^1$, $R^2$, $R^3$, and $R^{4b}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-I, $R^{4b1}$ is hydrogen, $R^{5a}$ and $R^{5b}$ are each hydrogen, n is 1, and $R^6$ is hydrogen, and $R^1$, $R^2$, and $R^3$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-I, $R^{4b}$ is hydrogen, $R^{5a}$ and $R^{5b}$ are each hydrogen, n is 1, and $R^6$ is hydrogen, and $R^1$, $R^2$, and $R^3$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ and $R^{4b1}$ are both $R^{4a}$-I, $R^{5a}$ and $R^{5b}$ are each hydrogen, n is 1, and $R^6$ is hydrogen, and $R^1$, $R^2$, and $R^3$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ and $R^{4b}$ are both $R^{4a}$-I, $R^{5a}$ and $R^{5b}$ are each hydrogen, n is 1, and $R^6$ is hydrogen, and $R^1$, $R^2$, and $R^3$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, i.e., $R^{4a1}$ is:

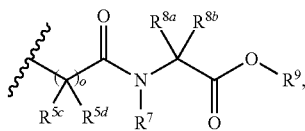

and $R^1$, $R^2$, $R^3$, $R^{4b1}$, $R^{5c}$, $R^{5d}$, $R^7$, $R^{8a}$, $R^{8b}$, o, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II, i.e., $R^{4a}$ is:

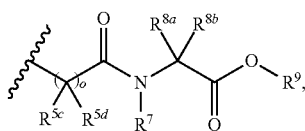

and $R^1$, $R^2$, $R^3$, $R^{4b}$, $R^{5c}$, $R^{5d}$, $R^7$, $R^{8a}$, $R^{8b}$, o, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II and $R^{5c}$ and $R^{5d}$ are each hydrogen, and $R^1$, $R^2$, $R^3$, $R^{4b1}$, $R^7$, $R^{8a}$, $R^{8b}$, o, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II and $R^{5c}$ and $R^{5d}$ are each hydrogen, and $R^1$, $R^2$, $R^3$, $R^{4b}$, $R^7$, $R^{8a}$, $R^{8b}$, o, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II and o is 1, and $R^1$, $R^2$, $R^3$, $R^{4b1}$, $R^{5c}$, $R^{5d}$, $R^7$, $R^{8a}$, $R^{8b}$, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II and o is 1, and $R^1$, $R^2$, $R^3$, $R^{4b}$, $R^{5c}$, $R^{5d}$, $R^7$, $R^{8a}$, $R^{8b}$, and $R^9$ are as defined above in connection with Formula I.

In another embodiment, Compounds of the Invention are compounds represented by any one of Formulae I-A-XII-A, and the pharmaceutically acceptable salts and solvates thereof, wherein $R^{4a1}$ is $R^{4a}$-II and $R^{8b}$ is hydrogen, and $R^1$, $R^2$, $R^3$, $R^{4b1}$, $R^{5c}$, $R^{5d}$, $R^7$, $R^{8a}$, o, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II and $R^{8b}$ is hydrogen, and $R^1$, $R^2$, $R^3$, $R^{4b}$, $R^{5c}$, $R^{5d}$, $R^7$, $R^{8a}$, o, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is:

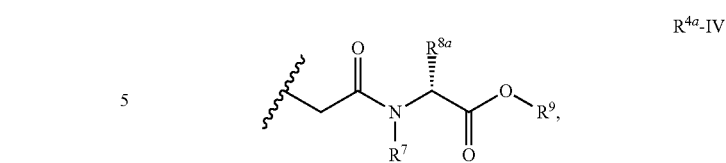

and $R^1$, $R^2$, $R^3$, $R^{4b1}$, $R^7$, $R^{8a}$, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is:

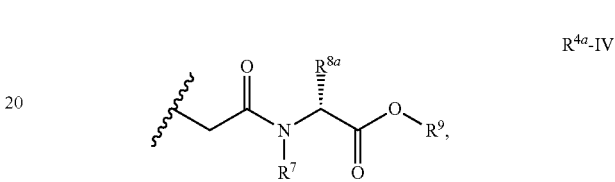

and $R^1$, $R^2$, $R^3$, $R^{4b}$, $R^7$, $R^{8a}$, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is:

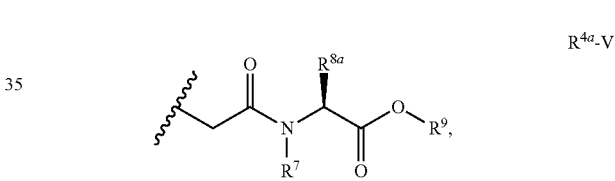

and $R^1$, $R^2$, $R^3$, $R^{4b1}$, $R^7$, $R^{8a}$, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is:

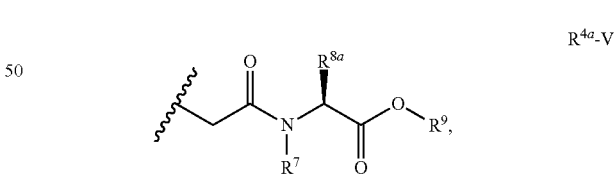

and $R^1$, $R^2$, $R^3$, $R^{4b}$, $R^7$, $R^{8a}$, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, $R^{8a}$ is hydrogen or $C_{1-4}$ alkyl, wherein the alkyl is optionally substituted with 1 or 2 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups, and $R^{8b}$ is hydrogen, and $R^1$, $R^2$, $R^3$, $R^{4b1}$, $R^{5c}$, $R^{5d}$, $R^7$, o, $R^9$, $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II, $R^{8a}$ is hydrogen or $C_{1-4}$ alkyl, wherein the alkyl is optionally substituted with 1 or 2 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups, and $R^{8b}$ is hydrogen, and $R^1$, $R^2$, $R^3$, $R^{4b}$, $R^{5c}$, $R^{5d}$, $R^7$, o, $R^9$, $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-IV or $R^{4a}$-V, $R^{4b1}$ is hydrogen, and $R^{8a}$ is hydrogen or $C_{1-4}$ alkyl, wherein the alkyl is optionally substituted with 1 or 2 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups, and $R^1$, $R^2$, $R^3$, $R^7$, $R^9$, and $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, and $R^{8a}$ is hydrogen or $C_{1-4}$ alkyl, wherein the alkyl is optionally substituted with 1 or 2 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups, and $R^1$, $R^2$, $R^3$, $R^7$, $R^9$, and $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, $R^{8a}$ is $C_{1-4}$ alkyl optionally substituted with 1 substituent selected from the group consisting of aryl, hydroxy, halo, haloalkyl, amino, alkylamino, dialkylamino, carboxy, alkoxy, alkoxycarbonyl, and aminocarbonyl, wherein the aryl is optionally substituted with 1, 2, or 3 independently selected $R^{11a}$ groups, and $R^{8b}$ is hydrogen, and $R^1$, $R^2$, $R^3$, $R^{4b1}$, $R^{5c}$, $R^{5d}$, $R^7$, o, $R^9$, $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II, $R^{8a}$ is $C_{1-4}$ alkyl optionally substituted with 1 substituent selected from the group consisting of aryl, hydroxy, halo, haloalkyl, amino, alkylamino, dialkylamino, carboxy, alkoxy, alkoxycarbonyl, and aminocarbonyl, wherein the aryl is optionally substituted with 1, 2, or 3 independently selected $R^{11}$ groups, and $R^{8b}$ is hydrogen, and $R^1$, $R^2$, $R^3$, $R^{4b}$, $R^{5c}$, $R^{5d}$, $R^7$, o, $R^9$, $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-IV or $R^{4a}$-V, $R^{4b1}$ is hydrogen, and $R^{8a}$ is $C_{1-4}$ alkyl optionally substituted with 1 substituent selected from the group consisting of aryl, hydroxy, halo, haloalkyl, amino, alkylamino, dialkylamino, carboxy, alkoxy, alkoxycarbonyl, and aminocarbonyl, wherein the aryl is optionally substituted with 1, 2, or 3 independently selected $R^{11a}$ groups, and $R^1$, $R^2$, $R^3$, $R^7$, $R^9$, and $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, and $R^{8a}$ is $C_{1-4}$ alkyl optionally substituted with 1 substituent selected from the group consisting of aryl, hydroxy, halo, haloalkyl, amino, alkylamino, dialkylamino, carboxy, alkoxy, alkoxycarbonyl, and aminocarbonyl, wherein the aryl is optionally substituted with 1, 2, or 3 independently selected $R^{11}$ groups, and $R^1$, $R^2$, $R^3$, $R^7$, $R^9$, and $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, $R^{4b1}$ is hydrogen, and $R^7$ is hydrogen, and $R^1$, $R^2$, $R^3$, $R^{5c}$, $R^{5d}$, $R^{8a}$, o, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, and $R^7$ is hydrogen, and $R^1$, $R^2$, $R^3$, $R^{8a}$, and $R^9$ are as defined above in connection with Formula I.

In another embodiment, Compounds of the Invention are compounds represented by any one of Formulae I-XIII, and the pharmaceutically acceptable salts and solvates thereof, wherein $R^{4a}$ is $R^{4a}$-II, $R^{4b}$ is hydrogen, and $R^7$ is hydrogen, and $R^1$, $R^2$, $R^3$, $R^{5c}$, $R^{5d}$, $R^{8a}$, o, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-IV or $R^{4a}$-V, $R^{4b1}$ is hydrogen, and $R^7$ is hydrogen, and $R^1$, $R^2$, $R^3$, $R^{8a}$, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, and $R^7$ is hydrogen, and $R^1$, $R^2$, $R^3$, $R^{8a}$, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, $R^{4b1}$ is hydrogen, $R^{8b}$ is hydrogen, and $R^7$ and $R^{8a}$ taken together with the atoms to which they are attached form a 5-membered heterocyclo, and $R^1$, $R^2$, $R^3$, $R^{5c}$, $R^{5d}$, o, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II, $R^{4b}$ is hydrogen, $R^{8b}$ is hydrogen, and $R^7$ and $R^{8a}$ taken together with the atoms to which they are attached form a 5-membered heterocyclo, and $R^1$, $R^2$, $R^3$, $R^{5c}$, $R^{5d}$, o, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-IV or $R^{4a}$-V, $R^{4b1}$ is hydrogen, and $R^7$ and $R^{8a}$ taken together with the atoms to which they are attached form a 5-membered heterocyclo, and $R^1$, $R^2$, $R^3$, and $R^9$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, and $R^7$ and $R^{8a}$ taken together with the atoms to which they are attached form a 5-membered heterocyclo, and $R^1$, $R^2$, $R^3$, and $R^9$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, $R^{4b1}$ is hydrogen, $R^7$ is hydrogen, $R^{8b}$ is hydrogen, and $R^9$ is hydrogen, and $R^1$, $R^2$, $R^3$, $R^{5c}$, $R^{5d}$, $R^{8a}$, and o are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II, $R^{4b}$ is hydrogen, $R^7$ is hydrogen, $R^{8b}$ is hydrogen, and $R^9$ is hydrogen, and $R^1$, $R^2$, $R^3$, $R^{5c}$, $R^{5d}$, $R^{8a}$, and o are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-IV or $R^{4a}$-V, $R^{4b1}$ is hydrogen, $R^7$ is hydrogen, and $R^9$ is hydrogen and $R^1$, $R^2$, $R^3$, and $R^{8a}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, $R^7$ is hydrogen, and $R^9$ is hydrogen and $R^1$, $R^2$, $R^3$, and $R^{8a}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, $R^{4b1}$ is hydrogen, $R^{8b}$ is hydrogen, $R^7$ and $R^{8a}$ taken together with the atoms to which they are attached form a 5-membered heterocyclo, and $R^9$ is hydrogen, and $R^1$, $R^2$, $R^3$, $R^{5c}$, $R^{5d}$, and o are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II, $R^{4b}$ is hydrogen, $R^{8b}$ is hydrogen, $R^7$ and $R^{8a}$ taken together with the atoms to which they are attached form a 5-membered heterocyclo, and $R^9$ is hydrogen, and $R^1$, $R^2$, $R^3$, $R^{5c}$, $R^{5d}$, and o are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-IV or $R^{4a}$-V, $R^{4b1}$ is hydrogen, $R^7$ and $R^{8a}$ taken together with the atoms to which they are attached form a 5-membered heterocyclo, and $R^9$ is hydrogen, and $R^1$, $R^2$, and $R^3$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, $R^7$ and $R^{8a}$ taken together with the atoms to which they are attached form a 5-membered heterocyclo, and $R^9$ is hydrogen, and $R^1$, $R^2$, and $R^3$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-II, $R^{4b1}$ is hydrogen, $R^7$ is hydrogen, $R^{8a}$ is $C_{1-4}$ alkyl, $R^{8b}$ is hydrogen, and $R^9$ is hydrogen, and $R^1$, $R^2$, $R^3$, $R^{5c}$, $R^{5d}$, and o are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-II, $R^{4b}$ is hydrogen, $R^7$ is hydrogen, $R^{8a}$ is $C_{1-4}$ alkyl, $R^{8b}$ is hydrogen, and $R^9$ is hydrogen, and $R^1$, $R^2$, $R^3$, $R^{5c}$, $R^{5d}$, and o are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-IV or $R^{4a}$-V, $R^{4b1}$ is hydrogen, $R^7$ is hydrogen, $R^{8a}$ is $C_{1-4}$ alkyl, and $R^9$ is hydrogen and $R^1$, $R^2$, and $R^3$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-IV or $R^{4a}$-V, $R^{4b}$ is hydrogen, $R^7$ is hydrogen, $R^{8a}$ is $C_{1-4}$ alkyl, and $R^9$ is hydrogen and $R^1$, $R^2$, and $R^3$ are as defined above in connection with Formula I.

In another embodiment, Compounds of the Invention are compounds represented by any one of Formulae I-A-XII-A, and the pharmaceutically acceptable salts and solvates thereof, wherein $R^{4a1}$ is selected from the group consisting of:

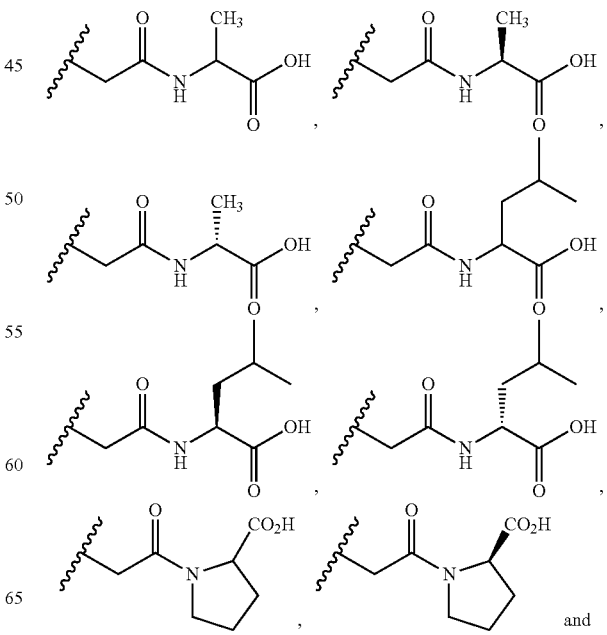

and

-continued

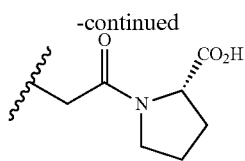

and $R^{4b1}$ is hydrogen, and $R^1$, $R^2$, and $R^3$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is selected from the group consisting of:

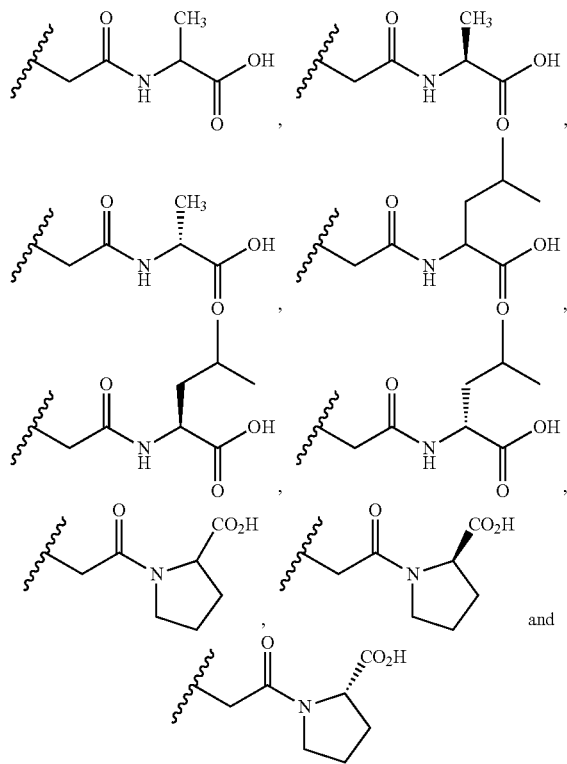

and $R^{4b}$ is hydrogen, and $R^1$, $R^2$, and $R^3$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-III, i.e., $R^{4a1}$ is:

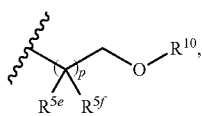

and $R^1$, $R^2$, $R^3$, $R^{4b1}$, $R^{5e}$, $R^{5f}$, p, and $R^{10}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-III, i.e., $R^{4a}$ is:

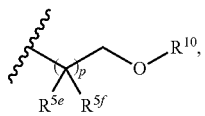

and $R^1$, $R^2$, $R^3$, $R^{4b}$, $R^{5e}$, $R^{5f}$, p, and $R^{10}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-III and $R^{5e}$ and $R^{5f}$ are each hydrogen, and $R^1$, $R^2$, $R^3$, $R^{4b1}$, p, and $R^{10}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-III and $R^{5e}$ and $R^{5f}$ are each hydrogen, and $R^1$, $R^2$, $R^3$, $R^{4b}$, p and $R^{10}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-III and p is 1, and $R^1$, $R^2$, $R^3$, $R^{4b1}$, $R^{5e}$, $R^{5f}$, and $R^{10}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-III and p is 1, and $R^1$, $R^2$, $R^3$, $R^{4b}$, $R^{5e}$, $R^{5f}$, and $R^{10}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-III and $R^{10}$ is hydrogen, or alkyl, cycloalkyl, aryl, heteroaryl, or arylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups, and $R^1$, $R^2$, $R^3$, $R^{4b1}$, $R^{5e}$, $R^{5f}$, p, and $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-III and $R^{10}$ is hydrogen, or alkyl, cycloalkyl, aryl, heteroaryl, or arylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups, and $R^1$, $R^2$, $R^3$, $R^{4b}$, $R^{5e}$, $R^{5f}$, p, and $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-III, $R^{4b1}$ is hydrogen, $R^{5e}$ and $R^{5f}$ are hydrogen, p is 1, and $R^{10}$ is hydrogen, or alkyl, cycloalkyl, aryl, heteroaryl, or arylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups, and $R^1$, $R^2$, $R^3$, and $R^{11a}$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-III, $R^{4b}$ is hydrogen, $R^{5e}$ and $R^{5f}$ are hydrogen, p is 1, and $R^{10}$ is hydrogen, or alkyl, cycloalkyl, aryl, heteroaryl, or arylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups, and $R^1$, $R^2$, $R^3$, and $R^{11}$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $R^{4a}$-III, $R^{4b1}$ is hydrogen, $R^{5e}$ and $R^{5f}$ are hydrogen, p is 1, and $R^{10}$ is selected from the group consisting of:

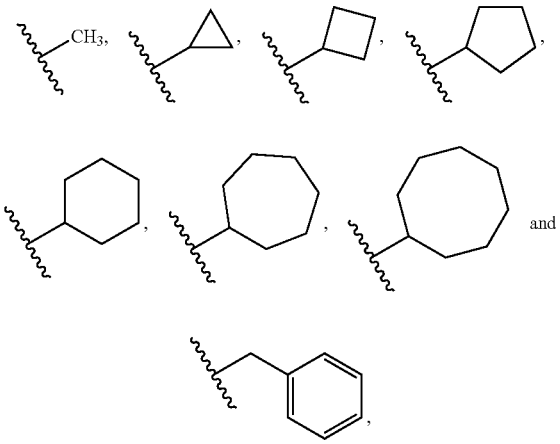

and $R^1$, $R^2$, and $R^3$ are as defined above in connection with Formula I-A.

In another embodiment, Compounds of the Invention are compounds represented by any one of Formulae I-XIII, and the pharmaceutically acceptable salts and solvates thereof, wherein $R^{4a}$ is $R^{4a}$-III, $R^{4b}$ is hydrogen, $R^{5e}$ and $R^{5f}$ are hydrogen, p is 1, and $R^{10}$ is selected from the group consisting of:

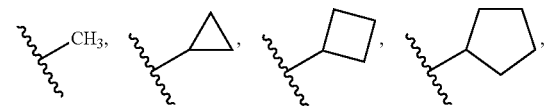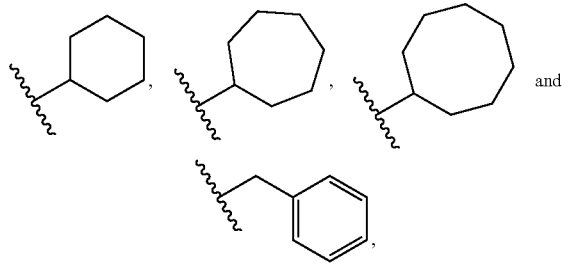

and $R^1$, $R^2$, and $R^3$ are as defined above in connection with Formula I.

In another embodiment, Compounds of the Invention are compounds represented by any one of Formulae I-A-XIII-A, and the pharmaceutically acceptable salts and solvates thereof, wherein $R^{4a1}$ is $C_3$-$C_6$ alkyl, $R^{4b1}$ is hydrogen, and $R^1$, $R^2$, and $R^3$ are as defined in connection with Formula I-A.

In another embodiment, Compounds of the Invention are compounds represented by any one of Formulae I-A-XIII-A, and the pharmaceutically acceptable salts and solvates thereof, wherein $R^{4a1}$ is arylalkyl, $R^{4b1}$ is hydrogen, and $R^1$, $R^2$, and $R^3$ are as defined in connection with Formula I-A.

In another embodiment, Compounds of the Invention are compounds represented by any one of Formulae I-A-XIII-A, and the pharmaceutically acceptable salts and solvates thereof, wherein $R^{4a1}$ is (cycloalkyl)alkyl, $R^{4b1}$ is hydrogen, and $R^1$, $R^2$, and $R^3$ are as defined in connection with Formula I-A.

In another embodiment, Compounds of the Invention are compounds represented by any one of Formulae I-A-XIII-A, and the pharmaceutically acceptable salts and solvates thereof, wherein $R^{4a1}$ is $C_3$-$C_6$ alkoxy, $R^{4b1}$ is hydrogen, and $R^1$, $R^2$, and $R^3$ are as defined in connection with Formula I-A.

In another embodiment, Compounds of the Invention are compounds represented by any one of Formulae I-A-XIII-A, and the pharmaceutically acceptable salts and solvates thereof, wherein $R^{4a1}$ is aralkyloxy, $R^{4b1}$ is hydrogen, and $R^1$, $R^2$, and $R^3$ are as defined in connection with Formula I-A.

In another embodiment, Compounds of the Invention are compounds represented by any one of Formulae I-A-XIII-A, and the pharmaceutically acceptable salts and solvates thereof, wherein $R^{4a1}$ is —N(H)COR$^{4c}$, $R^{4b1}$ is hydrogen, and $R^1$, $R^2$, $R^3$, and $R^{4c}$ are as defined in connection with Formula I-A. In another embodiment, $R^{4c}$ is alkyl, cycloalkyl, heterocyclo, arylalkyl, or aryl.

In another embodiment, Compounds of the Invention are compounds represented by any one of Formulae I-A-XIII-A, and the pharmaceutically acceptable salts and solvates thereof, wherein $R^{4a1}$ is —CH$_2$C(=O)NR$^{4d}$R$^{4e}$, $R^{4b1}$ is hydrogen, and $R^1$, $R^2$, $R^3$, $R^{4d}$ and $R^{4e}$ are as defined in connection with Formula I-A. In another embodiment, $R^{4d}$ and $R^{4e}$ are taken together with the nitrogen atom to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, alkoxy, aminocarbonyl, arylalkyl, and aryl, wherein the alkyl, arylalkyl, and aryl are optionally substituted with 1, 2, or 3 independently selected $R^{11a}$ groups. In another embodiment, $R^{4d}$ and $R^{4e}$ are taken together with the nitrogen atom to which they are attached form a 5- or 6-membered heterocyclo, wherein the heterocyclo is optionally substituted with one substituent, independently selected from the group consisting of alkyl, arylalkyl, and aryl, wherein the alkyl, arylalkyl, and aryl are optionally substituted with 1, 2, or 3 independently selected $R^{11a}$ groups.

In another embodiment, Compounds of the Invention are compounds represented by any one of Formulae I-A-XIII-A, and the pharmaceutically acceptable salts and solvates thereof, wherein $R^{4a1}$ is:

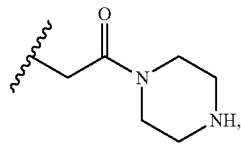 [SMILES: *CC(=O)N1CCNCC1]

i.e., $R^{4d}$ and $R^{4e}$ are taken together with the nitrogen atom to which they are attached form a piperazine, wherein the NH is optionally substituted with one substituent independently selected from the group consisting of alkyl, arylalkyl, and aryl, wherein the alkyl, arylalkyl, and aryl are optionally substituted with 1, 2, or 3 independently selected $R^{11a}$ groups.

In another embodiment, Compounds of the Invention are compounds represented by any one of Formulae I-A-XIII-A, and the pharmaceutically acceptable salts and solvates thereof, wherein $R^{4a1}$ is —N(H)SO$_2$R$^{4f}$, $R^{4b1}$ is hydrogen, and $R^1$, $R^2$, $R^3$, and $R^{4f}$ are as defined in connection with Formula I-A. In another embodiment, $R^{4f}$ is alkyl or aryl, wherein the aryl is optionally substituted with 1, 2, or 3 independently selected $R^{11a}$ groups.

In another embodiment, Compounds of the Invention are compounds represented by any one of Formulae I-A-XIII-A, and the pharmaceutically acceptable salts and solvates thereof, wherein $R^{4a1}$ and $R^{4b1}$ are taken together to form an alkenyl, and $R^1$, $R^2$, and $R^3$ are as defined in connection with Formula I-A. By way of example, $R^{4a1}$ and $R^{4b1}$ of Formula III-A are taken together to form an alkenyl to give a compound having Formula XIV:

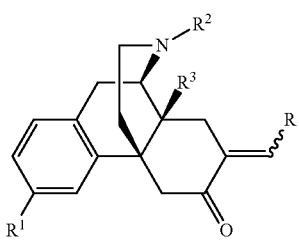

XIV and the pharmaceutically acceptable salts and solvates thereof, wherein R is hydrogen alkyl, or cycloalkyl, and $R^1$, $R^2$, and $R^3$ are as defined in connection with Formula I-A.

In another embodiment, Compounds of the Invention are compounds represented by Formula XV or Formula XVI:

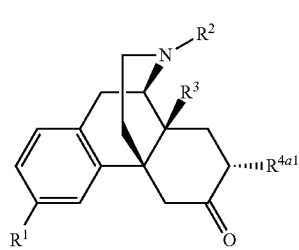

XV

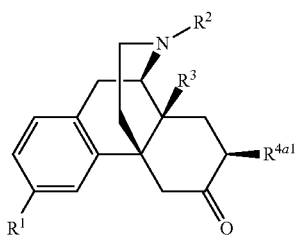

XVI and the pharmaceutically acceptable salts and solvates thereof, wherein:

$R^1$ is selected from the group consisting of OH and methoxy;

$R^2$ is selected from the group consisting of —CH$_3$ and —CH$_2$(cyclopropyl);

$R^3$ is selected from the group consisting of hydrogen and OH; and $R^{4a1}$ is as defined above in connection with Formula I-A.

In another embodiment, Compounds of the Invention are compounds represented by Formula XV or Formula XVI, and the pharmaceutically acceptable salts and solvates thereof, wherein:

$R^1$ is selected from the group consisting of OH and methoxy;

$R^2$ is selected from the group consisting of —CH$_3$ and —CH$_2$(cyclopropyl);

$R^3$ is selected from the group consisting of hydrogen and OH; and $R^{4a1}$ is selected from the group consisting of C$_3$-C$_6$ alkyl, (cycloalkyl)alkyl, C$_3$-C$_6$ alkoxy, aralkyloxy, —N(H)COR$^{4c}$, —CH$_2$C(=O)NR$^{4d}$R$^{4e}$, —N(H)SO$_2$R$^{4f}$,

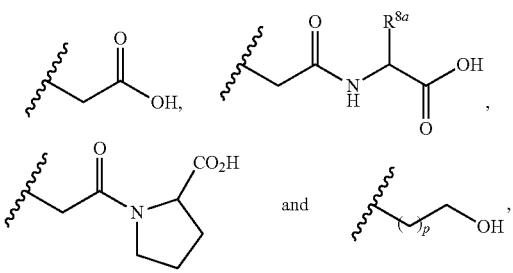

wherein $R^{4c}$, $R^{4d}$, $R^{4e}$, $R^{4f}$, $R^{8a}$ and p are defined above in connection with Formula I-A.

In another embodiment, Compounds of the Invention are compounds of Table 1, and the pharmaceutically acceptable salts and solvates thereof.

TABLE 1

| Compound No. | Structure |
|---|---|
| 1 | 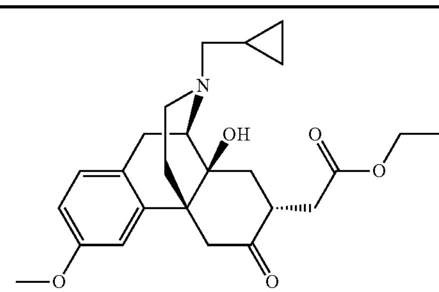 |

TABLE 1-continued

| Compound No. | Structure |
|---|---|
| 8 | 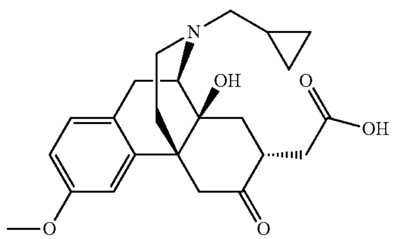 [SMILES: COc1ccc2c(c1)[C@]13CCN(CC4CC4)[C@H](C2)[C@]1(O)C[C@H](CC(=O)O)C(=O)C3] |
| 9 | 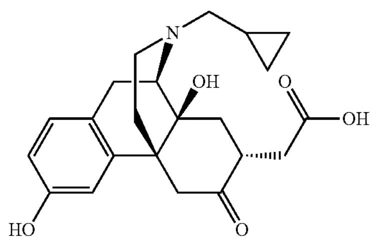 [SMILES: O=C(O)C[C@H]1C[C@@]2(O)[C@H]3Cc4ccc(O)cc4[C@@]2(CCN3CC2CC2)CC1=O] |
| 10 | 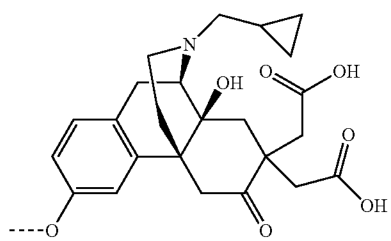 |
| 12 | 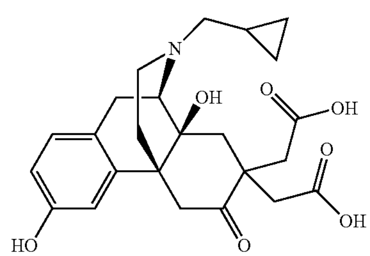 [SMILES: O=C(O)CC1(CC(=O)O)C[C@@]2(O)[C@H]3Cc4ccc(O)cc4[C@@]2(CCN3CC2CC2)CC1=O] |
| 13 | 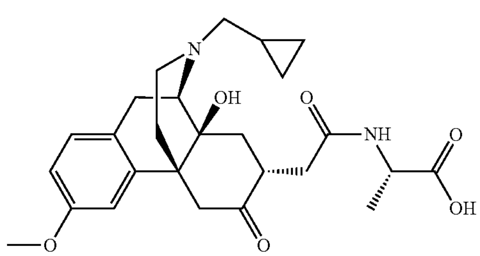 [SMILES: COc1ccc2c(c1)[C@]13CCN(CC4CC4)[C@H](C2)[C@]1(O)C[C@H](CC(=O)N[C@@H](C)C(=O)O)C(=O)C3] |
| 15 | 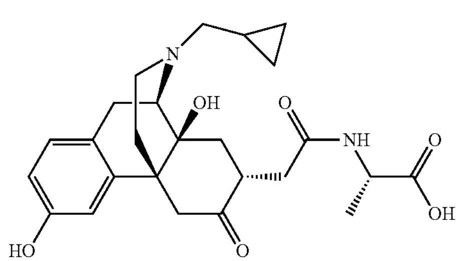 [SMILES: C[C@H](NC(=O)C[C@H]1C[C@@]2(O)[C@H]3Cc4ccc(O)cc4[C@@]2(CCN3CC2CC2)CC1=O)C(=O)O] |

TABLE 1-continued

| Compound No. | Structure |
|---|---|
| 16 | |
| 17 | |
| 18 | |
| 19 | |

In another embodiment, Compounds of the Invention are compounds of Table 1A, and the pharmaceutically acceptable salts and solvates thereof.

TABLE 1A

| Compound No. | Structure |
|---|---|
| 46 | 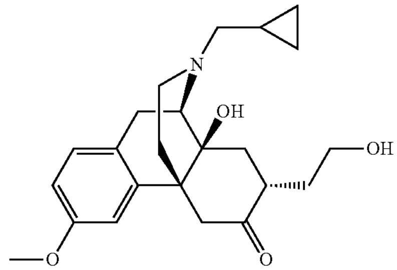 [SMILES: COc1ccc2c(c1)[C@]13CCN(CC4CC4)[C@H](C2)[C@]1(O)C[C@H](CCO)C(=O)C3] |
| 48 | 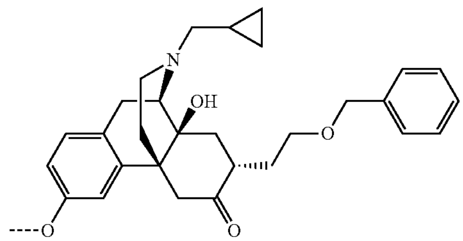 |
| 49 | 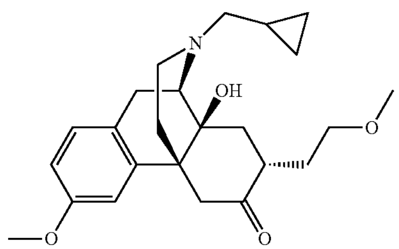 |
| 50 | 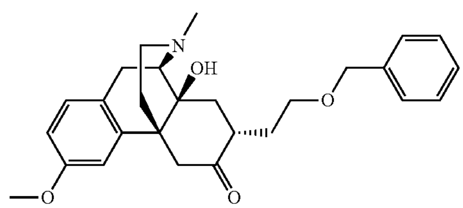 [SMILES: COc1ccc2c(c1)[C@]13CCN(C)[C@H](C2)[C@]1(O)C[C@H](CCOCc1ccccc1)C(=O)C3] |
| 54 | 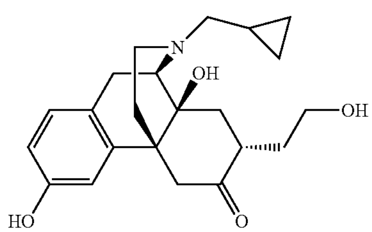 [SMILES: O=C1C[C@]23CCN(CC4CC4)[C@H](Cc4ccc(O)cc42)[C@]3(O)C[C@@H]1CCO] |
| 58 | 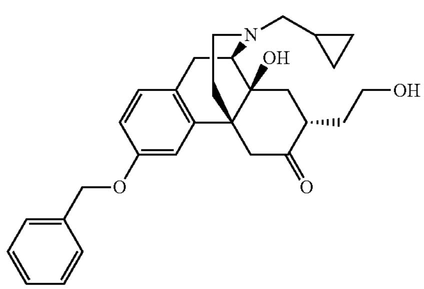 [SMILES: O=C1C[C@]23CCN(CC4CC4)[C@H](Cc4ccc(OCc5ccccc5)cc42)[C@]3(O)C[C@@H]1CCO] |

TABLE 1A-continued

| Compound No. | Structure |
|---|---|
| 59 | 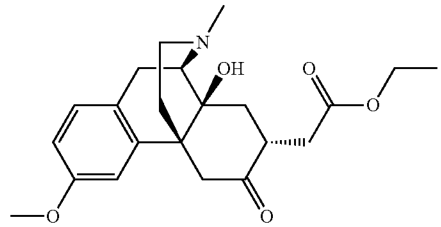 [SMILES: CCOC(=O)C[C@H]1C[C@@]2(O)[C@H]3Cc4ccc(OC)cc4[C@@]2(CCN3C)CC1=O] |
| 60 | 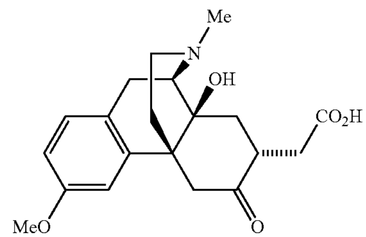 [SMILES: COc1ccc2c(c1)[C@]13CCN(C)[C@H](C2)[C@]1(O)C[C@H](CC(=O)O)C(=O)C3] |
| 61 | 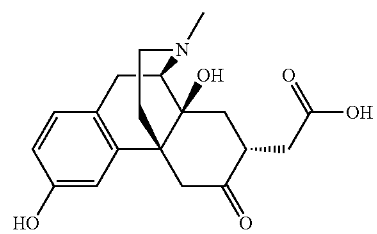 [SMILES: CN1CC[C@]23CC(=O)[C@@H](CC(=O)O)C[C@@]2(O)[C@H]1Cc1ccc(O)cc13] |
| 75 | 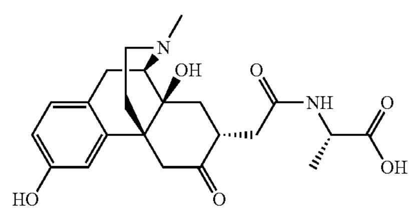 [SMILES: C[C@H](NC(=O)C[C@H]1C[C@@]2(O)[C@H]3Cc4ccc(O)cc4[C@@]2(CCN3C)CC1=O)C(=O)O] |

In another embodiment, Compounds of the Invention are compounds of Table 1B, and the pharmaceutically acceptable salts and solvates thereof.

TABLE 1B

| Compound No. | Structure |
|---|---|
| 23 | 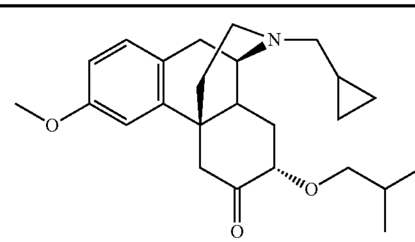 |

TABLE 1B-continued
| Compound No. | Structure |
|---|---|
| 24 | 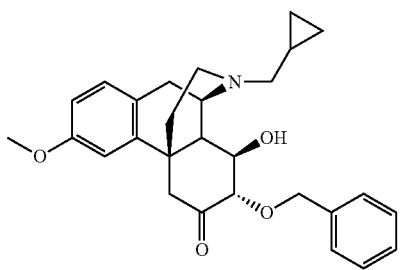 [SMILES: COc1ccc2c(c1)[C@]13CCN(CC4CC4)[C@H](C2)C1[C@@H](O)[C@H](OCc1ccccc1)C(=O)C3] |
| 25 | 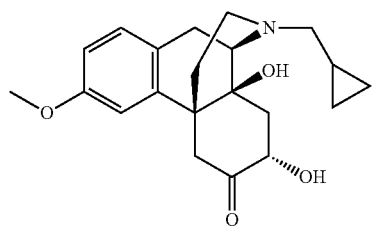 [SMILES: COc1ccc2c(c1)[C@]13CCN(CC4CC4)[C@H](C2)[C@]1(O)C[C@H](O)C(=O)C3] |
| 26 | 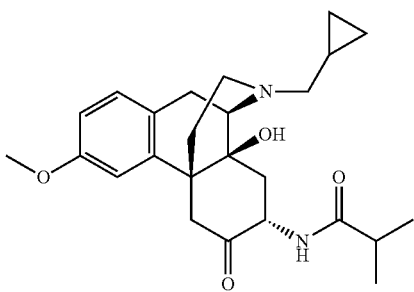 [SMILES: COc1ccc2c(c1)[C@]13CCN(CC4CC4)[C@H](C2)[C@]1(O)C[C@H](NC(=O)C(C)C)C(=O)C3] |
| 27 | 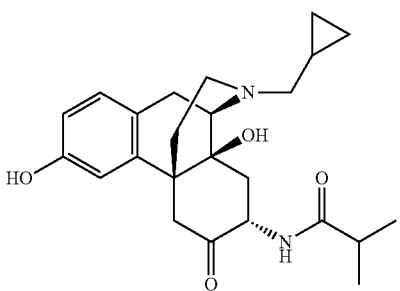 |
| 28 | 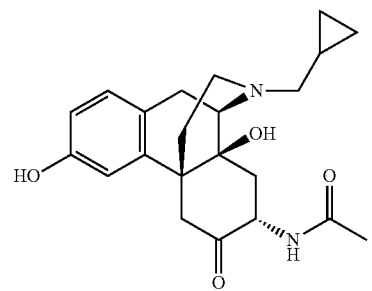 [SMILES: CC(=O)N[C@H]1C[C@@]2(O)[C@H]3Cc4ccc(O)cc4[C@@]2(CCN3CC2CC2)CC1=O] |
| 29 | 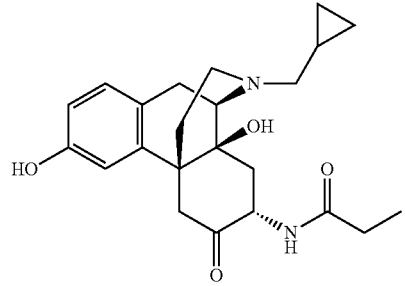 [SMILES: CCC(=O)N[C@H]1C[C@@]2(O)[C@H]3Cc4ccc(O)cc4[C@@]2(CCN3CC2CC2)CC1=O] |
| 30 | 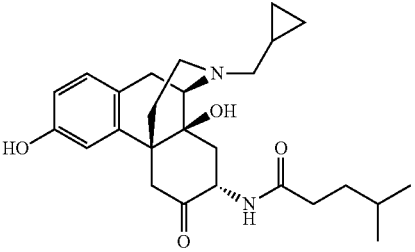 [SMILES: CC(C)CCC(=O)N[C@H]1C[C@@]2(O)[C@H]3Cc4ccc(O)cc4[C@@]2(CCN3CC2CC2)CC1=O] |
| 31 | 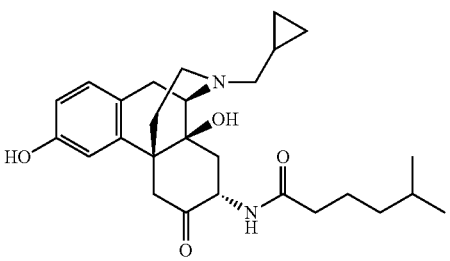 [SMILES: CC(C)CCCC(=O)N[C@H]1C[C@@]2(O)[C@H]3Cc4ccc(O)cc4[C@@]2(CCN3CC2CC2)CC1=O] |
| 32 | 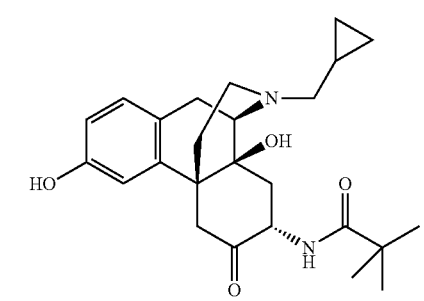 [SMILES: CC(C)(C)C(=O)N[C@H]1C[C@@]2(O)[C@H]3Cc4ccc(O)cc4[C@@]2(CCN3CC2CC2)CC1=O] |
| 33 | 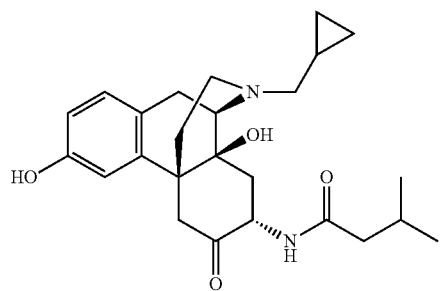 [SMILES: CC(C)CC(=O)N[C@H]1C[C@@]2(O)[C@H]3Cc4ccc(O)cc4[C@@]2(CCN3CC2CC2)CC1=O] |

TABLE 1B-continued

| Compound No. | Structure |
|---|---|
| 34 | 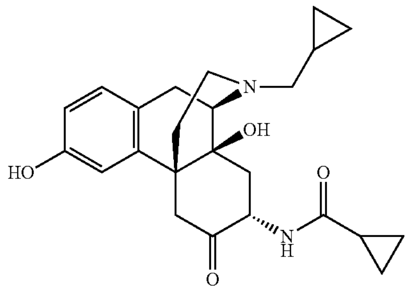 [SMILES: O=C(N[C@H]1C[C@@]2(O)[C@H]3Cc4ccc(O)cc4[C@@]2(CCN3CC2CC2)CC1=O)C1CC1] |
| 35 | 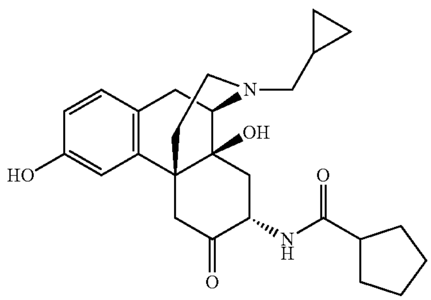 [SMILES: O=C(N[C@H]1C[C@@]2(O)[C@H]3Cc4ccc(O)cc4[C@@]2(CCN3CC2CC2)CC1=O)C1CCCC1] |
| 36 | 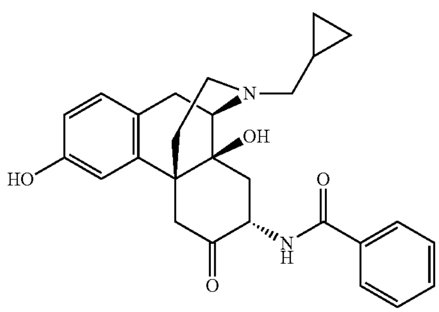 [SMILES: O=C(N[C@H]1C[C@@]2(O)[C@H]3Cc4ccc(O)cc4[C@@]2(CCN3CC2CC2)CC1=O)c1ccccc1] |
| 37 | 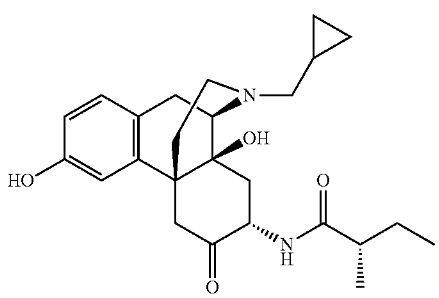 [SMILES: CC[C@H](C)C(=O)N[C@H]1C[C@@]2(O)[C@H]3Cc4ccc(O)cc4[C@@]2(CCN3CC2CC2)CC1=O] |
| 38 | 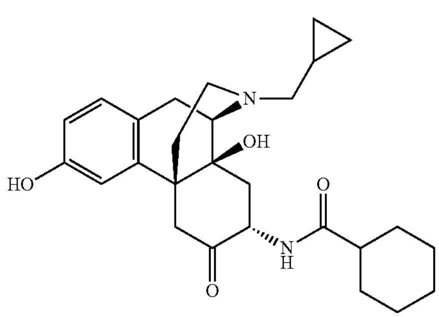 [SMILES: O=C(N[C@H]1C[C@@]2(O)[C@H]3Cc4ccc(O)cc4[C@@]2(CCN3CC2CC2)CC1=O)C1CCCCC1] |
| 42 | |
| 43 | |
| 62 | |
| 64 | |
| 65 | |

TABLE 1B-continued

| Compound No. | Structure |
|---|---|
| 66 | 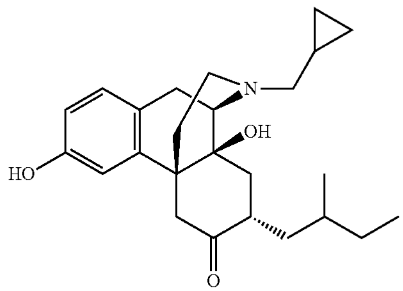 [SMILES: CCC(C)C[C@H]1C[C@@]2(O)[C@H]3Cc4ccc(O)cc4[C@@]2(CCN3CC2CC2)CC1=O] |
| 67 | 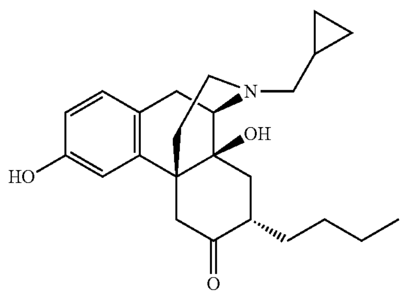 [SMILES: CCCC[C@H]1C[C@@]2(O)[C@H]3Cc4ccc(O)cc4[C@@]2(CCN3CC2CC2)CC1=O] |
| 68 | 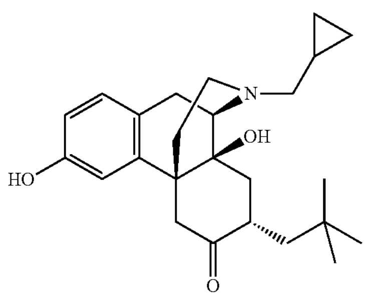 [SMILES: CC(C)(C)C[C@H]1C[C@@]2(O)[C@H]3Cc4ccc(O)cc4[C@@]2(CCN3CC2CC2)CC1=O] |
| 69 | 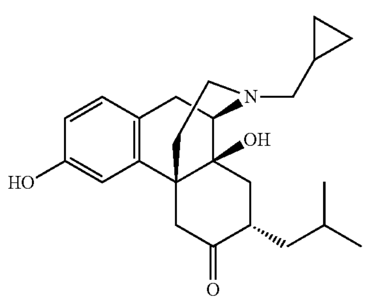 [SMILES: CC(C)C[C@H]1C[C@@]2(O)[C@H]3Cc4ccc(O)cc4[C@@]2(CCN3CC2CC2)CC1=O] |
| 70 | 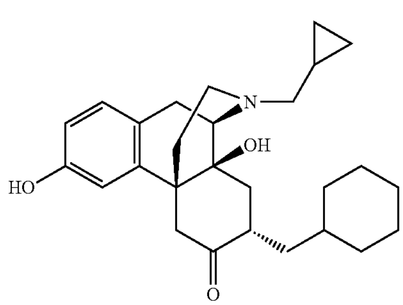 [SMILES: O=C1C[C@]23CCN(CC4CC4)[C@H](Cc4ccc(O)cc42)[C@]3(O)C[C@@H]1CC1CCCCC1] |
| 71 | 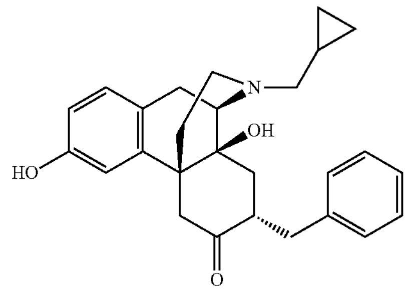 [SMILES: O=C1C[C@]23CCN(CC4CC4)[C@H](Cc4ccc(O)cc42)[C@]3(O)C[C@@H]1Cc1ccccc1] |
| 72 | 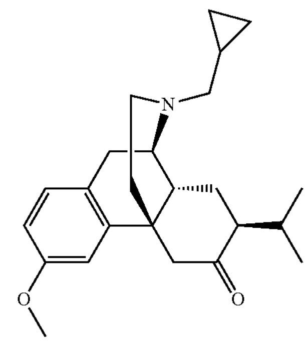 [SMILES: COc1ccc2c(c1)[C@]13CCN(CC4CC4)[C@H](C2)[C@@H]1C[C@@H](C(C)C)C(=O)C3] |
| 73 | 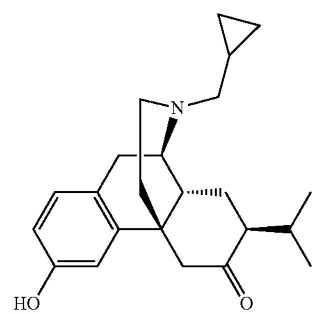 [SMILES: CC(C)[C@@H]1C[C@H]2[C@H]3Cc4ccc(O)cc4[C@@]2(CCN3CC2CC2)CC1=O] |
| 74 | 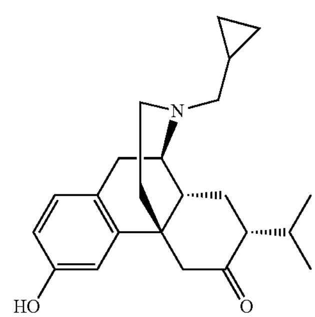 [SMILES: CC(C)[C@H]1C[C@H]2[C@H]3Cc4ccc(O)cc4[C@@]2(CCN3CC2CC2)CC1=O] |
| 76 | 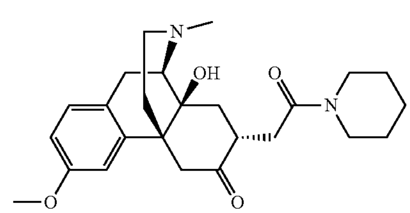 [SMILES: COc1ccc2c(c1)[C@]13CCN(C)[C@H](C2)[C@]1(O)C[C@H](CC(=O)N1CCCCC1)C(=O)C3] |

TABLE 1B-continued

| Compound No. | Structure |
|---|---|
| 77 | (structure) |
| 78 | (structure) |
| 79 | (structure) |
| 80 | (structure) |
| 81 | (structure) |
| 82 | (structure) |
| 83 | (structure) |
| 84 | (structure) |
| 85 | (structure) |
| 86 | (structure) |
| 87 | (structure) |
| 88 | (structure) |
| 89 | (structure) |

TABLE 1B-continued

| Compound No. | Structure |
|---|---|
| 90 | (structure) |
| 91 | (structure) |
| 92 | (structure) |
| 93 | (structure) |
| 94 | (structure) |
| 95 | (structure) |
| 96 | (structure) |
| 97 | (structure) |
| 98 | (structure) |
| 99 | (structure) |
| 100 | (structure) |
| 101 | (structure) |

TABLE 1B-continued

| Compound No. | Structure |
|---|---|
| 102 | (structure) |
| 103 | (structure) |
| 104 | (structure) |
| 105 | (structure) |
| 106 | (structure) |
| 107 | (structure) |
| 108 | (structure) |
| 109 | (structure) |
| 110 | (structure) |

The chemical names of the compound examples of Tables 1, 1A, and 1B are provided in Table 2.

TABLE 2

| Compound No. | Chemical Name |
|---|---|
| 1 | ethyl 2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetate |
| 8 | 2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetic acid |
| 9 | 2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetic acid |

TABLE 2-continued

| Compound No. | Chemical Name |
|---|---|
| 10 | 2,2'-((4bR,8aS,9R)-11-(cyclopropylmethyl)-8a-hydroxy-3-methoxy-6-oxo-6,7,8,8a,9,10-hexahydro-5H-9,4b-(epiminoethano)phenanthrene-7,7-diyl)diacetic acid |
| 12 | 2,2'-((4bR,8aS,9R)-11-(cyclopropylmethyl)-3,8a-dihydroxy-6-oxo-6,7,8,8a,9,10-hexahydro-5H-9,4b-(epiminoethano)phenanthrene-7,7-diyl)diacetic acid |
| 13 | (S)-2-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetamido)propanoic acid |
| 15 | (S)-2-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamido)propanoic acid |
| 16 | (S)-1-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetyl)pyrrolidine-2-carboxylic acid |
| 17 | (S)-1-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetyl)pyrrolidine-2-carboxylic acid |
| 18 | (S)-2-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetamido)-4-methylpentanoic acid |
| 19 | (S)-2-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamido)-4-methylpentanoic acid |
| 23 | (4bR,7S,8aS,9R)-11-(cyclopropylmethyl)-8a-hydroxy-7-isobutoxy-3-methoxy-8,8a,9,10-tetrahydro-5H-9,4b-(epiminoethano)phenanthren-6(7H)-one |
| 24 | (4bR,7S,8aS,9R)-7-(benzyloxy)-11-(cyclopropylmethyl)-8a-hydroxy-3-methoxy-8,8a,9,10-tetrahydro-5H-9,4b-(epiminoethano)phenanthren-6(7H)-one |
| 25 | (4bR,7S,8aS,9R)-11-(cyclopropylmethyl)-7,8a-dihydroxy-3-methoxy-8,8a,9,10-tetrahydro-5H-9,4b-(epiminoethano)phenanthren-6(7H)-one |
| 26 | N-((4bR,7S,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)isobutyramide |
| 27 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)isobutyramide |
| 28 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamide |
| 29 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)propionamide |
| 30 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-4-methylpentanamide |
| 31 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-5-methylhexanamide |
| 32 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)pivalamide |
| 33 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-3-methylbutanamide |
| 34 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopropanecarboxamide |
| 35 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopentanecarboxamide |
| 36 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzamide |
| 37 | (S)-N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-methylbutanamide |
| 38 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclohexanecarboxamide |

TABLE 2-continued

| Compound No. | Chemical Name |
|---|---|
| 42 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)ethanesulfonamide |
| 43 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzenesulfonamide |
| 46 | (4bR,7S,8aS,9R)-11-(cyclopropylmethyl)-8a-hydroxy-7-(2-hydroxyethyl)-3-methoxy-8,8a,9,10-tetrahydro-5H-9,4b-(epiminoethano)phenanthren-6(7H)-one |
| 48 | (4bR,7S,8aS,9R)-7-(2-(benzyloxy)ethyl)-11-(cyclopropylmethyl)-8a-hydroxy-3-methoxy-8,8a,9,10-tetrahydro-5H-9,4b-(epiminoethano)phenanthren-6(7H)-one |
| 49 | (4bR,7S,8aS,9R)-11-(cyclopropylmethyl)-8a-hydroxy-3-methoxy-7-(2-methoxyethyl)-8,8a,9,10-tetrahydro-5H-9,4b-(epiminoethano)phenanthren-6(7H)-one |
| 50 | (4bR,7S,8aS,9R)-7-(2-(benzyloxy)ethyl)-8a-hydroxy-3-methoxy-11-methyl-8,8a,9,10-tetrahydro-5H-9,4b-(epiminoethano)phenanthren-6(7H)-one |
| 54 | (4bR,7S,8aS,9R)-11-(cyclopropylmethyl)-3,8a-dihydroxy-7-(2-hydroxyethyl)-8,8a,9,10-tetrahydro-5H-9,4b-(epiminoethano)phenanthren-6(7H)-one |
| 58 | (4bR,7S,8aS,9R)-3-(benzyloxy)-11-(cyclopropylmethyl)-8a-hydroxy-7-(2-hydroxyethyl)-8,8a,9,10-tetrahydro-5H-9,4b-(epiminoethano)phenanthren-6(7H)-one |
| 59 | ethyl 2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetate |
| 60 | 2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetic acid |
| 61 | 2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetic acid |
| 62 | (4bR,8aS,9R,E)-11-(cyclopropylmethyl)-8a-hydroxy-3-methoxy-7-(3-methylbutylidene)-8,8a,9,10-tetrahydro-5H-9,4b-(epiminoethano)phenanthren-6(7H)-one |
| 64 | (4bR,7S,8aS,9R)-11-(cyclopropylmethyl)-3,8a-dihydroxy-7-isopentyl-8,8a,9,10-tetrahydro-5H-9,4b-(epiminoethano)phenanthren-6(7H)-one |
| 65 | (4bR,7S,8aS,9R)-7-(cyclopentylmethyl)-11-(cyclopropylmethyl)-3,8a-dihydroxy-8,8a,9,10-tetrahydro-5H-9,4b-(epiminoethano)phenanthren-6(7H)-one |
| 66 | (4bR,7S,8aS,9R)-11-(cyclopropylmethyl)-3,8a-dihydroxy-7-(2-methylbutyl)-8,8a,9,10-tetrahydro-5H-9,4b-(epiminoethano)phenanthren-6(7H)-one |
| 67 | (4bR,7S,8aS,9R)-7-butyl-11-(cyclopropylmethyl)-3,8a-dihydroxy-8,8a,9,10-tetrahydro-5H-9,4b-(epiminoethano)phenanthren-6(7H)-one |
| 68 | (4bR,7S,8aS,9R)-11-(cyclopropylmethyl)-3,8a-dihydroxy-7-neopentyl-8,8a,9,10-tetrahydro-5H-9,4b-(epiminoethano)phenanthren-6(7H)-one |
| 69 | (4bR,7S,8aS,9R)-11-(cyclopropylmethyl)-3,8a-dihydroxy-7-isobutyl-8,8a,9,10-tetrahydro-5H-9,4b-(epiminoethano)phenanthren-6(7H)-one |
| 70 | (4bR,7S,8aS,9R)-7-(cyclohexylmethyl)-11-(cyclopropylmethyl)-3,8a-dihydroxy-8,8a,9,10-tetrahydro-5H-9,4b-(epiminoethano)phenanthren-6(7H)-one |
| 71 | (4bR,7S,8aS,9R)-7-benzyl-11-(cyclopropylmethyl)-3,8a-dihydroxy-8,8a,9,10-tetrahydro-5H-9,4b-(epiminoethano)phenanthren-6(7H)-one |
| 72 | (4bS,7S,8aR,9R)-11-(cyclopropylmethyl)-7-isopropyl-3-methoxy-8,8a,9,10-tetrahydro-5H-9,4b-(epiminoethano)phenanthren-6(7H)-one |
| 73 | (4bS,7S,8aR,9R)-11-(cyclopropylmethyl)-3-hydroxy-7-isopropyl-8,8a,9,10-tetrahydro-5H-9,4b-(epiminoethano)phenanthren-6(7H)-one |
| 74 | (4bS,7R,8aR,9R)-11-(cyclopropylmethyl)-3-hydroxy-7-isopropyl-8,8a,9,10-tetrahydro-5H-9,4b-(epiminoethano)phenanthren-6(7H)-one |
| 75 | (2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetyl)-L-alanine |
| 76 | (4bR,7R,8aS,9R)-8a-hydroxy-3-methoxy-11-methyl-7-(2-oxo-2-(piperidin-1-yl)ethyl)-8,8a,9,10-tetrahydro-5H-9,4b-(epiminoethano)phenanthren-6(7H)-one |
| 77 | (4bR,7R,8aS,9R)-8a-hydroxy-3-methoxy-11-methyl-7-(2-oxo-2-(pyrrolidin-1-yl)ethyl)-8,8a,9,10-tetrahydro-5H-9,4b-(epiminoethano)phenanthren-6(7H)-one |

TABLE 2-continued

| Compound No. | Chemical Name |
| --- | --- |
| 78 | (4bR,7R,8aS,9R)-8a-hydroxy-7-(2-(4-hydroxypiperidin-1-yl)-2-oxoethyl)-3-methoxy-11-methyl-8,8a,9,10-tetrahydro-5H-9,4b-(epiminoethano)phenanthren-6(7H)-one |
| 79 | (4bR,7R,8aS,9R)-8a-hydroxy-3-methoxy-11-methyl-7-(2-morpholino-2-oxoethyl)-8,8a,9,10-tetrahydro-5H-9,4b-(epiminoethano)phenanthren-6(7H)-one |
| 80 | (4bR,7R,8aS,9R)-3,8a-dihydroxy-11-methyl-7-(2-oxo-2-(piperidin-1-yl)ethyl)-8,8a,9,10-tetrahydro-5H-9,4b-(epiminoethano)phenanthren-6(7H)-one |
| 81 | (4bR,7R,8aS,9R)-3,8a-dihydroxy-7-(2-(4-hydroxypiperidin-1-yl)-2-oxoethyl)-11-methyl-8,8a,9,10-tetrahydro-5H-9,4b-(epiminoethano)phenanthren-6(7H)-one |
| 82 | 2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-isobutylacetamide |
| 83 | N-benzyl-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide |
| 84 | N-(cyclopropylmethyl)-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide |
| 85 | 2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-(2-hydroxyethyl)acetamide |
| 86 | 2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-(3-hydroxypropyl)acetamide |
| 87 | 2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)-N-(2-hydroxyethyl)acetamide |
| 88 | 2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)-N-(3-hydroxypropyl)acetamide |
| 89 | (4bR,7R,8aS,9R)-3,8a-dihydroxy-11-methyl-7-(2-oxo-2-(piperazin-1-yl)ethyl)-8,8a,9,10-tetrahydro-5H-9,4b-(epiminoethano)phenanthren-6(7H)-one |
| 90 | (4bR,7R,8aS,9R)-3,8a-dihydroxy-11-methyl-7-(2-(4-methylpiperazin-1-yl)-2-oxoethyl)-8,8a,9,10-tetrahydro-5H-9,4b-(epiminoethano)phenanthren-6(7H)-one |
| 91 | (4bR,7R,8aS,9R)-7-(2-(4-benzylpiperazin-1-yl)-2-oxoethyl)-3,8a-dihydroxy-11-methyl-8,8a,9,10-tetrahydro-5H-9,4b-(epiminoethano)phenanthren-6(7H)-one |
| 92 | (4bR,7R,8aS,9R)-3,8a-dihydroxy-11-methyl-7-(2-oxo-2-(4-phenylpiperazin-1-yl)ethyl)-8,8a,9,10-tetrahydro-5H-9,4b-(epiminoethano)phenanthren-6(7H)-one |
| 93 | (4bR,7R,8aS,9R)-11-(cyclopropylmethyl)-3,8a-dihydroxy-7-(2-oxo-2-(piperazin-1-yl)ethyl)-8,8a,9,10-tetrahydro-5H-9,4b-(epiminoethano)phenanthren-6(7H)-one |
| 94 | (4bR,7R,8aS,9R)-11-(cyclopropylmethyl)-3,8a-dihydroxy-7-(2-(4-methylpiperazin-1-yl)-2-oxoethyl)-8,8a,9,10-tetrahydro-5H-9,4b-(epiminoethano)phenanthren-6(7H)-one |
| 95 | (4bR,7R,8aS,9R)-7-(2-(4-benzylpiperazin-1-yl)-2-oxoethyl)-11-(cyclopropylmethyl)-3,8a-dihydroxy-8,8a,9,10-tetrahydro-5H-9,4b-(epiminoethano)phenanthren-6(7H)-one |
| 96 | (4bR,7R,8aS,9R)-11-(cyclopropylmethyl)-3,8a-dihydroxy-7-(2-oxo-2-(4-phenylpiperazin-1-yl)ethyl)-8,8a,9,10-tetrahydro-5H-9,4b-(epiminoethano)phenanthren-6(7H)-one |
| 97 | N-((4bR,7S,8aS,9R)-3,8a-dihydroxy-11-methyl-6-oxo-6,7,8,8a,9,10-hexahydro-5H-9,4b-(epiminoethano)phenanthren-7-yl)acetamide |
| 98 | N-((4bR,7S,8aS,9R)-3,8a-dihydroxy-11-methyl-6-oxo-6,7,8,8a,9,10-hexahydro-5H-9,4b-(epiminoethano)phenanthren-7-yl)propionamide |
| 99 | N-((4bR,7S,8aS,9R)-3,8a-dihydroxy-11-methyl-6-oxo-6,7,8,8a,9,10-hexahydro-5H-9,4b-(epiminoethano)phenanthren-7-yl)isobutyramide |
| 100 | N-((4bR,7S,8aS,9R)-3,8a-dihydroxy-11-methyl-6-oxo-6,7,8,8a,9,10-hexahydro-5H-9,4b-(epiminoethano)phenanthren-7-yl)pivalamide |
| 101 | N-((4bR,7S,8aS,9R)-3,8a-dihydroxy-11-methyl-6-oxo-6,7,8,8a,9,10-hexahydro-5H-9,4b-(epiminoethano)phenanthren-7-yl)-4-methylpentanamide |
| 102 | N-((4bR,7S,8aS,9R)-3,8a-dihydroxy-11-methyl-6-oxo-6,7,8,8a,9,10-hexahydro-5H-9,4b-(epiminoethano)phenanthren-7-yl)-5-methylhexanamide |
| 103 | N-((4bR,7S,8aS,9R)-3,8a-dihydroxy-11-methyl-6-oxo-6,7,8,8a,9,10-hexahydro-5H-9,4b-(epiminoethano)phenanthren-7-yl)cyclohexanecarboxamide |

TABLE 2-continued

| Compound No. | Chemical Name |
|---|---|
| 104 | (4bS,7S,8aR,9R)-11-(cyclopropylmethyl)-3-hydroxy-7-isopentyl-8,8a,9,10-tetrahydro-5H-9,4b-(epiminoethano)phenanthren-6(7H)-one |
| 105 | (4bS,7S,8aR,9R)-7-(cyclopentylmethyl)-11-(cyclopropylmethyl)-3-hydroxy-8,8a,9,10-tetrahydro-5H-9,4b-(epiminoethano)phenanthren-6(7H)-one |
| 106 | (4bR,7S,8aS,9R)-3,8a-dihydroxy-7-isopentyl-11-methyl-8,8a,9,10-tetrahydro-5H-9,4b-(epiminoethano)phenanthren-6(7H)-one |
| 107 | (4bS,7S,8aR,9R)-7-(cyclopentylmethyl)-3-hydroxy-11-methyl-8,8a,9,10-tetrahydro-5H-9,4b-(epiminoethano)phenanthren-6(7H)-one |
| 108 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)methanesulfonamide |
| 109 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)piperidine-4-carboxamide |
| 110 | N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-(dimethylamino)acetamide |

In another embodiment, Compounds of the Invention are compounds represented by any one of Formulae I-A-XIII-A, and the pharmaceutically acceptable salts and solvates thereof, wherein $R^1$ is —O—PG, wherein PG is a hydroxyl protecting group, and $R^2$, $R^3$, $R^{4a1}$, and $R^{4b1}$ are as defined above in connection with Formula I-A.

In another embodiment, Compounds of the Invention are compounds represented by any one of Formulae I-XIII, and the pharmaceutically acceptable salts and solvates thereof, wherein $R^1$ is —O—PG, wherein PG is a hydroxyl protecting group, and $R^2$, $R^3$, $R^{4a}$, and $R^{4b}$ are as defined above in connection with Formula I.

In one aspect, the present disclosure is drawn to the following particular embodiments:

Embodiment I

A compound having the Formula I-A:

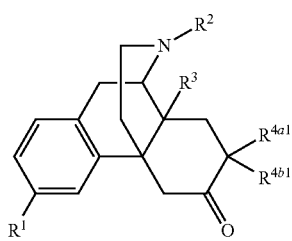

I-A or a pharmaceutically acceptable salt or solvate thereof, wherein:

$R^1$ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups; or —O—PG, wherein PG is a hydroxyl protecting group;

$R^2$ is:
(a) hydrogen or carboxamido; or
(b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^3$ is hydrogen, OH, or halo; or alkoxy, alkylamino, or dialkylamino, any of which is optionally substituted with 1, 2, or 3 substituents, each independently selected from the group consisting of hydroxyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^{4a1}$ is selected from the group consisting of $C_3$-$C_6$ alkyl, aralkyl, (cycloalkyl)alkyl, $C_3$-$C_6$ alkoxy, aralkyloxy, —N(H)COR$^{4c}$, —CH$_2$C(=O)NR$^{4d}$R$^{4e}$, —N(H)SO$_2$R$^{4f}$,

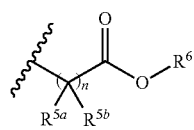

R4a-I

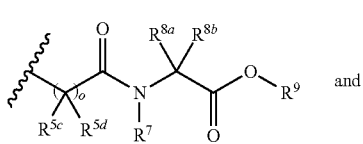

R4a-II and

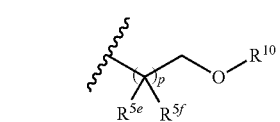

R4a-III $R^{4b1}$ is selected from the group consisting of hydrogen and $R^{4a}$-I; or $R^{4a1}$ and $R^{4b1}$ taken together form an alkenyl, $R^{4c}$ is alkyl, cycloalkyl, heterocyclo, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl and cycloalkyl are optionally substituted with 1, 2, or 3 independently selected $R^{11a}$ groups;

$R^{4d}$ is hydrogen; or alkyl, cycloalkyl, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^{4e}$ is hydrogen; or alkyl, optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl; or $R^{4d}$ and $R^{4e}$ taken together with the nitrogen atom to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, alkoxy, aminocarbonyl, arylalkyl, and aryl, wherein the alkyl, arylalkyl, and aryl are optionally substituted with 1, 2, or 3 independently selected $R^{11a}$ groups;

$R^{4f}$ is alkyl, cycloalkyl, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl and cycloalkyl are optionally substituted with 1, 2, or 3 independently selected $R^{11a}$ groups;

each $R^{5a}$, $R^{5b}$, $R^{5c}$, $R^{5d}$, $R^{5e}$, and $R^{5f}$ is independently selected from the group consisting of hydrogen and alkyl;

$R^6$ is hydrogen or alkyl;

$R^7$ is hydrogen or alkyl;

$R^{8a}$ is hydrogen or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^{8b}$ is hydrogen or alkyl, wherein the alkyl is optionally substituted with 1, 2, or 3 substituents, each independently selected from the group consisting of alkyl, hydroxy, halo, haloalkyl, amino, alkylamino, dialkylamino, carboxy, alkoxy, alkoxycarbonyl, and aminocarbonyl; or $R^{8a}$ and $R^{8b}$ taken together with the carbon atom to which they are attached form a 3- to 8-membered cycloalkyl; or $R^7$ and $R^{8a}$ taken together with the atoms to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, carboxy, alkoxy, alkoxycarbonyl, and aminocarbonyl;

$R^9$ is hydrogen or alkyl;

$R^{10}$ is hydrogen, or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

each $R^{11a}$ is independently selected from the group consisting of hydroxy, halo, alkyl, haloalkyl, cyano, nitro, amino, alkylamino, dialkylamino, carboxy, alkoxy, and alkoxycarbonyl;

n is 1, 2, or 3;

o is 1, 2, or 3; and p is 1, 2, or 3.

Embodiment II

The compound of Embodiment I, or a pharmaceutically acceptable salt or solvate thereof, wherein:

$R^{4a1}$ is selected from the group consisting of:

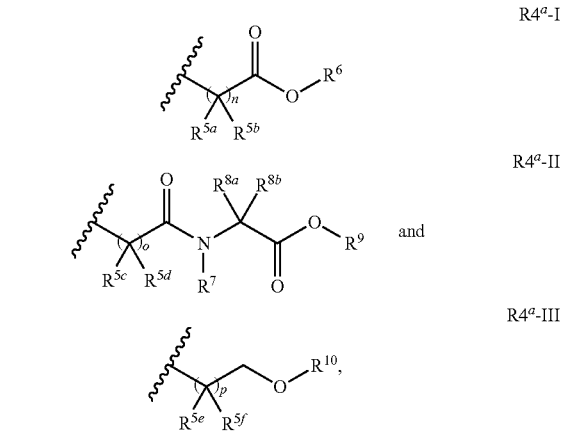

and $R^{4b1}$ is selected from the group consisting of hydrogen and $R^{4a}$-I.

Embodiment III

The compound of Embodiment I or II, having the Formula II-A:

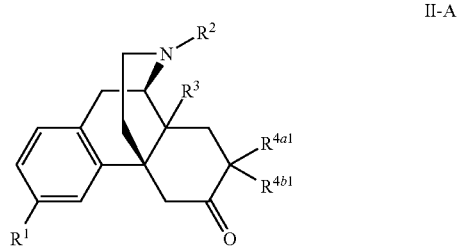

or a pharmaceutically acceptable salt or solvate thereof.

Embodiment IV

The compound of Embodiment III, having the Formula III-A:

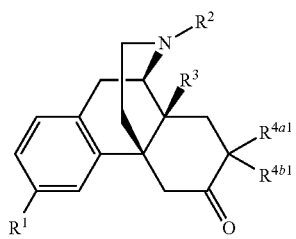

III-A or a pharmaceutically acceptable salt or solvate thereof.

Embodiment V

The compound of Embodiment IV, having the Formula IV-A:

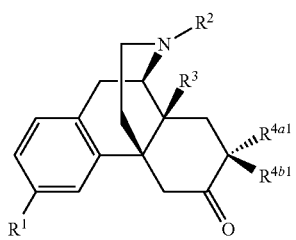

IV-A or a pharmaceutically acceptable salt or solvate thereof.

Embodiment VI

The compound of Embodiment IV, having the Formula V-A:

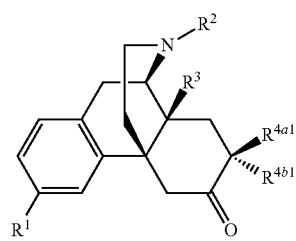

V-A or a pharmaceutically acceptable salt or solvate thereof.

Embodiment VII

The compound of Embodiment III, having the Formula VI-A:

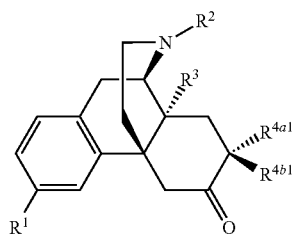

VI-A or a pharmaceutically acceptable salt or solvate thereof.

Embodiment VIII

The compound of Embodiment III, having the Formula VII-A:

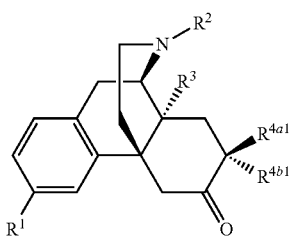

VII-A or a pharmaceutically acceptable salt or solvate thereof.

Embodiment IX

The compound of Embodiment I or II, having the Formula VIII-A:

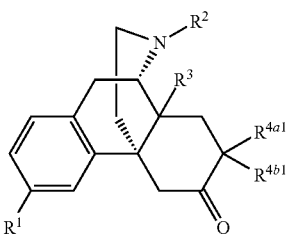

VIII-A or a pharmaceutically acceptable salt or solvate thereof.

Embodiment X

The compound of Embodiment IX, having the Formula IX-A:

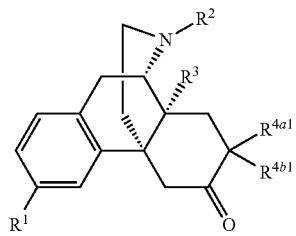

IX-A or a pharmaceutically acceptable salt or solvate thereof.

Embodiment XI

The compound of Embodiment X, having the Formula X-A:

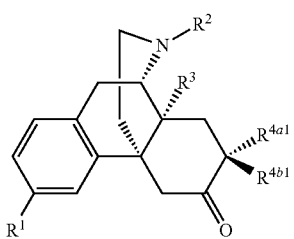

X-A or a pharmaceutically acceptable salt or solvate thereof.

Embodiment XII

The compound of Embodiment X, having the Formula XI-A:

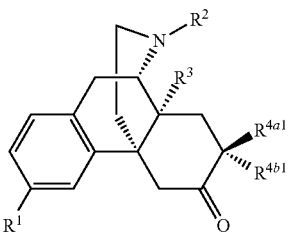

XI-A or a pharmaceutically acceptable salt or solvate thereof.

Embodiment XIII

The compound of Embodiment IX, having the Formula XII-A:

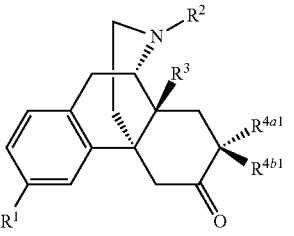

XII-A or a pharmaceutically acceptable salt or solvate thereof.

Embodiment XIV

The compound of Embodiment IX, having the Formula XIII-A:

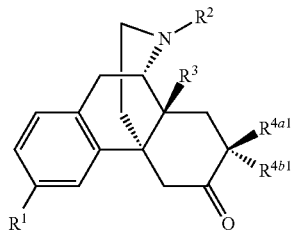

XIII-A or a pharmaceutically acceptable salt or solvate thereof.

Embodiment XV

The compound of any one of Embodiments I-IV, or a pharmaceutically acceptable salt or solvate thereof, wherein $R^1$ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups.

Embodiment XVI

The compound of any one of Embodiments I-XV, or a pharmaceutically acceptable salt or solvate thereof, wherein $R^1$ is OH or unsubstituted $C_{1-6}$ alkoxy.

Embodiment XVII

The compound of any one of Embodiments I-XVI, or a pharmaceutically acceptable salt or solvate thereof, wherein $R^2$ is hydrogen or carboxamido.

Embodiment XVIII

The compound of any one of Embodiments I-XVI, or a pharmaceutically acceptable salt or solvate thereof, wherein $R^2$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups.

Embodiment XIX

The compound of Embodiment XVIII, or a pharmaceutically acceptable salt or solvate thereof, wherein $R^2$ is $C_{3-7}$ (cycloalkyl)($C_{1-4}$)alkyl or $C_{3-7}$ (cycloalkenyl)($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

Embodiment XX

The compound of Embodiment XIX, or a pharmaceutically acceptable salt or solvate thereof, wherein $R^2$ is cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, amino, $C_{1-4}$ alkylamino, di($C_{1-4}$)alkylamino, carboxy, $C_{1-4}$ alkoxy, and $C_{1-4}$ alkoxycarbonyl.

Embodiment XXI

The compound of any one of Embodiments I-XX, or a pharmaceutically acceptable salt or solvate thereof, wherein $R^3$ is hydrogen.

Embodiment XXII

The compound of any one of Embodiments I-XX, or a pharmaceutically acceptable salt or solvate thereof, wherein $R^3$ is hydroxy.

Embodiment XXIII

The compound of any one of Embodiments I-XXII, or a pharmaceutically acceptable salt or solvate thereof, wherein $R^{4a1}$ is $C_3$-$C_6$ alkyl.

Embodiment XXIV

The compound of any one of Embodiments I-XXII, or a pharmaceutically acceptable salt or solvate thereof, wherein $R^{4a1}$ is arylalkyl.

Embodiment XXV

The compound of any one of Embodiments I-XXII, or a pharmaceutically acceptable salt or solvate thereof wherein $R^{4a1}$ is (cycloalkyl)alkyl.

Embodiment XXVI

The compound of any one of Embodiments I-XXII, or a pharmaceutically acceptable salt or solvate thereof, wherein $R^{4a1}$ is $C_3$-$C_6$ alkoxy.

Embodiment XXVII

The compound of any one of Embodiments I-XXII, or a pharmaceutically acceptable salt or solvate thereof, wherein $R^{4a1}$ is aralkyloxy.

Embodiment XXVIII

The compound of any one of Embodiments I-XXII, or a pharmaceutically acceptable salt or solvate thereof, wherein $R^{4a1}$ is N(H)COR$^{4c}$.

Embodiment XXIX

The compound of Embodiment XXVIII, or a pharmaceutically acceptable salt or solvate thereof, wherein $R^{4c}$ is alkyl, cycloalkyl, heterocyclo, arylalkyl, or aryl.

Embodiment XXX

The compound of any one of Embodiments I-XXII, or a pharmaceutically acceptable salt or solvate thereof, wherein $R^{4a1}$ is —CH$_2$C(=O)NR$^{4d}$R$^{4e}$.

Embodiment XXXI

The compound of Embodiment XXX, or a pharmaceutically acceptable salt or solvate thereof, wherein $R^{4d}$ and $R^{4e}$ are taken together with the nitrogen atom to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, alkoxy, aminocarbonyl, arylalkyl, and aryl, wherein the alkyl, arylalkyl, and aryl are optionally substituted with 1, 2, or 3 independently selected $R^{11a}$ groups.

Embodiment XXXII

The compound of Embodiment XXXI, or a pharmaceutically acceptable salt or solvate thereof, wherein $R^{4d}$ and $R^{4e}$ are taken together with the nitrogen atom to which they are attached form a 5- or 6-membered heterocyclo, wherein the heterocyclo is optionally substituted with one substituent, independently selected from the group consisting of alkyl, arylalkyl, and aryl, wherein the alkyl, arylalkyl, and aryl are optionally substituted with 1, 2, or 3 independently selected $R^{11a}$ groups.

Embodiment XXXIII

The compound of Embodiment XXX, or a pharmaceutically acceptable salt or solvate thereof, wherein $R^{4d}$ is alkyl, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups; and $R^{4e}$ is hydrogen.

Embodiment XXXIV

The compound of any one of Embodiments I-XXII, or a pharmaceutically acceptable salt or solvate thereof, wherein $R^{4a1}$ is —N(H)SO$_2$R$^{4f}$.

Embodiment XXXV

The compound of Embodiment XXXIV, or a pharmaceutically acceptable salt or solvate thereof, wherein $R^{4f}$ is alkyl or aryl, wherein the aryl is optionally substituted with 1, 2, or 3 independently selected $R^{11a}$ groups.

Embodiment XXXVI

The compound of any one of Embodiments I-XXII, or a pharmaceutically acceptable salt or solvate thereof, wherein $R^{4a1}$ is:

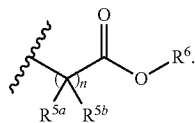

Embodiment XXXVII

The compound of Embodiment XXXVI, or a pharmaceutically acceptable salt or solvate thereof, wherein $R^{5a}$ and $R^{5b}$ are each hydrogen.

Embodiment XXXVIII

The compound of Embodiment XXXVI or XXXVII, or a pharmaceutically acceptable salt or solvate thereof, wherein n is 1.

Embodiment XXXIX

The compound of any one of Embodiments XXXVI-XXXVIII, or a pharmaceutically acceptable salt or solvate thereof, wherein $R^6$ is selected from the group consisting of hydrogen and $C_{1-4}$ alkyl.

Embodiment XL

The compound of Embodiment XXXIX, or a pharmaceutically acceptable salt or solvate thereof, wherein $R^6$ is hydrogen.

Embodiment XLI

The compound of any one of Embodiments I-XXII, or a pharmaceutically acceptable salt or solvate thereof, wherein $R^{4a1}$ is:

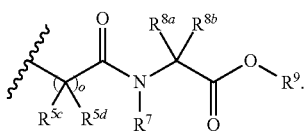

Embodiment XLII

The compound of Embodiment XLI, or a pharmaceutically acceptable salt or solvate thereof, wherein $R^{5c}$ and $R^{5d}$ are each hydrogen.

Embodiment XLIII

The compound of Embodiment XLI or XLII, or a pharmaceutically acceptable salt or solvate thereof, wherein o is 1.

Embodiment XLIV

The compound of any one of Embodiments XLI-XLIII, or a pharmaceutically acceptable salt or solvate thereof, wherein $R^{8b}$ is hydrogen.

Embodiment XLV

The compound of Embodiment XLI, or a pharmaceutically acceptable salt or solvate thereof, wherein $R^{4a}$ is:

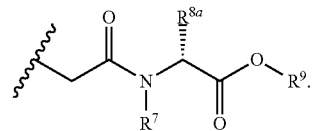

Embodiment XLVI

The compound of Embodiment XLI, or a pharmaceutically acceptable salt or solvate thereof, wherein $R^{4a}$ is:

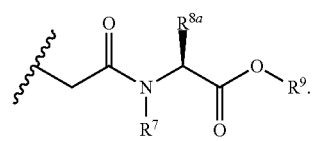

Embodiment XLVII

The compound of any one of Embodiments XLI-XLVI, or a pharmaceutically acceptable salt or solvate thereof, wherein $R^{8a}$ is hydrogen or $C_{1-4}$ alkyl, wherein the alkyl is optionally substituted with 1 or 2 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups.

Embodiment XLVIII

The compound of any one of Embodiments XLI-XLVII, or a pharmaceutically acceptable salt or solvate thereof, wherein $R^7$ is hydrogen.

Embodiment XLIX

The compound of any one of Embodiments XLI-XLVI, or a pharmaceutically acceptable salt or solvate thereof, wherein $R^7$ and $R^{8a}$ taken together with the atoms to which they are attached form a 5-membered heterocyclo.

Embodiment L

The compound of any one of Embodiments XLI-XLIX, or a pharmaceutically acceptable salt or solvate thereof, wherein $R^9$ is hydrogen.

Embodiment LI

The compound of Embodiment XLI, wherein $R^{4a1}$ is selected from the group consisting of:

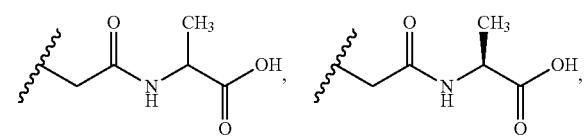

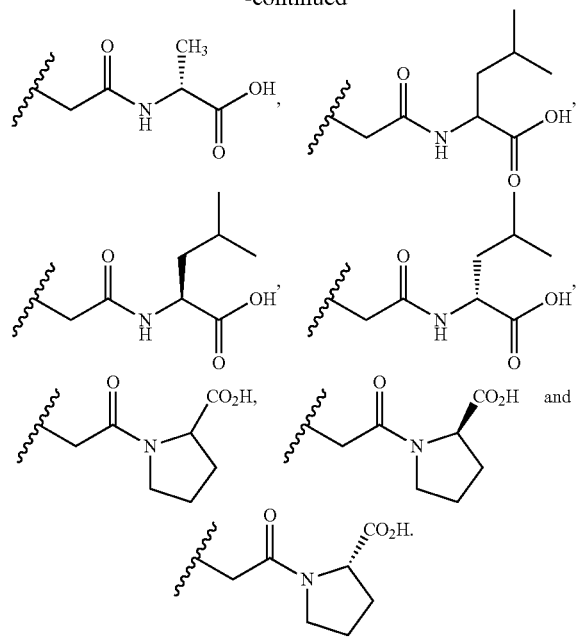

Embodiment LII

The compound of any one of Embodiments I-XXII, or a pharmaceutically acceptable salt or solvate thereof, wherein $R^{4a1}$ is:

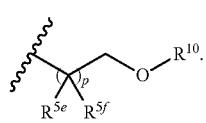

Embodiment LIII

The compound of Embodiment LII, or a pharmaceutically acceptable salt or solvate thereof, wherein $R^{5e}$ and $R^{5f}$ are each hydrogen.

Embodiment LIV

The compound of Embodiments LII or LIII, or a pharmaceutically acceptable salt or solvate thereof, wherein p is 1.

Embodiment LV

The compound of any one of Embodiments LII-LIV, or a pharmaceutically acceptable salt or solvate thereof, wherein $R^{10}$ is hydrogen, or alkyl, cycloalkyl, aryl, heteroaryl, or arylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups.

Embodiment LVI

The compound of Embodiment LV, or a pharmaceutically acceptable salt or solvate thereof, wherein $R^{10}$ is hydrogen

Embodiment LVII

The compound of Embodiment LV, or a pharmaceutically acceptable salt or solvate thereof, wherein $R^{10}$ is selected from the group consisting of:

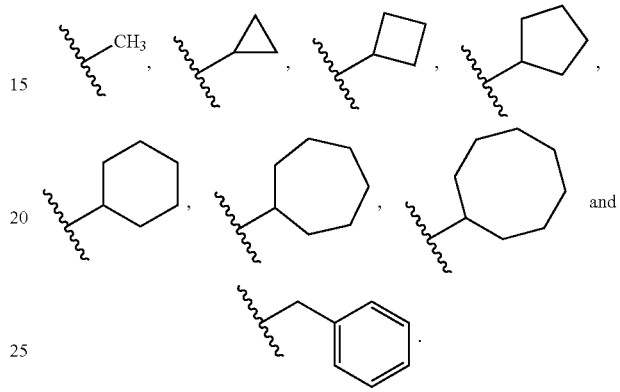

Embodiment LVIII

The compound of any one of Embodiments I-LVII, or a pharmaceutically acceptable salt or solvate thereof, wherein $R^{4b1}$ is hydrogen.

Embodiment LIX

The compound of any one of Embodiments I-LVII, or a pharmaceutically acceptable salt or solvate thereof, wherein $R^{4b1}$ is:

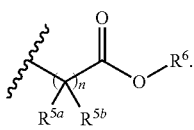

Embodiment LX

The compound of Embodiment IV having the Formula XIV:

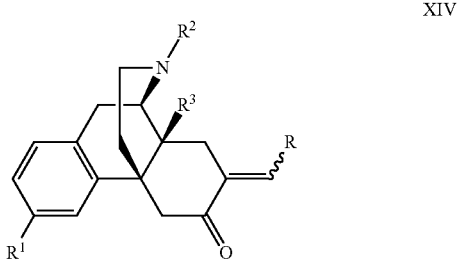

and the pharmaceutically acceptable salts and solvates thereof, wherein R is hydrogen, alkyl, or cycloalkyl.

Embodiment LXI

The compound of Embodiment I having the Formula XV:

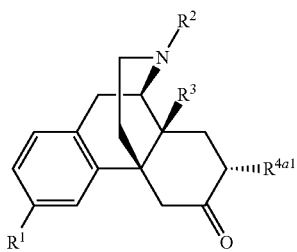

XV and the pharmaceutically acceptable salts and solvates thereof.

Embodiment LXII

The compound of Embodiment I having the Formula XVI:

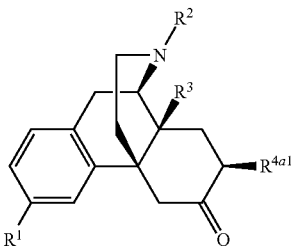

XVI and the pharmaceutically acceptable salts and solvates thereof.

Embodiment LXIII

The compound of Embodiments LXI or LXII, wherein $R^1$ is selected from the group consisting of OH and methoxy; $R^2$ is selected from the group consisting of —$CH_3$ and —$CH_2$(cyclopropyl); and $R^3$ is selected from the group consisting of hydrogen and OH, and the pharmaceutically acceptable salts and solvates thereof.

Embodiment LXIV

The compound of any one of Embodiments LXI-LXIII, wherein $R^{4a1}$ is selected from the group consisting of $C_3$-$C_6$ alkyl, (cycloalkyl)alkyl, $C_3$-$C_6$ alkoxy, aralkyloxy, —N(H)COR$^{4c}$, —$CH_2$C(=O)NR$^{4d}$R$^{4e}$, —N(H)SO$_2$R$^{4f}$,

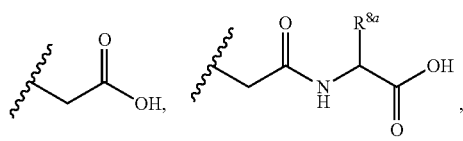

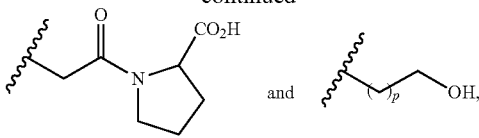

and the pharmaceutically acceptable salts and solvates thereof.

Embodiment LXV

The compound of Embodiment I selected from the group consisting of:
(4bR,7S,8aS,9R)-11-(cyclopropylmethyl)-8a-hydroxy-7-isobutoxy-3-methoxy-8,8a,9,10-tetrahydro-5H-9,4b-(epiminoethano)phenanthren-6(7H)-one;
(4bR,7S,8aS,9R)-7-(benzyloxy)-11-(cyclopropylmethyl)-8a-hydroxy-3-methoxy-8,8a,9,10-tetrahydro-5H-9,4b-(epiminoethano)phenanthren-6(7H)-one;
N-((4bR,7S,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)isobutyramide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)isobutyramide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamide;
N-((4bR,7 S,8aS,9R)-11-(cyclopropylmethyl)-3,8a-dihydroxy-6-oxo-6,7,8,8a,9,10-hexahydro-5H-9,4b-(epiminoethano)phenanthren-7-yl)propionamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-4-methylpentanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-5-methylhexanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)pivalamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-3-methylbutanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopropanecarboxamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopentanecarboxamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzamide;
(S)—N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-methylbutanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclohexanecarboxamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)ethanesulfonamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzenesulfonamide;

(4bR,7S,8aS,9R)-11-(cyclopropylmethyl)-8a-hydroxy-7-(2-hydroxyethyl)-3-methoxy-8,8a,9,10-tetrahydro-5H-9,4b-(epiminoethano)phenanthren-6(7H)-one;

(4bR,7S,8aS,9R)-7-(2-(benzyloxy)ethyl)-11-(cyclopropylmethyl)-8a-hydroxy-3-methoxy-8,8a,9,10-tetrahydro-5H-9,4b-(epiminoethano)phenanthren-6(7H)-one;

(4bR,7S,8aS,9R)-11-(cyclopropylmethyl)-8a-hydroxy-3-methoxy-7-(2-methoxyethyl)-8,8a,9,10-tetrahydro-5H-9,4b-(epiminoethano)phenanthren-6(7H)-one;

(4bR,7S,8aS,9R)-7-(2-(benzyloxy)ethyl)-8a-hydroxy-3-methoxy-11-methyl-8,8a,9,10-tetrahydro-5H-9,4b-(epiminoethano)phenanthren-6(7H)-one;

(4bR,7S,8aS,9R)-11-(cyclopropylmethyl)-3,8a-dihydroxy-7-(2-hydroxyethyl)-8,8a,9,10-tetrahydro-5H-9,4b-(epiminoethano)phenanthren-6(7H)-one;

(4bR,7S,8aS,9R)-3-(benzyloxy)-11-(cyclopropylmethyl)-8a-hydroxy-7-(2-hydroxyethyl)-8,8a,9,10-tetrahydro-5H-9,4b-(epiminoethano)phenanthren-6 (7H)-one;

ethyl 2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetate;

2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetic acid;

2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetic acid;

(4bR,8aS,9R,E)-11-(cyclopropylmethyl)-8a-hydroxy-3-methoxy-7-(3-methylbutylidene)-8,8a,9,10-tetrahydro-5H-9,4b-(epiminoethano)phenanthren-6(7H)-one;

(4bR,7S,8aS,9R)-11-(cyclopropylmethyl)-3,8a-dihydroxy-7-isopentyl-8,8a,9,10-tetrahydro-5H-9,4b-(epiminoethano)phenanthren-6(7H)-one;

(4bR,7S,8aS,9R)-7-(cyclopentylmethyl)-11-(cyclopropylmethyl)-3,8a-dihydroxy-8,8a,9,10-tetrahydro-5H-9,4b-(epiminoethano)phenanthren-6(7H)-one;

(4bR,7S,8aS,9R)-11-(cyclopropylmethyl)-3,8a-dihydroxy-7-(2-methylbutyl)-8,8a,9,10-tetrahydro-5H-9,4b-(epiminoethano)phenanthren-6(7H)-one;

(4bR,7S,8aS,9R)-7-butyl-11-(cyclopropylmethyl)-3,8a-dihydroxy-8,8a,9,10-tetrahydro-5H-9,4b-(epiminoethano)phenanthren-6(7H)-one;

(4bR,7S,8aS,9R)-11-(cyclopropylmethyl)-3,8a-dihydroxy-7-neopentyl-8,8a,9,10-tetrahydro-5H-9,4b-(epiminoethano)phenanthren-6(7H)-one;

(4bR,7S,8aS,9R)-11-(cyclopropylmethyl)-3,8a-dihydroxy-7-isobutyl-8,8a,9,10-tetrahydro-5H-9,4b-(epiminoethano)phenanthren-6(7H)-one;

(4bR,7S,8aS,9R)-7-(cyclohexylmethyl)-11-(cyclopropylmethyl)-3,8a-dihydroxy-8,8a,9,10-tetrahydro-5H-9,4b-(epiminoethano)phenanthren-6(7H)-one;

(4bR,7S,8aS,9R)-7-benzyl-11-(cyclopropylmethyl)-3,8a-dihydroxy-8,8a,9,10-tetrahydro-5H-9,4b-(epiminoethano)phenanthren-6(7H)-one;

(4bS,7S,8aR,9R)-11-(cyclopropylmethyl)-7-isopropyl-3-methoxy-8,8a,9,10-tetrahydro-5H-9,4b-(epiminoethano)phenanthren-6(7H)-one;

(4bS,7S,8aR,9R)-11-(cyclopropylmethyl)-3-hydroxy-7-isopropyl-8,8a,9,10-tetrahydro-5H-9,4b-(epiminoethano)phenanthren-6(7H)-one;

(4bS,7R,8aR,9R)-11-(cyclopropylmethyl)-3-hydroxy-7-isopropyl-8,8a,9,10-tetrahydro-5H-9,4b-(epiminoethano)phenanthren-6(7H)-one;

(2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetyl)-L-alanine;

(4bR,7R,8aS,9R)-8a-hydroxy-3-methoxy-11-methyl-7-(2-oxo-2-(piperidin-1-yl)ethyl)-8,8a,9,10-tetrahydro-5H-9,4b-(epiminoethano)phenanthren-6(7H)-one;

(4bR,7R,8aS,9R)-8a-hydroxy-3-methoxy-11-methyl-7-(2-oxo-2-(pyrrolidin-1-yl)ethyl)-8,8a,9,10-tetrahydro-5H-9,4b-(epiminoethano)phenanthren-6(7H)-one;

(4bR,7R,8aS,9R)-8a-hydroxy-7-(2-(4-hydroxypiperidin-1-yl)-2-oxoethyl)-3-methoxy-11-methyl-8,8a,9,10-tetrahydro-5H-9,4b-(epiminoethano)phenanthren-6(7H)-one;

(4bR,7R,8aS,9R)-8a-hydroxy-3-methoxy-11-methyl-7-(2-morpholino-2-oxoethyl)-8,8a,9,10-tetrahydro-5H-9,4b-(epiminoethano)phenanthren-6(7H)-one;

(4bR,7R,8aS,9R)-3,8a-dihydroxy-11-methyl-7-(2-oxo-2-(piperidin-1-yl)ethyl)-8,8a,9,10-tetrahydro-5H-9,4b-(epiminoethano)phenanthren-6(7H)-one;

(4bR,7R,8aS,9R)-3,8a-dihydroxy-7-(2-(4-hydroxypiperidin-1-yl)-2-oxoethyl)-11-methyl-8,8a,9,10-tetrahydro-5H-9,4b-(epiminoethano)phenanthren-6(7H)-one;

2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-isobutylacetamide;

N-benzyl-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide;

N-(cyclopropylmethyl)-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide;

2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-(2-hydroxyethyl)acetamide;

2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-(3-hydroxypropyl)acetamide;

2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)-N-(2-hydroxyethyl)acetamide;

2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)-N-(3-hydroxypropyl)acetamide;

(4bR,7R,8aS,9R)-3,8a-dihydroxy-11-methyl-7-(2-oxo-2-(piperazin-1-yl)ethyl)-8,8a,9,10-tetrahydro-5H-9,4b-(epiminoethano)phenanthren-6(7H)-one;

(4bR,7R,8aS,9R)-3,8a-dihydroxy-11-methyl-7-(2-(4-methylpiperazin-1-yl)-2-oxoethyl)-8,8a,9,10-tetrahydro-5H-9,4b-(epiminoethano)phenanthren-6(7H)-one;

(4bR,7R,8aS,9R)-7-(2-(4-benzylpiperazin-1-yl)-2-oxoethyl)-3,8a-dihydroxy-11-methyl-8,8a,9,10-tetrahydro-5H-9,4b-(epiminoethano)phenanthren-6(7H)-one;

(4bR,7R,8aS,9R)-3,8a-dihydroxy-11-methyl-7-(2-oxo-2-(4-phenylpiperazin-1-yl)ethyl)-8,8a,9,10-tetrahydro-5H-9,4b-(epiminoethano)phenanthren-6(7H)-one;

(4bR,7R,8aS,9R)-11-(cyclopropylmethyl)-3,8a-dihydroxy-7-(2-oxo-2-(piperazin-1-yl)ethyl)-8,8a,9,10-tetrahydro-5H-9,4b-(epiminoethano)phenanthren-6(7H)-one;

(4bR,7R,8aS,9R)-11-(cyclopropylmethyl)-3,8a-dihydroxy-7-(2-(4-methylpiperazin-1-yl)-2-oxoethyl)-8,8a,9,10-tetrahydro-5H-9,4b-(epiminoethano)phenanthren-6(7H)-one;

(4bR,7R,8aS,9R)-7-(2-(4-benzylpiperazin-1-yl)-2-oxoethyl)-11-(cyclopropylmethyl)-3,8a-dihydroxy-8,8a,9,10-tetrahydro-5H-9,4b-(epiminoethano)phenanthren-6(7H)-one;

(4bR,7R,8aS,9R)-11-(cyclopropylmethyl)-3,8a-dihydroxy-7-(2-oxo-2-(4-phenylpiperazin-1-yl)ethyl)-8,8a,9,10-tetrahydro-5H-9,4b-(epiminoethano)phenanthren-6(7H)-one;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)acetamide;
N-((4bR,7S,8aS,9R)-3,8a-dihydroxy-11-methyl-6-oxo-6,7,8,8a,9,10-hexahydro-5H-9,4b-(epiminoethano)phenanthren-7-yl)propionamide;
N-((4bR,7S,8aS,9R)-3,8a-dihydroxy-11-methyl-6-oxo-6,7,8,8a,9,10-hexahydro-5H-9,4b-(epiminoethano)phenanthren-7-yl)isobutyramide;
N-((4bR,7S,8aS,9R)-3,8a-dihydroxy-11-methyl-6-oxo-6,7,8,8a,9,10-hexahydro-5H-9,4b-(epiminoethano)phenanthren-7-yl)pivalamide;
N-((4bR,7S,8aS,9R)-3,8a-dihydroxy-11-methyl-6-oxo-6,7,8,8a,9,10-hexahydro-5H-9,4b-(epiminoethano)phenanthren-7-yl)-4-methylpentanamide;
N-((4bR,7S,8aS,9R)-3,8a-dihydroxy-11-methyl-6-oxo-6,7,8,8a,9,10-hexahydro-5H-9,4b-(epiminoethano)phenanthren-7-yl)-5-methylhexanamide;
N-((4bR,7S,8aS,9R)-3,8a-dihydroxy-11-methyl-6-oxo-6,7,8,8a,9,10-hexahydro-5H-9,4b-(epiminoethano)phenanthren-7-yl)cyclohexanecarboxamide;
(4bS,7S,8aR,9R)-11-(cyclopropylmethyl)-3-hydroxy-7-isopentyl-8,8a,9,10-tetrahydro-5H-9,4b-(epiminoethano)phenanthren-6(7H)-one;
(4bS,7S,8aR,9R)-7-(cyclopentylmethyl)-11-(cyclopropylmethyl)-3-hydroxy-8,8a,9,10-tetrahydro-5H-9,4b-(epiminoethano)phenanthren-6(7H)-one;
(4bR,7S,8aS,9R)-3,8a-dihydroxy-7-isopentyl-11-methyl-8,8a,9,10-tetrahydro-5H-9,4b-(epiminoethano)phenanthren-6(7H)-one;
(4bS,7S,8aR,9R)-7-(cyclopentylmethyl)-3-hydroxy-11-methyl-8,8a,9,10-tetrahydro-5H-9,4b-(epiminoethano)phenanthren-6(7H)-one;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)methanesulfonamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)piperidine-4-carboxamide; and
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-(dimethylamino)acetamide,
and the pharmaceutically acceptable salts and solvates thereof.

Embodiment LXVI

The compound of Embodiment II selected from the group consisting of:
ethyl 2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetate;
2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetic acid;
2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetic acid;
2,2'-((4bR,8aS,9R)-11-(cyclopropylmethyl)-8a-hydroxy-3-methoxy-6-oxo-6,7,8,8a,9,10-hexahydro-5H-9,4b-(epiminoethano)phenanthrene-7,7-diyl)diacetic acid;
2,2'-((4bS,8aS,9R)-11-(cyclopropylmethyl)-3,8a-dihydroxy-6-oxo-6,7,8,8a,9,10-hexahydro-5H-9,4b-(epiminoethano)phenanthrene-7,7-diyl)diacetic acid;
(S)-2-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetamido)propanoic acid;
(S)-2-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamido)propanoic acid;
(S)-1-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetyl)pyrrolidine-2-carboxylic acid;
(S)-1-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetyl)pyrrolidine-2-carboxylic acid;
(S)-2-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetamido)-4-methylpentanoic acid;
(S)-2-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamido)-4-methylpentanoic acid,
and the pharmaceutically acceptable salts and solvates thereof.

Embodiment LXVII

A pharmaceutical composition, comprising a compound of any one of Embodiments I-LXVI, or a pharmaceutically acceptable salt or solvate thereof, and one or more pharmaceutically acceptable carriers.

Embodiment LXVIII

A method of treating or preventing a disorder responsive to the modulation of one or more opioid receptors in a patient, comprising administering to a patient in need of such treatment or prevention an effective amount of a compound of any one of Embodiments I-LXVI, or a pharmaceutically acceptable salt or solvate thereof.

Embodiment LXIX

The method of Embodiment LXVIII, wherein the disorder is responsive to modulation of μ-opioid receptor or the κ-opioid receptor, or to modulation of a combination thereof.

Embodiment LXX

The method of Embodiment LXIX, wherein the disorder is responsive to modulation of κ-opioid receptor.

Embodiment LXXI

The method of any one of Embodiments LXVIII-LXX, wherein the disorder is pain.

Embodiment LXXII

A method of treating or preventing pain, constipation, diarrhea, pruritis, an addictive disorder, withdrawal from alcohol addiction or withdrawal from drug addiction in a patient, comprising administering an effective amount of a compound of any one of Embodiments I-LXVI, or a pharmaceutically acceptable salt or solvate thereof, to a patient in need of such treatment or prevention.

Embodiment LXXIII

The method of Embodiment LXXII, wherein the method is for treating pain.

Embodiment LXXIV

The method of Embodiment LXXIII, wherein said pain is acute pain, chronic pain or surgical pain.

Embodiment LXXV

The method of Embodiment LXXIV, wherein said pain is chronic pain.

Embodiment LXXVI

The method of Embodiment LXXV, wherein said chronic pain is neuropathic pain, postoperative pain, or inflammatory pain.

Embodiment LXXVII

A method of modulating one or more opioid receptors in a patient, comprising administering to the patient an effective amount of a compound of any one of Embodiments I-LXVI, or a pharmaceutically acceptable salt or solvate thereof.

Embodiment LXXVIII

The method of Embodiment LXXVII, wherein the μ- or κ-opioid receptor is modulated, or both the μ- and κ-opioid receptors are modulated.

Embodiment LXXIX

A compound of any one of Embodiments I-LXVI, or a pharmaceutically acceptable salt or solvate thereof, for use in treatment or prevention of a disorder responsive to the modulation of one or more opioid receptors in a patient.

Embodiment LXXX

The compound of Embodiment LXXIX, wherein the disorder is responsive to modulation of the μ-opioid receptor or the κ-opioid receptor, or to modulation of a combination thereof.

Embodiment LXXXI

The compound of Embodiment LXXIX or LXXX, wherein the disorder is responsive to modulation of the κ-opioid receptor.

Embodiment LXXXII

The compound of any one of Embodiments LXXIX-LXXXI, wherein the disorder is pain.

Embodiment LXXXIII

A compound of any one of Embodiments I-LXVI, or a pharmaceutically acceptable salt or solvate thereof, for use in treatment or prevention of pain, constipation, diarrhea, pruritis, an addictive disorder, withdrawal from alcohol addiction or withdrawal from drug addiction in a patient.

Embodiment LXXXIV

The compound of Embodiment LXXXIII, wherein said use is for the treatment or prevention of pain.

Embodiment LXXXV

The compound of Embodiment LXXXIV, wherein said pain is acute pain, chronic pain or surgical pain.

Embodiment LXXXVI

The compound of Embodiment LXXXV, wherein said chronic pain is neuropathic pain, postoperative pain, or inflammatory pain.

Embodiment LXXXVII

A compound of any one of Embodiments I-LXVI, or a pharmaceutically acceptable salt or solvate thereof, for use in modulating of one or more opioid receptors in a patient.

Embodiment LXXXVIII

The compound of Embodiment LXXXVII, wherein the μ- or κ-opioid receptor is modulated, or both the μ- and κ-opioid receptors are modulated.

Embodiment LXXXIX

Use of a compound of any one of Embodiments I-LXVI, or a pharmaceutically acceptable salt or solvate thereof, in the manufacture of a medicament for treating or preventing a disorder responsive to the modulation of one or more opioid receptors.

Embodiment XC

The use of Embodiment LXXXIX, wherein the disorder is responsive to modulation of the μ-opioid receptor or the κ-opioid receptor, or to modulation of a combination thereof.

Embodiment XCI

The use of Embodiment XC, wherein the disorder is responsive to modulation of the κ-opioid receptor.

Embodiment XCII

The use of any one of Embodiments LXXXIX-XCI, wherein the disorder is pain.

Embodiment XCIII

Use of a compound of any one of Embodiments I-LXVI, or a pharmaceutically acceptable salt or solvate thereof, in the manufacture of a medicament for treating or preventing pain, constipation, diarrhea, pruritis, an addictive disorder, withdrawal from alcohol addiction or withdrawal from drug addiction.

Embodiment XCIV

The use of Embodiment XCIII, wherein said use is for treating or preventing pain.

Embodiment XCV

The use of Embodiment XCIV, wherein said pain is acute pain, chronic pain or surgical pain.

Embodiment XCVI

The use of Embodiment XCV, wherein said chronic pain is neuropathic pain, postoperative pain, or inflammatory pain Embodiment XCVII Use of a compound of any one of Embodiments I-LXVI, or a pharmaceutically acceptable salt or solvate thereof, in the manufacture of a medicament for modulating of one or more opioid receptor.

Embodiment XCVIII

The use of Embodiment XCVII, wherein the μ- or κ-opioid receptor is modulated, or both the μ- and κ-opioid receptors are modulated.

Embodiment XCIX

A compound of any one of Embodiments I-LXVI, or a pharmaceutically acceptable salt or solvate thereof, for use as a medicament.

Embodiment C

A compound of any one of Embodiments I-LXVI, or a pharmaceutically acceptable salt or solvate, wherein the compound is $^{3}H$, $^{11}C$, or $^{14}C$ radiolabeled.

Embodiment CI

A method of screening a candidate compound for the ability to bind to an opioid receptor using a radiolabeled compound of Embodiment C, comprising a) introducing a fixed concentration of the radiolabeled compound to the receptor to form a complex; b) titrating the complex with a candidate compound; and c) determining the binding of the candidate compound to said receptor.

Embodiment CII

A method of preparing a pharmaceutical composition, comprising admixing a therapeutically effective amount of a compound of any one of Embodiments I-LXVI, or a pharmaceutically acceptable salt or solvate thereof, with a pharmaceutically acceptable carrier.

Embodiment CIII

A kit, comprising a sterile container containing an effective amount of a compound of any one of Embodiments I-LXVI, or a pharmaceutically acceptable salt or solvate thereof, and instructions for therapeutic use.

Suitable hydroxyl protecting groups for PG are well known and include, for example, any suitable hydroxyl protecting group disclosed in Wuts, P. G. M. & Greene, T. W., *Greene's Protective Groups in Organic Synthesis,* 4rd Ed., pp. 16-430 (J. Wiley & Sons, 2007), herein incorporated by reference in its entirety. The term "hydroxyl protecting group" as used herein refers to a group that blocks (i.e., protects) the hydroxy functionality while reactions are carried out on other functional groups or parts of the molecule. Those skilled in the art will be familiar with the selection, attachment, and cleavage of protecting groups and will appreciate that many different protective groups are known in the art, the suitability of one protective group or another being dependent on the particular synthetic scheme planned. Suitable hydroxy protecting groups are generally able to be selectively introduced and removed using mild reaction conditions that do not interfere with other portions of the subject compounds. These protecting groups can be introduced or removed at a convenient stage using methods known in the art. The chemical properties of such groups, methods for their introduction and removal are known in the art and can be found, for example, in Greene, T. W. and Wuts, P. G. M., above. Additional hydroxyl protecting groups can be found, for example, in U.S. Pat. No. 5,952,495, U.S. Patent Appl. Pub. No. 2008/0312411, WO 2006/035195, and WO 98/02033, which are herein incorporated in their entireties. Suitable hydroxyl protecting groups include the methoxymethyl, tetrahydropyranyl, tert-butyl, allyl, tert-butyldimethylsilyl, tert-butyldiphenylsilyl, acetyl, pivaloyl, benzoyl, benzyl (Bn), and p-methoxybenzyl group.

It will be apparent to a person of ordinary skill in the art in view of this disclosure that certain groups included in the definitions of —O—PG overlap with the other definitions for $R^1$, such as methoxy, tert-butoxy, etc., and, thus, certain Compounds of the Invention having $R^1$ groups that include groups acting as hydroxyl protecting groups can be pharmaceutically active as described herein.

In one embodiment, the hydroxyl protecting group PG is selected from the group consisting of alkyl, arylalkyl, heterocyclo, (heterocyclo)alkyl, acyl, silyl, and carbonate, any of which are optionally substituted.

In another embodiment, the hydroxyl protecting group PG is an alkyl group, typically an optionally substituted $C_{1-6}$ alkyl group, and suitably unsubstituted methyl or tert-butyl.

In another embodiment, the hydroxyl protecting group PG is an arylalkyl group. Suitable arylalkyl groups include, for example, an unsubstituted benzyl group, substituted benzyl groups, such as p-methoxybenzyl, and naphthylmethyl.

In another embodiment, the hydroxyl protecting group PG is a heterocyclo group, such as unsubstituted tetrahydropyranyl or optionally substituted tetrahydropyranyl.

In another embodiment, the hydroxyl protecting group PG is a (heterocyclo)alkyl group. Suitable (heterocyclo)alkyl groups include, for example, 4-morpholinyl($C_{1-4}$)alkyl groups, such as, 2-(4-morpholinyl)ethyl.

In another embodiment, the hydroxyl protecting group PG is a silyl group. The term "silyl" as employed herein refers to the group having the following structure:

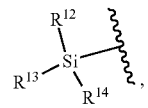

wherein $R^{12}$, $R^{13}$, and $R^{14}$ are each independently selected from the group consisting of alkyl, cycloalkyl, aryl, (cycloalkyl)alkyl, or arylalkyl, any of which is optionally substituted. In one embodiment, the silyl group is trimethyl silyl, tert-butyldimethyl silyl, tert-butyldiphenyl silyl, or tri-isopropyl silyl.

In another embodiment, the hydroxyl protecting group PG is an acyl group. The term "acyl" as employed herein refers to the following structure:

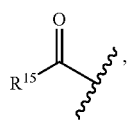

wherein $R^{15}$ is alkyl, cycloalkyl, aryl, (cycloalkyl)alkyl, or arylalkyl, any of which is optionally substituted. The acyl group can be, for example, $C_{1-4}$ alkylcarbonyl (such as, for example, acetyl), arylcarbonyl (such as, for example, benzoyl), levulinoyl, or pivaloyl. In another embodiment, the acyl group is benzoyl.

In another embodiment, the hydroxyl protecting group is a carbonate group. The term "carbonate" as employed herein refers to the following structure:

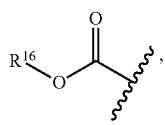

wherein $R^{16}$ is alkyl, alkenyl, cycloalkyl, aryl, (cycloalkyl)alkyl, or arylalkyl, any of which is optionally substituted. Typically, $R^{16}$ is $C_{1-10}$ alkyl (e.g., 2,4-dimethylpent-3-yl), $C_{2-6}$ alkenyl (e.g., ethenyl or prop-2-enyl, i.e., allyl), $C_{3-12}$ cycloalkyl (e.g., adamantyl), phenyl, or benzyl.

In another embodiment, the present disclosure provides a pharmaceutical composition comprising a Compound of the Invention and one or more pharmaceutically acceptable carriers.

In another embodiment, the present disclosure provides a pharmaceutical composition comprising a Compound of the Invention in a therapeutically effective amount and one or more pharmaceutically acceptable carriers.

In another embodiment, the present disclosure provides a method of treating or preventing a disorder responsive to the modulation of one or more opioid receptors in a patient, comprising administering to a patient in need of such treatment or prevention an effective amount of a Compound of the Invention. In another embodiment, the disorder is responsive to modulation of the μ-opioid receptor or the κ-opioid receptor, or to modulation of a combination thereof. In another embodiment, the disorder is responsive to modulation of the κ-opioid receptor. In another embodiment, the disorder is pain.

In another embodiment, the present disclosure provides a method of treating or preventing pain, constipation, diarrhea, pruritis, an addictive disorder, withdrawal from alcohol addiction or withdrawal from drug addiction in a patient, comprising administering an effective amount of a Compound of the Invention to a patient in need of such treatment or prevention. In another embodiment, the method is for treating pain. In another embodiment, the pain is acute pain, chronic pain or surgical pain. In another embodiment, the pain is chronic pain. In another embodiment, the chronic pain is neuropathic pain, postoperative pain, or inflammatory pain.

In another embodiment, the present disclosure provides a method of modulating one or more opioid receptors in a patient, comprising administering to the patient an effective amount of Compound of the Invention. In another embodiment, the μ- or κ-opioid receptor is modulated, or both the μ- and κ-opioid receptors are modulated.

In another embodiment, the present disclosure provides a Compound of the Invention for use in treatment or prevention of a disorder responsive to the modulation of one or more opioid receptors in a patient. In another embodiment, the disorder is responsive to modulation of the μ-opioid receptor or the κ-opioid receptor, or to modulation of a combination thereof. In another embodiment, the disorder is responsive to modulation of the κ-opioid receptor. In another embodiment, the disorder is pain.

In another embodiment, the present disclosure provides a Compound of the Invention for use in treatment or prevention of pain, constipation, diarrhea, pruritis, an addictive disorder, withdrawal from alcohol addiction or withdrawal from drug addiction in a patient. In another embodiment, the use is for the treatment or prevention of pain. In another embodiment, the pain is acute pain, chronic pain or surgical pain. In another embodiment, the chronic pain is neuropathic pain, postoperative pain, or inflammatory pain. In another embodiment, the present disclosure provides a Compound of the Invention for use in modulating of one or more opioid receptors in a patient. In another embodiment, the μ- or κ-opioid receptor is modulated, or both the μ- and κ-opioid receptors are modulated.

In another embodiment, the present disclosure provides the use of a Compound of the Invention in the manufacture of a medicament for treating or preventing a disorder responsive to the modulation of one or more opioid receptors. In another embodiment, the disorder is responsive to modulation of the μ-opioid receptor or the κ-opioid receptor, or to modulation of a combination thereof. In another embodiment, the disorder is responsive to modulation of the κ-opioid receptor. In another embodiment, the disorder is pain.

In another embodiment, the present disclosure provides the use of a Compound of the Invention in the manufacture of a medicament for treating or preventing pain, constipation, diarrhea, pruritis, an addictive disorder, withdrawal from alcohol addiction or withdrawal from drug addiction. In another embodiment, the use is for treating or preventing pain. In another embodiment, the pain is acute pain, chronic pain or surgical pain. In another embodiment, the chronic pain is neuropathic pain, postoperative pain, or inflammatory pain.

In another embodiment, the present disclosure provides the use of a Compound of the Invention in the manufacture of a medicament for modulating one or more opioid receptors. In another embodiment, the μ- or κ-opioid receptor is modulated, or both the μ- and κ-opioid receptors are modulated.

In another embodiment, the present disclosure provides a Compound of the Invention for use as a medicament.

In another embodiment, the present disclosure provides a $^3$H, $^{11}$C, or $^{14}$C radiolabeled Compound of the Invention.

In another embodiment, the present disclosure provides a method of screening a candidate compound for the ability to bind to an opioid receptor using a radiolabeled Compound of the Invention, comprising a) introducing a fixed concentration of the radiolabeled compound to the receptor to form a complex; b) titrating the complex with a candidate compound; and c) determining the binding of the candidate compound to said receptor.

In another embodiment, the present disclosure provides a method of preparing a pharmaceutical composition, comprising admixing a therapeutically effective amount of a Compound of the Invention with a pharmaceutically acceptable carrier.

In another embodiment, the present disclosure provides a kit, comprising a sterile container containing an effective amount of a Compound of the Invention and instructions for therapeutic use.

Optional substituents attached to aryl, phenyl and heteroaryl rings each take the place of a hydrogen atom that would otherwise be present in any position on the aryl, phenyl or heteroaryl rings.

Useful halo or halogen groups include fluorine, chlorine, bromine and iodine.

Useful alkyl groups are selected from straight-chain and branched-chain $C_{1-10}$ alkyl groups. Typical $C_{1-10}$ alkyl groups include methyl, ethyl, n-propyl, n-butyl, n-pentyl, n-hexyl, n-heptyl, n-octyl, n-nonyl, and n-decyl, isopropyl, sec-butyl, tert-butyl, iso-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl, among others. In one embodiment, useful alkyl groups are selected from straight chain $C_{1-6}$ alkyl groups and branched chain $C_{3-6}$ alkyl groups. Typical $C_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight chain $C_{2-6}$ alkyl groups and branched chain $C_{3-6}$ alkyl groups. Typical $C_{2-6}$ alkyl groups include ethyl, propyl, isopropyl, butyl, sec-butyl, tert-butyl, iso-butyl, pentyl, 3-pentyl, hexyl among others. In one embodiment, useful alkyl groups are selected from straight chain $C_{1-4}$ alkyl groups and branched chain $C_{3-4}$ alkyl groups. Typical $C_{1-4}$ alkyl groups include methyl, ethyl, propyl, isopropyl, butyl, sec-butyl, tert-butyl, and iso-butyl.

Useful alkenyl groups are selected from straight-chain and branched-chain $C_{2-6}$ alkenyl groups, preferably $C_{2-4}$ alkenyl. Typical $C_{2-6}$ alkenyl groups include ethenyl, propenyl, isopropenyl, butenyl, sec-butenyl, pentenyl, and hexenyl. Typical $C_{2-4}$ alkenyl groups include ethenyl, propenyl, isopropenyl, butenyl, and sec-butenyl.

Useful alkynyl groups are selected from straight-chain and branched-chain $C_{2-4}$ alkynyl groups, preferably $C_{2-4}$ alkynyl. Typical $C_{2-6}$ alkynyl groups include ethynyl, propynyl, butynyl, 2-butynyl, pentynyl, and hexynyl groups. Typical $C_{2-4}$ alkynyl groups include ethynyl, propynyl, butynyl, and 2-butynyl groups.

Useful haloalkyl groups include any of the above-mentioned $C_{1-10}$ alkyl groups, and preferably $C_{1-6}$ alkyl groups, and preferably any of the above-mentioned $C_{1-4}$ alkyl groups, substituted by one or more fluorine, chlorine, bromine or iodine atoms (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups).

Useful hydroxyalkyl groups include any of the above-mentioned $C_{1-10}$ alkyl groups, and preferably any of the abovementioned $C_{1-6}$ alkyl groups, and preferably any of the above-mentioned $C_{1-4}$ alkyl groups, substituted by one or more hydroxy groups, such as monohydroxyalkyl and dihydroxyalkyl groups (e.g., hydroxymethyl, hydroxyethyl, hydroxypropyl, hydroxybutyl, hydroxypentyl, and hydroxyhexyl groups groups, and especially hydroxymethyl, 1-hydroxyethyl, 2-hydroxyethyl, 1,2-dihydroxyethyl, 2-hydroxypropyl, 2-hydroxyprop-2-yl, 3-hydroxypropyl, 2,3-dihydroxypropyl, 3-hydroxybutyl, 4-hydroxybutyl, 2-hydroxy-1-methylpropyl, and 1,3-dihydroxyprop-2-yl).

Useful cycloalkyl groups are selected from saturated cyclic hydrocarbon groups containing 1, 2, or 3 rings having 3, 4, 5, 6, 7, 8, 9, 10, 11, or 12 carbon atoms (i.e., $C_3$-$C_{12}$ cycloalkyl) or the number of carbons designated. In one embodiment, the cycloalkyl has one or two rings. In another embodiment, the cycloalkyl is a $C_3$-$C_8$ cycloalkyl. In another embodiment, the cycloalkyl is a $C_{3-7}$ cycloalkyl. In another embodiment, the cycloalkyl is a $C_{3-6}$ cycloalkyl. Exemplary cycloalkyl groups include cyclopropyl, cyclobutyl, cyclopentyl, cyclohexyl, cycloheptyl, cyclooctyl, norbornyl, decalin, and adamantyl.

Useful cycloalkenyl groups are selected from partially unsaturated (i.e., containing, e.g., one or two double bonds) cyclic hydrocarbon groups containing 1, 2, or 3 rings having 4, 5, 6, 7, 8, 9, 10, 11, or 12 carbon atoms (i.e., $C_4$-$C_{12}$ cycloalkenyl) or the number of carbons designated. In one embodiment, the cycloalkenyl has one or two rings. In another embodiment, the cycloalkenyl is a $C_3$-$C_8$ cycloalkenyl. In another embodiment, the cycloalkenyl is a $C_{3-7}$ cycloalkenyl. In another embodiment, the cycloalkenyl is a $C_{3-6}$ cycloalkenyl. In one embodiment, the cycloalkenyl group contains one double bond. Exemplary cycloalkenyl groups containing one double bond include cyclobutenyl, cyclopentenyl, cyclohexenyl, cycloheptenyl, cyclooctenyl, cyclononenyl, and cyclodecenyl. In another embodiment, the cycloalkenyl group contains two double bonds. Preferably, the cycloalkenyl groups containing two double bonds have 5, 6, 7, 8, 9, 10, 11, or 12 carbon atoms (i.e., $C_5$-$C_{12}$ cycloalkadienyl). Exemplary cycloalkenyl groups having two double bonds include cyclopentadienyl, cyclohexadienyl, cycloheptadienyl, cyclooctadienyl, cyclononadienyl, and cyclodecadienyl.

Useful alkoxy groups include oxygen substituted by one of the $C_{1-10}$ alkyl groups mentioned above (e.g., methoxy, ethoxy, propoxy, iso-propoxy, butoxy, tert-butoxy, iso-butoxy, sec-butoxy, pentyloxy, hexyloxy, heptyloxy, octyloxy, nonyloxy and decyloxy), preferably by one of the $C_{1-6}$ alkyl groups, and preferably by one of the $C_{1-4}$ alkyl groups.

Useful alkenyloxy groups include oxygen substituted by one of the $C_{2-6}$ alkenyl groups, and preferably by one of the $C_{2-4}$ alkenyl groups, mentioned above (e.g., ethenyloxy, propenyloxy, isopropenyloxy, butenyloxy, sec-butenyloxy, pentenyloxy, and hexenyloxy).

Useful alkynyloxy groups include oxygen substituted by one of the $C_{2-6}$ alkynyl groups, preferably by one of the $C_{2-4}$ alkynyl groups, mentioned above (e.g., ethynyloxy, propynyloxy, butynyloxy, 2-butynyloxy, pentynyloxy, and hexynyloxy).

Useful alkoxyalkyl groups include any of the above-mentioned $C_{1-10}$ alkyl groups, and preferably any of the above-mentioned $C_{1-6}$ alkyl groups, substituted with any of the above-mentioned alkoxy groups (e.g., methoxymethyl, methoxyethyl, methoxypropyl, methoxybutyl, ethoxymethyl, 2-ethoxyethyl, 3-ethoxypropyl, 4-ethoxybutyl, propoxymethyl, iso-propoxymethyl, 2-propoxyethyl, 3-propoxypropyl, butoxymethyl, tert-butoxymethyl, isobutoxymethyl, sec-butoxymethyl, and pentyloxymethyl).

Useful haloalkoxy groups include oxygen substituted by one of the $C_{1-10}$ haloalkyl groups, and preferably one of the $C_{1-6}$ haloalkyl groups, mentioned above (e.g., fluoromethoxy, difluoromethoxy, trifluoromethoxy, and 2,2,2-trifluoroethoxy).

Useful (cycloalkyl)alkyl groups include any of the above-mentioned $C_{1-10}$ alkyl groups, and preferably any of the above-mentioned $C_{1-6}$ alkyl groups, substituted with any of the above-mentioned cycloalkyl groups (e.g., (cyclopropyl)

methyl, 2-(cyclopropyl)ethyl, (cyclopropyl)propyl, (cyclobutyl)methyl, (cyclopentyl)methyl, and (cyclohexyl)methyl).

Useful (cycloalkenyl)alkyl groups include any of the above-mentioned $C_{1-10}$ alkyl groups, and preferably any of the above-mentioned $C_{1-6}$ alkyl groups, substituted with any of the above-mentioned cycloalkenyl groups (e.g., (cyclobutenyl)methyl, 2-(cyclobutenyl)ethyl, (cyclobutenyl) propyl, (cyclopentenyl)methyl, (cyclohexenyl)methyl, and (cyclopentadienyl)methyl).

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

Useful aryloxy groups include oxygen substituted by one of the aryl groups mentioned above (e.g., phenoxy).

Useful arylalkyl groups include any of the above-mentioned $C_{1-10}$ alkyl groups, and preferably any of the above-mentioned $C_{1-6}$ alkyl groups, substituted by any of the above-mentioned aryl groups (e.g., benzyl and phenethyl).

Useful arylalkenyl groups include any of the above-mentioned $C_{2-6}$ alkenyl groups substituted by any of the above-mentioned aryl groups (e.g., phenylethenyl).

Useful arylalkynyl groups include any of the above-mentioned $C_{2-6}$ alkynyl groups substituted by any of the above-mentioned aryl groups (e.g., phenylethynyl).

Useful aralkyloxy or arylalkoxy groups include oxygen substituted by one of the above-mentioned arylalkyl groups (e.g., benzyloxy).

Useful (arylalkoxy)carbonyl groups include a carbonyl group substituted by any of the above-mentioned arylalkoxy groups (e.g., (benzyloxy)carbonyl).

The term "heteroaryl" or "heteroaromatic" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. In one embodiment, the heteroaryl group is a 5- to 10-membered heteroaryl group. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Typical heteroaryl groups include thienyl (e.g., thien-2-yl and thien-3-yl), furyl (e.g., 2-furyl and 3-furyl), pyrrolyl (e.g., pyrrol-1-yl, 1H-pyrrol-2-yl and 1H-pyrrol-3-yl), imidazolyl (e.g., imidazol-1-yl, 1H-imidazol-2-yl and 1H-imidazol-4-yl), tetrazolyl (e.g., tetrazol-1-yl and tetrazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). A 5-membered heteroaryl can contain up to 4 heteroatoms. A 6-membered heteroaryl can contain up to 3 heteroatoms. Each heteroatom is independently selected from nitrogen, oxygen and sulfur.

Useful heteroarylalkyl groups include any of the above-mentioned $C_{1-10}$ alkyl groups substituted by any of the above-mentioned heteroaryl groups (e.g., (thien-2-yl)methyl, 2-furylmethyl, (pyrrol-1-yl)methyl, and 2-(1H-pyrrol-2-yl) ethyl).

Useful heteroarylalkoxy groups include oxygen substituted by one of the above-mentioned heteroaryl groups.

Useful (heteroarylalkoxy)carbonyl groups include a carbonyl group substituted by any of the above-mentioned heteroarylalkoxy groups.

The terms "heterocyclic" and "heterocyclo" are used herein to mean saturated or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. In one embodiment, the 3- to 7-membered monocyclic heterocyclic ring is either a saturated, or unsaturated non-aromatic ring. A 3-membered heterocyclo can contain up to 1 heteroatom, a 4-membered heterocyclo can contain up to 2 heteroatoms, a 5-membered heterocyclo can contain up to 4 heteroatoms, a 6-membered heterocyclo can contain up to 4 heteroatoms, and a 7-membered heterocyclo can contain up to 5 heteroatoms. Each heteroatom is independently selected from nitrogen, which can be quaternized; oxygen; and sulfur, including sulfoxide and sulfone. The 3- to 7-membered heterocyclo can be attached via a nitrogen or carbon atom. A 7- to 10-membered bicyclic heterocyclo contains from 1 to 4 heteroatoms independently selected from nitrogen, which can be quaternized; oxygen; and sulfur, including sulfoxide and sulfone. The 7- to 10-membered bicyclic heterocyclo can be attached via a nitrogen or carbon atom. Examples of the heterocyclic rings include, but are not limited to, pyrrolidinyl, piperidinyl, piperazinyl, morpholinyl, imidazolinyl, pyrazolidinyl, tetrahydrofuranyl, oxazolidinyl, 2-oxooxazolidinyl, tetrahydrothienyl, imidazolidinyl, hexahydropyrimidinyl, and benzodiazepines.

Useful (heterocyclo)alkyl groups include any of the above-mentioned $C_{1-10}$ alkyl groups, and preferably any of the above-mentioned $C_{1-6}$ alkyl groups, substituted by any of the above-mentioned heterocyclic groups (e.g., (pyrrolidin-2-yl) methyl, (pyrrolidin-1-yl)methyl, (piperidin-1-yl)methyl, (morpholin-4-yl)methyl, (2-oxooxazolidin-4-yl)methyl, 2-(2-oxooxazolidin-4-yl)ethyl, (2-oxo-imidazolidin-1-yl) methyl, (2-oxo-imidazolidin-1-yl)ethyl, and (2-oxo-imidazolidin-1-yl)propyl).

As used herein, the term "amino" or "amino group" refers to —$NH_2$.

Useful aminoalkyl groups include any of the above-mentioned $C_{1-10}$ alkyl groups, and preferably any of the above-mentioned $C_{1-6}$ alkyl groups, substituted with one or more amino group.

Useful alkylamino and dialkylamino groups are —$NHR^{17}$ and —$NR^{17}R^{18}$, respectively, wherein $R^{17}$ and $R^{18}$ are each independently selected from a $C_{1-10}$ alkyl group.

As used herein, the term "aminocarbonyl" refers to —$C(=O)NH_2$.

Useful alkylcarbonyl groups include a carbonyl group, i.e., —$C(=O)$—, substituted by any of the above-mentioned $C_{1-10}$ alkyl groups.

Useful alkoxycarbonyl groups include a carbonyl group substituted by any of the above-mentioned alkoxy groups (e.g., methoxycarbonyl, ethoxycarbonyl, propoxycarbonyl, iso-propoxycarbonyl, butoxycarbonyl, tert-butoxycarbonyl, iso-butoxycarbonyl, sec-butoxycarbonyl, and pentyloxycarbonyl).

Useful arylcarbonyl groups include a carbonyl group substituted by any of the above-mentioned aryl groups (e.g., benzoyl).

Useful alkylcarbonyloxy or acyloxy groups include oxygen substituted by one of the above-mentioned alkylcarbonyl groups.

Useful alkylcarbonylamino or acylamino groups include any of the above-mentioned alkylcarbonyl groups attached to an amino nitrogen, such as methylcarbonylamino.

As used herein, the term "carboxamido" refers to a radical of formula —C(=O)NR$^{19}$R$^{20}$, wherein R$^{19}$ and R$^{20}$ are each independently hydrogen, optionally substituted $C_{1-10}$ alkyl, or optionally substituted aryl. Exemplary carboxamido groups include —CONH$_2$, —CON(H)CH$_3$, —CON(CH$_3$)$_2$, and —CON(H)Ph.

Useful alkylaminocarbonyl and dialkylaminocarbonyl groups are any of the above-mentioned carboxamido groups, where R$^{19}$ is H and R$^{20}$ is $C_{1-10}$ alkyl or where R$^{19}$ and R$^{20}$ are each independently selected from a $C_{1-10}$ alkyl group, respectively.

As used herein, the term "sulfonamido" refers to a radical of formula —SO$_2$NR$^{21}$R$^{22}$, wherein R$^{21}$ and R$^{22}$ are each independently hydrogen, optionally substituted $C_{1-10}$ alkyl, or optionally substituted aryl. Exemplary sulfonamido groups include —SO$_2$NH$_2$, —SO$_2$N(H)CH$_3$, and —SO$_2$N(H)Ph.

As used herein, the term "thiol" refers to —SH.

Useful mercaptoalkyl groups include any of the above-mentioned $C_{1-10}$ alkyl groups, and preferably any of the above-mentioned $C_{1-6}$ alkyl groups, substituted by a —SH group.

As used herein, the term "carboxy" refers to —COOH.

Useful carboxyalkyl groups include any of the above-mentioned $C_{1-10}$ alkyl groups, and preferably any of the above-mentioned $C_{1-6}$ alkyl groups, substituted by —COOH.

As used herein, the terms "hydroxyl" or "hydroxy" refer to —OH.

As used herein, the term "cyano" refers to —CN.

Useful cyanoalkyl groups include any of the above-mentioned $C_{1-10}$ alkyl groups, and preferably any of the above-mentioned $C_{1-6}$ alkyl groups, substituted by a CN group. Exemplary cyanoalkyl groups include —CH$_2$CN, —CH$_2$CH$_2$CN, and —CH$_2$CH$_2$CH$_2$CN.

As used herein, the term "nitro" refers to —NO$_2$.

As used herein, the term "ureido" refers to —NH—C(=O)—NH$_2$.

As used herein, the term "azido" refers to —N$_3$.

The term "ambient temperature" as used herein means the temperature of the surroundings. The ambient temperature indoors is the same as room temperature, which is from about 20° C. to about 25° C.

The term "about," as used herein in connection with a measured quantity, refers to the normal variations in that measured quantity, as expected by the skilled artisan making the measurement and exercising a level of care commensurate with the objective of measurement and the precision of the measuring equipment. Typically, the term "about" includes the recited number±10%. Thus, "about 10" means 9 to 11.

As used herein, the term "optionally substituted" refers to a group that may be unsubstituted or substituted.

Optional substituents on optionally substituted groups, when not otherwise indicated, include one or more groups, typically 1, 2, or 3 groups, independently selected from the group consisting of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$) alkyl, aryl($C_{2-6}$)alkenyl, aryl($C_{2-6}$)alkynyl, cycloalkyl($C_{1-6}$) alkyl, heterocyclo($C_{1-6}$)alkyl, hydroxy($C_{1-6}$)alkyl, amino ($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, aryloxy, ar($C_{1-6}$)alkyloxy, carboxamido, sulfonamido, azido, $C_{1-6}$ alkoxy, halo($C_{1-6}$)alkoxy, carboxy, aminocarbonyl, (=O), and mercapto($C_{1-6}$)alkyl groups mentioned above. Preferred optional substituents include halo, halo($C_{1-6}$)alkyl, hydroxy($C_{1-6}$)alkyl, amino($C_{1-6}$)alkyl, hydroxy, nitro, $C_{1-6}$ alkyl, $C_{1-6}$ alkoxy, halo($C_{1-6}$)alkoxy, and amino.

Compounds of the Invention encompass all the salts of the disclosed compounds of Formulae I-XIII, I-A-XIII-A, and XIV-XVI. The present invention preferably includes all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, aspariginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

Compounds of the Invention also encompass solvates of any of the disclosed compounds of Formulae I-XIII, I-A-XIII-A, and XIV-XVI. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g., a disolvate, monosolvate or hemisolvate, where the ratio of solvent molecule to compound of the present invention is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Invention may be present as solvated forms with a pharmaceutically acceptable solvent, such as water, methanol, ethanol, and the like, and it is intended that the invention includes both solvated and unsolvated forms of compounds of any of Formulae I-XIII, I-A-XIII-A, and XIV-XVI. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*: 603-604 (2001). A typical, non-limiting, process of preparing a solvate would involve dissolving a compound of any of Formulae I-XIII, I-A-XIII-A, and XIV-XVI in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Isotopically labeled Compounds of the Invention, as well as the pharmaceutically acceptable salts and solvates thereof, can be used as radioligands to test for the binding of compounds to an opioid receptor. For example, a radio-labeled Compound of the Invention can be used to characterize specific binding of a test or candidate compound to the receptor. Binding assays utilizing such radio-labeled compounds can provide an in vitro alternative to animal testing for the evaluation of chemical structure-activity relationships. For example, the receptor assay may be performed at a fixed concentration of a radiolabeled Compound of the Invention and at increasing concentrations of a test compound in a competition assay. In a non-limiting embodiment, the present invention provides a method for screening a candidate compound for the ability to bind to an opioid receptor, comprising a) introducing a fixed concentration of a radio-labeled Compound of the Invention to the receptor under conditions that permit binding of the radio-labeled compound to the receptor to form a complex; b) titrating the complex with a candidate compound; and c) determining the binding of the candidate compound to said receptor.

Some of the compounds disclosed herein may contain one or more asymmetric centers and may thus give rise to enantiomers, diastereomers, and other stereoisomeric forms, such as epimers. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "epimer" refers to diastereomers that have opposite configuration at only one of two or more tetrahedral streogenic centres present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

Open terms such as "include," "including," "contain," "containing" and the like mean "comprising."

As used herein, compounds that bind to receptors and mimic the regulatory effects of endogenous ligands are defined as "agonists". Compounds that bind to receptors and are only partly effective as agonists are defined as "partial agonists". Compounds that bind to a receptor but produce no regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in Goodman & Gilman's the *Pharmacological Basis of Therapeutics*, 10th Ed. (J. G. Hardman, L. E. Limbird and A. Goodman-Gilman eds., 2001)).

In certain embodiments, the Compound of the Invention is an agonist at one or more of the µ, δ and/or κ opioid receptors. In certain non-limiting embodiments, the Compound of the Invention produces fewer side effects and/or less severe side effects than currently available analgesic opioid compounds when administered at doses producing equivalent levels of analgesia and/or anti-hyperalgesia. In certain embodiments, the Compound of the Invention is an agonist at ORL-1 opioid receptor.

In certain embodiments, Compounds of the Invention can be used in combination with at least one other therapeutic agent. The other therapeutic agent can be, but is not limited to, a µ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

Compounds of the Invention potently bind to the μ and/or κ and/or δ and/or ORL-1 opioid receptors. Compounds of the Invention can be modulators at the μ and/or κ and/or δ and/or ORL-1 opioid receptors, and therefore Compounds of the Invention can be used/administered to treat, ameliorate, or prevent pain.

In some embodiments, Compounds of the Invention are antagonists of one or more opioid receptors. In another embodiment, Compounds of the Invention are antagonists of the μ and/or κ opioid receptors.

In some embodiments, Compounds of the Invention are partial agonists of one or more opioid receptors. In another embodiment, Compounds of the Invention are partial agonists of the μ and/or κ opioid receptors.

In another embodiment, Compounds of the Invention are agonists of one or more opioid receptors. In another embodiment, Compounds of the Invention are agonists of the μ and/or κ opioid receptors.

In some embodiments, Compounds of the Invention have both: (i) antagonist activity at the ORL-1 receptor; and (ii) agonist activity at one or more of the μ, δ and/or κ receptors. In another embodiment, Compounds of the Invention have both: (i) antagonist activity at the ORL-1 receptor; and (ii) agonist activity at the μ receptor. In another embodiment, Compounds of the Invention have both: (i) antagonist activity at the μ receptor; and (ii) agonist activity at the κ receptor. In another embodiment, Compounds of the Invention have: (i) antagonist activity at the ORL-1 receptor; (ii) antagonist activity at the μ receptor; and (iii) agonist activity at the κ receptor. In another embodiment, Compounds of the Invention have: (i) antagonist activity at the μ receptor; (ii) agonist activity at the κ receptor; and (iii) antagonist activity at the δ receptor.

Compounds of the Invention that are antagonists of the μ-opioid receptor or agonists of κ-opioid receptor, or both, can be used/administered to treat or ameliorate constipation. Compounds of the Invention that are agonists of μ-opioid receptor can be used/administered to treat or ameliorate diarrhea.

Compounds of the Invention can be used to treat or prevent acute, chronic pain (which includes but is not limited to, neuropathic pain, postoperative pain, and inflammatory pain), or surgical pain. Examples of pain that can be treated or prevented using a Compound of the Invention include, but are not limited to, cancer pain, neuropathic pain, labor pain, myocardial infarction pain, pancreatic pain, colic pain, postoperative pain, headache pain, muscle pain, arthritic pain, and pain associated with a periodontal disease, including gingivitis and periodontitis.

Acute pain includes, but is not limited to, perioperative pain, postoperative pain, post-traumatic pain, acute disease related pain, and pain related to diagnostic procedures, orthopedic manipulations, and myocardial infarction. Acute pain in the perioperative setting includes pain because of pre-existing disease, the surgical procedure, e.g., associated drains, chest or nasogastric tubes, or complications, or a combination of disease-related and procedure-related sources.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Compounds of the Invention can be used to treat or prevent pain associated with inflammation or with an inflammatory disease in a patient. Such pain can arise where there is an inflammation of the body tissue which can be a local inflammatory response or a systemic inflammation. For example, a Compound of the Invention can be used to treat or prevent pain associated with inflammatory diseases including, but not limited to, organ transplant rejection; reoxygenation injury resulting from organ transplantation (see Grupp et al., *J. Mol, Cell Cardiol*. 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. Compounds of the Invention can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

Compounds of the Invention can be used to treat or prevent pain associated with nerve injury (i.e., neuropathic pain). Chronic neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Chronic neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

Compounds of the Invention can be used to treat or prevent pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

Compounds of the Invention can also be used as an agent to treat withdrawal from alcohol addiction or drug addiction; as an agent to treat or prevent addictive disorders; an agent to treat a pruritic condition; and in treating or ameliorating constipation and diarrhea.

The present invention also provides the use of a compound represented by any of defined Formulae I-XIII, I-A-XIII-A, and XIV-XVI, or a pharmaceutically acceptable salt or solvate thereof, in the manufacture of a medicament for treating a disorder responsive to the modulation of one or more opioids receptors (e.g., any of the disorders listed above) in a patient suffering from said disorder.

Furthermore, the present invention provides a method of modulating, in particular activating, one or more opioid receptors in a patient in need thereof, said method comprising administering to the patient at least one compound represented by any of defined Formulae I-XIII, I-A-XIII-A, and XIV-XVI, or a pharmaceutically acceptable salt or solvate thereof.

The present invention also provides the use of a compound represented by any of defined Formulae I-XIII, I-A-XIII-A, and XIV-XVI, or a pharmaceutically acceptable salt or solvate thereof, in the manufacture of a medicament, in particular a medicament for modulating, in particular activating, one or more opioid receptors, in a patient in need thereof.

Synthesis of Compounds

Compounds of the Invention can be prepared using methods known to those skilled in the art in view of this disclosure, or by illustrative methods shown in the schemes below. For example, compounds of Formula IV wherein $R^1$ is methoxy, $R^3$ is hydroxy, and $R^{4b}$ is hydrogen can be prepared as shown in Scheme 1. Additional methods of synthesis are described in Schemes 2-5 and illustrated in the working examples set forth below.

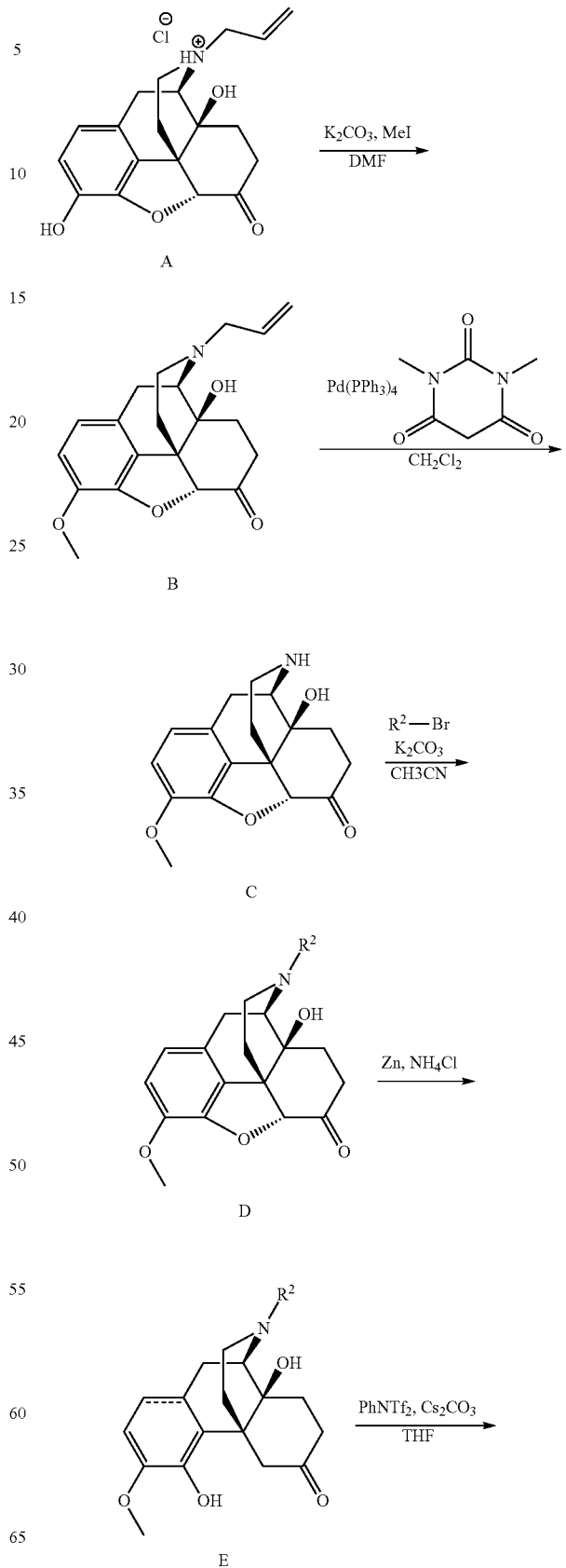

Scheme 1

-continued

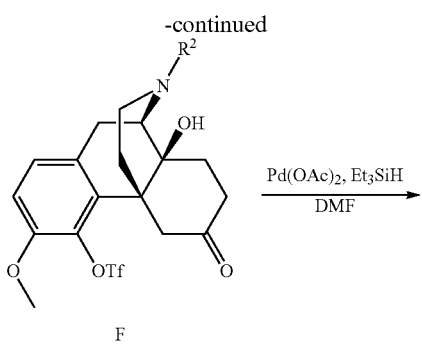

F

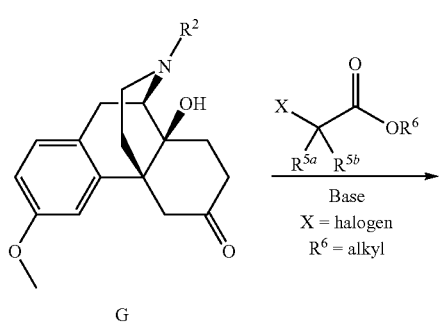

G

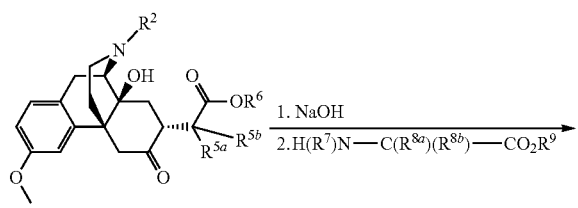

Formula IV
(wherein $R^{4a}$ is $R^{4a}$-I and n is 1)

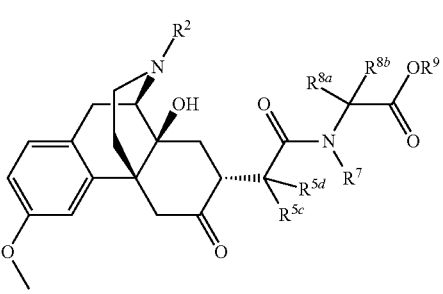

Formula IV
(wherein $R^{4a}$ is $R^{4a}$-II, and o is 1)

Briefly, naloxone, A, is methylated by reaction with a suitable reagent such as methyl iodide (MeI) in a suitable solvent such as dimethylformamide (DMF) in the presence of an inorganic base such as potassium carbonate ($K_2CO_3$) or an organic base such as diisopropylethylamine to provide the methyl ether B. Compound C is prepared by deallylation of compound B with a palladium catalyst such as palladium tetrakistriphenylphosphine ($Pd(PPh_3)_4$) in the presence of a suitable acid source such as dimethylbarbituric acid. Compound D is prepared by alkylation of compound C with an alkyl halide in a suitable solvent such as acetonitrile (AcCN), dimethylformamide (DMF) or dimethyl sulfoxide (DMSO) in the presence of an inorganic base such as potassium carbonate or an organic base such as diisopropylethylamine. Compound D can also be prepared by reductive amination of compound C with an aldehyde or ketone using sodium cyanoborohydride or sodium triacetoxyborohydride in a suitable solvent such as dichloromethane (DCM). Compound E is prepared by reaction of compound D with an excess of zinc dust and aqueous ammonium chloride ($NH_4Cl$). Compound F is prepared by triflation of compound E in a suitable solvent such as tetrahydrofuran (THF) in the presence of an inorganic base such as cesium carbonate ($Cs_2CO_3$). Compound G is prepared via palladium-catalyzed aryl triflate reduction with triethylsilane. A compound having Formula IV (wherein $R^{4a}$ is $R^{4a}$-I and n is 1) is prepared by reaction of compound G with an alkyl halide or other electrophile in a suitable solvent such as THF or DMF in the presence of a base such as sodium hydride or sodium hexamethyldisilazide (NaHMDS). (U.S. Pat. No. 4,423,221; Kawamura, *Chem. Pharm. Bull.* 52:747 (2004)). Conversion of the ester to the acid and coupling with a compound having $H(R^7)N-C(R^{8a})(R^{8b})-CO_2R^9$, e.g., an amino acid or amino ester, provides a compound having Formula IV (wherein $R^{4a}$ is $R^{4a}$-II and o is 1).

The opposite isomers of the compounds described in Scheme 1 can be prepared starting from compounds of Formula G':

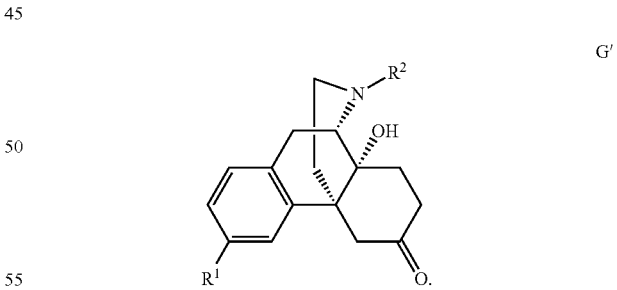

G'

Compounds of Formula G' can be prepared according methods described in the art, such as, for example, in US 2009/0156818, US 2009/0156820, and Hupp C. D., et al., *Tetrahedron Letters* 51:2359-2361 (2010). Accordingly, for example, a compound of Formula X wherein $R^1$ is OMe, $R^3$ is hydroxy, and $R^{4b}$ is hydrogen can be prepared as described in Scheme 2 starting from CAS #6080-33-7.

Scheme 2

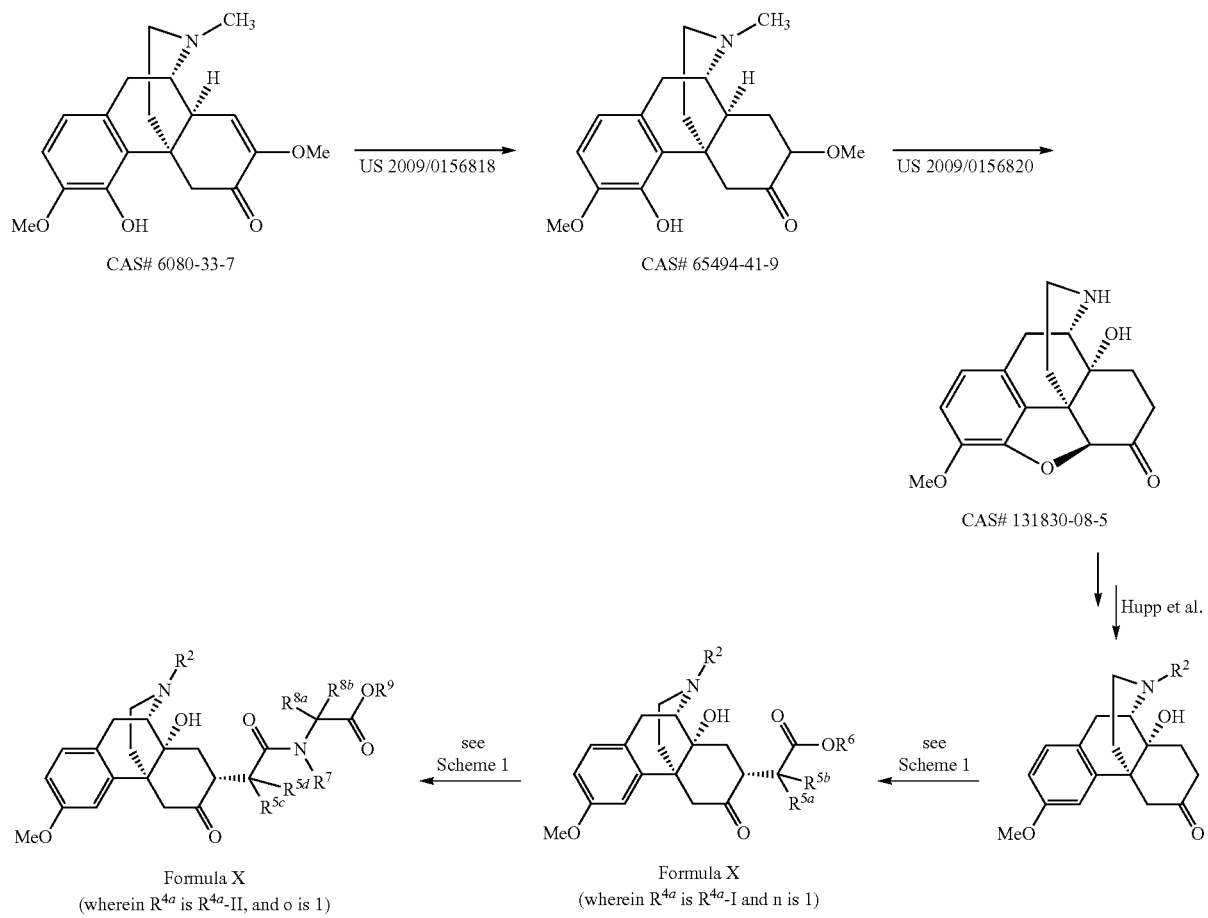

Scheme 3

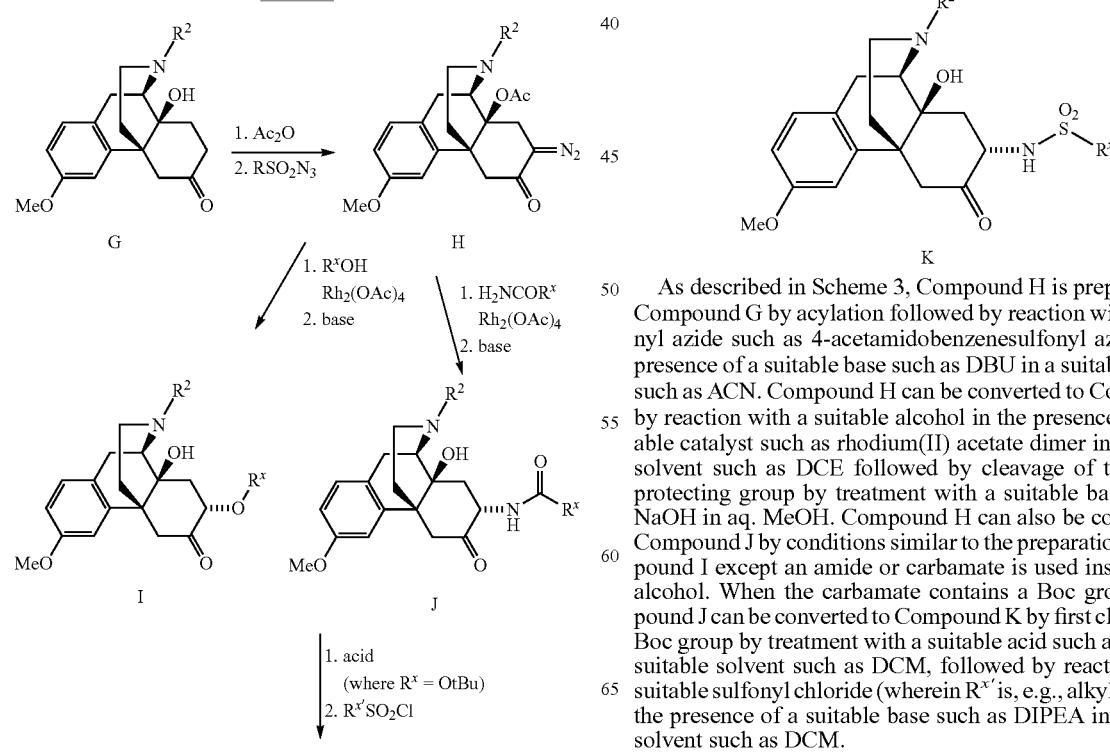

As described in Scheme 3, Compound H is prepared from Compound G by acylation followed by reaction with a sulfonyl azide such as 4-acetamidobenzenesulfonyl azide in the presence of a suitable base such as DBU in a suitable solvent such as ACN. Compound H can be converted to Compound I by reaction with a suitable alcohol in the presence of a suitable catalyst such as rhodium(II) acetate dimer in a suitable solvent such as DCE followed by cleavage of the acetate protecting group by treatment with a suitable base such as NaOH in aq. MeOH. Compound H can also be converted to Compound J by conditions similar to the preparation of Compound I except an amide or carbamate is used instead of an alcohol. When the carbamate contains a Boc group, Compound J can be converted to Compound K by first cleaving the Boc group by treatment with a suitable acid such as TFA in a suitable solvent such as DCM, followed by reaction with a suitable sulfonyl chloride (wherein $R^{x'}$ is, e.g., alkyl or aryl) in the presence of a suitable base such as DIPEA in a suitable solvent such as DCM.

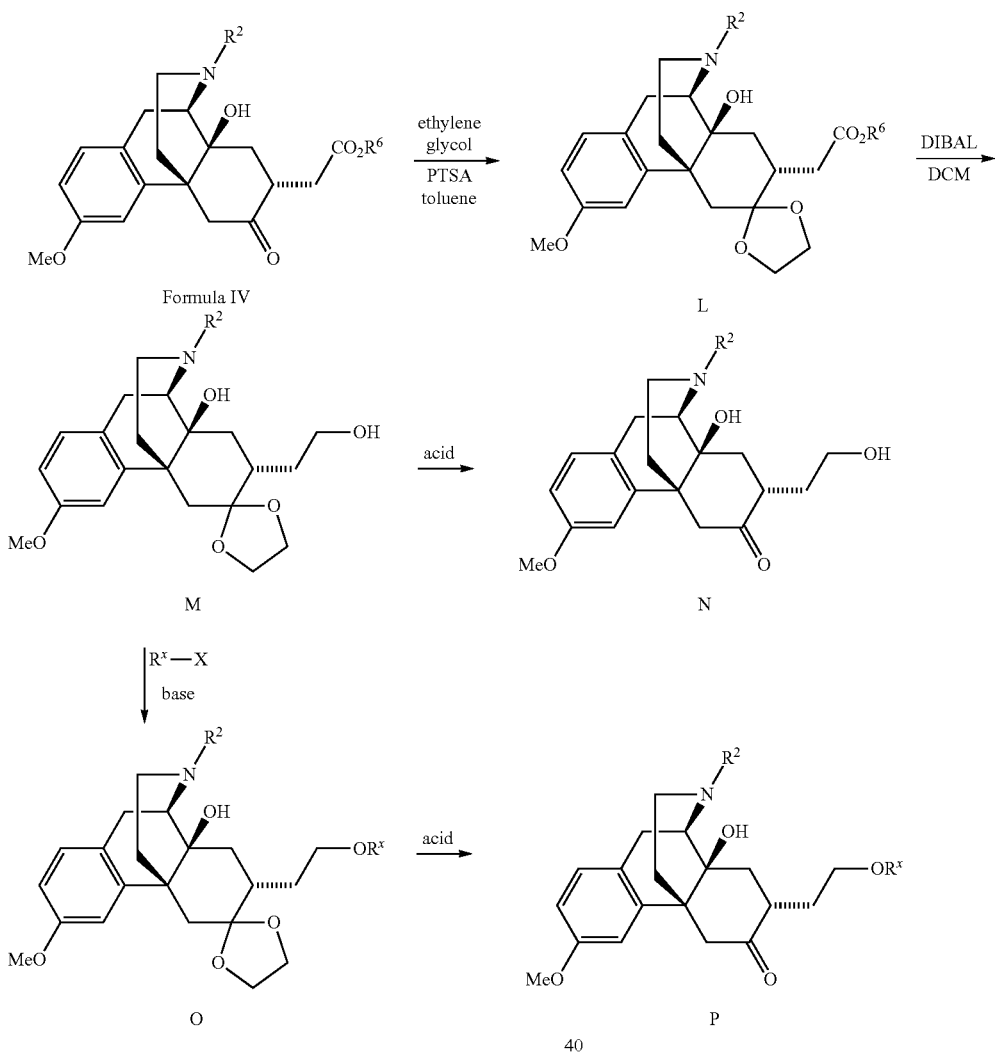

In Scheme 4, Compound L can be prepared from a compound having Formula IV (see Scheme 1) by reaction of the ketone group with a suitable diol such as ethylene glycol in the presence of an acid catalyst such as PTSA in a suitable solvent such as toluene. Treatment of Compound L with a suitable reducing agent such as DIBAL in a suitable solvent such as DCM gives Compound M. Treatment of Compound M with a suitable acid such as aq. HCl gives Compound N. Compound M can be converted to Compound O by treatment with a suitable base such as NaH and a suitable alkylating agent in a suitable solvent such as DMF. Treatment of Compound O with a suitable acid such as aq. HCl gives Compound P.

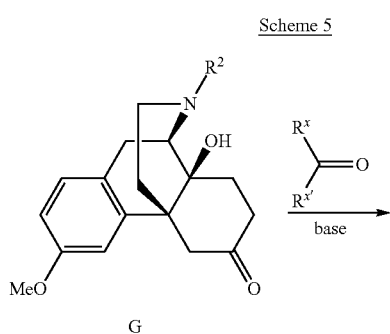

Scheme 5

-continued

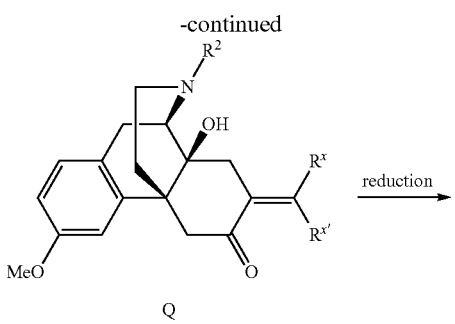

In Scheme 5, Compound Q can be prepared from Compound G by treatment with a suitable aldehyde or ketone in the presence of a suitable base such as NaOH in a suitable solvent such as aq. MeOH. Compound R can be prepared from Compound Q by reduction under suitable conditions such as hydrogenation over a suitable catalyst such as Pd/C in a suitable solvent such as MeOH.

Subsequent side chain modifications can be accomplished via appropriate functional group manipulations known to one skilled in the art.

In Vitro Assay Protocols

μ-Opioid Receptor Binding Assay Procedures:

Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hours at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-Opioid Receptor Binding Data:

Generally, the lower the $K_i$ value, the more effective Compounds of the Invention will be at treating or preventing pain or another Condition. In certain embodiments, Compounds of the Invention exhibit a $K_i$ (nM) of about 30,000 or less, e.g., about 10,000 or less, for binding to μ-opioid receptors. Typically, Compounds of the Invention exhibit a $K_i$ (nM) of about 1,000 or less, or about 300 or less, or about 100 or less, or about 10 or less, or about 1 or less, or about 0.1 or less.

μ-Opioid Receptor Functional Assay Procedures:

[$^{35}$S]GTPγS functional assays were conducted using freshly thawed μ-receptor membranes prepared from a cell line expressing recombinant μ opioid receptor in a HEK-293, CHO or U-2 OS cell background or purchased from a commercial source (Perkin Elmer, Shelton, Conn.; or DiscovRx, Fremont, Calif.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hours. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data:

μ GTP $EC_{50}$ is the concentration of a compound providing 50% of the maximal response for the compound at a μ-opioid receptor. Typically, Compounds of the Invention exhibit a μ GTP $EC_{50}$ (nM) of about 5,000 or less, or about 2000 or less, or about 1,000 or less, or about 100 or less, or about 10 or less, or about 1 or less, or about 0.1 or less.

μ GTP $E_{max}$ (%) is the maximal effect elicited by a compound relative to the effect elicited by DAMGO, a standard μ agonist. Generally, the μ GTP $E_{max}$ (%) value measures the efficacy of a compound to treat or prevent pain or other Conditions. Typically, Compounds of the Invention exhibit a μ GTP $E_{max}$ (%) of greater than about 10%, or greater than about 20%, or greater than about 50%, or greater than about 65%, or greater than about 75%, or greater than about 85%, or greater than about 100%.

κ-Opioid Receptor Binding Assay Procedures:

Membranes from HEK-293 cells, CHO or U-2 OS cells expressing the recombinant human kappa opioid receptor (κ) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hour at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data:

In certain embodiments, Compounds of the Invention exhibit a $K_i$ (nM) for κ receptors of about 10,000 or more (which, for purposes of this invention, is interpreted as having no binding to the κ receptors). Certain Compounds of the Invention exhibit a $K_i$ (nM) of about 20,000 or less, or about 10,000 or less, or about 5,000 or less, or about 1,000 or less, or about 500 or less, or about 450 or less, or about 350 or less, or about 200 or less, or about 100 or less, or about 50 or less, or about 10 or less, or about 1 or less, or about 0.1 or less.

κ-Opioid Receptor Functional Assay Procedures:

Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) was transferred to 96-shallow well polypropylene plates containing 10 µl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM $NaH_2PO_4$, 10 mM $Na_2HPO_4$, pH 7.4). Filter plates were subsequently dried at 50° C. for 2-3 hours. Fifty µl/well scintillation cocktail (Perkin Elmer, Shelton, Conn.) was added and plates were counted in a Packard Top-Count for 1 min/well.

κ-Opioid Receptor Functional Data:

κ GTP $EC_{50}$ is the concentration of a compound providing 50% of the maximal response for the compound at a κ receptor. Certain Compounds of the Invention exhibit a κ GTP $EC_{50}$ (nM) of about 20,000 or less to stimulate κ opioid receptor function, or about 10,000 or less, or about 5,000 or less, or about 2,000 or less, or about 1,500 or less, or about 1,000 or less, or about 600 or less, or about 100 or less, or about 50 or less, or about 25 or less, or about 10 or less, or about 1 or less, or about 0.1 or less.

κ GTP $E_{max}$ (%) is the maximal effect elicited by a compound relative to the effect elicited by U69,593. Certain Compounds of the Invention exhibit a κ GTP $E_{max}$ (%) of greater than about 1%, or greater than about 5%, or greater than about 10%, or greater than about 20%, or greater than about 50%, or greater than about 75%, or greater than about 90%, or greater than about 100%.

δ-Opioid Receptor Binding Assay Procedures:

δ-Opioid Receptor Binding Assay Procedures can be conducted as follows. Radioligand dose-displacement assays use 0.3 nM [$^3$H]-Naltrindole (Perkin Elmer, Shelton, Conn.; 33.0 Ci/mmole) with 5 µg membrane protein (Perkin Elmer, Shelton, Conn.) in a final volume of 500 µl binding buffer (5 mM $MgCl_2$, 5% DMSO, 50 mM Trizma base, pH 7.4). Non-specific binding is determined in the presence of 25 µM unlabeled naloxone. All reactions are performed in 96-deep well polypropylene plates for 1 hour at a temperature of about 25° C. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by five filtration washes with 500 µl ice-cold binding buffer. Filter plates are subsequently dried at 50° C. for 1-2 hours. Fifty µl/well scintillation cocktail (Perkin Elmer, Shelton, Conn.) are added and plates are counted in a Packard Top-Count for 1 min/well.

δ-Opioid Receptor Binding Data:

In certain embodiments, Compounds of the Invention can exhibit a $K_i$ (nM) for δ receptors of about 10,000 or more (which, for the purposes of this invention, is interpreted as having no binding to the δ receptors). Certain Compounds of the Invention can exhibit a $K_i$ (nM) of about 20,000 or less, or about 10,000 or less, or about 9,000 or less, or about 7,500 or less, or about 6,500 or less, or about 5,000 or less, or about 3,000 or less, or about 2,500 or less, or about 1,000 or less, or about 500 or less, or about 350 or less, or about 250 or less, or about 100 or less, or about 10 or less for δ receptors.

δ-Opioid Receptor Functional Assay Procedures:

Functional [$^{35}$S]GTPγS binding assays are conducted as follows. δ opioid receptor membrane solution is prepared by sequentially adding final concentrations of 0.026 µg/µl δ membrane protein (Perkin Elmer, Shelton, Conn.), 10 µg/mL saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µl/well) is transferred to 96-shallow well polypropylene plates containing 10 µl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 µl ice-cold binding buffer (10 mM $NaH_2PO_4$, 10 mM $Na_2HPO_4$, pH 7.4). Filter plates are subsequently dried at 50° C. for 1-2 hours. Fifty µl/well scintillation cocktail (Perkin Elmer, Shelton, Conn.) are added and plates are counted in a Packard Top-count for 1 min/well.

δ-Opioid Receptor Functional Data:

δ GTP $EC_{50}$ is the concentration of a compound providing 50% of the maximal response for the compound at a δ receptor. Certain Compounds of the Invention can exhibit a δ GTP $EC_{50}$ (nM) of about 20,000 or less, or about 10,000 or less, or about 3,500 or less, or about 1,000 or less, or about 500 or less, or about 100 or less, or about 90 or less, or about 50 or less, or about 25 or less, or about 10 or less.

δ GTP $E_{max}$ (%) is the maximal effect elicited by a compound relative to the effect elicited by met-enkephalin. Certain Compounds of the Invention can exhibit a δ GTP $E_{max}$ (%) of greater than about 1%, or greater than about 5%, or greater than about 10%, or greater than about 30%, or greater than about 50%, or greater than about 75%, or greater than about 90%, or greater than about 100%.

ORL-1 Receptor Binding Assay Procedure:

Membranes from recombinant HEK-293 cells expressing the human opioid receptor-like receptor (ORL-1) (Perkin Elmer, Shelton, Conn.) can be prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^3$H]-nociceptin (Perkin Elmer, Shelton, Conn.; 87.7 Ci/mmole) with 12 µg membrane protein in a final volume of 500 µl binding buffer (10 mM $MgCl_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by three filtration washes with 500 µl ice-cold binding buffer. Filter plates are subsequently dried at 50° C. for 2-3 hours. Fifty µl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data:

Certain Compounds of the Invention can have a $K_i$ (nM) of about 20,000 or less, e.g., about 5,000 or less. In certain embodiments, Compounds of the Invention have a $K_i$ (nM) of about 1,000 or less, or about 500 or less, or about 300 or less, or about 100 or less, or about 50 or less, or about 20 or less, or about 10 or less, or about 1 or less, or about 0.1 or less.

ORL-1 Receptor Functional Assay Procedure:

Membranes from recombinant HEK-293 cells expressing the human opioid receptor-like (ORL-1) (Perkin Elmer, Shelton, Conn.) can be prepared by lysing cells in ice-cold hypotonic buffer (2.5 mM Mg $Cl_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the Bio-Rad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) is transferred to 96-shallow well polypropylene plates containing 10 μl of 20× concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates are subsequently dried at 50° C. for 2-3 hours. Fifty μl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data:

ORL-1 GTP $EC_{50}$ is the concentration of a compound providing 50% of the maximal response for the compound at an ORL-1 receptor. In certain embodiments, the Compounds of the Invention that have a high binding affinity (i.e. low $K_i$ value) can have an ORL-1 GTP $EC_{50}$ (nM) of greater than about 10,000 (i.e. will not stimulate at therapeutic concentrations) In certain embodiments, Compounds of the Invention have an ORL-1 GTP $EC_{50}$ (nM) of about 20,000 or less, or about 10,000 or less, or about 5000 or less, or about 1000 or less, or about 100 or less, or about 10 or less, or about 1 or less, or about 0.1 or less.

ORL-1 GTP $E_{max}$% is the maximal effect elicited by a compound relative to the effect elicited by nociceptin, a standard ORL-1 agonist. In certain embodiments, Compounds of the Invention have an ORL-1 GTP $E_{max}$ of less than 10% (which, for the purposes of this invention, is interpreted as having antagonist activity at ORL-1 receptors). Certain Compounds of the Invention can have an ORL-1 GTP $E_{max}$ (%) of greater than about 1%, or greater than about 5%, or greater than about 10%, or greater than about 20%, or greater than about 50%, or greater than about 75%, or greater than about 88%, or of greater than about 100%.

In Vivo Assays for Pain

Test Animals:

Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain:

To assess the actions of a Compound of the Invention for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\% \ MPE = \frac{\left[\begin{array}{c}(\text{post administration latency}) - \\ (\text{pre-administration latency})\end{array}\right]}{(20 \ s - \text{pre-administration latency})} \times 100$$

The rat tail flick test is described in F. E. D'Amour et al., "A Method for Determining Loss of Pain Sensation," *J Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rat is placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) escape or attempted escape from the testing device; or 4) vocalization. Data are expressed as response latency(s) and the percentage of the maximal possible effect is calculated as described above for the tail flick test. The hot plate test is described in G. Woolfe and A. D. MacDonald, *J. Pharmacol. Exp. Ther.* 80:300-307 (1944).

Inflammatory Pain:

To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. Prior to injection of FCA (baseline)

and 24 hour post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \text{ Reversal} = \frac{\left[\begin{array}{c}(\text{post administration } PWT) - \\ (\text{pre-administration } PWT)\end{array}\right]}{[(\text{baseline } PWT) - (\text{pre-administration } PWT)]} \times 100$$

Neuropathic Pain:

To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{ Reversal} = \frac{\left[\begin{array}{c}(\text{post administration } PWT) - \\ (\text{pre-administration } PWT)\end{array}\right]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The rat is gently restrained, its hindpaw is placed on a small round platform, and punctate pressure is applied to the dorsal surface of the hindpaw in a graded manner. The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus applied to the plantar surface of the hindpaw are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., *Intensive Care Med.* (26): 585-591 (2000).

Assessment of Gastric Motility.

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in a patient in need thereof. The Compounds of the Invention can be administered to any patient requiring modulation of the opioid receptors. The term "patient" as used herein refers to any animal that may experience the beneficial effects of a Compound of the Invention. Foremost such animals are mammals, e.g., humans and companion animals, although the invention is not intended to be so limited.

When administered to a patient, a Compound of the Invention can be administered as a component of a composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, powders, multi-particulates, capsules, capsules containing liquids, capsules containing powders, capsules containing multi-particulates, lozenges, sustained-release formulations, suppositories, transdermal patches, transmucosal films, sublingual tablets or tabs, aerosols, sprays, or any other form suitable for use. In one embodiment, the composition is in the form of a tablet. In another embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the patient. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, Science 249:1527-1533 (1990); and Treat et al., Liposomes in the Therapy of Infectious Disease and Cancer 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially immediately release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol. 2, Applications and Evaluation*, R. S. Langer and D. L. Wise eds., CRC Press (1984). Other controlled- or sustained-release systems that are discussed in the review by Langer, Science 249:1527-1533 (1990) can be selected for use according to the present invention. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each patient's circumstances. Variations in dosing may occur depending upon typical factors such as the weight, age, gender and physical condition (e.g., hepatic and renal function) of the patient being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the patient per day, although they are typically from about 0.01 mg/kg of body weight to about 2500 mg/kg of body weight of the patient per day or from about 0.01 mg/kg of body weight to about 1000 mg/kg of body weight of the patient per day. In one embodiment, the effective dosage amount is about 100 mg/kg of body weight of the patient per day or less. In another embodiment, the effective dosage amount ranges from about 0.01 mg/kg of body weight to about 100 mg/kg of body weight of the patient per day of a Compound of the Invention, in another embodiment, about 0.02 mg/kg of body weight to about 50 mg/kg of body weight of the patient per day, and in another embodiment, about 0.025 mg/kg of body weight to about 20 mg/kg of body weight of the patient per day.

Administration can be as a single dose or as a divided dose. In one embodiment, an effective dosage amount is administered about every 24 hours until the Condition is abated. In another embodiment, an effective dosage amount is administered about every 12 hours until the Condition is abated. In another embodiment, an effective dosage amount is administered about every 8 hours until the Condition is abated. In another embodiment, an effective dosage amount is administered about every 6 hours until the Condition is abated. In another embodiment, an effective dosage amount is administered about every 4 hours until the Condition is abated. The effective dosage amounts described herein refer to total amounts administered; that is, if more than one Compound of the Invention is administered, the effective dosage amounts correspond to the total amount administered.

Where a cell capable of expressing the μ-opioid receptors is contacted with a Compound of the Invention in vitro, the amount effective for inhibiting or activating the μ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the δ-opioid receptors is contacted with a Compound of the Invention in vitro, the amount effective for inhibiting or activating the δ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the κ-opioid receptors is contacted with a Compound of the Invention in vitro, the amount effective for inhibiting or activating the κ-opioid receptors function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Where a cell capable of expressing the ORL-1 receptor is contacted with a Compound of the Invention in vitro, the amount effective for inhibiting or activating the ORL-1 receptor function in a cell can typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention can be from about 0.01 μL to about 1 mL. In another embodiment, the volume of solution or suspension can be about 200 μL.

Compounds of the Invention can be assayed in vitro or in vivo for the desired therapeutic or prophylactic activity prior to use in humans. Animal model systems can be used to demonstrate safety and efficacy. Certain Compounds of the Invention are expected to have an $ED_{50}$ for treating inflammatory pain ranging from about 0.5 mg/kg to about 20 mg/kg. Certain Compounds of the Invention are expected to produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the present invention, methods for treating or preventing a Condition in a patient in need thereof can further comprise co-administering to the patient an effective amount of a second therapeutic agent in addition to a Compound of the Invention (i.e., a first therapeutic agent). An effective amount of the second therapeutic agent can be known or determinable by a medical practitioner in view of this disclosure and published clinical studies. In one embodiment of the invention, where a second therapeutic agent is administered to a patient for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-IA inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

A composition of the invention is prepared by a method comprising admixing a Compound of the Invention with a pharmaceutically acceptable carrier or excipient. Admixing can be accomplished using methods known for admixing a compound (or derivative) and a pharmaceutically acceptable carrier or excipient. In one embodiment, the Compound of the Invention is present in the composition in an effective amount.

The present invention also relates to a kit, comprising a sterile container containing an effective amount of a Compound of the Invention and instructions for therapeutic use.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

Synthesis of ethyl 2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetate (Compound 1)

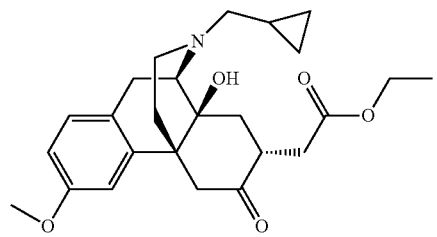 [SMILES: CCOC(=O)C[C@H]1C[C@@]2(O)[C@H]3Cc4ccc(OC)cc4[C@@]2(CCN3CC2CC2)CC1=O]

Step A: (4R,4aS,7aR,12bS)-3-allyl-4a-hydroxy-9-methoxy-2,3,4,4a,5,6-hexahydro-1H-4,12-methanobenzofuro[3,2-e]isoquinolin-7(7aH)-one (Compound 2)

To a solution of naloxone (50 g, 125 mmol) in 50 mL of DMF was added $K_2CO_3$ (51.8 g, 375 mmol). The resulting suspension was stirred at ambient temperature for 30 min whereupon methyl iodide (7.82 mL, 125 mmol) in 7 mL of DMF was added dropwise via an addition funnel. The suspension was maintained overnight at ambient temperature. The reaction mixture was added to 1 L of $H_2O$ and a white precipitate formed. The mixture was stirred for 1 h then filtered to give a white solid. The solid was dissolved in $CH_2Cl_2$ (700 mL) and washed with 1 N NaOH (400 mL). The layers were separated and the organic layer was concentrated to give a wet solid. Water was added and the solid was subsequently filtered and dried overnight in a vacuum oven to afford 28.1 g (66%) of Compound 2 as a white solid. LC/MS, m/z=342.2 $[M+H]^+$ (Calc: 342.40).

Step B: (4R,4aS,7aR,12bS)-4a-hydroxy-9-methoxy-2,3,4,4a,5,6-hexahydro-1H-4,12-methanobenzofuro[3,2-e]isoquinolin-7(7aH)-one (Compound 3)

Allylamine (36 g, 105 mmol) and 1,3-dimethylbarbituric acid (49.4 g, 316 mmol) were added to a flask containing Compound 2 from Step A then dissolved in 180 mL $CH_2Cl_2$. Nitrogen was bubbled into the mixture for 10 min. $Pd(PPh_3)_4$ (3.66 g, 3.16 mmol) was added and the yellow reaction mixture was heated at 40° C. under $N_2$ for 2 h. LC-MS revealed that the reaction was complete. The reaction mixture was transferred to a separatory funnel and extracted with 1 N HCl (3×200 mL). The combined aqueous layers were back extracted with $CH_2Cl_2$ (2×200 mL). The aqueous layer was basified to pH=10 with 2.5 N NaOH. The basified aqueous was extracted with $CH_2Cl_2$/MeOH (9:1) (3×300 mL). The combined organics were dried over $MgSO_4$, filtered, and concentrated to afford 12 g of a white solid. The pH of the aqueous layer was checked and found to be neutral. The aqueous layer was then basified to pH 10 with 2.5 N NaOH. The basified aqueous layer was again extracted with $CH_2Cl_2$/MeOH (9:1) (3×300 mL). The combined organics were dried over $MgSO_4$, filtered, and concentrated to afford 17 g of Compound 3 as a white solid. LC/MS, m/z=302.2 $[M+H]^+$ (Calc: 302.34).

Step C: (4R,4aS,7aR,12bS)-3-(cyclopropylmethyl)-4a-hydroxy-9-methoxy-2,3,4,4a,5,6-hexahydro-1H-4,12-methanobenzofuro[3,2-e]isoquinolin-7(7aH)-one (Compound 4)

To a suspension of Compound 3 (9.5 g, 31.5 mmol) in 80 mL of $CH_3CN$ was added $K_2CO_3$ (10.9 g, 79.0 mmol) portionwise followed by cyclopropylmethyl bromide (3.97 mL, 41.0 mmol) dropwise via syringe. The suspension was heated at reflux for 18 h. LC-MS showed a single peak corresponding to the desired product (Tr=0.830 min, M+H=356). The mixture was cooled to ambient temperature and the solid was filtered off and washed with $CH_3CN$. The filtrate was concentrated and the golden yellow residue was diluted with $CH_2Cl_2$ and $H_2O$. The layers were separated and the aqueous was further extracted with $CH_2Cl_2$. The combined organics were washed with brine, dried over $MgSO_4$, filtered, and concentrated to provide 9.76 g (87%) of Compound 4 as a white foam that turned to a light yellow oily foam overnight. LC/MS, m/z=356.2 $[M+H]^+$ (Calc: 356.43).

Step D: (4bR,8aS,9R)-11-(cyclopropylmethyl)-4,8a-dihydroxy-3-methoxy-8,8a,9,10-tetrahydro-5H-9,4b-(epiminoethano)phenanthren-6(7H)-one (Compound 5)

To a solution of Compound 4 (9.7 g, 12.7 mmol) in 100 mL of acetone was added saturated aqueous ammonium chloride solution (27 mL, 191 mmol) and zinc powder (7.14 g, 109 mmol). The resulting mixture was maintained at 60° C. for 4.5 h. LC-MS analysis showed the reaction was complete. The reaction mixture was cooled to ambient temperature and then filtered through Celite. The filter cake was rinsed with acetone and the filtrate was concentrated. The crude product was diluted with 300 mL $CH_2Cl_2$ and 150 mL concentrated $NH_4OH$ solution. The layers were separated and the aqueous layer was further extracted with $CH_2Cl_2$. The combined organics were washed with brine, dried over $Na_2SO_4$, filtered and concentrated. Purification by flash chromatography on $SiO_2$ (ISCO ReadySep Rf 220 g 0-50% acetone/hexanes) afforded 6.9 g (71%) of Compound 5 as a white foam. LC/MS, m/z=358.2 $[M+H]^+$ (Calc: 358.44).

Step E: (4bR,8aS,9R)-11-(cyclopropylmethyl)-8a-hydroxy-3-methoxy-6-oxo-6,7,8,8a,9,10-hexahydro-5H-9,4b-(epiminoethano)phenanthren-4-yl trifluoromethane sulfonate (Compound 6)

To a solution of Compound 5 (20.0 g, 56.0 mmol) in 370 mL of THF was added $Cs_2CO_3$ (23.7 g, 72.7 mmol) followed by $PhNTf_2$ (24.0 g, 67.1 mmol). The resulting yellow-orange mixture was maintained overnight at 70° C. LC-MS analysis showed the reaction was complete. The mixture was concentrated and diluted with $CH_2Cl_2$ and $H_2O$. The layers were separated. The aqueous layer was further extracted with $CH_2Cl_2$. The combined organics were washed with brine, dried over $Na_2SO_4$, filtered, and concentrated to give 24.9 g (91%) of Compound 6 as an off-white/beige solid. LC/MS, m/z=490.2 $[M+H]^+$ (Calc: 490.51).

Step F: (4bR,8aS,9R)-11-(cyclopropylmethyl)-8a-hydroxy-3-methoxy-8,8a,9,10-tetrahydro-5H,4b-(epiminoethano)phenanthren-6(7H)-one (Compound 7)

To a solution of Compound 6 (15.0 g, 30.6 mmol) in 306 mL of THF was added $Pd(OAc)_2$ (0.688 g, 3.06 mmol) and dppp (1.26 g, 3.06 mmol). $Et_3SiH$ (12.2 mL, 77.0 mmol) was dissolved in THF (30 mL) and added slowly dropwise via dropping funnel. The orange solution was maintained overnight at ambient temperature. The resultant dark red/brown reaction mixture was then diluted with 300 mL $Et_2O$ and extract three times with 150 mL 1N HCl. The combined aqueous layers were washed with $CH_2Cl_2$ (2×150 mL). LC-MS showed the product was in the acidic aqueous layer (pH=1). The aqueous was basified with concentrated $NH_4OH$. The white, milky aqueous layer was extracted with $CH_2Cl_2$ (3×200 mL). The combined organics were washed with brine, dried over $Na_2SO_4$, filtered and concentrated. Purification by flash chromatography (ISCO ReadySep Rf, 220 g, 0-40% acetone/hexanes) afforded 7.4 g (71%) of Compound 7 as a white solid. LC/MS, m/z=342.2 $[M+H]^+$ (Calc: 342.44).

Step G: Ethyl 2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl) acetate (Compound 1)

To a −78° C. solution of sodium hexamethyldisilazide (17.6 mL, 17.6 mmol) in 34 mL of anhydrous THF was added a solution of Compound 7 (1.5 g, 4.39 mmol) in 10 mL of THF dropwise via syringe. The pale yellow solution was maintained at −10° C. for 20 min. The solution was cooled to −78° C. whereupon ethyl iodoacetate (2.1 mL, 17.6 mmol—passed through basic alumnina) was added dropwise (neat). The resulting yellow reaction mixture was allowed to slowly warm to ambient temperature overnight. LC-MS analysis showed the reaction was complete. The reaction was quenched with saturated aqueous $NaHCO_3$ and diluted with EtOAc. The layers were separated and the aqueous layer was further extracted with EtOAc (3×). The combined organics were washed with brine, dried over $Na_2SO_4$, filtered, and concentrated. Purification by flash chromatography (ISCO ReadySep Rf 80 g 0-50% EtOAc/hexanes) afforded 0.800 g (43%) of Compound 1 as a light yellow oil. Compound 1 was further purified by mass-directed reverse phase preparative HPLC (20-90% AcCN/$H_2O$, 0.1% TFA) to provide 15 mg of a light yellow solid (after neutralization with ammonium carbonate resin and lyophilization). $^1H$ NMR: $\delta_H$ (400 MHz, $CD_3OD$): 7.04 (d, 1H), 6.79 (s, 1H), 6.72 (d, 1H), 4.10-3.95 (m, 2H), 3.74 (s, 3H), 3.41-3.31 (m, 1H), 3.20-3.00 (m, 2H), 2.90-2.55 (m, 3H), 2.55-2.30 (m, 3H), 2.30-2.05 (m, 2H), 2.00 (dd, 1H), 1.95-1.85 (m, 1H), 1.68 (app t, 1H), 1.17 (t, 3H), 1.00-0.85 (m, 1H), 0.65-0.45 (m, 2H), 0.25-0.10 (m, 2H). LC/MS, m/z=428.1 $[M+H]^+$ (Calc: 428.53).

Example 2

Synthesis of 2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetic acid (Compound 8)

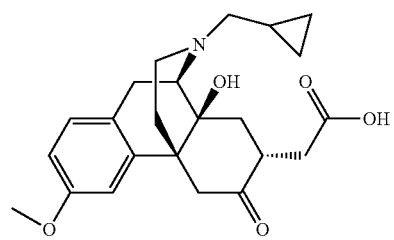 [SMILES: COc1ccc2c(c1)[C@]13CCN(CC4CC4)[C@H](C2)[C@]1(O)C[C@H](CC(=O)O)C(=O)C3]

To a solution of Compound 1 (0.127 g, 0.297 mmol) from EXAMPLE 1 in 3.7 mL of MeOH was added 1.78 mL of 2.5 N NaOH dropwise via syringe. The resulting yellow solution was maintained for 18 h at ambient temperature. LC-MS analysis showed that the reaction was complete. The volatiles were concentrated and the crude residue was purified by reverse phase mass-directed preparative HPLC (0-60% AcCN/$H_2$O, 0.1% TFA). The fractions were combined and lyophilized to afford 81 mg (68%) of Compound 8 as a white, fluffy solid (TFA salt). $^1$H NMR: $\delta_H$ (400 MHz, CD$_3$OD): 7.06 (d, 1H), 6.79 (brs, 1H), 6.75 (dd, 1H), 3.93 (d, 1H), 3.68 (s, 3H), 3.31 3.22 (3H), 3.10 (d, 1H), 3.00-2.82 (m, 3H), 2.62-2.45 (m, 2H), 2.42 (dd, 1H), 2.03 (dd, 1H), 1.88 (dd, 1H), 1.64 (app t, 1H), 1.33 (d, 1H), 1.10-0.95 (m, 1H), 0.80-0.60 (m, 2H), 0.50-0.35 (m, 2H). LC/MS, m/z=400.2 [M+H]$^+$ (Calc: 400.48).

Example 3

Synthesis of 2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetic acid (Compound 9)

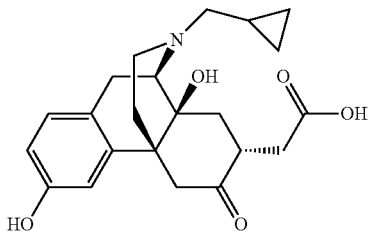 [SMILES: O=C(O)C[C@H]1C[C@@]2(O)[C@H]3Cc4ccc(O)cc4[C@@]2(CCN3CC2CC2)CC1=O]

To a -10° C. solution of Compound 8 (0.055 g, 0.138 mmol) from EXAMPLE 2 in CH$_2$Cl$_2$ was added a 1.0 M solution of BBr$_3$ in CH$_2$Cl$_2$ (0.690 mL, 0.688 mmol) dropwise via syringe. The resulting yellow suspension was maintained at -10° C. for 2 h. LC-MS showed that the reaction was mostly complete. The reaction was quenched with 5 mL of MeOH and left overnight at ambient temperature. LC-MS analysis of the mixture after being left at ambient temperature overnight now showed the formation of the methyl ester. The solution was concentrated and then redissolved in 3 mL MeOH and treated with 1 mL of 2.5 N NaOH and stirred for 3 h. Purification of the crude reaction mixture by mass-directed reverse-phase prep HPLC (0-40% AcCN/H$_2$O, 0.1% TFA) and subsequent lyophilization afforded 13 mg (25%) of Compound 9 as a fluffy, white solid (TFA salt). $^1$H NMR: $\delta_H$ (400 MHz, CD$_3$OD): 7.05 (d, 1H), 6.78 (d, 1H), 6.68 (dd, 1H), 3.99 (d, 1H), 3.40-3.20 (m, 4H), 3.16 (d, 1H) 3.10-3.00 (m, 1H), 3.00-2.85 (m, 2H), 2.11 (dd, 1H), 1.99 (dd, 1H), 1.76 (app t, 1H), 1.38 (d, 1H), 1.18-1.03 (m, 2H), 0.90-0.70 (m, 2H), 0.55-0.42 (m, 2H). LC/MS, m/z=386.3 [M+H]$^+$ (Calc: 386.45).

Example 4

Synthesis of 2,2'-((4bR,8aS,9R)-11-(cyclopropylmethyl)-8a-hydroxy-3-methoxy-6-oxo-6,7,8,8a,9,10-hexahydro-5H-9,4b-(epiminoethano)phenanthrene-7,7-diyl)diacetic acid (Compound 10)

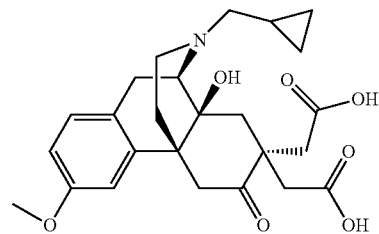

Step A: Diethyl 2,2'-((4bR,8aS,9R)-11-(cyclopropylmethyl)-8a-hydroxy-3-methoxy-6-oxo-6,7,8,8a,9,10-hexahydro-5H-9,4b-(epiminoethano)phenanthrene-7,7-diyl)diacetate (Compound 11)

To a -78° C. solution of NaHMDS (40 mL, 40 mmol) in 70 mL of anhydrous THF was added a solution of Compound 7 (3.0 g, 8.79 mmol) from EXAMPLE 1 in 30 mL of THF dropwise via syringe. The pale yellow solution was maintained at -10° C. for 15 min. The solution was cooled to -78° C. whereupon ethyl iodoacetate (4.67 mL, 40 mmol—passed through basic alumnina) was added dropwise (neat). The resulting yellow reaction mixture was allowed to slowly warm to ambient temperature overnight. The reaction was quenched with saturated aqueous NaHCO$_3$ and diluted with EtOAc. The layers were separated and the aqueous layer was further extracted with EtOAc (3×). The combined organics were washed with brine, dried over Na$_2$SO$_4$, filtered, and concentrated. Purification by flash chromatography (ISCO ReadySep Rf 80 g 0-50% EtOAc/hexanes) afforded 0.290 g of Compound 11 as a light yellow oil. LC/MS, m/z=514.3 [M+H]$^+$ (Calc: 514.45).

Step B: 2,2'-((4bR,8aS,9R)-11-(cyclopropylmethyl)-8a-hydroxy-3-methoxy-6-oxo-6,7,8,8a,9,10-hexahydro-5H-9,4b-(epiminoethano)phenanthrene-7,7-diyl)diacetic acid (Compound 10)

To a solution of Compound 11 (0.250 g, 0.487 mmol) from Step A in 8 mL of MeOH was added 1.0 mL of 2.5 N NaOH dropwise via syringe. The reaction was maintained at ambient temperature for 7 h. LC-MS analysis showed that the reaction was complete. Purification of the crude reaction mixture by reverse-phase preparative HPLC (0-60% AcCN/H$_2$O, 0.1% TFA) and subsequent lyophilization afforded 116 mg (52%) of Compound 10 as a fluffy, white solid (TFA salt). $^1$H NMR: $\delta_H$ (400 MHz, D2O): 7.15 (d, 1H), 6.94 (d, 1H), 6.89 (dd, 1H), 3.35-3.22 (m, 3H), 3.20-3.08 (m, 2H), 3.08-2.90 (m, 3H), 2.75-2.55 (m, 2H), 2.50 (ddd, 1H), 2.41 (d, 1H), 2.15 (d, 1H), 1.48 (dd, 1H), 1.1-1.0 (m, 1H), 0.85-0.65 (m, 2H), 0.48-0.35 (m, 2H). LC/MS, m/z=458.4 [M+H]$^+$ (Calc: 458.52).

Example 5

Synthesis of 2,2'-((4bR,8aS,9R)-11-(cyclopropylmethyl)-3,8a-dihydroxy-6-oxo-6,7,8,8a,9,10-hexahydro-5H-9,4b-(epiminoethano)phenanthrene-7,7-diyl) diacetic acid (Compound 12)

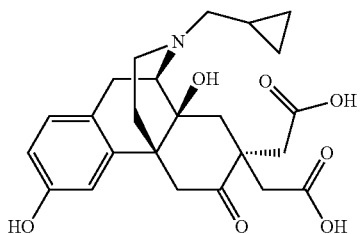

To a −10° C. solution of Compound 10 (0.050 g, 0.109 mmol) from EXAMPLE 4 in 2.78 mL of anhydrous $CH_2Cl_2$ was added a 1.0 M solution of $BBr_3$ in $CH_2Cl_2$ (0.550 mL, 0.550 mmol) dropwise via syringe. The resulting yellow suspension was maintained at −10° C. for 2 h. LC-MS showed that the reaction was mostly complete The reaction was quenched with 5 mL of $H_2O$ and concentrated. The crude residue was dissolved in 1.3 mL of MeOH and treated with 0.13 mL of 2.5 N NaOH dropwise via syringe. The reaction was maintained overnight at ambient temperature. LC-MS showed that the reaction was complete. Purification of the reaction mixture by mass-directed reverse-phase prep HPLC (0-40% $AcCN/H_2O$, 0.1% TFA) and subsequent lyophilization afforded 9 mg (32%) of Compound 12 as a fluffy, white solid (TFA salt). $^1$H NMR: $\delta_H$ (400 MHz, $D_2O$): 7.05 (d, 1H), 6.81 (d, 1H), 6.74 (dd, 1H), 4.01 (brs, 1H), 3.30-3.18 (m, 3H), 3.12-3.01 (m, 2H), 3.00-2.85 (m, 3H), 2.70-2.52 (m, 2H), 2.50-2.33 (m, 2H), 2.15-2.05 (m, 2H), 1.42 (dd, 1H), 1.10-0.95 (m, 1H), 0.80-0.60 (m, 2H), 0.45-0.30 (m, 2H). LC/MS, m/z=444.1 $[M+H]^+$ (Calc: 444.49).

Example 6

Synthesis of (S)-2-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetamido)propanoic acid (Compound 13)

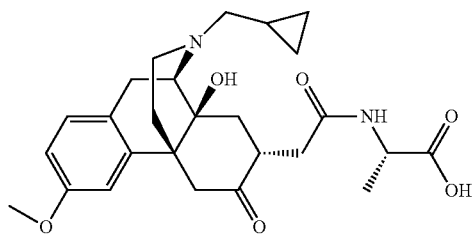 [SMILES: COc1ccc2c(c1)[C@]13CCN(CC4CC4)[C@H](C2)[C@]1(O)C[C@H](CC(=O)N[C@@H](C)C(=O)O)C(=O)C3]

Step A: (S)-methyl 2-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)acetamido)propanoate (Compound 14)

To a suspension of Compound 8 (0.150 g, 0.375 mmol) from EXAMPLE 2 in 3 mL of DMF was added (S)-methyl 2-aminopropanoate hydrochloride (0.079 g, 0.563 mmol) HATU (0.286 g, 0.751 mmol), and diisopropylethylamine (0.200 mL, 1.13 mmol). The resulting yellow suspension was maintained overnight at ambient temperature. LC-MS analysis showed the reaction was complete. The crude reaction was concentrated on a Genevac at 50° C. for 18 h. The residue was diluted with $CH_2Cl_2$/MeOH, filtered, and concentrated. Purification by flash chromatography (ISCO ReadySep Rf, 40 g, 0-25% MeOH/$CH_2Cl_2$) afforded 0.166 g (91%) of Compound 14. LC/MS, m/z=485.4 $[M+H]^+$ (Calc: 485.58).

Step B: (S)-2-(2-((4bR,7R,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl) acetamido)propanoic acid (Compound 13)

To a solution of Compound 14 (0.166 g, 0.343 mmol) in 3.5 mL of MeOH was added 0.69 mL of 2.5 N NaOH dropwise via syringe. The reaction was maintained at ambient temperature for 24 h. LC-MS analysis showed that the reaction was complete. Purification by reverse-phase preparative HPLC (0-60% $AcCN/H_2O$, 0.1% TFA) and subsequent lyophilization afforded 46 mg (28%) of Compound 13 as a fluffy, white solid (TFA salt). 1H NMR: $\delta_H$ (400 MHz, $CD_3OD$): 7.15 (d, 1H), 6.89 (d, 1H), 6.83 (dd, 1H), 4.32 (q, 1H), 4.01 (d, 1H), 3.76 (s, 3H), 3.40-3.22 (m, 4H), 3.20 (d, 1H), 3.06 (dd, 1H), 3.02-2.90 (m, 2H), 2.72-2.50 (m, 3H), 2.13 (dd, 1H), 1.87 (dd, 1H), 1.69 (app t, 1H), 1.42 (d, 1H), 1.35 (d, 3H), 1.18-1.05 (m, 1H), 0.90-0.80 (m, 1H), 0.80-0.70 (m, 1H), 0.58-0.45 (m, 2H). LC/MS, m/z=471.3 $[M+H]^+$ (Calc: 471.56).

Example 7

Synthesis of (S)-2-(2-((4bR,7R,8aS,9R)-11-(cyclopropylmethyl)-3,8a-dihydroxy-6-oxo-6,7,8,8a,9,10-hexahydro-5H-9,4b-(epimnoethano)phenanthren-7-yl)acetamido)propanoic acid (Compound 15)

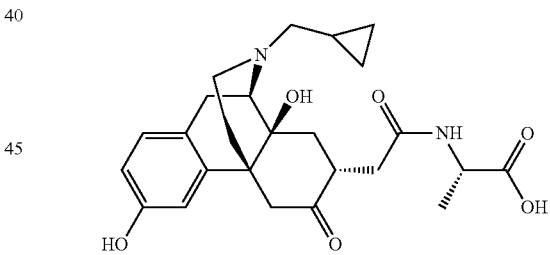

To a 0° C. solution of Compound 13 (0.030 g, 0.064 mmol) from EXAMPLE 6 in 2 mL of anhydrous $CH_2Cl_2$ was added a 1.0 M solution of $BBr_3$ in $CH_2Cl_2$ (0.320 mL, 0.320 mmol) dropwise via syringe. The resulting yellow suspension was maintained at 0° C. for 3 h. LC-MS showed that the reaction was mostly complete. The reaction was quenched with 5 mL of MeOH and stirred at ambient temperature for 1 h. LC-MS showed a mixture of phenol acid and the corresponding methyl ester. The solution was concentrated.

The crude residue was redissolved in 3 mL of MeOH and treated with 1 mL of 2.5 N NaOH. The reaction was maintained overnight at ambient temperature. LC-MS analysis showed the reaction was complete with the phenol acid as the major product. Purification by mass-directed reverse-phase prep HPLC (0-40% $AcCN/H_2O$, 0.1% TFA) and subsequent lyophilization afforded 12 mg (41%) of Compound 15 as a fluffy, white solid (TFA salt). $^1$H NMR: $\delta_H$ (400 MHz, CD$_3$OD): 7.05 (d, 1H), 6.78 (d, 1H), 6.68 (dd, 1H), 4.32 (q, 1H), 3.99 (d, 1H), 3.38-3.32 (m, 2H), 3.28-3.13 (m, 3H), 3.05 (dd, 1H), 3.00-2.85 (m, 2H), 2.68 (ddd, 1H), 2.60-2.48 (m, 2H), 2.12 (dd, 1H), 1.88 (dd, 1H), 1.72 (app t, 1H), 1.45-1.30 (m, 4H), 1.18-1.05 (m, 1H), 0.88-0.80 (m, 1H), 0.80-0.70 (m, 1H), 0.55-0.45 (m, 2H). LC/MS, m/z=457.2 [M+H]$^+$ (Calc: 457.56).

Example 8

Synthesis of (S)-1-(2-((4bR,7R,8aS,9R)-11-(cyclopropylmethyl)-8a-hydroxy-3-methoxy-6-oxo-6,7,8, 8a,9,10-hexahydro-5H-9,4b-(epiminoethano)phenanthren-7-yl)acetyl)pyrrolidine-2-carboxylic acid (Compound 16)

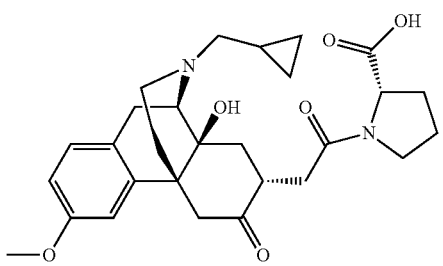 [SMILES: COc1ccc2c(c1)[C@]13CCN(CC4CC4)[C@H](C2)[C@]1(O)C[C@H](CC(=O)N1CCC[C@H]1C(=O)O)C(=O)C3]

Compound 16 was prepared from Compound 8 in a similar manner as described in EXAMPLE 6 employing (S)-methyl pyrrolidine-2-carboxylate hydrochloride in the initial amide coupling step. Compound 16 was obtained after purification by reverse-phase preparative HPLC (0-60% AcCN/H$_2$O, 0.1% TFA) and subsequent lyophilization to give 46 mg (28%) as a fluffy, white solid (TFA salt). $^1$H NMR: δ$_H$ (400 MHz, CD$_3$OD): 7.15 (d, 1H), 6.89 (d, 1H), 6.83 (dd, 1H), 4.38 (dd, 1H), 4.01 (d, 1H), 3.76 (s, 3H), 3.63-3.40 (m, 3H), 3.40-3.30 (m, 2H), 3.28-3.15 (m, 2H), 3.10-3.02 (m, 1H), 3.10-2.90 (m, 2H), 2.75-2.50 (m, 3H), 2.30-2.17 (m, 1H), 2.13 (dd, 1H), 2.05-1.90 (m, 4H), 1.71 (app t, 1H), 1.42 (d, 1H), 1.18-1.05 (m, 1H), 0.88-0.80 (m, 1H), 0.80-0.70 (m, 1H), 0.55-0.45 (m, 2H). LC/MS, m/z=497.3 [M+H]$^+$ (Calc: 497.60).

Example 9

Synthesis of (S)-1-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetyl)pyrrolidine-2-carboxylic acid (Compound 17)

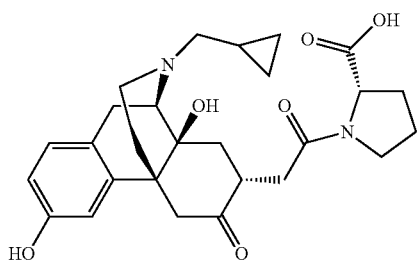 [SMILES: O=C1C[C@]23CCN(CC4CC4)[C@H](Cc4ccc(O)cc42)[C@]3(O)C[C@@H]1CC(=O)N1CCC[C@H]1C(=O)O]

To a 0° C. solution of Compound 16 (0.040 g, 0.081 mmol) from EXAMPLE 8 in 3 mL of anhydrous CH$_2$Cl$_2$ was added a 1.0 M solution of BBr$_3$ in CH$_2$Cl$_2$ (0.400 mL, 0.400 mmol) dropwise via syringe. The resulting yellow suspension was maintained at 0° C. for 2 h. LC-MS showed that the reaction was mostly complete. The reaction was quenched with 5 mL of MeOH and stirred at ambient temperature for 1 h. The solution was concentrated then redissolved in 3 mL of MeOH and treated with 1 mL of 2.5 N NaOH. The reaction was maintained overnight at ambient temperature. LC-MS analysis showed the reaction was complete with the phenol acid as the major product. Purification by mass-directed reverse-phase prep HPLC (0-60% AcCN/H$_2$O, 0.1% TFA) and subsequent lyophilization afforded 17 mg (44%) of Compound 17 as a fluffy, white solid (TFA salt). $^1$H NMR: δ$_H$ (400 MHz, CD$_3$OD): 7.05 (d, 1H), 6.78 (d, 1H), 6.68 (dd, 1H), 4.39 (dd, 1H), 3.99 (d, 1H), 3.63-3.40 (m, 3H), 3.40-3.30 (m, 2H), 3.27-3.12 (m, 3H), 3.04 (dd, 1H), 3.08-2.85 (m, 2H), 2.75-2.62 (m, 2H), 2.62-2.50 (m, 1H), 2.30-2.17 (m, 1H), 2.12 (dd, 1H), 2.03-1.90 (m, 4H), 1.74 (app t, 1H), 1.38 (d, 1H), 1.17-1.05 (m, 1H), 0.88-0.80 (m, 1H), 0.80-0.70 (m, 1H), 0.58-0.45 (m, 2H). LC/MS, m/z=483.3 [M+H]$^+$ (Calc: 483.57).

Example 10

Synthesis of (S)-2-(2-((4bR,7R,8aS,9R)-11-(cyclopropylmethyl)-8a-hydroxy-3-methoxy-6-oxo-6,7,8, 8a,9,10-hexahydro-5H-9,4b-(epiminoethano)phenanthren-7-yl)acetamido)-4-methylpentanoic acid (Compound 18)

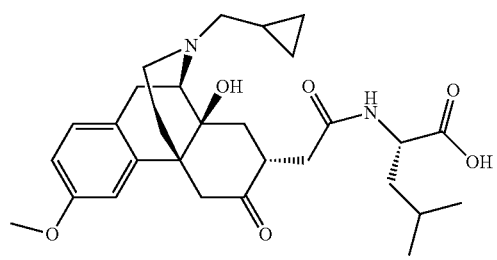 [SMILES: COc1ccc2c(c1)[C@]13CCN(CC4CC4)[C@H](C2)[C@]1(O)C[C@H](CC(=O)N[C@@H](CC(C)C)C(=O)O)C(=O)C3]

Compound 18 was prepared from Compound 8 in a similar manner as described in EXAMPLE 6 employing (S)-methyl 2-amino-4-methylpentanoate hydrochloride in the initial amide coupling step. Compound 18 was obtained after purification by reverse-phase preparative HPLC (0-60% AcCN/H$_2$O, 0.1% TFA) and subsequent lyophilization to give 89 mg (46%) as a fluffy, white solid. $^1$H NMR: δ$_H$ (400 MHz, CD$_3$OD): 8.18 (d, 1H), 7.15 (d, 1H), 6.89 (d, 1H), 6.83 (dd, 1H), 4.42-4.30 (m, 1H), 4.01 (d, 1H), 3.76 (s, 3H), 3.42-3.32 (m, 3H), 3.27-3.15 (m, 2H), 3.05 (dd, 1H), 3.02-2.90 (m, 2H), 2.72-2.47 (m, 3H), 2.12 (dd, 1H), 1.88 (dd, 1H), 1.80-1.65 (m, 2H), 1.63-1.50 (m, 2H), 1.42 (d, 1H), 1.18-1.05 (m, 1H), 0.94 (d, 3H), 0.90 (d, 3H), 0.87-0.80 (m, 1H), 0.80-0.70 (m, 1H), 0.67-0.45 (m, 2H). LC/MS, m/z=513.3 [M+H]$^+$ (Calc: 513.64).

Example 11

Synthesis of (S)-2-(2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamido)-4-methylpentanoic acid (Compound 19)

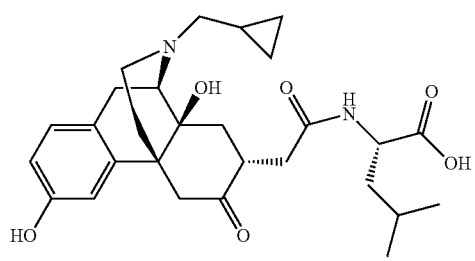 [SMILES: CC(C)C[C@H](NC(=O)C[C@H]1C[C@@]2(O)[C@H]3Cc4ccc(O)cc4[C@@]2(CCN3CC2CC2)CC1=O)C(=O)O]

To a 0° C. solution of Compound 18 (0.074 g, 0.144 mmol) from EXAMPLE 10 in 4 mL of anhydrous CH$_2$Cl$_2$ was added a 1.0 M solution of BBr$_3$ in CH$_2$Cl$_2$ (0.722 mL, 0.722 mmol) dropwise via syringe. The resulting yellow suspension was maintained at 0° C. for 1.25 h. LC-MS showed that the reaction was mostly complete. The reaction was quenched with 5 mL of MeOH and maintained for 1 h at ambient temperature. The solution was concentrated then redissolved in 3 mL of MeOH and treated with 1 mL of 2.5 N NaOH. The reaction was maintained overnight at ambient temperature. LC-MS analysis showed the reaction was complete with the phenol acid as the major product. Purification by mass-directed reverse-phase preparative HPLC (0-60% AcCN/H$_2$O, 0.1% TFA) and subsequent lyophilization afforded 42 mg (58%) of Compound 19 as a fluffy, white solid (TFA salt). $^1$H NMR: $\delta_H$ (400 MHz, CD$_3$OD): 8.19 (d, 1H), 7.05 (d, 1H), 6.78 (d, 1H), 6.68 (dd, 1H), 4.43-4.30 (m, 1H), 3.99 (d, 1H), 3.40-3.30 (m, 2H), 3.25-3.12 (m, 2H), 3.05 (dd, 1H), 3.00-2.85 (m, 2H), 2.68 (ddd, 1H), 2.60-2.48 (m, 2H), 2.11 (dd, 1H), 1.89 (dd, 1H), 1.80-1.67 (m, 2H), 1.65-1.50 (m, 2H), 1.38 (d, 1H), 1.18-1.05 (m, 1H), 0.94 (d, 3H), 0.90 (d, 3H), 0.88-0.80 (m, 1H), 0.80-0.70 (m, 1H), 0.57-0.45 (m, 2H). LC/MS, m/z=499.2 [M+H]$^+$ (Calc: 499.61).

Example 12

Synthesis of (4bR,7S,8aS,9R)-11-(cyclopropylmethyl)-8a-hydroxy-7-isobutoxy-3-methoxy-8,8a,9,10-tetrahydro-5H-9,4b-(epiminoethano)phenanthren-6(7H)-one (TFA salt) (Compound 23)

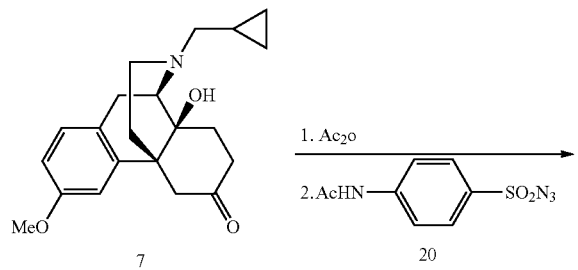

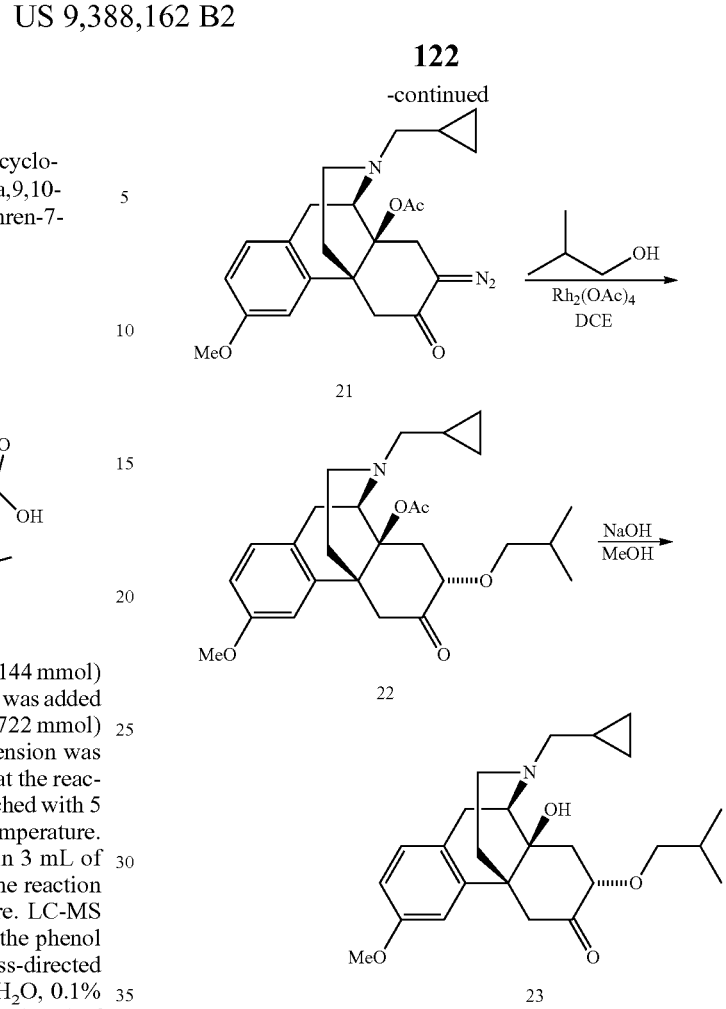

DIPEA (13.3 mL, 76 mmol) was added to Compound 7 (27.4 g, 72.5 mmol) in Ac$_2$O (68.4 mL, 725 mmol) and the solution was heated at 120° C. for 2 h. The reaction mixture was diluted with EtOAc, and the mixture washed with satd. aq. NaHCO$_3$ (2×), dried over Na$_2$SO$_4$, and dried under vacuum. ACN (300 mL) and 4-acetamidobenzenesulfonyl azide (34.8 g, 145 mmol, Compound 20) were added, followed by DBU (32.8 mL, 218 mmol) at 0° C. The reaction was allowed to warm to RT over 18 h and concentrated. EtOAc was added, washed with two portions of 1M aq. NaOH, dried over Na$_2$SO$_4$ and concentrated. The resulting brown solid was triturated with acetone, filtered and concentrated to give 17.28 g of Compound 21 as a yellow solid which was used in subsequent steps without further purification. LC/MS, m/z=410 [M+H]$^+$ (Calc: 409).

A solution of Compound 21 (409 mg, 1 mmol) in DCE (3 mL) was added dropwise to 2-methyl-1-propanol (0.11 mL, 1.2 mmol) and rhodium(II) acetate dimer (8 mg, 0.02 mmol) in DCE (2 mL) at 80° C. The solution was stirred at 80° C. for 45 min, concentrated, and purified by MPLC (SiO$_2$, 0-50% acetone/hexanes) to give 380 mg of Compound 22 as a clear oil. LC/MS, m/z=456 [M+H]$^+$ (Calc: 455).

To a solution of Compound 22 (380 mg, 0.83 mmol) in MeOH (3 mL) was added 2.5 M aq. NaOH (1.2 mL, 3 mmol) and the solution was heated at 80° C. for 75 min. EtOAc was added, and the mixture washed with satd. aq. NaHCO$_3$, dried over Na$_2$SO$_4$ and concentrated to yield crude product. Purification by reverse-phase prep HPLC (C18, 0-60% 0.1% TFA in ACN/0.1% TFA in water) gave Compound 23 as its TFA salt. $^1$H NMR $\delta_H$ (400 MHz, DMSO-d$_6$): 8.92 (br. s., 1H), 7.05 (d, J=8.4 Hz, 1H), 6.75-6.85 (m, 2H), 6.53 (s, 1H), 4.22 (dd, J=12.1, 6.8 Hz, 1H), 3.86 (d, J=5.9 Hz, 1H), 3.66 (s, 3H), 3.22-3.38 (m, 3H), 3.07-3.16 (m, 1H), 2.90-3.02 (m, 3H), 2.89-2.76 (m, 2H), 2.18-2.39 (m, 3H), 1.56-1.70 (m, 1H), 1.52 (t, J=12.7 Hz, 1H), 1.30 (d, J=12.3 Hz, 1H), 0.93-1.05 (m, 1H), 0.73 (d, J=1.5 Hz, 3H), 0.72 (d, J=1.5 Hz, 3H), 0.59-0.67 (m, 1H), 0.50-0.58 (m, 1H), 0.38-0.46 (m, 1H), 0.31-0.38 (m, 1H). LC/MS, m/z=414 [M+H]$^+$ (Calc: 413).

In a similar manner, the following compounds were prepared:

(4bR,7S,8aS,9R)-7-(benzyloxy)-11-(cyclopropylmethyl)-8a-hydroxy-3-methoxy-8,8a,9,10-tetrahydro-5H-9,4b-(epiminoethano)phenanthren-6(7H)-one (TFA salt (Compound 24): $^1$H NMR $\delta_H$ (400 MHz, DMSO-d$_6$): 8.92 (br. s., 1H), 7.28-7.17 (m, 5H), 7.05 (d, J=8.6 Hz, 1H), 6.85 (d, J=2.6 Hz, 1H), 6.79 (dd, J=8.4, 2.4 Hz, 1H), 6.52 (s, 1H), 4.59 (d, J=12.1 Hz, 1H), 4.39 (dd, J=12.0, 6.9 Hz, 1H), 4.33 (d, J=12.1 Hz, 1H), 3.87 (d, J=5.9 Hz, 1H), 3.67 (s, 3H), 3.33-3.23 (m, 2H), 3.11 (dd, J=20.5, 7.3 Hz, 1H), 3.03-2.88 (m, 3H), 2.86-2.77 (m, 1H), 2.40-2.20 (m, 3H), 1.59 (t, J=12.7 Hz, 1H), 1.32 (d, J=12.5 Hz, 1H), 1.05-0.94 (m, 1H), 0.67-0.58 (m, 1H), 0.58-0.50 (m, 1H), 0.45-0.38 (m, 1H), 0.38-0.30 (m, 1H). LC/MS, m/z=448 [M+H]$^+$ (Calc: 447); and (4bR,7S,8aS,9R)-11-(cyclopropylmethyl)-7,8a-dihydroxy-3-methoxy-8,8a,9,10-tetrahydro-5H-9,4b-(epiminoethano)phenanthren-6(7H)-one (TFA salt) (Compound 25) (which was produced as a byproduct during preparation of Compound 24): $^1$H NMR $\delta_H$ (400 MHz, DMSO-d$_6$): 8.95 (br. s., 1H), 7.18 (d, J=8.6 Hz, 0.4H), 7.15-7.10 (m, 1H), 6.95-6.88 (m, 1H), 6.85 (dd, J=8.5, 2.3 Hz, 0.6H), 6.50 (s, 0.6H), 6.33 (s, 0.4H), 4.42 (dd, J=11.9, 7.0 Hz, 0.6H), 3.93-3.85 (m, 1.6H), 3.78 (s, 1.6H), 3.73 (s, 2H), 3.41-3.26 (m, 3.6H), 3.18 (d, J=6.8 Hz, 1.6H), 3.05-2.94 (m, 2.5H), 2.92-2.81 (m, 1.2H), 2.74 (dd, J=13.3, 6.1 Hz, 0.5H), 2.46-2.17 (m, 3.2H), 2.11 (t, J=12.9 Hz, 0.4H), 1.58 (t, J=12.7 Hz, 0.6H), 1.44-1.33 (m, 1H), 1.13-0.98 (m, 1H), 0.74-0.55 (m, 2H), 0.54-0.36 (m, 2H). LC/MS, m/z=358 [M+H]$^+$ (Calc: 357).

Example 13

Synthesis of N-((4bR,7S,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)isobutyramide (TFA salt) (Compound 26) and N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)isobutyramide (TFA salt) (Compound 27)

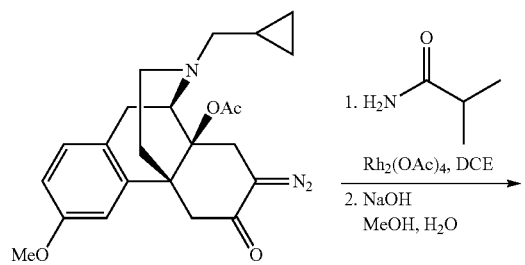

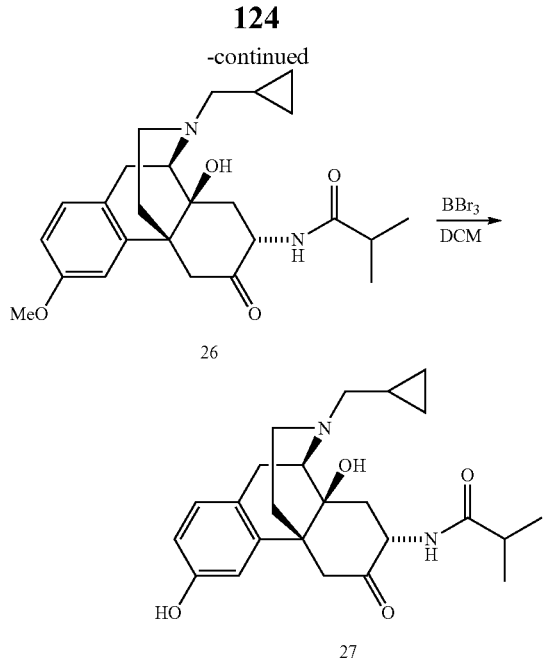

A solution of Compound 21 (500 mg, 1.2 mmol) in DCE (2 mL) was added dropwise to isobutyramide (177 mg, 1.34 mmol) and rhodium(II) acetate dimer (11 mg, 0.02 mmol) in DCE (2 mL) at 80° C. The solution was stirred at 80° C. for 90 min. then concentrated. MeOH (2 mL) was added followed by 2.5 M aq. NaOH (1.5 mL, 3.7 mmol) and the resulting solution stirred at RT for 72 h. DCM was added followed by satd. aq. NaHCO$_3$ and the mixture was passed through a phase separation column (Biotage Isolute 120-1906-D). Concentration followed by purification by MPLC (SiO$_2$, 0-60% acetone/hexanes) and reverse-phase prep HPLC (C18, 0-60% 0.1% TFA in ACN/0.1% TFA in water) gave Compound 26 as its TFA salt. $^1$H NMR $\delta_H$ (400 MHz, DMSO-d$_6$): 8.96 (br. s., 1H), 7.73 (d, J=8.6 Hz, 1H), 7.06 (d, J=8.6 Hz, 1H), 6.84 (d, J=2.4 Hz, 1H), 6.77 (dd, J=8.4, 2.4 Hz, 1H), 6.56 (s, 1H), 4.90-4.81 (m, 1H), 3.89 (d, J=5.9 Hz, 1H), 3.66 (s, 3H), 3.35-3.23 (m, 2H), 3.06 (dd, J=19.7, 6.3 Hz, 1H), 2.99 (d, J=2.2 Hz, 2H), 2.94 (d, J=8.1 Hz, 1H), 2.85-2.77 (m, 1H), 2.39-2.22 (m, 3H), 2.10 (dd, J=13.3, 6.5 Hz, 1H), 1.64 (t, J=13.0 Hz, 1H), 1.31 (d, J=10.3 Hz, 1H), 1.03-0.95 (m, 1H), 0.89 (d, J=6.8 Hz, 3H), 0.85 (d, J=6.8 Hz, 3H), 0.66-0.58 (m, 1H), 0.58-0.50 (m, 1H), 0.45-0.30 (m, 2H). LC/MS, m/z=427 [M+H]$^+$ (Calc: 426).

A 1 M solution of BBr$_3$ in DCM (2.9 mL, 2.9 mmol) was added slowly to Compound 26 (308 mg, 0.72 mmol) in DCM (2 mL). The solution was stirred at RT for 90 min. then slowly quenched with 1.6 mL of 7 M NH$_3$ in MeOH (11.5 mmol). The resulting salts were filtered off and the filtrate purified by MPLC (SiO$_2$, 0-20% (10% NH$_4$OH/MeOH)/DCM) followed by reverse-phase prep HPLC (C18, 0-60% 0.1% TFA in ACN/0.1% TFA in water) to give Compound 27 as its TFA salt. $^1$H NMR $\delta_H$ (400 MHz, DMSO-d$_6$): 9.40 (br. s., 1H), 8.99 (br. s., 1H), 7.82 (d, J=8.6 Hz, 1H), 7.00 (d, J=8.4 Hz, 1H), 6.75 (d, J=2.2 Hz, 1H), 6.65 (dd, J=8.3, 2.3 Hz, 1H), 6.59 (s, 1H), 4.96-4.87 (m, 1H), 3.94 (d, J=5.9 Hz, 1H), 3.41-3.26 (m, 2H), 3.13-2.96 (m, 3H), 2.94-2.82 (m, 2H), 2.47-2.29 (m, 3H), 2.16 (dd, J=13.2, 6.4 Hz, 1H), 1.75 (t, J=13.0 Hz, 1H), 1.34 (d, J=11.4 Hz, 1H), 1.10-1.01 (m, 1H), 0.97 (d, J=6.8 Hz, 3H), 0.93 (d, J=6.8 Hz, 3H), 0.72-0.65 (m, 1H), 0.65-0.56 (m, 1H), 0.56-0.44 (m, 1H), 0.44-0.33 (m, 1H). LC/MS, m/z=413 [M+H]$^+$ (Calc: 412).

In a similar manner, the following compounds were prepared:

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamide (Compound 28): ¹H NMR δ$_H$ (400 MHz, DMSO-d$_6$): 9.33 (br. s., 1H), 8.91 (br. s., 1H), 7.87 (d, J=8.4 Hz, 1H), 6.93 (d, J=8.4 Hz, 1H), 6.68 (d, J=2.4 Hz, 1H), 6.57 (dd, J=8.3, 2.3 Hz, 1H), 6.53 (s, 1H), 4.83 (dt, J=12.8, 7.5 Hz, 1H), 3.86 (d, J=5.9 Hz, 1H), 3.33-3.19 (m, 2H), 3.06-2.96 (m, 2H), 2.92 (d, J=10.1 Hz, 1H), 2.86-2.73 (m, 2H), 2.38-2.22 (m, 2H), 2.11 (dd, J=13.2, 6.6 Hz, 1H), 1.70 (s, 3H), 1.63 (t, J=13.0 Hz, 1H), 1.27 (d, J=11.9 Hz, 1H), 0.98 (d, J=4.8 Hz, 1H), 0.66-0.58 (m, 1H), 0.58-0.48 (m, 1H), 0.48-0.26 (m, 2H). LC/MS, m/z=385 [M+H]⁺ (Calc: 384);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)propionamide (Compound 29): ¹H NMR δ$_H$ (400 MHz, DMSO-d$_6$): 9.40 (br. s., 1H), 8.99 (br. s., 1H), 7.85 (d, J=8.4 Hz, 1H), 7.00 (d, J=8.4 Hz, 1H), 6.75 (d, J=2.2 Hz, 1H), 6.65 (dd, J=8.4, 2.2 Hz, 1H), 6.60 (s, 1H), 4.96-4.87 (m, 1H), 3.93 (d, J=5.9 Hz, 1H), 3.39-3.28 (m, 2H), 3.14-2.96 (m, 3H), 2.92-2.82 (m, 2H), 2.47-2.31 (m, 2H), 2.18 (dd, J=13.3, 6.5 Hz, 1H), 2.11-1.98 (m, 2H), 1.72 (t, J=13.1 Hz, 1H), 1.34 (d, J=11.7 Hz, 1H), 1.12-1.01 (m, 1H), 0.95 (t, J=7.6 Hz, 3H), 0.72-0.57 (m, 2H), 0.52-0.36 (m, 2H). LC/MS, m/z=399 [M+H]⁺ (Calc: 398);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-4-methylpentanamide (Compound 30): ¹H NMR δ$_H$ (400 MHz, DMSO-d$_6$): 9.39 (s, 1H), 8.98 (br. s., 1H), 7.88 (d, J=8.6 Hz, 1H), 7.00 (d, J=8.4 Hz, 1H), 6.75 (d, J=2.2 Hz, 1H), 6.65 (dd, J=8.3, 2.3 Hz, 1H), 6.59 (s, 1H), 4.97-4.87 (m, 1H), 3.93 (d, J=5.7 Hz, 1H), 3.40-3.28 (m, 2H), 3.13-2.96 (m, 3H), 2.91-2.82 (m, 2H), 2.46-2.31 (m, 2H), 2.16 (dd, J=13.0, 6.4 Hz, 1H), 2.03 (t, J=7.7 Hz, 2H), 1.72 (t, J=13.0 Hz, 1H), 1.46 (dquin, J=13.2, 6.6 Hz, 1H), 1.38-1.30 (m, 3H), 1.10-1.02 (m, 1H), 0.83 (d, J=1.8 Hz, 3H), 0.81 (d, J=2.0 Hz, 3H), 0.72-0.57 (m, 2H), 0.51-0.44 (m, 1H), 0.44-0.38 (m, 1H). LC/MS, m/z=441 [M+H]⁺ (Calc: 440);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-5-methylhexanamide (Compound 31): ¹H NMR δ$_H$ (400 MHz, DMSO-d$_6$): 9.40 (s, 1H), 8.98 (br. s., 1H), 7.87 (d, J=8.6 Hz, 1H), 7.00 (d, J=8.4 Hz, 1H), 6.75 (d, J=2.2 Hz, 1H), 6.65 (dd, J=8.3, 2.3 Hz, 1H), 6.59 (s, 1H), 4.97-4.88 (m, 1H), 3.93 (d, J=5.7 Hz, 1H), 3.39-3.28 (m, 2H), 3.12-2.96 (m, 3H), 2.92-2.81 (m, 2H), 2.45-2.30 (m, 2H), 2.16 (dd, J=13.2, 6.4 Hz, 1H), 2.01 (t, J=7.0 Hz, 2H), 1.73 (t, J=13.0 Hz, 1H), 1.53-1.39 (m, 3H), 1.34 (d, J=11.9 Hz, 1H), 1.15-1.00 (m, 3H), 0.83 (d, J=0.9 Hz, 3H), 0.82 (d, J=1.1 Hz, 3H), 0.72-0.57 (m, 2H), 0.52-0.36 (m, 2H). LC/MS, m/z=455 [M+H]⁺ (Calc: 454);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)pivalamide (Compound 32): ¹H NMR δ$_H$ (400 MHz, DMSO-d$_6$): 9.31 (s, 1H), 8.91 (br. s., 1H), 7.34 (d, J=8.6 Hz, 1H), 6.94 (d, J=8.4 Hz, 1H), 6.68 (d, J=2.2 Hz, 1H), 6.58 (dd, J=8.1, 2.2 Hz, 1H), 6.47 (s, 1H), 4.96-4.84 (m, 1H), 3.85 (d, J=5.7 Hz, 1H), 3.32-3.20 (m, 2H), 3.05-2.89 (m, 3H), 2.88-2.75 (m, 2H), 2.40-2.23 (m, 2H), 2.05-1.98 (m, 1H), 1.89 (t, J=12.8 Hz, 1H), 1.25 (d, J=11.2 Hz, 1H), 1.04-0.93 (m, 10H), 0.66-0.58 (m, 1H), 0.57-0.50 (m, 1H), 0.45-0.29 (m, 2H). LC/MS, m/z:=427 [M+H]⁺ (Calc: 426);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-3-methylbutanamide (Compound 33): ¹H NMR δ$_H$ (400 MHz, DMSO-d$_6$): 9.33 (br. s., 1H), 8.92 (br. s., 1H), 7.80 (d, J=8.6 Hz, 1H), 6.93 (d, J=8.4 Hz, 1H), 6.68 (d, J=2.2 Hz, 1H), 6.58 (dd, J=8.3, 2.3 Hz, 1H), 6.53 (s, 1H), 4.93-4.82 (m, 1H), 3.87 (d, J=5.9 Hz, 1H), 3.33-3.20 (m, 2H), 3.08-2.89 (m, 3H), 2.87-2.73 (m, 2H), 2.38-2.24 (m, 2H), 2.09 (dd, J=13.2, 6.4 Hz, 1H), 1.90-1.79 (m, 3H), 1.67 (t, J=13.0 Hz, 1H), 1.27 (d, J=11.7 Hz, 1H), 1.05-0.93 (m, 1H), 0.79 (d, J=6.8 Hz, 3H), 0.75 (d, J=6.4 Hz, 3H), 0.65-0.50 (m, 2H), 0.44-0.30 (m, 2H). LC/MS, m/z=427 [M+H]⁺ (Calc: 426);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopropanecarboxamide (Compound 34): ¹H NMR δ$_H$ (400 MHz, DMSO-d$_6$): 9.34 (br. s., 1H), 8.91 (br. s., 1H), 8.11 (d, J=8.6 Hz, 1H), 6.93 (d, J=8.4 Hz, 1H), 6.69 (d, J=2.2 Hz, 1H), 6.58 (dd, J=8.3, 2.3 Hz, 1H), 6.52 (s, 1H), 4.93-4.84 (m, 1H), 3.86 (d, J=5.9 Hz, 1H), 3.34-3.17 (m, 2H), 3.10-2.89 (m, 3H), 2.86-2.74 (m, 2H), 2.38-2.23 (m, 2H), 2.12 (dd, J=13.2, 6.4 Hz, 1H), 1.66 (t, J=12.9 Hz, 1H), 1.48 (quin, J=6.3 Hz, 1H), 1.27 (d, J=11.9 Hz, 1H), 1.04-0.93 (m, 1H), 0.64-0.49 (m, 6H), 0.44-0.28 (m, 2H). LC/MS, m/z=411 [M+H]⁺ (Calc: 410);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopentanecarboxamide (Compound 35): ¹H NMR δ$_H$ (400 MHz, DMSO-d$_6$): 9.32 (br. s., 1H), 8.91 (br. s., 1H), 7.76 (d, J=8.6 Hz, 1H), 6.93 (d, J=8.4 Hz, 1H), 6.68 (d, J=2.0 Hz, 1H), 6.58 (dd, J=8.3, 2.3 Hz, 1H), 6.51 (s, 1H), 4.92-4.81 (m, 1H), 3.86 (d, J=5.7 Hz, 1H), 3.33-3.19 (m, 2H), 3.06-2.88 (m, 3H), 2.85-2.74 (m, 2H), 2.51-2.45 (m, 1H), 2.38-2.24 (m, 2H), 2.09 (dd, J=13.3, 6.5 Hz, 1H), 1.74-1.33 (m, 9H), 1.26 (d, J=11.7 Hz, 1H), 1.04-0.93 (m, 1H), 0.66-0.58 (m, 1H), 0.58-0.49 (m, 1H), 0.45-0.29 (m, 2H). LC/MS, m/z=439 [M+H]⁺ (Calc: 438);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzamide (Compound 36): ¹H NMR δ$_H$ (400 MHz, DMSO-d$_6$): 9.33 (s, 1H), 8.95 (br. s., 1H), 8.37 (d, J=8.4 Hz, 1H), 7.76 (d, J=7.3 Hz, 2H), 7.48-7.41 (m, 1H), 7.40-7.32 (m, 2H), 6.96 (d, J=8.4 Hz, 1H), 6.70 (d, J=2.2 Hz, 1H), 6.63-6.56 (m, 2H), 5.16-5.05 (m, 1H), 3.89 (d, J=5.9 Hz, 1H), 3.35-3.23 (m, 2H), 3.09-2.76 (m, 5H), 2.40-2.25 (m, 2H), 2.14 (dd, J=13.6, 6.4 Hz, 1H), 2.03 (t, J=13.6 Hz, 1H), 1.29 (d, J=11.0 Hz, 1H), 1.07-0.95 (m, 1H), 0.66-0.58 (m, 1H), 0.58-0.51 (m, 1H), 0.46-0.38 (m, 1H), 0.38-0.30 (m, 1H). LC/MS, m/z=447 [M+H]⁺ (Calc: 446);

(S)—N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-methylbutanamide (Compound 37): ¹H NMR δ$_H$ (400 MHz, DMSO-d$_6$): 9.33 (br. s., 1H), 8.92 (br. s., 1H), 7.77 (d, J=8.6 Hz, 1H), 6.94 (d, J=8.4 Hz, 1H), 6.68 (d, J=2.0 Hz, 1H), 6.58 (dd, J=8.4, 2.2 Hz, 1H), 6.52 (s, 1H), 4.88 (dd, J=13.0, 7.5 Hz, 1H), 3.86 (d, J=5.9 Hz, 2H), 3.33-3.21 (m, 2H), 3.07-2.89 (m, 3H), 2.87-2.75 (m, 2H), 2.40-2.23 (m, 3H), 2.14-2.01 (m, 2H), 1.70 (t, J=0.7 Hz, 1H), 1.45-1.32 (m, 1H), 1.27 (d, J=11.4 Hz, 1H), 1.23-1.08 (m, 1H), 1.03-0.94 (m, 1H), 0.84 (d, J=6.8 Hz, 3H), 0.75 (t, J=7.5 Hz, 3H), 0.65-0.57 (m, 1H), 0.57-0.49 (m, 1H), 0.45-0.29 (m, 2H). LC/MS, m/z=427 [M+H]⁺ (Calc: 426);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclohexanecarboxamide (Compound 38): ¹H NMR δ$_H$ (400 MHz, DMSO-d$_6$): 9.32 (br. s., 1H), 8.91 (br. s., 1H), 7.68 (d, J=8.6 Hz, 1H), 6.93 (d, J=8.4 Hz, 1H), 6.67 (d, J=2.2 Hz, 1H), 6.58 (dd, J=8.3, 2.3 Hz, 1H), 6.50 (s, 1H), 4.89-4.78 (m, 1H), 3.85 (d, J=5.9 Hz, 1H), 3.33-3.20 (m, 2H), 3.05-2.89 (m, 3H), 2.83-2.74 (m, 2H), 2.38-2.23 (m, 2H), 2.11-1.96 (m, 2H), 1.68 (t, J=13.0 Hz, 2H), 1.63-1.45 (m, 5H), 1.29-0.93 (m, 7H), 0.65-0.58 (m, 1H), 0.58-0.49 (m, 1H), 0.45-0.29 (m, 2H). LC/MS, m/z=453 [M+H]$^+$ (Calc: 452);

N-((4bR,7S,8aS,9R)-3,8a-dihydroxy-11-methyl-6-oxo-6,7,8,8a,9,10-hexahydro-5H-9,4b-(epiminoethano)phenanthren-7-yl)acetamide (TFA salt) (Compound 97): $^1$H NMR (DMSO-d$_6$) δ: 9.34 (s, 1H), 9.23 (br. s., 1H), 7.87 (d, J=8.6 Hz, 1H), 6.95 (d, J=8.4 Hz, 1H), 6.67 (d, J=2.0 Hz, 1H), 6.57 (dd, J=8.1, 2.2 Hz, 1H), 6.44 (s, 1H), 4.88-4.74 (m, 1H), 3.51 (d, J=5.7 Hz, 1H), 3.26 (d, J=19.8 Hz, 1H), 3.03-2.90 (m, 3H), 2.80 (d, J=13.9 Hz, 1H), 2.76 (d, J 4.6 Hz, 3H), 2.43-2.31 (m, 1H), 2.30-2.19 (m, 1H), 2.04 (dd, J=13.2, 6.4 Hz, 1H), 1.70 (s, 3H), 1.62 (t, J=13.0 Hz, 1H), 1.26 (d, J=12.5 Hz, 1H). LC/MS, m/z=345.2 [M+H]$^+$ (Calc: 344.4);

N-((4bR,7S,8aS,9R)-3,8a-dihydroxy-11-methyl-6-oxo-6,7,8,8a,9,10-hexahydro-5H-9,4b-(epiminoethano)phenanthren-7-yl)propionamide (TFA salt) (Compound 98): $^1$H NMR (DMSO-d$_6$) δ: 9.33 (s, 1H), 9.22 (br. s., 1H), 7.78 (d, J=8.6 Hz, 1H), 6.95 (d, J=8.4 Hz, 1H), 6.67 (d, J=2.0 Hz, 1H), 6.57 (dd, J=8.3, 2.1 Hz, 1H), 6.43 (s, 1H), 4.88-4.76 (m, 1H), 3.51 (d, J=6.2 Hz, 1H), 3.27-3.23 (m, 1H), 3.04-2.90 (m, 3H), 2.80 (d, J=13.9 Hz, 1H), 2.76 (d, J=4.8 Hz, 3H), 2.43-2.31 (m, 1H), 2.29-2.17 (m, 1H), 2.08-1.91 (m, 3H), 1.64 (t, J=13.1 Hz, 1H), 1.26 (d, J=13.2 Hz, 1H), 0.87 (t, J=7.6 Hz, 3H). LC/MS, m/z=359.2 [M+H]$^+$ (Calc: 358.43);

N-((4bR,7S,8aS,9R)-3,8a-dihydroxy-11-methyl-6-oxo-6,7,8,8a,9,10-hexahydro-5H-9,4b-(epiminoethano)phenanthren-7-yl)isobutyramide (TFA salt) (Compound 99): $^1$H NMR (DMSO-d$_6$) δ: 9.33 (s, 1H), 9.23 (br. s., 1H), 7.74 (d, J=8.6 Hz, 1H), 6.95 (d, J=8.4 Hz, 1H), 6.67 (d, J=2.2 Hz, 1H), 6.58 (dd, J=8.3, 2.1 Hz, 1H), 6.41 (s, 1H), 4.86-4.75 (m, 1H), 3.50 (d, J=5.7 Hz, 1H), 3.28-3.20 (m, 1H), 3.02-2.90 (m, 3H), 2.79 (d, J=14.1 Hz, 1H), 2.76 (d, J=4.6 Hz, 3H), 2.39-2.30 (m, 1H), 2.30-2.18 (m, 2H), 2.01 (dd, J=13.2, 6.4 Hz, 1H), 1.67 (t, J=13.1 Hz, 1H), 1.26 (d, J=13.0 Hz, 1H), 0.90 (d, J=6.8 Hz, 3H), 0.86 (d, J=6.8 Hz, 3H). LC/MS, m/z=373.4 [M+H]$^+$ (Calc: 372.46);

N-((4bR,7S,8aS,9R)-3,8a-dihydroxy-11-methyl-6-oxo-6,7,8,8a,9,10-hexahydro-5H-9,4b-(epiminoethano)phenanthren-7-yl)pivalamide (TFA salt) (Compound 100): $^1$H NMR (DMSO-d$_6$) δ: 9.33 (s, 1H), 9.23 (br. s., 1H), 7.33 (d, J=8.6 Hz, 1H), 6.96 (d, J=8.4 Hz, 1H), 6.67 (d, J=2.2 Hz, 1H), 6.58 (dd, J=8.3, 2.1 Hz, 1H), 6.37 (s, 1H), 4.85 (dt, J=12.5, 5.7 Hz, 1H), 3.50 (d, J=5.3 Hz, 1H), 3.28-3.21 (m, 1H), 3.00-2.88 (m, 3H), 2.82-2.73 (m, 4H), 2.40-2.18 (m, 2H), 1.98-1.83 (m, 2H), 1.24 (d, J=12.5 Hz, 1H), 0.98 (s, 9H). LC/MS, m/z=387.2 [M+H]$^+$ (Calc: 386.48);

N-((4bR,7S,8aS,9R)-3,8a-dihydroxy-11-methyl-6-oxo-6,7,8,8a,9,10-hexahydro-5H-9,4b-(epiminoethano)phenanthren-7-yl)-4-methylpentanamide (TFA salt) (Compound 101): $^1$H NMR (DMSO-d$_6$) δ: 9.34 (s, 1H), 9.23 (br. s., 1H), 7.80 (d, J=8.6 Hz, 1H), 6.95 (d, J=8.4 Hz, 1H), 6.67 (d, J=2.2 Hz, 1H), 6.58 (dd, J=8.1, 2.2 Hz, 1H), 6.43 (s, 1H), 4.87-4.75 (m, 1H), 3.51 (d, J=5.5 Hz, 1H), 3.28-3.20 (m, 1H), 3.03-2.89 (m, 3H), 2.79 (d, J=13.9 Hz, 1H), 2.76 (d, J=4.8 Hz, 3H), 2.40-2.30 (m, 1H), 2.29-2.19 (m, 1H), 2.04-1.91 (m, 3H), 1.65 (t, J=13.1 Hz, 1H), 1.39 (dquin, J=13.3, 6.7 Hz, 1H), 1.31-1.21 (m, 3H), 0.76 (d, J=1.5 Hz, 3H), 0.74 (d, J=1.5 Hz, 3H). LC/MS, m/z=401.4 [M+H]$^+$ (Calc: 400.51);

N-((4bR,7S,8aS,9R)-3,8a-dihydroxy-11-methyl-6-oxo-6,7,8,8a,9,10-hexahydro-5H-9,4b-(epiminoethano)phenanthren-7-yl)-5-methylhexanamide (TFA salt) (Compound 102): $^1$H NMR (DMSO-d$_6$) δ: 9.34 (s, 1H), 9.23 (br. s., 1H), 7.79 (d, J=8.6 Hz, 1H), 6.95 (d, J=8.4 Hz, 1H), 6.67 (d, J=2.0 Hz, 1H), 6.57 (dd, J=8.3, 2.1 Hz, 1H), 6.43 (s, 1H), 4.88-4.77 (m, 1H), 3.51 (d, J=5.9 Hz, 1H), 3.28-3.20 (m, 1H), 3.02-2.91 (m, 3H), 2.79 (d, J=13.9 Hz, 1H), 2.76 (d, J=4.8 Hz, 3H), 2.41-2.31 (m, 1H), 2.30-2.19 (m, 1H), 2.01 (dd, J=13.2, 6.4 Hz, 1H), 1.96-1.90 (m, 2H), 1.65 (t, J=13.0 Hz, 1H), 1.46-1.31 (m, 3H), 1.26 (d, J=13.0 Hz, 1H), 1.08-0.95 (m, 2H), 0.76 (d, J=0.9 Hz, 3H), 0.74 (d, J=0.9 Hz, 3H). LC/MS, m/z=415.4 [M+H]$^+$ (Calc: 414.54);

N-((4bR,7S,8aS,9R)-3,8a-dihydroxy-11-methyl-6-oxo-6,7,8,8a,9,10-hexahydro-5H-9,4b-(epiminoethano)phenanthren-7-yl)cyclohexanecarboxamide (TFA salt) (Compound 103): $^1$H NMR (DMSO-d$_6$) δ: 9.34 (s, 1H), 9.24 (br. s., 1H), 6.95 (d, J=8.4 Hz, 1H), 6.66 (d, J=2.2 Hz, 1H), 6.58 (dd, J=8.4, 2.2 Hz, 1H), 6.41 (s, 1H), 4.85-4.75 (m, 1H), 3.51 (d, J=5.7 Hz, 1H), 3.26 (d, J=18.5 Hz, 1H), 3.00-2.89 (m, 3H), 2.81-2.73 (m, 4H), 2.41-2.31 (m, 1H), 2.31-2.19 (m, 1H), 2.05-1.93 (m, 2H), 1.72-1.63 (m, 1H), 1.63-1.46 (m, 5H), 1.28-1.16 (m, 3H), 1.16-1.00 (m, 3H). LC/MS, m/z=413.4 [M+H]$^+$ (Calc: 412.52);

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)piperidine-4-carboxamide (TFA salt) (Compound 109): $^1$H NMR (DMSO-d$_6$) δ: 9.40 (s, 1H), 8.99 (br. s., 1H), 8.55-8.45 (m, 1H), 8.29-8.15 (m, 1H), 8.01 (d, J=8.6 Hz, 1H), 7.00 (d, J=8.4 Hz, 1H), 6.74 (d, J=2.2 Hz, 1H), 6.65 (dd, J=8.4, 2.2 Hz, 1H), 6.59 (s, 1H), 4.95-4.85 (m, 1H), 3.93 (d, J=5.9 Hz, 1H), 3.40-3.19 (m, 3H), 3.12-2.97 (m, 3H), 2.93-2.73 (m, 5H), 2.45-2.29 (m, 3H), 2.16 (dd, J=13.2, 6.6 Hz, 1H), 1.87-1.59 (m, 6H), 1.34 (d, J=11.4 Hz, 1H), 1.12-1.01 (m, 1H), 0.74-0.64 (m, 1H), 0.64-0.56 (m, 1H), 0.53-0.45 (m, 1H), 0.45-0.36 (m, 1H). LC/MS, m/z=454 [M+H]$^+$ (Calc: 453); and N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-(dimethylamino)acetamide (TFA salt) (Compound 110): $^1$H NMR (DMSO-d$_6$) δ: 9.72 (br. s., 1H), 9.44 (br. s., 1H), 9.03 (br. s., 1H), 8.68 (d, J=8.1 Hz, 1H), 7.01 (d, J=8.4 Hz, 1H), 6.75 (d, J=2.2 Hz, 2H), 6.66 (dd, J=8.4, 2.2 Hz, 1H), 4.99-4.85 (m, 1H), 3.97 (d, J=5.9 Hz, 1H), 3.86 (s, 2H), 3.41-3.29 (m, 2H), 3.17-2.84 (m, 5H), 2.77 (s, 6H), 2.46-2.32 (m, 2H), 2.26 (dd, J=13.1, 6.5 Hz, 1H), 1.75 (t, J=13.0 Hz, 1H), 1.36 (d, J=12.1 Hz, 1H), 1.11-1.00 (m, 1H), 0.74-0.65 (m, 1H), 0.65-0.57 (m, 1H), 0.54-0.35 (m, 2H). LC/MS, m/z=428 [M+H]$^+$ (Calc: 427).

Example 14

Synthesis of N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)ethanesulfonamide TFA salt (Compound 42)

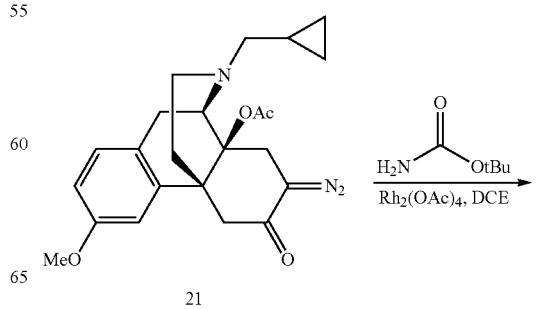

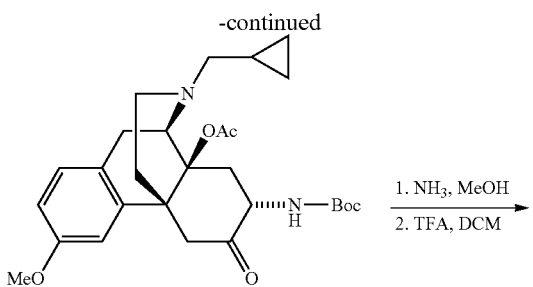

39

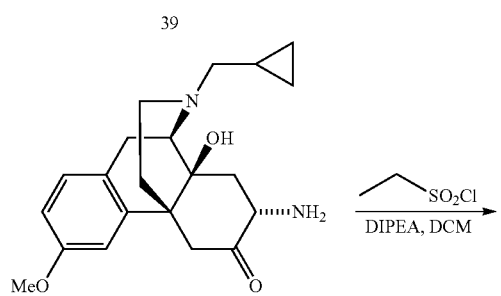

40

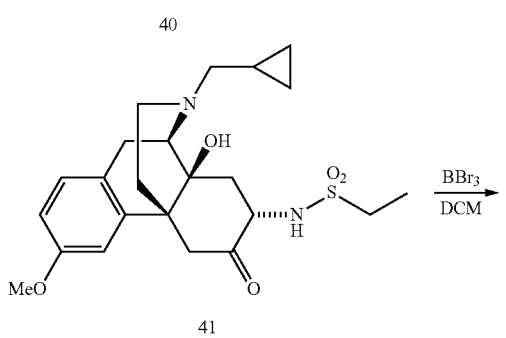

41

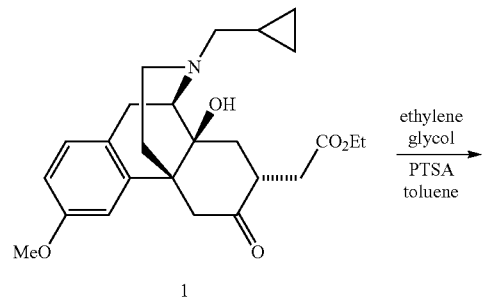

42

A solution of Compound 21 (4.47 g, 10.8 mmol) in DCE (24 mL) was added dropwise to O-t-butyl carbamate (1.52 g, 13 mmol) and rhodium(II) acetate dimer (95 mg, 0.216 mmol) in DCE (24 mL) at 80° C. The solution was stirred at 80° C. for 15 min, then concentrated. Purification by MPLC (SiO$_2$, 0-40% acetone/hexanes) gave 3.75 g of Compound 39 as a white foam. LC/MS, m/z=499 [M+H]$^+$ (Calc: 498).

MeOH (50 mL) was added to Compound 39 (3.75 g, 7.5 mmol) followed by 7 M NH$_3$ in MeOH (0.77 mL, 5.4 mmol). The solution was heated at reflux for 19 h then concentrated. DCM (45 mL) was added followed by TFA (10 mL) and the solution was stirred at RT for 40 min then concentrated. The resulting material was subjected to the following sequence three times: the material was taken up in 25 mL DCM, 2 M HCl in Et$_2$O (25 mL, 50 mmol) added and the solution briefly swirled then concentrated. Final drying under vacuum gave 4.60 g of Compound 40 (2 HCl salt) as a brown foam. LC/MS, m/z=357 [M+H]$^+$ (Calc: 356).

DIPEA (0.49 mL, 2.8 mmol) was added slowly to Compound 40 (2 HCl salt) (400 mg, 0.9 mmol) and ethanesulfonyl chloride (0.11 mL, 1.1 mmol) in DCM (2 mL) and the resulting solution was stirred at RT for 2 h. DCM was added followed by 10% aq. NH$_4$OH and the mixture was passed through a phase separation column (Biotage Isolute 120-1906-D). Concentration and purification by MPLC (SiO$_2$, 0-10% MeOH/DCM) gave 223 mg of Compound 41. LC/MS, m/z=449 [M+H]$^+$ (Calc: 448).

A 1 M solution of BBr$_3$ in DCM (2.0 mL, 2.0 mmol) was added slowly to Compound 41 (223 mg, 0.50 mmol) in DCM (2 mL). The solution was stirred at RT for 75 min then slowly quenched with 1.1 mL of 7 M NH$_3$ in MeOH (8 mmol). The resulting salts were filtered off and the filtrate purified by MPLC (SiO$_2$, 0-15% (10% NH$_4$OH/MeOH)/DCM) followed by reverse-phase prep HPLC (C18, 0-40% 0.1% TFA in ACN/0.1% TFA in water) to give Compound 42 as its TFA salt. $^1$H NMR δ$_H$ (400 MHz, DMSO-d$_6$): 9.40 (br. s., 1H), 8.97 (br. s., 1H), 7.33 (d, J=9.0 Hz, 1H), 7.00 (d, J=8.4 Hz, 1H), 6.74 (d, J=2.2 Hz, 1H), 6.64 (dd, J=8.4, 2.4 Hz, 1H), 4.43 (ddd, J=12.7, 8.9, 6.6 Hz, 1H), 3.94 (d, J=5.9 Hz, 1H), 3.42-3.35 (m, 1H), 3.31 (d, J=19.6 Hz, 1H), 3.13-3.04 (m, 2H), 3.03-2.80 (m, 6H), 2.56 (t, J=5.1 Hz, 1H), 2.47-2.28 (m, 2H), 2.24 (dd, J=13.3, 6.3 Hz, 1H), 1.78 (t, J=13.0 Hz, 1H), 1.33 (d, J=12.5 Hz, 1H), 1.18 (t, J=7.4 Hz, 3H), 1.12-1.00 (m, 1H), 0.74-0.65 (m, 1H), 0.65-0.56 (m, 1H), 0.53-0.46 (m, 1H), 0.45-0.36 (m, 1H). LC/MS, m/z=435 [M+H]$^+$ (Calc: 434).

In a similar manner, the following compounds were prepared:

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzenesulfonamide (TFA salt) (Compound 43) was prepared: $^1$H NMR δ$_H$ (400 MHz, DMSO-d$_6$): 9.37 (br. s., 1H), 8.93 (br. s., 1H), 7.96 (d, J=8.6 Hz, 1H), 7.78-7.71 (m, 2H), 7.63-7.50 (m, 3H), 6.98 (d, J=8.4 Hz, 1H), 6.70-6.60 (m, 3H), 4.49-4.39 (m, 1H), 3.91 (d, J=5.9 Hz, 1H), 3.39-3.25 (m, 2H), 3.10-2.93 (m, 3H), 2.89-2.78 (m, 2H), 2.45-2.25 (m, 2H), 2.20 (dd, J=13.3, 6.5 Hz, 1H), 1.75 (t, J=12.9 Hz, 1H), 1.30 (d, J=12.5 Hz, 1H), 1.10-1.00 (m, 1H), 0.72-0.64 (m, 1H), 0.64-0.56 (m, 1H), 0.51-0.43 (m, 1H), 0.43-0.34 (m, 1H). LC/MS, m/z=483 [M+H]$^+$ (Calc: 482); and N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)methanesulfonamide (TFA salt) (Compound 108): $^1$H NMR (DMSO-d$_6$) δ: 9.39 (s, 1H), 8.97 (br. s., 1H), 7.37 (d, J=9.0 Hz, 1H), 7.00 (d, J=8.4 Hz, 1H), 6.74 (d, J=2.2 Hz, 1H), 6.64 (dd, J=8.3, 2.3 Hz, 1H), 6.62 (s, 1H), 4.52-4.40 (m, 1H), 3.94 (d, J=5.9 Hz, 1H), 3.31 (d, J=19.8 Hz, 1H), 3.15-2.90 (m, 4H), 2.88 (s, 3H), 2.85-2.80 (m, 1H), 2.45-2.31 (m, 2H), 2.26 (dd, J=13.4, 6.6 Hz, 1H), 1.75 (t, J=13.0 Hz, 1H), 1.34 (d, J=12.1 Hz, 1H), 1.12-1.01 (m, 1H), 0.73-0.64 (m, 1H), 0.64-0.56 (m, 1H), 0.56-0.44 (m, 1H), 0.44-0.36 (m, 1H). LC/MS, m/z=421 [M+H]$^+$ (Calc: 420).

Example 15

Synthesis of (4bR,7S,8aS,9R)-11-(cyclopropylmethyl)-8a-hydroxy-7-(2-hydroxyethyl)-3-methoxy-8,8a,9,10-tetrahydro-5H-9,4b-(epiminoethano)phenanthren-6(7H)-one (Compound 46)

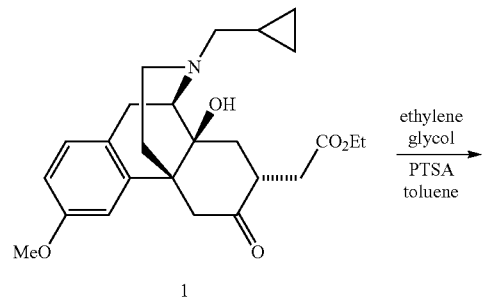

1

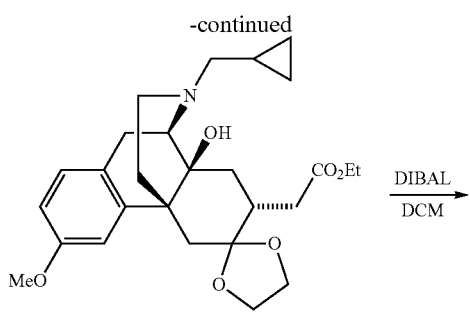

44

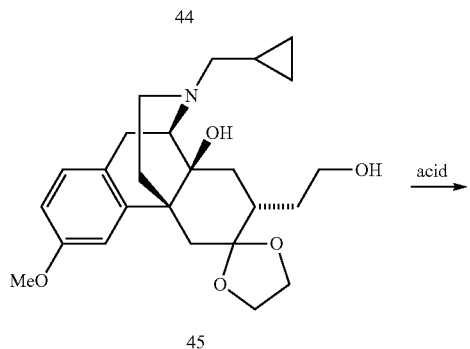

45

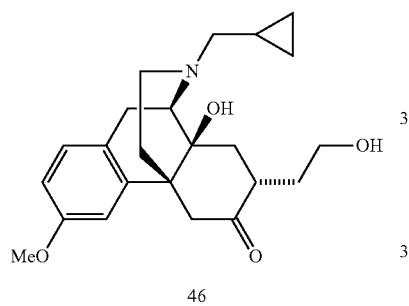

46

To a solution of Compound 1 (1.3 g, 3.04 mmol) in 30 mL of toluene was added PTSA.H₂O (0.636 g, 3.34 mmol) followed by ethylene glycol (0.5 mL, 9.12 mmol) dropwise via syringe. The resulting mixture was heated at reflux with a Dean-Stark trap. After 24 h, LC/MS analysis revealed a 4:1 mixture of product to starting material. An additional 0.5 mL of ethylene glycol (0.912 mmol) was added to the reaction and the mixture was heated at reflux for 3 days. The mixture was cooled to 0° C. then quenched with solid NaHCO₃. Satd. aq. NaHCO₃ was added and the organic layer was separated. The aqueous layer was extracted with Et₂O (3x) and the combined organics were washed with brine. The organic layer was dried over Na₂SO₄, filtered, and concentrated to give crude Compound 44 as an oil that was used in the next step without further purification. LC/MS, m/z=472.4 [M+H]⁺ (Calc: 471.6).

To a −78° C. solution of Compound 44 (0.788 g, 1.67 mmol) in 17 mL of anhydrous DCM was added a 1.0 M solution of DIBAL in hexanes (8.4 mL, 8.4 mmol) dropwise via syringe. The reaction was allowed to warm slowly to −30° C. over 2 h. LC/MS showed that the reaction was complete. MeOH (0.35 mL) was added dropwise and the reaction mixture warmed to RT. The mixture was diluted with satd. aq. Rochelle's salt and DCM and stirred vigorously for 1 h. The layers were separated. The aqueous layer was extracted with DCM (2x). The combined organics were washed with brine, dried over Na₂SO₄, filtered, and concentrated. Crude Compound 45 (0.670 g, 93%) was used in the next step without further purification. LC/MS, m/z=430.2 [M+H]⁺ (Calc: 429.6).

To Compound 45 (0.137 g, 0.319 mmol) was added 1.6 mL of 1 N aq. HCl. The resulting solution was maintained at RT for 60 h. The reaction mixture was cooled to 0° C. and basified with conc. NH₄OH. The mixture was diluted with EtOAc, the layers were separated and the aqueous layer was extracted with EtOAc (2x). The combined organics were washed with brine, dried over Na₂SO₄, filtered, and concentrated. Purification by reverse-phase prep HPLC (C18, 0-60% 0.1% TFA in ACN/0.1% TFA in water) with subsequent neutralization with ammonium carbonate resin and lyophilization gave 31 mg (25%) of Compound 46 as a fluffy, white solid (as the TFA salt). ¹H NMR δ_H (400 MHz, CD₃OD): 7.00 (d, J=8.3 Hz, 1H), 6.83 (s, 1H), 6.71 (d, J=8.3 Hz, 1H), 3.78 (s, 3H), 3.67-3.53 (m, 2H), 3.41-3.18 (m, 1H), 3.14 (d, J=13.6 Hz, 1H), 3.08 (d, J=18.3 Hz, 2H), 2.87 (d, J=13.6 Hz, 2H), 2.74-2.60 (m, 1H), 2.59-2.39 (m, 2H), 2.34-2.21 (m, 1H), 2.20-2.09 (m, 1H), 2.07-1.83 (m, 2H), 1.60 (t, J=12.9 Hz, 1H), 1.32-1.11 (m, 2H), 1.03-0.83 (m, 1H), 0.71-0.50 (m, 2H), 0.34-0.10 (m, 2H). LC/MS, m/z=386.3 [M+H]⁺ (Calc: 385.50).

Example 16

Synthesis of (4bR,7S,8aS,9R)-7-(2-(benzyloxy)ethyl)-11-(cyclopropylmethyl)-8a-hydroxy-3-methoxy-8,8a,9,10-tetrahydro-5H-9,4b-(epiminoethano)phenanthren-6(7H)-one (Compound 48)

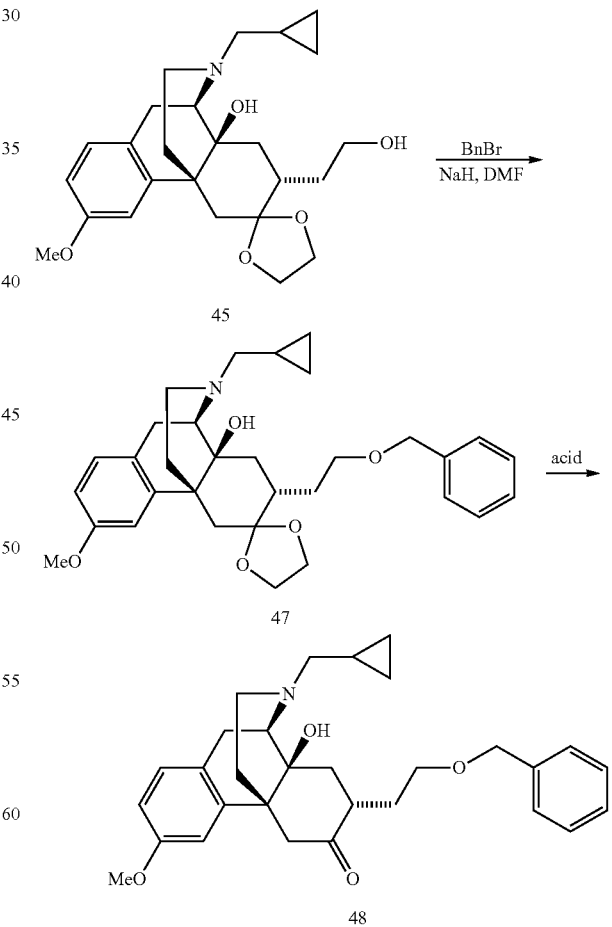

To a suspension of NaH (0.028 g, 1.19 mmol) in 3 mL of anhydrous DMF cooled to 0° C. was added Compound 45

(0.170 g, 0.396 mmol) in 1 mL of anhydrous DMF dropwise via syringe. The suspension was maintained for 0.5 h whereupon benzyl bromide (0.052 mL, 0.435 mmol) was added dropwise. The reaction was maintained for 24 h at RT. LC/MS analysis showed that the reaction was not complete. An additional 10 mg (~1 equiv) of NaH was added and the reaction was maintained for another 24 h. LC/MS now showed that the reaction was mostly complete. The reaction was slowly quenched with $H_2O$ then diluted with EtOAc. The layers were separated and the aqueous layer was further extracted with EtOAc (2×). The combined organics were washed with brine, dried over $Na_2SO_4$, filtered, and concentrated. Crude Compound 47 (176 mg) was used in the next step without further purification. LC/MS, m/z=520.4 $[M+H]^+$ (Calc: 519.7).

To Compound 47 (0.176 g, 0.339 mmol) in 1.0 mL of THF was added 1.7 mL of 1 N aq. HCl. The resulting light orange solution was maintained for 60 h at RT. LC/MS analysis showed the reaction was complete. The reaction mixture was cooled to 0° C. and basified with conc. $NH_4OH$. The mixture was diluted with EtOAc, the layers separated and the aqueous layer was extracted with EtOAc (2×). The combined organics were washed with brine, dried over $Na_2SO_4$, filtered, and concentrated. Purification by reverse-phase prep HPLC (C18, 20-90% 0.1% TFA in ACN/0.1% TFA in water) with subsequent neutralization with ammonium carbonate resin and lyophilization gave 31 mg (19%) of the Compound 48 as a fluffy, white solid. $^1$H NMR $\delta_H$ (400 MHz, $CD_3OD$): 7.40-7.18 (m, 5H), 7.02 (d, J=8.4 Hz, 1H), 6.80 (s, 1H), 6.72 (d, J=8.1 Hz, 1H), 4.41 (s, 2H), 3.75 (s, 3H), 3.41 (t, J=6.4 Hz, 2H), 3.27-2.95 (m, 4H), 2.87-2.58 (m, 3H), 2.57-2.34 (m, 2H), 2.34-2.01 (m, 2H), 2.01-1.86 (m, 2H), 1.57 (t, J=13.1 Hz, 1H), 1.31-1.09 (m, 2H), 1.04-0.83 (m, 1H), 0.71-0.47 (m, 2H), 0.33-0.09 (m, 214). LC/MS, m/z=476.3 $[M+H]^+$ (Calc: 475.6).

In a similar manner, the following compounds were prepared:

(4bR,7S,8aS,9R)-11-(cyclopropylmethyl)-8a-hydroxy-3-methoxy-7-(2-methoxyethyl)-8,8a,9,10-tetrahydro-5H-9,4b-(epiminoethano)phenanthren-6(7H)-one (Compound 49): $^1$H NMR $\delta_H$ (400 MHz, $CD_3OD$): 7.04 (d, J=8.4 Hz, 1H), 6.81 (d, J=2.2 Hz, 1H), 6.72 (dd, J=8.4, 2.0 Hz, 1H), 3.75 (s, 3H), 3.37-3.33 (m, 3H), 3.24 (s, 3H), 3.18-2.92 (m, 3H), 2.89-2.75 (m, 2H), 2.74-2.61 (m, 1H), 2.59-2.37 (m, 2H), 2.32-2.03 (m, 2H), 1.90-1.80 (m, 2H), 1.67-1.47 (m, 1H), 1.24-1.06 (m, 2H), 1.02-0.82 (m, TH), 0.68-0.46 (m, 2H), 0.34-0.11 (m, 2H). LC/MS, m/z=400.2 $[M+H]^+$ (Calc: 399.5); and (4bR,7S,8aS,9R)-7-(2-(benzyloxy)ethyl)-8a-hydroxy-3-methoxy-11-methyl-8,8a,9,10-tetrahydro-5H-9,4b-(epiminoethano)phenanthren-6(7H)-one (Compound 50): $^1$H NMR $\delta_H$ (400 MHz, $CD_3OD$): 7.41-7.21 (m, 5H), 7.14 (d, J=8.4 Hz, 1H), 6.89 (d, J=2.4 Hz, 1H), 6.84 (dd, J=8.5, 2.5 Hz, 1H), 4.39 (s, 2H), 3.78 (s, 3H), 3.57 (d, J=6.4 Hz, 1H), 3.48-3.35 (m, 3H), 3.27-3.16 (m, 1H), 3.15-3.06 (m, 2H), 3.05-2.94 (m, 2H), 2.92 (s, 3H), 2.74-2.62 (m, 1H), 2.58-2.44 (m, 1H), 2.07 (dd, J=13.9, 6.4 Hz, 1H), 2.00-1.86 (m, 1H), 1.75-1.63 (m, 1H), 1.50-1.38 (m, 1H), 1.35-1.22 (m, 1H). LC/MS, m/z=436.2 $[M+H]^+$ (Calc: 435.6).

Example 17

Synthesis of (4bR,7S,8aS,9R)-11-(cyclopropylmethyl)-3,8a-dihydroxy-7-(2-hydroxyethyl)-8,8a,9,10-tetrahydro-5H-9,4b-(epiminoethano)phenanthren-6(7H)-one (Compound 54)

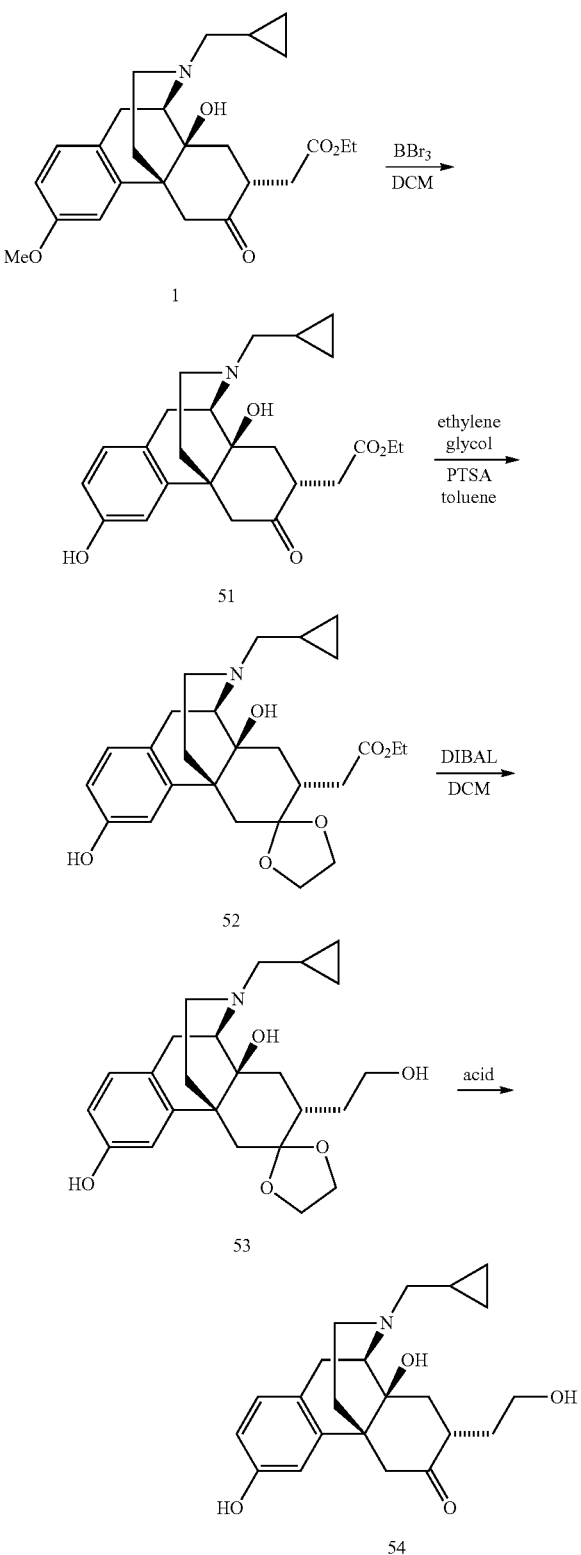

To a 0° C. solution of Compound 1 (1.4 g, 3.27 mmol) in 33 mL of anhydrous DCM was added 13.1 mL (13.1 mmol) of a 1.0 M solution of BBr₃ in DCM dropwise via syringe. The resulting yellow suspension was maintained at 0° C. for 15 min. LC/MS analysis showed that the reaction was complete. The reaction was quenched with 10 mL of EtOH then diluted with DCM and saturated aqueous NaHCO₃. The layers were separated and the aqueous layer was extracted with DCM (2×). The combined organics were washed with brine, dried over Na₂SO₄, filtered, and concentrated to afford 1.08 g (80%) of Compound 51. LC/MS, m/z=414.2 [M+H]⁺ (Calc: 413.5).

To a solution of Compound 51 (0.260 g, 0.629 mmol) in 6.3 mL of benzene was added ethlyene glycol (0.140 mL, 2.52 mmol) followed by PTSA (0.132 g, 0.692 mmol). The reaction was heated at reflux with a Dean-Stark trap for 1 h. LC/MS analysis showed that the reaction was complete. The mixture was quenched with solid NaHCO₃ at 0° C. Satd. aq. NaHCO₃ was added and the organic layer was separated. The aqueous layer was extracted with EtOAc (3×) and the combined organics were washed with brine. The organic layer was dried over Na₂SO₄, filtered, and concentrated. Purification by flash chromatography (SiO₂, 0-5% MeOH/DCM) gave 108 mg (38%) of Compound 52. LC/MS, m/z=458.2 [M+H]⁺ (Calc: 457.6).

To a −78° C. solution of Compound 52 (0.108 g, 0.236 mmol) in 2.4 mL of anhydrous DCM was added a 1.0 M solution of DIBAL in hexanes (1.18 mL, 1.18 mmol) dropwise via syringe. The reaction was allowed to warm slowly to −30° C. over 2 h. LC/MS showed that the reaction was complete. MeOH (0.5 mL) was added dropwise and the reaction mixture warmed to RT. The mixture was diluted with satd. aq. Rochelle's salt and DCM and stirred vigorously for 1 h. The layers were separated and the aqueous layer was extracted with DCM (2×). The combined organics were washed with brine, dried over Na₂SO₄, filtered, and concentrated. The crude Compound 53 (0.097 g, 99%) was used in the next step without further purification. LC/MS, m/z=416.4 [M+H]⁺ (Calc: 415.5).

To Compound 53 (0.097 g, 0.233 mmol) was added 1.2 mL of 1 N aq. HCl. The resulting solution was maintained at RT for 18 h. LC/MS showed the reaction was complete. The reaction mixture was cooled to 0° C. and basified with conc. NH₄OH. The reaction was diluted with EtOAc and H₂O, the layers separated and the aqueous layer was extracted with EtOAc (2×). The combined organics were washed with brine, dried over Na₂SO₄, filtered, and concentrated. Purification by reverse-phase prep HPLC (C18, 0-40% 0.1% TFA in ACN/0.1% TFA in water) with subsequent neutralization with ammonium carbonate resin and lyophilization afforded 37 mg (43%) of Compound 54 as a fluffy, white solid. ¹H NMR δ_H (400 MHz, CD₃OD): 6.94 (d, J=8.4 Hz, 1H), 6.71 (d, J=2.4 Hz, 1H), 6.59 (dd, J=8.3, 2.3 Hz, 1H), 3.65-3.42 (m, 2H), 3.08 (d, J=13.2 Hz, 3H), 3.04-2.93 (m, 1H), 2.79 (d, J=13.6 Hz, 2H), 2.72-2.60 (m, 1H), 2.58-2.36 (m, 2H), 2.31-2.05 (m, 2H), 1.99-1.79 (m, 2H), 1.67-1.51 (m, 1H), 1.29-1.03 (m, 2H), 0.99-0.84 (m, 1H), 0.68-0.49 (m, 2H), 0.27-0.13 (m, 2H). LC/MS, m/z=372.2 [M+H]⁺ (Calc: 371.5).

Example 18

Synthesis of (4bR,7S,8aS,9R)-3-(benzyloxy)-11-(cyclopropylmethyl)-8a-hydroxy-7-(2-hydroxyethyl)-8,8a,9,10-tetrahydro-5H-9,4b-(epiminoethano)phenanthren-6(7H)-one (Compound 58)

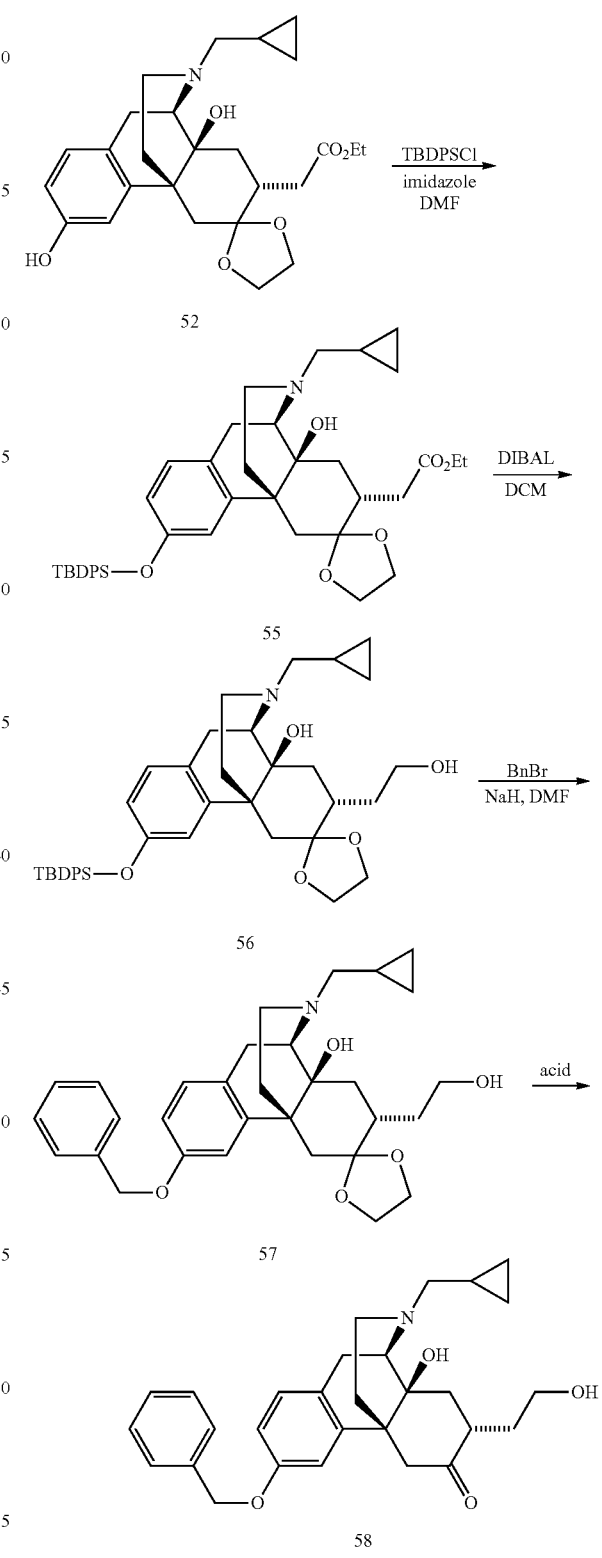

To a solution of Compound 52 (0.457 g, 1.00 mmol) in 4 mL of anhydrous DMF was added imidazole (170 mg, 2.50 mmol) followed by TBDPSCl (0.462 mL, 1.80 mmol) via syringe. The reaction was maintained for 5 days at RT. LC/MS analysis showed that the reaction was mostly complete. Satd. aq. NaHCO$_3$ and EtOAc were added, the layers separated and the aqueous layer was extracted with EtOAc (2×). The combined organics were washed with brine, dried over Na$_2$SO$_4$, filtered, and concentrated. Purification by flash chromatography (SiO$_2$, 0-5% MeOH/DCM) gave 0.610 g (88%) of Compound 55. LC/MS, m/z=696.4 [M+H]$^+$ (Calc: 695.9).

To a −78° C. solution of Compound 55 (0.310 g, 0.445 mmol) in 4 mL of anhydrous DCM was added a 1.0 M solution of DIBAL in hexanes (2.23 mL, 2.23 mmol) dropwise via syringe. The reaction was allowed to warm slowly to −30° C. over 2 h. LC/MS showed that the reaction was complete. MeOH (0.3 mL) was added dropwise and the reaction mixture warmed to RT. The mixture was diluted with satd. aq. Rochelle's salt and DCM and stirred vigorously for 1 h. The layers were separated. The aqueous layer was extracted with DCM (2×). The combined organics were washed with brine, dried over Na$_2$SO$_4$, filtered, and concentrated. Purification by flash chromatography (SiO$_2$, 0-10% MeOH/DCM) gave 0.265 g (91%) of Compound 56. LC/MS, m/z=654.4 [M+H]$^+$ (Calc: 653.9).

To a 0° C. suspension of NaH (0.039 g, 1.62 mmol) in 3 mL of anhydrous DMF was added Compound 56 (0.265 g, 0.405 mmol) in 1 mL of anhydrous DMF dropwise via syringe. The suspension was maintained at 0° C. for 0.5 h whereupon benzyl bromide (0.058 mL, 0.486 mmol) was added dropwise. The reaction was maintained for 4 h at RT. The reaction was slowly quenched with H$_2$O and diluted with EtOAc. The layers were separated and the aqueous layer was extracted with EtOAc (2×). The combined organics were washed with brine, dried over Na$_2$SO$_4$, filtered, and concentrated. Purification by flash chromatography (SiO$_2$, 0-5% MeOH/DCM) gave 29 mg of Compound 57 as a clear colorless residue. LC/MS, m/z=506.3 [M+H]$^+$ (Calc: 505.7).

To Compound 57 (0.029 g, 0.057 mmol) in 0.5 mL of THF was added 1.2 mL of 1 N aq. HCl. The resulting solution was maintained at RT for 18 h. LC-MS showed the reaction was complete. The reaction mixture was cooled to 0° C. and basified with conc. NH$_4$OH. The mixture was diluted with EtOAc, the layers were separated and the aqueous layer was extracted with EtOAc (2×). The combined organics were washed with brine, dried over Na$_2$SO$_4$, filtered, and concentrated. Purification by reverse-phase prep HPLC (C18, 0-60% 0.1% TFA in ACN/0.1% TFA in water) with subsequent neutralization with ammonium carbonate resin and lyophilization afforded 11 mg (42%) of Compound 58 as a fluffy, white solid. $^1$H NMR $\delta_H$ (400 MHz, DMSO-d$_6$): 7.53-7.27 (m, 5H), 7.03 (d, J=8.4 Hz, 1H), 6.86 (d, J=2.4 Hz, 1H), 6.79 (dd, J=8.4, 2.6 Hz, 1H), 5.06-4.92 (m, 2H), 4.81 (s, 1H), 4.30 (t, J=5.2 Hz, 1H), 3.09 (d, J=5.9 Hz, 1H), 3.06-2.84 (m, 3H), 2.80-2.63 (m, 2H), 2.58-2.52 (m, 1H), 2.43-2.22 (m, 3H), 2.16-2.03 (m, 1H), 1.97-1.79 (m, 2H), 1.79-1.66 (m, 1H), 1.43-1.28 (m, 1H), 1.06 (d, J=12.1 Hz, 1H), 0.99-0.77 (m, 3H), 0.37-0.59 (m, 2H), 0.01-0.21 (m, 2H). LC/MS, m/z=462.3 [M+H]$^+$ (Calc: 461.6).

Example 19

In a manner similar to that described in EXAMPLES 1-3, the following compounds were prepared:

ethyl 2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetate (TFA salt) (Compound 59): $^1$H NMR $\delta_H$ (400 MHz, CD$_3$OD): 7.16 (d, J=8.4 Hz, 1H), 6.89 (d, J=2.4 Hz, 1H), 6.85 (dd, J=8.5, 2.5 Hz, 1H), 3.97-4.13 (m, 2H), 3.78 (s, 3H), 3.60 (d, J=6.4 Hz, 1H), 3.33-3.47 (m, 2H), 3.19-3.28 (m, 1H), 3.17 (d, J=13.9 Hz, 1H), 3.10 (dd, J=12.5, 4.4 Hz, 1H), 2.99 (d, J=13.9 Hz, 1H), 2.93 (s, 3H), 2.62-2.75 (m, 1H), 2.50-2.62 (m, 1H), 2.45 (dd, J=16.8, 7.8 Hz, 1H), 2.00-2.14 (m, 2H), 1.70-1.86 (m, 1H), 1.38-1.49 (m, 1H), 1.18 (t, J=7.2 Hz, 3H). LC/MS, m/z=388.2 [M+H]$^+$ (Calc: 387.5);

2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetic acid (TFA salt) (Compound 60): $^1$H NMR $\delta_H$ (400 MHz, CD$_3$OD): 7.16 (d, J=8.6 Hz, 1H), 6.89 (d, J=2.4 Hz, 1H), 6.85 (dd, J=8.5, 2.5 Hz, 1H), 3.78 (s, 3H), 3.60 (d, J=6.4 Hz, 1H), 3.38 (s, 1H), 3.33-3.37 (m, 1H), 3.20-3.28 (m, 1H), 3.18 (d, J=13.9 Hz, 1H), 3.10 (dd, J=12.7, 4.3 Hz, 1H), 2.99 (d, J=13.9 Hz, 1H), 2.93 (s, 3H), 2.62-2.79 (m, 1H), 2.45-2.60 (m, 2H), 2.09 (dd, J=13.9, 6.2 Hz, 1H), 1.98 (dd, J=16.9, 5.7 Hz, 1H), 1.66-1.79 (m, 1H), 1.37-1.52 (m, 1H). LC/MS, m/z=360.2 [M+H]$^+$ (Calc: 359.4); and 2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetic acid (Compound 61): $^1$H NMR $\delta_H$ (400 MHz, CD$_3$OD): 7.06 (d, J=8.4 Hz, 1H), 6.78 (d, J=2.2 Hz, 1H), 6.70 (dd, J=8.4, 2.4 Hz, 1H), 3.58 (d, J=6.2 Hz, 1H), 3.35 (s, 3H), 3.03-3.27 (m, 3H), 2.86-3.00 (m, 4H), 2.63-2.77 (m, 1H), 2.44-2.61 (m, 2H), 2.09 (dd, J=13.6, 6.2 Hz, 1H), 1.98 (dd, J=16.9, 5.7 Hz, 1H), 1.66-1.83 (m, 1H), 1.34-1.47 (m, 1H). LC/MS, m/z=346.2 [M+H]$^+$ (Calc: 345.4).

Example 20

Synthesis of (4bR,8aS,9R,E)-11-(cyclopropylmethyl)-8a-hydroxy-3-methoxy-7-(3-methylbutylidene)-8,8a,9,10-tetrahydro-5H-9,4b-(epiminoethano)phenanthren-6(7H)-one (TFA salt) (Compound 62) and (4bR,7S,8aS,9R)-11-(cyclopropylmethyl)-3,8a-dihydroxy-7-isopentyl-8,8a,9,10-tetrahydro-5H-9,4b-(epiminoethano)phenanthren-6(7H)-one (TFA salt) (Compound 64)

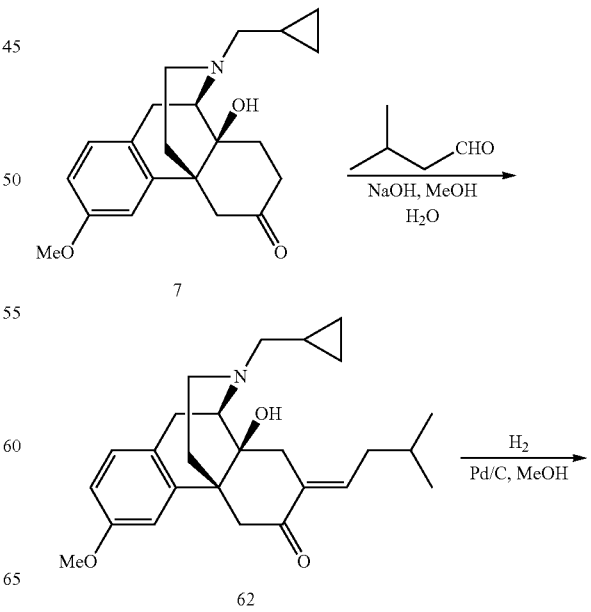

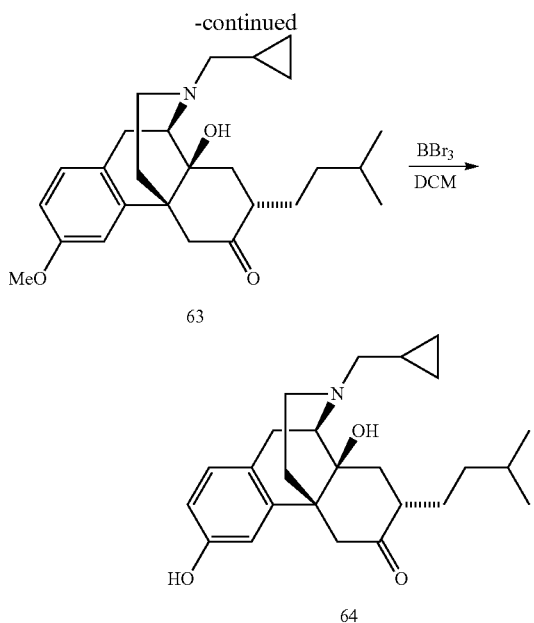

Isovaleraldehyde (0.57 mL, 5.3 mmol) was added to Compound 7 (1 g, 2.5 mmol) and 2.5 M aq. NaOH (3.2 mmol, 7.9 mmol) in MeOH (6 mL). The solution was stirred at RT for 45 h, and an additional aliquot of isovaleraldehyde (0.57 mL, 5.3 mmol) was added. After 3 days EtOAc was added, the resulting mixture was washed with sat. NaHCO$_3$, dried with Na$_2$SO$_4$, and concentrated. The crude material was purified by MPLC (SiO$_2$, 0-30% acetone/hexanes) followed by purification by prep-HPLC (C18, 0-60% 0.1% TFA in ACN/0.1% TFA in water) to give Compound 62 as its TFA salt. $^1$H NMR $\delta_H$ (400 MHz, DMSO-d$_6$): 8.76 (br. s., 1H), 6.89 (d, J=8.4 Hz, 1H), 6.61 (dd, J=8.4, 2.4 Hz, 1H), 6.56 (d, J=2.4 Hz, 1H), 6.25 (t, J=7.0 Hz, 1H), 6.07 (br. s., 1H), 3.79 (d, J=5.9 Hz, 1H), 3.46 (s, 3H), 3.02-3.21 (m, 3H), 2.87 (d, J=16.9 Hz, 1H), 2.53-2.80 (m, 4H), 2.11 (d, J=17.4 Hz, 1H), 2.03 (td, J=13.8, 4.8 Hz, 1H), 1.64-1.75 (m, 1H), 1.54-1.63 (m, 1H), 1.35-1.47 (m, 1H), 1.15 (d, J=12.1 Hz, 1H), 0.77-0.88 (m, 1H), 0.62-0.71 (m, 1H), 0.60 (d, J=6.6 Hz, 3H), 0.53 (d, J=6.6 Hz, 3H), 0.44-0.51 (m, 1H), 0.35-0.43 (m, 1H), 0.14-0.28 (m, 2H). LC/MS, m/z=410 [M+H]$^+$ (Calc: 409).

To a crude solution of Compound 62 (600 mg, 1.5 mmol) in MeOH (30 mL) was carefully added 90 mg of 10% Pd/C. The solution was evacuated and filled with 1 atm of H$_2$ three times, after which it was stirred under 1 atm of H$_2$ at RT for 66 h. Filtration through Celite followed by concentration yielded 600 mg of Compound 63 as a clear oil which was used in subsequent steps without purification. LC/MS, m/z=412 [M+H]$^+$ (Calc: 411).

A 1M solution of BBr$_3$ in DCM (5.8 mL, 5.8 mmol) was added slowly to Compound 63 (600 mmol, 1.5 mmol) in DCM (2 mL). The solution was stirred at RT for 75 min. then slowly quenched with 3.3 mL of 7M NH$_3$ in MeOH (23.1 mmol). The resulting salts were filtered off and the filtrate purified by MPLC (SiO$_2$, 0-20% (10% NH$_4$OH/MeOH)/DCM) followed by prep-HPLC (C18, 0-60% 0.1% TFA in ACN/0.1% TFA in water) to give Compound 64 as its TFA salt. $^1$H NMR $\delta_H$ (400 MHz, DMSO-d$_6$): 9.29 (s, 1H), 8.87 (br s., 1H), 6.91 (d, J=8.4 Hz, 1H), 6.63 (d, J=2.2 Hz, 1H), 6.57 (dd, J=8.4, 2.4 Hz, 1H), 6.28 (s, 1H), 3.82 (d, J=5.7 Hz, 1H), 3.33-3.26 (m, 1H), 3.22 (d, J=19.6 Hz, 1H), 3.04 (dd, J=23.5, 12.1 Hz, 1H), 2.90 (d, J=13.6 Hz, 2H), 2.85-2.74 (m, 1H), 2.67 (d, J=13.6 Hz, 1H), 2.65-2.59 (m, 1H), 2.40-2.21 (m, 2H), 2.05 (dd, J=13.6, 6.2 Hz, 1H), 1.59-1.47 (m, 1H), 1.42-1.30 (m, 2H), 1.21 (d, J=12.5 Hz, 1H), 1.06-0.88 (m, 3H), 0.81-0.70 (m, 7H), 0.67-0.59 (m, 1H), 0.59-0.51 (m, 1H), 0.45-0.31 (m, 2H). LC/MS, m/z=398 [M+H]$^+$ (Calc: 397).

In a similar manner, the following compounds were prepared:

(4bR,7S,8aS,9R)-7-(cyclopentylmethyl)-11-(cyclopropylmethyl)-3,8a-dihydroxy-8,8a,9,10-tetrahydro-5H-9,4b-(epiminoethano)phenanthren-6(7H)-one (TFA salt) (Compound 65): $^1$H NMR $\delta_H$ (400 MHz, DMSO-d$_6$): 9.29 (br. s., 1H), 8.86 (br. s., 1H), 6.90 (d, J=8.1 Hz, 1H), 6.62 (d, J=2.2 Hz, 1H), 6.57 (dd, J=8.4, 2.4 Hz, 1H), 6.30 (s, 1H), 3.83 (d, J=5.9 Hz, 1H), 3.33-3.17 (m, 2H), 3.04 (dd, J=19.8, 6.2 Hz, 1H), 2.96-2.87 (m, 2H), 2.85-2.76 (m, 1H), 2.67 (d, J=13.6 Hz, 2H), 2.39-2.20 (m, 2H), 2.08 (dd, J=13.6, 6.2 Hz, 1H), 1.72-1.25 (m, 9H), 1.21 (d, J=12.5 Hz, 1H), 1.05-0.74 (m, 4H), 0.67-0.59 (m, 1H), 0.59-0.50 (m, 1H), 0.46-0.38 (m, 1H), 0.38-0.29 (m, 1H). LC/MS, m/z=410 [M+H]$^+$ (Calc: 409);

(4bR,7S,8aS,9R)-11-(cyclopropylmethyl)-3,8a-dihydroxy-7-(2-methylbutyl)-8,8a,9,10-tetrahydro-5H-9,4b-(epiminoethano)phenanthren-6(7H)-one (TFA salt) (Compound 66): $^1$H NMR $\delta_H$ (400 MHz, DMSO-d$_6$): 8.98-8.87 (m, 1H), 6.98 (d, J=8.4 Hz, 1H), 6.69 (d, J=2.2 Hz, 1H), 6.64 (dd, J=8.3, 2.3 Hz, 1H), 6.38 (br. s., 1H), 3.90 (t, J=5.7 Hz, 1H), 3.32-3.07 (m, 3H), 3.04-2.92 (m, 2H), 2.91-2.70 (m, 3H), 2.46-2.27 (m, 2H), 2.08 (td, J=14.0, 6.4 Hz, 1H), 1.59 (dt, J=13.6, 6.6 Hz, 1H), 1.48-1.38 (m, 1H), 1.38-1.14 (m, 4H), 1.06 (d, J=7.3 Hz, 2H), 0.84-0.73 (m, 7H), 0.72-0.66 (m, 1H), 0.66-0.54 (m, 2H), 0.54-0.45 (m, 1H), 0.45-0.37 (m, 1H). LC/MS, m/z=398 [M+H]$^+$ (Calc: 397);

(4bR,7S,8aS,9R)-7-butyl-11-(cyclopropylmethyl)-3,8a-dihydroxy-8,8a,9,10-tetrahydro-5H-9,4b-(epiminoethano)phenanthren-6(7H)-one (TFA salt) (Compound 67): $^1$H NMR $\delta_H$ (400 MHz, DMSO-d$_6$): 9.36 (s, 1H), 8.93 (br. s., 1H), 6.98 (d, J=8.1 Hz, 1H), 6.69 (d, J=2.0 Hz, 1H), 6.64 (dd, J=8.1, 2.2 Hz, 1H), 6.34 (s, 2H), 3.89 (d, J=5.5 Hz, 1H), 3.33-3.20 (m, 2H), 3.11 (dd, J=18.5, 5.9 Hz, 1H), 2.98 (d, J=13.6 Hz, 2H), 2.91-2.82 (m, 1H), 2.78-2.69 (m, 2H), 2.45-2.28 (m, 2H), 2.11 (dd, J=13.8, 6.1 Hz, 1H), 1.57 (td, J=13.3, 7.4 Hz, 1H), 1.42 (t, J=13.3 Hz, 1H), 1.33-1.01 (m, 7H), 0.90-0.84 (m, 1H), 0.81 (t, J=7.0 Hz, 3H), 0.74-0.65 (m, 1H), 0.65-0.57 (m, 1H), 0.54-0.45 (m, 1H), 0.44-0.36 (m, 1H). LC/MS, m/z=384 [M+H]$^+$ (Calc: 383);

(4bR,7S,8aS,9R)-11-(cyclopropylmethyl)-3,8a-dihydroxy-7-neopentyl-8,8a,9,10-tetrahydro-5H-9,4b-(epiminoethano)phenanthren-6(7H)-one (TFA salt) (Compound 68) $^1$H NMR $\delta_H$ (400 MHz, DMSO-d$_6$): 9.37 (br. s., 1H), 8.92 (br. s., 1H), 6.98 (d, J=8.1 Hz, 1H), 6.70 (d, J=2.0 Hz, 1H), 6.64 (dd, J=8.1, 2.2 Hz, 1H), 6.43 (s, 1H), 3.90 (d, J=5.7 Hz, 1H), 3.40-3.32 (m, 1H), 3.29 (d, J=19.6 Hz, 1H), 3.14-2.96 (m, 3H), 2.93-2.85 (m, 1H), 2.81-2.72 (m, 2H), 2.47-2.30 (m, 2H), 2.09 (dd, J=13.6, 6.4 Hz, 1H), 1.95 (dd, J=14.0, 4.7 Hz, 1H), 1.52 (t, J=13.3 Hz, 1H), 1.28 (d, J=11.9 Hz, 1H), 1.12-1.00 (m, 1H), 0.80 (s, 9H), 0.74-0.58 (m, 2H), 0.54-0.37 (m, 3H). LC/MS, m/z=398 [M+H]$^+$ (Calc: 397);

(4bR,7S,8aS,9R)-11-(cyclopropylmethyl)-3,8a-dihydroxy-7-isobutyl-8,8a,9,10-tetrahydro-5H-9,4b-(epiminoethano)phenanthren-6(7H)-one (TFA salt) (Compound 69) $^1$H NMR $\delta_H$ (400 MHz, DMSO-d$_6$): 9.29 (s, 1H), 8.85 (br. s., 1H), 6.91 (d, J=8.4 Hz, 1H), 6.62 (d, J=2.4 Hz, 1H), 6.57 (dd, J=8.3, 2.3 Hz, 1H), 6.31 (s, 1H), 3.83 (d, J=5.9 Hz, 1H), 3.33-3.25 (m, 1H), 3.22 (d, J=19.6 Hz, 1H), 3.04 (dd, J=22.0, 8.1 Hz, 1H), 2.96-2.87 (m, 2H), 2.85-2.76 (m, 2H), 2.75-2.65 (m, 2H), 2.39-2.21 (m, 2H), 2.02 (dd, J=13.8, 6.3 Hz, 1H), 1.48-1.28 (m, 3H), 1.21 (d, J=12.8 Hz, 1H), 1.06-0.94 (m, 1H), 0.73 (d, J=2.6 Hz, 3H), 0.72 (d, J=2.9 Hz, 3H), 0.68-0.58 (m, 2H), 0.59-0.51 (m, 1H), 0.47-0.38 (m, 1H), 0.38-0.30 (m, 1H). LC/MS, m/z=384 [M+H]+ (Calc: 383);

(4bR,7S,8aS,9R)-7-(cyclohexylmethyl)-11-(cyclopropylmethyl)-3,8a-dihydroxy-8,8a,9,10-tetrahydro-5H-9,4b-(epiminoethano)phenanthren-6(7H)-one (TFA salt) (Compound 70): $^1$H NMR $\delta_H$ (400 MHz, DMSO-d$_6$): 9.29 (br. s., 1H), 8.86 (br. s., 1H), 6.90 (d, J=8.4 Hz, 1H), 6.62 (d, J=2.2 Hz, 1H), 6.57 (dd, J=8.3, 2.3 Hz, 1H), 6.30 (s, 1H), 3.84 (d, J:=0.5.9 Hz, 1H), 3.32-3.17 (m, 2H), 3.05 (dd, J=22.2, 7.9 Hz, 1H), 2.97-2.86 (m, 2H), 2.84-2.70 (m, 2H), 2.67 (d, J=13.9 Hz, 1H), 2.40-2.20 (m, 2H), 2.03 (dd, J=13.6, 6.2 Hz, 1H), 1.70-1.37 (m, 6H), 1.31 (t, J=13.2 Hz, 1H), 1.21 (d, J=12.5 Hz, 1H), 1.14-0.94 (m, 5H), 0.79-0.68 (m, 1H), 0.68-0.51 (m, 4H), 0.47-0.38 (m, 1H), 0.38-0.29 (m, 1H). LC/MS, m/z=424 [M+H]+ (Calc: 423);

(4bR,7S,8aS,9R)-7-benzyl-11-(cyclopropylmethyl)-3,8a-dihydroxy-8,8a,9,10-tetrahydro-5H-9,4b-(epiminoethano) phenanthren-6(7H)-one (TFA salt) (Compound 71) $^1$H NMR $\delta_H$(400 MHz, DMSO-d$_6$): 9.33 (br. s., 1H), 8.80 (br. s., 1H), 7.20-7.13 (m, 2H), 7.13-7.03 (m, 3H), 6.92 (d, J=8.4 Hz, 1H), 6.67 (d, J=2.4 Hz, 1H), 6.59 (dd, J=8.3, 2.3 Hz, 1H), 6.20 (s, 1H), 3.76 (d, J=5.9 Hz, 1H), 3.30-3.16 (m, 2H), 3.05-2.94 (m, 4H), 2.88 (d, J=10.8 Hz, 1H), 2.81-2.70 (m, 2H), 2.39-2.20 (m, 2H), 1.98 (dd, J=14.7, 10.1 Hz, 1H), 1.84 (dd, J=13.6, 5.7 Hz, 1H), 1.42 (t, J=13.1 Hz, 1H), 1.22 (d, J=12.3 Hz, 1H), 1.01-0.90 (m, 1H), 0.63-0.54 (m, 1H), 0.54-0.44 (m, 1H), 0.42-0.34 (m, 1H), 0.34-0.25 (m, 1H). LC/MS, m/z=418 [M+H]+ (Calc: 417);

(4bS,7S,8aR,9R)-11-(cyclopropylmethyl)-7-isopropyl-3-methoxy-8,8a,9,10-tetrahydro-5H-9,4b-(epiminoethano) phenanthren-6(7H)-one (TFA salt) (Compound 72): $^1$H NMR $\delta_H$(400 MHz, CD$_3$OD): 7.05 (d, J=8.6 Hz, 1H), 6.80 (s, 1H), 6.69-6.76 (m, 1H), 4.05 (br. s., 1H), 3.67 (s, 3H), 3.30 (d, J=12.7 Hz, 1H), 2.95-3.12 (m, 3H), 2.48-2.61 (m, 3H), 2.28-2.39 (m, 1H), 1.81-2.10 (m, 3H), 1.67 (d, J=14.3 Hz, 1H), 1.00-1.25 (m, 2H), 0.76 (d, J=6.8 Hz, 3H), 0.69 (d, J=7.0 Hz, 2H), 0.64-0.72 (m, 2H), 0.34-0.53 (m, 5H). LC/MS, m/z=368.3 [M+H]+ (Calc: 367.5);

(4bS,7S,8aR,9R)-11-(cyclopropylmethyl)-3-hydroxy-7-isopropyl-8,8a,9,10-tetrahydro-5H-9,4b-(epiminoethano) phenanthren-6(7H)-one (TFA salt) (Compound 73): $^1$H NMR $\delta_H$(400 MHz, CD$_3$OD): 6.95 (d, J=8.1 Hz, 1H), 6.66-6.71 (m, 1H), 6.54-6.62 (m, 1H), 4.03 (br. s., 1H), 3.24-3.34 (m, 1H), 3.11-3.18 (m, 1H), 2.95-3.08 (m, 4H), 2.45-2.61 (m, 3H), 2.26-2.37 (m, 1H), 1.88-2.08 (m, 3H), 1.63 (d, J=13.8 Hz, 1H), 1.14-1.29 (m, 1H), 1.00-1.11 (m, 1H), 0.64-0.80 (m, 5H), 0.52 (d, J=6.8 Hz, 1H), 0.35-0.44 (m, 2H). LC/MS, m/z=354.1 [M+H]+ (Calc: 353.5); and (4bS,7R,8aR,9R)-11-(cyclopropylmethyl)-3-hydroxy-7-isopropyl-8,8a,9,10-tetrahydro-5H-9,4b-(epiminoethano) phenanthren-6(7H)-one (TFA salt) (Compound 74): $^1$H NMR $\delta_H$(400 MHz, CD$_3$OD): 6.98 (d, J=8.3 Hz, 1H), 6.61 (d, J=8.3 Hz, 1H), 6.54 (s, 1H), 4.07 (br. s., 1H), 3.25-3.29 (m, 1H), 3.15-3.22 (m, 3H), 2.74-2.89 (m, 2H), 2.50-2.70 (m, 3H), 2.37-2.47 (m, 1H), 1.92-2.12 (m, 4H), 1.37 (d, J=14.7 Hz, 1H), 1.02 (d, J=6.6 Hz, 1H), 0.89 (t, J=7.5 Hz, 6H), 0.59-0.74 (m, 2H), 0.29-0.43 (m, 2H). LC/MS, m/z: 354.1 [M+H]+ (Calc: 353.5);

(4bS,7S,8aR,9R)-11-(cyclopropylmethyl)-3-hydroxy-7-isopentyl-8,8a,9,10-tetrahydro-5H-9,4b-(epiminoethano) phenanthren-6(7H)-one (TFA salt) (Compound 104): $^1$H NMR (DMSO-d$_6$) δ: 9.43 (br. s., 0.7H), 9.34 (br. s., 0.3H), 9.31-9.21 (m, 1H), 6.95-6.85 (m, 1H), 6.64 (d, J=2.0 Hz, 1H), 6.56 (dd, J=8.4, 2.4 Hz, 1H), 3.97 (br. s., 0.7H), 3.85 (br. s., 0.3H), 3.42-3.32 (m, 0.6H), 3.29-2.83 (m, 6H), 2.71-2.47 (m, 2H), 2.41-2.24 (m, 1H), 2.17-2.06 (m, 0.5H), 2.02-1.81 (m, 2H), 1.55 (d, J=13.4 Hz, 1H), 1.51-1.41 (m, 1H), 1.41-1.28 (m, 1H), 1.10-0.83 (m, 5H), 0.83-0.76 (m, 1H), 0.74 (d, J=6.8 Hz, 3H), 0.72 (d, J=6.8 Hz, 3H), 0.65-0.53 (m, 2H), 0.40-0.25 (m, 2H). LC/MS, m/z=382.4 [M+H]+ (Calc: 381.55);

(4bS,7S,8aR,9R)-7-(cyclopentylmethyl)-11-(cyclopropylmethyl)-3-hydroxy-8,8a,9,10-tetrahydro-5H-9,4b-(epiminoethano)phenanthren-6(7H)-one (TFA salt) (Compound 105): $^1$H NMR (DMSO-d$_6$) δ: 9.37 (br. s., 0.7H), 9.31-9.23 (m, 1.3H), 6.94-6.86 (m, 1H), 6.64 (d, J=2.2 Hz, 1H), 6.56 (dd, J=8.4, 2.4 Hz, 1H), 3.98 (br. s., 0.7H), 3.84 (br. s., 0.3H), 3.43-3.33 (m, 0.7H), 3.33-2.82 (m, 7H), 2.76-2.58 (m, 1.7H), 2.56-2.46 (m, 1H), 2.41-2.30 (m, 1H), 2.16-2.08 (m, 0.6H), 2.08-1.87 (m, 2H), 1.73-1.30 (m, 10H), 1.10-0.74 (m, 6H), 0.68-0.53 (m, 2H), 0.41-0.26 (m, 2H). LC/MS, m/z=394.4 [M+H]+ (Calc: 393.56);

(4bR,7S,8aS,9R)-3,8a-dihydroxy-7-isopentyl-11-methyl-8,8a,9,10-tetrahydro-5H-9,4b-(epiminoethano)phenanthren-6(7H)-one (TFA salt) (Compound 106): $^1$H NMR (DMSO-d$_6$) δ: 9.37 (s, 1H), 9.24 (br. s., 1H), 6.99 (d, J=8.1 Hz, 1H), 6.69 (d, J=2.2 Hz, 1H), 6.64 (dd, J=8.4, 2.2 Hz, 1H), 6.26 (s, 1H), 3.54 (d, J=5.7 Hz, 1H), 3.29 (d, J=19.8 Hz, 1H), 3.08 (dd, J=19.8, 6.4 Hz, 1H), 3.00 (d, J=12.3 Hz, 1H), 2.96 (d, J=13.9 Hz, 1H), 2.83 (d, J=4.8 Hz, 3H), 2.73 (d, J:=13.9 Hz, 1H), 2.71-2.63 (m, 1H), 2.48-2.38 (m, 1H), 2.34-2.24 (m, 1H), 2.03 (dd, J=13.6, 6.2 Hz, 1H), 1.61-1.49 (m, 1H), 1.48-1.35 (m, 2H), 1.27 (d, J=12.5 Hz, 1H), 1.11-0.92 (m, 2H), 0.88-0.82 (m, 1H), 0.80 (d, J=6.8 Hz, 3H), 0.78 (d, J=6.6 Hz, 3H). LC/MS, m/z=358.2 [M+H]+ (Calc: 357.49); and (4bS,7S,8aR,9R)-7-(cyclopentylmethyl)-3-hydroxy-11-methyl-8,8a,9,10-tetrahydro-5H-9,4b-(epiminoethano) phenanthren-6(7H)-one (TFA salt) (Compound 107): $^1$H NMR (DMSO-d$_6$) δ: 9.37 (br. s., 1H), 9.24 (br. s., 1H), 6.99 (d, J=8.4 Hz, 1H), 6.69 (d, J=2.2 Hz, 1H), 6.63 (dd, J=8.1, 2.2 Hz, 1H), 6.30 (s, 1H), 3.54 (d, J=5.9 Hz, 1H), 3.29 (d, J=19.8 Hz, 1H), 3.13-3.01 (m, 2H), 2.97 (d, J=13.9 Hz, 1H), 2.83 (d, J=4.8 Hz, 3H), 2.79-2.65 (m, 2H), 2.47-2.37 (m, 1H), 2.37-2.24 (m, 1H), 2.06 (dd, J=13.6, 6.2 Hz, 1H), 1.78-1.32 (m, 9H), 1.27 (d, J=12.8 Hz, 1H), 1.05-0.75 (m, 3H). LC/MS, m/z=370.4 [M+H]+ (Calc: 369.5).

Example 21

In a manner similar to that described in EXAMPLES 6 and 7, the following compounds were prepared:

(2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetyl)-L-alanine (TFA salt) (Compound 75): $^1$H NMR $\delta_H$ (400 MHz, CD$_3$OD): 8.22 (d, J=6.8 Hz, 1H), 7.06 (d, J=8.4 Hz, 1H), 6.78 (d, J=2.2 Hz, 1H), 6.69 (dd, J=8.3, 2.3 Hz, 1H), 4.39-4.25 (m, 1H), 3.57 (d, J=5.9 Hz, 1H), 3.43-3.33 (m, 2H), 3.15 (d, J=14.1 Hz, 2H), 3.09 (dd, J=12.8, 4.2 Hz, 1H), 2.97-2.88 (m, 4H), 2.77-2.63 (m, 1H), 2.62-2.45 (m, 2H), 2.11 (dd, J=13.8, 6.3 Hz, 1H), 1.88 (dd, J=15.2, 7.7 Hz, 1H), 1.77-1.64 (m, 1H), 1.45-1.37 (m, 1H), 1.36 (d, J=7.5 Hz, 3H). LC/MS, m/z=417.2 [M+H]+ (Calc: 416.47);

(4bR,7R,8aS,9R)-8a-hydroxy-3-methoxy-11-methyl-7-(2-oxo-2-(piperidin-1-yl)ethyl)-8,8a,9,10-tetrahydro-5H-9, 4b-(epiminoethano)phenanthren-6(7H)-one (TFA salt) (Compound 76): $^1$H NMR $\delta_H$ (400 MHz, CD$_3$OD): 7.16 (d, J=8.4 Hz, 1H), 6.91 (d, J=2.6 Hz, 1H), 6.84 (dd, J=8.5, 2.5 Hz, 1H), 3.77 (s, 3H), 3.59 (d, J=6.2 Hz, 1H), 3.57-3.50 (m, 1H), 3.49-3.33 (m, 6H), 3.19 (s, 2H), 3.10 (dd, J=12.7, 4.3 Hz, 1H), 2.98 (d, J=13.6 Hz, 1H), 2.95-2.90 (m, 3H), 2.76 (dd, J=16.4, 6.9 Hz, 1H), 2.72-2.63 (m, 1H), 2.62-2.50 (m, 1H), 2.09 (dd, J=13.6, 6.2 Hz, 1H), 1.90 (dd, J=16.5, 5.7 Hz, 1H), 1.75-1.57 (m, 4H), 1.57-1.38 (m, 4H). LC/MS, m/z=427.2 [M+H]+ (Calc: 426.6);

(4bR,7R,8aS,9R)-8a-hydroxy-3-methoxy-11-methyl-7-(2-oxo-2-(pyrrolidin-1-yl)ethyl)-8,8a,9,10-tetrahydro-5H-9,4b-(epiminoethano)phenanthren-6(7H)-one (TFA salt) (Compound 77): $^1$H NMR $\delta_H$ (400 MHz, CD$_3$OD): 7.16 (d, J=8.6 Hz, 1H), 6.90 (d, J=2.4 Hz, 1H), 6.84 (dd, J=8.4, 2.4 Hz, 1H), 3.77 (s, 3H), 3.60 (d, J=6.2 Hz, 1H), 3.47 (d, J=6.8 Hz, 2H), 3.45-3.33 (m, 5H), 3.27-3.16 (m, 2H), 3.10 (dd, J=12.5, 4.4 Hz, 1H), 2.98 (d, J=13.9 Hz, 1H), 2.93 (s, 3H), 2.74-2.61 (m, 2H), 2.61-2.49 (m, 1H), 2.10 (dd, J=13.8, 6.1 Hz, 1H), 2.00-1.81 (m, 5H), 1.76-1.65 (m, 1H), 1.50-1.39 (m, 1H). LC/MS, m/z=413.3 [M+H]$^+$ (Calc: 412.5);

(4bR,7R,8aS,9R)-8a-hydroxy-7-(2-(4-hydroxypiperidin-1-yl)-2-oxoethyl)-3-methoxy-11-methyl-8,8a,9,10-tetrahydro-5H-9,4b-(epiminoethano)phenanthren-6(7H)-one (TFA salt) (Compound 78): $^1$H NMR $\delta_H$ (400 MHz, CD$_3$OD): 7.16 (d, J=8.4 Hz, 1H), 6.93-6.88 (m, 1H), 6.84 (dd, J=8.5, 2.5 Hz, 1H), 4.11-3.91 (m, 1H), 3.88-3.68 (m, 5H), 3.59 (d, J=6.2 Hz, 1H), 3.52-3.33 (m, 2H), 3.28-3.01 (m, 5H), 2.98 (d, J=13.6 Hz, 1H), 2.93 (s, 3H), 2.82-2.73 (m, 1H), 2.73-2.62 (m, 1H), 2.62-2.49 (m, 1H), 2.14-2.03 (m, 1H), 1.97-1.86 (m, 1H), 1.86-1.75 (m, 2H), 1.75-1.66 (m, 1H), 1.58-1.31 (m, 3H). LC/MS, m/z=443.3 [M+H]$^+$ (Calc: 442.6);

(4bR,7R,8aS,9R)-8a-hydroxy-3-methoxy-11-methyl-7-(2-morpholino-2-oxoethyl)-8,8a,9,10-tetrahydro-5H-9,4b-(epiminoethano)phenanthren-6(7H)-one (TFA salt) (Compound 79): $^1$H NMR $\delta_H$ (400 MHz, CD$_3$OD): 7.16 (d, J=8.6 Hz, 1H), 6.90 (d, J=2.4 Hz, 1H), 6.84 (dd, J=8.5, 2.5 Hz, 1H), 3.77 (s, 3H), 3.69-3.57 (m, 5H), 3.57-3.37 (m, 6H), 3.27-3.16 (m, 2H), 3.11 (dd, J=12.8, 4.2 Hz, 1H), 2.98 (d, J=13.6 Hz, 1H), 2.92 (s, 3H), 2.80-2.64 (m, 2H), 2.61-2.51 (m, 1H), 2.09 (dd, J=13.8, 6.1 Hz, 1H), 1.91 (dd, J:=16.4, 5.6 Hz, 1H), 1.79-1.63 (m, 1H), 1.51-1.37 (m, 1H). LC/MS, m/z=429.2 [M+H]$^+$ (Calc: 428.5);

(4bR,7R,8aS,9R)-3,8a-dihydroxy-11-methyl-7-(2-oxo-2-(piperidin-1-yl)ethyl)-8,8a,9,10-tetrahydro-5H-9,4b-(epiminoethano)phenanthren-6(7H)-one (TFA salt) (Compound 80): $^1$H NMR $\delta_H$ (400 MHz, CD$_3$OD): 7.06 (d, J=8.4 Hz, 1H), 6.79 (d, J=2.4 Hz, 1H), 6.69 (dd, J=8.4, 2.4 Hz, 1H), 3.57 (d, J=6.2 Hz, 1H), 3.55-3.33 (m, 6H), 3.26-3.13 (m, 2H), 3.09 (dd, J=12.7, 4.3 Hz, 1H), 2.93 (s, 4H), 2.78 (dd, J=16.5, 6.8 Hz, 1H), 2.74-2.63 (m, 1H), 2.61-2.47 (m, 1H), 2.08 (dd, J=13.8, 6.1 Hz, 1H), 1.91 (dd, J=16.5, 5.9 Hz, 1H), 1.78-1.68 (m, 1H), −1.68-1.44 (m, 6H), 1.43-1.34 (m, 1H). LC/MS, m/z=413.4 [M+H]$^+$ (Calc: 412.5);

(4bR,7R,8aS,9R)-3,8a-dihydroxy-7-(2-(4-hydroxypiperidin-1-yl)-2-oxoethyl)-11-methyl-8,8a,9,10-tetrahydro-5H-9,4b-(epiminoethano)phenanthren-6(7H)-one (Compound 81): $^1$H NMR $\delta_H$ (400 MHz, DMSO-d$_6$): 9.13 (br. s., 1H), 6.91 (d, J=8.1 Hz, 1H), 6.68-6.57 (m, 1H), 6.55-6.47 (m, 1H), 4.87-4.72 (m, 1H), 4.69 (t, J=4.6 Hz, 1H), 3.95-3.75 (m, 1H), 3.70-3.50 (m, 2H), 3.44-3.35 (m, 1H), 3.14-3.00 (m, 2H), 3.00-2.70 (m, 3H), 2.70-2.54 (br s, 3H), 2.42-2.25 (m, 3H), 2.20-2.06 (m, 1H), 2.02-1.85 (m, 1H), 1.85-1.56 (m, 4H), 1.52-1.40 (m, 1H), 1.36-1.09 (m, 3H), 1.02 (d, J=11.9 Hz, 1H). LC/MS, m/z=429.2 [M+H]$^+$ (Calc: 428.5);

2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-isobutylacetamide (Compound 82): $^1$H NMR $\delta_H$ (400 MHz, DMSO-d$_6$): 9.14 (br. s., 1H), 7.67 (t, J=5.8 Hz, 1H), 6.92 (d, J=8.1 Hz, 1H), 6.62 (d, J=2.2 Hz, 1H), 6.57-6.49 (m, 1H), 4.79 (br. s., 1H), 3.25-3.14 (m, 1H), 3.07 (d, J=18.3 Hz, 1H), 2.93 (d, J=13.4 Hz, 1H), 2.84-2.73 (m, 3H), 2.65 (d, J=13.4 Hz, 2H), 2.42-2.24 (m, 5H), 2.20-2.04 (m, 1H), 2.01-1.84 (m, 1H), 1.84-1.69 (m, 1H), 1.61 (s, 2H), 1.47-1.33 (m, 1H), 1.10-0.93 (m, 1H), 0.81 (s, 3H), 0.79 (s, 3H). LC/MS, m/z=401.4 [M+H]$^+$ (Calc: 400.5);

N-benzyl-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide (TFA salt) (Compound 83): $^1$H NMR $\delta_H$ (400 MHz, CD$_3$OD): 8.33 (br s, 1H), 7.28 (d, J=5.7 Hz, 4H), 7.06 (d, J=8.4 Hz, 1H), 6.79 (d, J=2.2 Hz, 1H), 6.69 (dd, J=8.4, 2.4 Hz, 1H), 4.24-4.42 (m, 2H), 3.56 (d, J=6.2 Hz, 1H), 3.45-3.33 (m, 3H), 3.23-3.06 (m, 3H), 2.96-2.89 (m, 4H), 2.77-2.64 (m, 1H), 2.61-2.47 (m, 2H), 2.05 (dd, J=13.6, 6.2 Hz, 1H), 1.90 (dd, J=15.3, 6.5 Hz, 1H), 1.78-1.65 (m, 1H), 1.48-1.33 (m, 1H). LC/MS, m/z=435.2 [M+H]$^+$ (Calc: 434.53); and N-(cyclopropylmethyl)-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide (TFA salt) (Compound 84): $^1$H NMR $\delta_H$ (400 MHz, DMSO-d$_6$): 9.37 (s, 1H), 9.24 (br s, 1H), 7.79 (t, J=5.5 Hz, 1H), 7.00 (d, J=8.1 Hz, 1H), 6.68 (d, J=2.4 Hz, 1H), 6.64 (dd, J=8.4, 2.4 Hz, 1H), 6.34 (s, 1H), 3.56 (d, J=5.9 Hz, 1H), 3.33-3.21 (m, 2H), 3.09-2.94 (m, 3H), 2.92-2.85 (m, 2H), 2.82 (d, J=5.1 Hz, 3H), 2.76 (d, J=13.6 Hz, 1H), 2.47-2.37 (m, 1H), 2.36-2.23 (m, 2H), 1.98 (dd, J=13.6, 6.4 Hz, 1H), 1.63 (dd, J=15.0, 6.8 Hz, 1H), 1.54-1.40 (m, 1H), 1.28 (d, J=13.2 Hz, 1H), 0.90-0.74 (m, 1H), 0.43-0.30 (m, 2H), 0.17-0.04 (m, 2H). LC/MS, m/z=399.2 [M+H]$^+$ (Calc: 398.5).

In the foregoing Examples the following abbreviations are used:

| | |
|---|---|
| Ac | acetyl |
| ACN | acetonitrile |
| AcOH | acetic acid |
| Ac$_2$O | acetic anhydride |
| aq. | aqueous |
| atm | atmosphere(s) |
| Bn | benzyl |
| Boc | tert-butoxycarbonyl |
| ° C. | degrees Celcius |
| conc. | concentrated |
| DBU | 1,8-diazabicyclo[5.4.0]undec-7-ene |
| DCE | 1,2-dichloroethane |
| DCM | dichloromethane |
| DIBAL | diisobutylaluminum hydride |
| DIPEA | diisopropylethylamine |
| DMF | dimethylformamide |
| DMSO | dimethylsulfoxide |
| Et$_2$O | diethyl ether |
| EtOAc | ethyl acetate |
| EtOH | ethanol |
| h | hour(s) |
| HATU | 2-(7-aza-1H-benzotriazole-1-yl)-1,1,3,3-tetramethyluronium hexafluorophosphate |
| HPLC | high pressure liquid chromatography |
| MeOH | methanol |
| min | minute(s) |
| MPLC | medium pressure liquid chromatography |
| NaHMDS | sodium hexamethyldisilazide |
| Pd/C | palladium on carbon |
| Pd(Ph$_3$P)$_4$ | tetrakis(triphenylphosphine)palladium(0) |
| psi | pounds per square inch |
| PTSA | p-toluenesulfonic acid |
| RT | room temperature |
| satd. | saturated |
| TBDPS | tert-butyldiphenylsilyl |
| TFA | trifluoroacetic acid |
| THF | tetrahydrofuran |

Example 22

The following tables provide results on the efficacy of binding and activity response of exemplified Compounds of the Invention at the μ- and κ-opioid receptors. In TABLE 3, binding affinity of certain Compounds of the Invention to the μ- and κ-opioid receptors was determined as described above. In TABLE 4, activity response of certain Compounds of the Invention to the μ- and κ-opioid receptors was determined as described above for functional assays using HEK-293 cells. In TABLE 5, activity response of certain Compounds of the Invention to the μ- and κ-opioid receptors was determined as described above using U-2 OS cells.

TABLE 3

Binding Affinity

| Compound No. | Opioid Receptor $K_i$ (nM) [mean ± SEM] | |
|---|---|---|
| | κ | μ |
| 1 | 407.78 ± 34.14 | |
| 8 | 260.85 ± 97.28 | |
| 9 | 0.97 ± 0.19 | 6.18 ± 0.76 |
| 10 | >20000 | |
| 12 | 3410.66 ± 537.83 | |
| 13 | >20000 | |
| 15 | 190.65 ± 45.81 | |
| 16 | >20000 | |
| 17 | 128.06 ± 18.10 | |
| 18 | 15905.72 | |
| 19 | 145.53 ± 29.67 | |
| 24 | 249.2 ± 104.2 | 668.0 ± 118.5 |
| 46 | 394.2 ± 85.2 | 591.0 ± 80.3 |
| 48 | 65.3 ± 4.49 | 222.8 ± 32.5 |
| 49 | 324.4 ± 48.0 | 1959 ± 638.1 |
| 72 | 82.9 ± 1.96 | 476.0 ± 117.8 |
| 73 | 0.32 ± 0.11 | 1.98 ± 0.44 |
| 74 | 0.33 ± 0.041 | 7.42 ± 2.25 |

TABLE 4

Activity Response

| Compound No. | μ | | κ | |
|---|---|---|---|---|
| | $EC_{50}$ (nM) [mean ± SEM] | $E_{max}$ (%) | $EC_{50}$ (nM) [mean ± SEM] | $E_{max}$ (%) |
| Opioid Receptor (HEK-293 cells) | | | | |
| 1 | 3397.92 ± 584.13 | 59.33 ± 3.38 | 5114.25 ± 1261.73 | 72.00 ± 3.21 |
| 8 | 702.68 ± 72.01 | 59.67 ± 8.69 | 4435.58 ± 678.77 | 66.67 ± 6.84 |
| 9 | >200000 | −1.00 ± 0.00 | 17.30 ± 3.73 | 40.75 ± 1.93 |
| 10 | 14670.57 ± 1534.34 | 16.00 ± 2.65 | | |
| 12 | >200000 | — | | |
| 13 | 4604.07 ± 471.18 | 66.00 ± 2.65 | | |
| 15 | 43.75 ± 14.65 | 36.25 ± 3.75 | 220.91 ± 59.35 | 36.00 ± 2.00 |
| 16 | 6770.22 ± 1369.30 | 28.67 ± 1.86 | | |
| 17 | >200000 | 0.00 ± 0.58 | >200000 | — |
| 18 | 2749.52 ± 220.89 | 50.00 ± 1.53 | | |
| 19 | 49.72 ± 7.48 | 37.50 ± 3.93 | 201.13 ± 25.95 | 41.33 ± 2.85 |
| 42 | >200000 | 5.50 | | |
| 43 | >200000 | 0.00 | | |
| 48 | 463.0 ± 32.6 | 139.0 ± 3.21 | 362.3 ± 36.6 | 70.3 ± 6.94 |
| 54 | 14.2 ± 3.39 | 25.0 ± 2.04 | 5.02 ± 0.14 | 34.3 ± 0.67 |
| 64 | >200000 | 1.00 | 4.30 ± 1.55 | 33.0 ± 1.73 |
| 72 | 212 ± 48.8 | 100.7 ± 5.55 | 1052 ± 192.8 | 69.3 ± 6.77 |
| 73 | 2.85 ± 0.60 | 53.2 ± 5.71 | 6.07 ± 1.92 | 61.0 ± 8.62 |
| 74 | 2.31 ± 0.60 | 90.3 ± 3.84 | 3.52 ± 1.00 | 34.0 ± 5.86 |
| 82 | 2331 ± 199.6 | 67.8 ± 4.01 | | |
| 83 | 456.5 ± 36.7 | 75.0 ± 5.51 | | |
| 84 | 1258 ± 301.1 | 57.7 ± 2.73 | | |
| Opioid Receptor (U-2 OS cells) | | | | |
| 23 | 2102 ± 735.1 | 15.7 ± 3.71 | 5560 ± 480.7 | 90.0 ± 1.00 |
| 24 | 463.0 ± 120.9 | 43.2 ± 7.97 | 317.1 ± 21.1 | 102.0 ± 5.86 |
| 25 | 578.2 ± 91.8 | 36.0 ± 3.51 | 876.5 ± 18.8 | 105.7 ± 3.28 |
| 26 | 7112 ± 632.8 | 31.0 ± 2.08 | 7213 ± 437.5 | 104.0 ± 2.52 |
| 27 | >200000 | 8.00 ± 2.12 | 24.7 ± 3.18 | 92.7 ± 3.18 |
| 28 | >200000 | 2.50 | 27.1 ± 3.29 | 86.7 ± 2.40 |
| 29 | >200000 | 7.25 ± 1.89 | 14.6 ± 1.86 | 98.7 ± 5.21 |
| 30 | 9.61 ± 0.83 | 51.0 ± 2.65 | 1.61 ± 0.12 | 97.7 ± 3.18 |
| 31 | 9.65 ± 0.22 | 73.7 ± 2.60 | 2.59 ± 0.14 | 90.7 ± 6.57 |
| 32 | 18.6 ± 8.05 | 11.3 ± 0.88 | 17.5 ± 2.66 | 113.0 ± 3.61 |
| 33 | >200000 | 2.50 | 36.1 ± 3.14 | 52.0 ± 4.93 |
| 34 | >200000 | 6.33 ± 2.19 | 12.6 ± 2.04 | 100.7 ± 3.33 |
| 35 | >200000 | 2.00 | 13.6 ± 1.04 | 85.7 ± 2.40 |
| 36 | 12.7 ± 2.92 | 20.3 ± 0.33 | 4.28 ± 0.60 | 99.0 ± 4.73 |
| 37 | >200000 | 6.00 ± 1.53 | 42.1 ± 7.56 | 71.3 ± 5.70 |
| 38 | 10.3 ± 1.72 | 40.3 ± 1.45 | 2.30 ± 0.25 | 95.3 ± 5.21 |
| 46 | 408.7 ± 88.5 | 68.7 ± 4.10 | 1016 ± 110.1 | 109.3 ± 4.84 |
| 48 | 38.6 ± 2.85 | 98.0 ± 2.65 | 225.1 ± 20.1 | 118.7 ± 4.91 |

TABLE 4-continued

| | Activity Response | | | |
|---|---|---|---|---|
| | μ | | κ | |
| Compound No. | $EC_{50}$ (nM) [mean ± SEM] | $E_{max}$ (%) | $EC_{50}$ (nM) [mean ± SEM] | $E_{max}$ (%) |
| 49 | | | 1282 ± 159.6 | 108.0 ± 5.57 |
| 50 | 147.8 ± 10.4 | 101.7 ± 1.67 | 7896 ± 706.9 | 74.0 ± 5.29 |
| 54 | 1.81 ± 0.57 | 26.3 ± 2.33 | 4.82 ± 0.71 | 88.2 ± 2.53 |
| 58 | 787.3 ± 242.1 | 43.7 ± 3.93 | 838.8 ± 9.90 | 96.0 ± 6.35 |
| 59 | 11549 ± 902.8 | 100.0 ± 4.62 | >200000 | 59.0 ± 1.53 |
| 60 | | | 14890 ± 1323 | 84.3 ± 0.67 |
| 61 | 466.1 ± 81.0 | 77.3 ± 2.03 | 963.2 ± 83.0 | 90.0 ± 10.0 |
| 62 | >200000 | 27.5 | 3067 ± 233.4 | 62.7 ± 4.37 |
| 64 | >200000 | 7.50 | 4.71 ± 0.12 | 87.3 ± 2.60 |
| 65 | >200000 | 4.00 | 2.57 ± 0.24 | 101.0 ± 5.51 |
| 66 | >200000 | 2.50 | 7.57 ± 1.14 | 101.7 ± 1.33 |
| 67 | >200000 | 2.00 | 3.00 ± 0.12 | 101.0 ± 1.73 |
| 68 | >200000 | 3.00 | 20.5 ± 0.40 | 69.0 ± 3.21 |
| 69 | >200000 | 2.00 | 9.52 ± 1.41 | 95.2 ± 1.89 |
| 70 | >200000 | 3.50 | 4.01 ± 0.47 | 105.5 ± 3.80 |
| 71 | 6.76 ± 1.73 | 17.7 ± 0.88 | 5.60 ± 0.72 | 109.0 ± 5.45 |
| 72 | 269.7 ± 48.2 | 60.0 ± 6.00 | 302.8 ± 40.4 | 102.0 ± 2.52 |
| 73 | 0.84 ± 0.13 | 28.3 ± 4.06 | 1.92 ± 0.28 | 100.7 ± 3.38 |
| 74 | 3.66 ± 0.82 | 46.0 ± 11.0 | 1.42 ± 0.15 | 91.3 ± 3.76 |
| 75 | 1153 ± 102.8 | 95.0 ± 1.53 | 16592 ± 1193 | 66.7 ± 1.20 |
| 76 | 16697 ± 2272 | 61.7 ± 1.86 | >200000 | 47.7 ± 2.19 |
| 77 | 17630 ± 3649 | 77.0 ± 2.08 | >200000 | 49.0 ± 9.45 |
| 78 | 10398 ± 4813 | 36.7 ± 9.17 | >200000 | 53.3 ± 1.45 |
| 79 | 11657 ± 3625 | 60.0 ± 10.2 | >200000 | 51.0 ± 0.58 |
| 80 | 580.8 ± 22.1 | 74.0 ± 0.58 | 1198 ± 114.1 | 43.0 ± 1.73 |
| 81 | 1005 ± 276.2 | 84.3 ± 3.84 | 6508 ± 1194 | 34.0 ± 2.65 |

The in vitro test results of TABLES 3-5 show that representative Compounds of the Invention have binding affinity for opioid receptors, and that these compounds activate these receptors as partial to full agonists. Compounds of the Invention are therefore expected to be useful to treat Conditions, particularly pain, that are responsive to the activation of one or more opioid receptors.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents, patent applications, and publications cited herein are fully incorporated by reference herein in their entirety.

What is claimed is:

1. A compound having the Formula I-A:

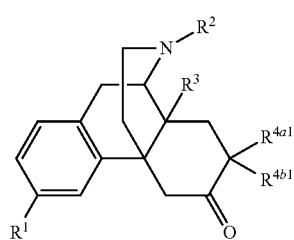

I-A or a pharmaceutically acceptable salt or solvate thereof, wherein:

$R^1$ is hydrogen, OH, halo, cyano, carboxy, or aminocarbonyl; or alkyl, alkenyl, alkynyl, alkoxy, alkenyloxy, or alkynyloxy, any of which is optionally substituted with 1, 2, or 3 substituents, each independently selected from the group consisting of hydroxy, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups; or —O-PG, wherein PG is a hydroxyl protecting group;

$R^2$ is:
(a) hydrogen or carboxamido; or
(b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^3$ is hydrogen, OH, or halo; or alkoxy, alkylamino, or dialkylamino, any of which is optionally substituted with 1, 2, or 3 substituents, each independently selected from the group consisting of hydroxyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^{4a1}$ is selected from the group consisting of $C_3$-$C_6$ alkyl, arylalkyl, (cycloalkyl)alkyl, $C_3$-$C_6$ alkoxy, aralkyloxy, —N(H)COR$^{4c}$, —CH$_2$C(=O)NR$^{4d}$R$^{4e}$, and —N(H)SO$_2$R$^{4f}$,

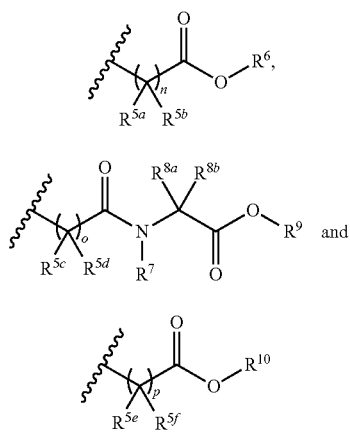

$R^{4b1}$ is selected from the group consisting of hydrogen and $R^{4a}$—I; or $R^{4a1}$ and $R^{4b1}$ taken together form an alkenyl;

$R^{4c}$ is alkyl, cycloalkyl, heterocyclo, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl and cycloalkyl are optionally substituted with 1, 2, or 3 independently selected $R^{11a}$ groups;

$R^{4d}$ is hydrogen; or alkyl, cycloalkyl, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^{4e}$ is hydrogen; or alkyl, optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl; or $R^{4d}$ and $R^{4e}$ taken together with the nitrogen atom to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, alkoxy, aminocarbonyl, arylalkyl, and aryl, wherein the alkyl, arylalkyl, and aryl are optionally substituted with 1, 2, or 3 independently selected $R^{11a}$ groups;

$R^{4f}$ is alkyl, cycloalkyl, arylalkyl, or aryl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl and cycloalkyl are optionally substituted with 1, 2, or 3 independently selected $R^{11a}$ groups;

each $R^{5a}$, $R^{5b}$, $R^{5c}$, $R^{5d}$, $R^{5e}$, and $R^{5f}$ is independently selected from the group consisting of hydrogen and alkyl;

$R^6$ is hydrogen or alkyl;

$R^7$ is hydrogen or alkyl;

$R^{8a}$ is hydrogen, or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

$R^{8b}$ is hydrogen or alkyl, wherein the alkyl is optionally substituted with 1, 2, or 3 substituents, each independently selected from the group consisting of alkyl, hydroxy, halo, haloalkyl, amino, alkylamino, dialkylamino, carboxy, alkoxy, alkoxycarbonyl, and aminocarbonyl; or $R^{8a}$ and $R^{8b}$ taken together with the carbon atom to which they are attached form a 3- to 8-membered cycloalkyl; or $R^7$ and $R^{8a}$ taken together with the atoms to which they are attached form a 4- to 8-membered heterocyclo, wherein the heterocyclo is optionally substituted with 1 or 2 substituents, each independently selected from the group consisting of alkyl, hydroxy, halo, haloalkyl, amino, alkylamino, dialkylamino, carboxy, alkoxy, alkoxycarbonyl, and aminocarbonyl;

$R^9$ is hydrogen or alkyl;

$R^{10}$ is hydrogen, or alkyl, cycloalkyl, cycloalkenyl, heterocyclo, aryl, heteroaryl, (cycloalkyl)alkyl, (cycloalkenyl)alkyl, (heterocyclo)alkyl, arylalkyl, or heteroarylalkyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11a}$ groups;

each $R^{11a}$ is independently selected from the group consisting of hydroxy, halo, alkyl, haloalkyl, cyano, nitro, amino, alkylamino, dialkylamino, carboxy, alkoxy, and alkoxycarbonyl;

n is 1, 2, or 3;

o is 1, 2, or 3; and p is 1, 2, or 3.

2. The compound of claim 1 having the Formula IV-A:

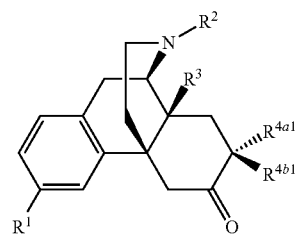

or a pharmaceutically acceptable salt or solvate thereof.

3. The compound of claim 1 having the Formula V-A:

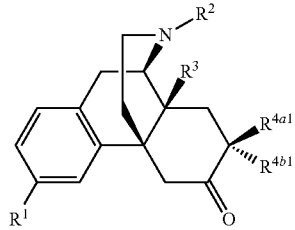

V-A or a pharmaceutically acceptable salt or solvate thereof.

4. The compound of claim 1, or a pharmaceutically acceptable salt or solvate thereof, wherein $R^{4a1}$ is selected from the group consisting of:

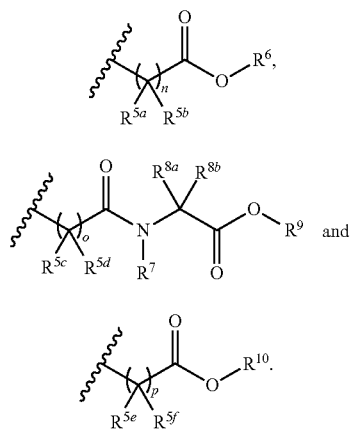

$R^{4a}$-I $R^{4a}$-II and $R^{4a}$-III

5. The compound of claim 1, or a pharmaceutically acceptable salt or solvate thereof, wherein $R^{4a1}$ is selected from the group consisting of $C_3$-$C_6$ alkyl, arylalkyl, (cycloalkyl)alkyl, $C_3$-$C_6$ alkoxy, aralkyloxy, —N(H)COR$^{4c}$, —CH$_2$C(=O)NR$^{4d}$R$^{4e}$, and —N(H)SO$_2$R$^{4f}$.

6. The compound of claim 5, or a pharmaceutically acceptable salt or solvate thereof, wherein:
$R^1$ is OH or unsubstituted $C_{1-6}$ alkoxy;
$R^2$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, alkylcarbonyl, alkoxycarbonyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, amino, alkylamino, dialkylamino, carboxy, alkoxy, alkoxycarbonyl, aryl, heteroaryl, heterocyclo, cycloalkyl, and cycloalkenyl, wherein the aryl, heteroaryl, heterocyclo, cycloalkyl, and cycloalkenyl are optionally substituted with 1, 2, or 3 independently selected $R^{11}$ groups; and
$R^3$ is hydrogen or hydroxy.

7. The compound of claim 6, or a pharmaceutically acceptable salt or solvate thereof, wherein $R^{4a1}$ is selected from the group consisting of $C_3$-$C_6$ alkyl, arylalkyl, and (cycloalkyl)alkyl.

8. The compound of claim 6, or a pharmaceutically acceptable salt or solvate thereof, wherein $R^{4a1}$ is selected from the group consisting of $C_3$-$C_6$ alkoxy and aralkyloxy.

9. The compound of claim 6, or a pharmaceutically acceptable salt or solvate thereof, wherein $R^{4a1}$ is selected from the group consisting of N(H)COR$^{4c}$, CH$_2$C(=O)NR$^{4d}$R$^{4e}$, and —N(H)SO$_2$R$^{4f}$.

10. The compound of claim 1 having the Formula XIV:

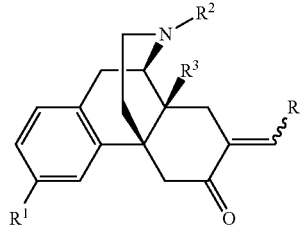

XIV or a pharmaceutically acceptable salt or solvate thereof, wherein R is hydrogen, alkyl, or cycloalkyl.

11. The compound of claim 1 having the Formula XV:

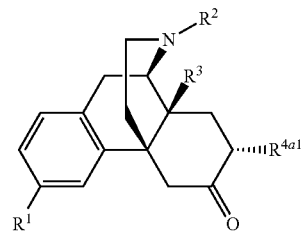

XV or a pharmaceutically acceptable salt or solvate thereof.

12. The compound of claim 11, or a pharmaceutically acceptable salt or solvate thereof, wherein:
$R^1$ is selected from the group consisting of OH and methoxy;
$R^2$ is selected from the group consisting of —CH$_3$ and —CH$_2$(cyclopropyl); and
$R^3$ is selected from the group consisting of hydrogen and OH; and
$R^{4a1}$ is selected from the group consisting of $C_3$-$C_6$ alkyl, (cycloalkyl)alkyl, $C_3$-$C_6$ alkoxy, aralkyloxy, —N(H)COR$^{4c}$, —CH$_2$C(=O)NR$^{4d}$R$^{4e}$, —N(H)SO$_2$R$^{4f}$,

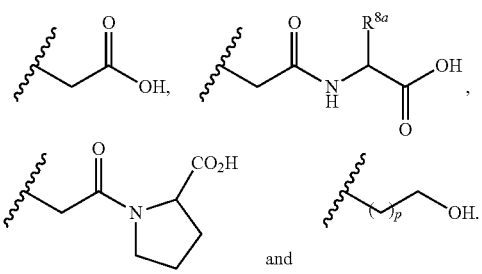

and

13. The compound of claim 12, or a pharmaceutically acceptable salt or solvate thereof, wherein $R^{4a1}$ is selected from the group consisting of $C_3$-$C_6$ alkyl, (cycloalkyl)alkyl, $C_3$-$C_6$ alkoxy, aralkyloxy, —N(H)COR$^{4c}$, —CH$_2$C(=O)NR$^{4d}$R$^{4e}$, and —N(H)SO$_2$R$^{4f}$.

14. The compound of claim 1 having the Formula XVI:

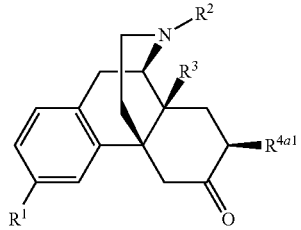

or a pharmaceutically acceptable salt or solvate thereof; wherein
$R^1$ is selected from the group consisting of OH and methoxy;
$R^2$ is selected from the group consisting of —$CH_3$ and —$CH_2$(cyclopropyl); and
$R^3$ is selected from the group consisting of hydrogen and OH; and
$R^{4a1}$ is selected from the group consisting of $C_3$-$C_6$ alkyl, (cycloalkyl)alkyl, $C_3$-$C_6$ alkoxy, aralkyloxy, —N(H)COR$^{4c}$, —$CH_2$C(=O)NR$^{4d}$R$^{4e}$, —N(H)SO$_2$R$^{4f}$,

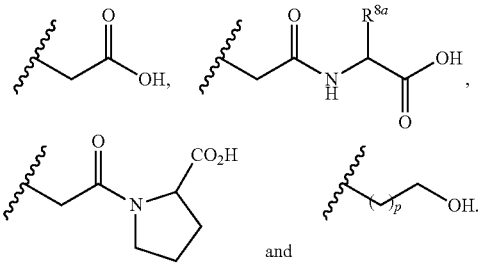

and

15. The compound of claim 1 selected from the group consisting of:
(4bR,7S,8aS,9R)-11-(cyclopropylmethyl)-8a-hydroxy-7-isobutoxy-3-methoxy-8,8a,9,10-tetrahydro-5H-9,4b-(epiminoethano)phenanthren-6(7H)-one;
(4bR,7S,8aS,9R)-7-(benzyloxy)-11-(cyclopropylmethyl)-8a-hydroxy-3-methoxy-8,8a,9,10-tetrahydro-5H-9,4b-(epiminoethano)phenanthren-6(7H)-one;
N-((4bR,7S,8aS,9R)-11-(cyclopropylmethyl)-8a-hydroxy-3-methoxy-6-oxo-6,7,8,8a,9,10-hexahydro-5H-9,4b-(epiminoethano)phenanthren-7-yl)isobutyramide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)isobutyramide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)acetamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)propionamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-4-methylpentanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-5-methylhexanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)pivalamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-3-methylbutanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopropanecarboxamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclopentanecarboxamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzamide;
(S)-N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-methylbutanamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)cyclohexanecarboxamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)ethanesulfonamide;
N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)benzenesulfonamide;
(4bR,7S,8aS,9R)-11-(cyclopropylmethyl)-8a-hydroxy-7-(2-hydroxyethyl)-3-methoxy-8,8a,9,10-tetrahydro-5H-9,4b-(epiminoethano)phenanthren-6(7H)-one;
(4bR,7S,8aS,9R)-7-(2-(benzyloxy)ethyl)-11-(cyclopropylmethyl)-8a-hydroxy-3-methoxy-8,8a,9,10-tetrahydro-5H-9,4b-(epiminoethano)phenanthren-6(7H)-one;
(4bR,7S,8aS,9R)-11-(cyclopropylmethyl)-8a-hydroxy-3-methoxy-7-(2-methoxyethyl)-8,8a,9,10-tetrahydro-5H-9,4b-(epiminoethano)phenanthren-6(7H)-one;
(4bR,7S,8aS,9R)-7-(2-(benzyloxy)ethyl)-8a-hydroxy-3-methoxy-11-methyl-8,8a,9,10-tetrahydro-5H-9,4b-(epiminoethano)phenanthren-6(7H)-one;
(4bR,7S,8aS,9R)-11-(cyclopropylmethyl)-3,8a-dihydroxy-7-(2-hydroxyethyl)-8,8a,9,10-tetrahydro-5H-9,4b-(epiminoethano)phenanthren-6(7H)-one;
(4bR,7S,8aS,9R)-3-(benzyloxy)-11-(cyclopropylmethyl)-8a-hydroxy-7-(2-hydroxyethyl)-8,8a,9,10-tetrahydro-5H-9,4b-(epiminoethano)phenanthren-6(7H)-one;
ethyl 2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetate;
2-((4bR,7R,8aS,9R)-8a-hydroxy-3-methoxy-11-methyl-6-oxo-6,7,8,8a,9,10-hexahydro-5H-9,4b-(epiminoethano)phenanthren-7-yl)acetic acid;
2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetic acid;
(4bR,8aS,9R,E)-11-(cyclopropylmethyl)-8a-hydroxy-3-methoxy-7-(3-methylbutylidene)-8,8a,9,10-tetrahydro-5H-9,4b-(epiminoethano)phenanthren-6(7H)-one;
(4bR,7S,8aS,9R)-11-(cyclopropylmethyl)-3,8a-dihydroxy-7-isopentyl-8,8a,9,10-tetrahydro-5H-9,4b-(epiminoethano)phenanthren-6(7H)-one;
(4bR,7S,8aS,9R)-7-(cyclopentylmethyl)-11-(cyclopropylmethyl)-3,8a-dihydroxy-8,8a,9,10-tetrahydro-5H-9,4b-(epiminoethano)phenanthren-6(7H)-one;
(4bR,7S,8aS,9R)-11-(cyclopropylmethyl)-3,8a-dihydroxy-7-(2-methylbutyl)-8,8a,9,10-tetrahydro-5H-9,4b-(epiminoethano)phenanthren-6(7H)-one;

(4bR,7S,8aS,9R)-7-butyl-11-(cyclopropylmethyl)-3,8a-dihydroxy-8,8a,9,10-tetrahydro-5H-9,4b-(epiminoethano)phenanthren-6(7H)-one;

(4bR,7S,8aS,9R)-11-(cyclopropylmethyl)-3,8a-dihydroxy-7-neopentyl-8,8a,9,10-tetrahydro-5H-9,4b-(epiminoethano)phenanthren-6(7H)-one;

(4bR,7S,8aS,9R)-11-(cyclopropylmethyl)-3,8a-dihydroxy-7-isobutyl-8,8a,9,10-tetrahydro-5H-9,4b-(epiminoethano)phenanthren-6(7H)-one;

(4bR,7S,8aS,9R)-7-(cyclohexylmethyl)-11-(cyclopropylmethyl)-3,8a-dihydroxy-8,8a,9,10-tetrahydro-5H-9,4b-(epiminoethano)phenanthren-6(7H)-one;

(4bR,7S,8aS,9R)-7-benzyl-11-(cyclopropylmethyl)-3,8a-dihydroxy-8,8a,9,10-tetrahydro-5H-9,4b-(epiminoethano)phenanthren-6(7H)-one;

(4bS,7S,8aR,9R)-11-(cyclopropylmethyl)-7-isopropyl-3-methoxy-8,8a,9,10-tetrahydro-5H-9,4b-(epiminoethano)phenanthren-6(7H)-one;

(4bS,7S,8aR,9R)-11-(cyclopropylmethyl)-3-hydroxy-7-isopropyl-8,8a,9,10-tetrahydro-5H-9,4b-(epiminoethano)phenanthren-6(7H)-one;

(4bS,7R,8aR,9R)-11-(cyclopropylmethyl)-3-hydroxy-7-isopropyl-8,8a,9,10-tetrahydro-5H-9,4b-(epiminoethano)phenanthren-6(7H)-one;

(2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetyl)-L-alanine;

(4bR,7R,8aS,9R)-8a-hydroxy-3-methoxy-11-methyl-7-(2-oxo-2-(piperidin-1-yl)ethyl)-8,8a,9,10-tetrahydro-5H-9,4b-(epiminoethano)phenanthren-6(7H)-one;

(4bR,7R,8aS,9R)-8a-hydroxy-3-methoxy-11-methyl-7-(2-oxo-2-(pyrrolidin-1-yl)ethyl)-8,8a,9,10-tetrahydro-5H-9,4b-(epiminoethano)phenanthren-6(7H)-one;

(4bR,7R,8aS,9R)-8a-hydroxy-7-(2-(4-hydroxypiperidin-1-yl)-2-oxoethyl)-3-methoxy-11-methyl-8,8a,9,10-tetrahydro-5H-9,4b-(epiminoethano)phenanthren-6(7H)-one;

(4bR,7R,8aS,9R)-8a-hydroxy-3-methoxy-11-methyl-7-(2-morpholino-2-oxoethyl)-8,8a,9,10-tetrahydro-5H-9,4b-(epiminoethano)phenanthren-6(7H)-one;

(4bR,7R,8aS,9R)-3,8a-dihydroxy-11-methyl-7-(2-oxo-2-(piperidin-1-yl)ethyl)-8,8a,9,10-tetrahydro-5H-9,4b-(epiminoethano)phenanthren-6(7H)-one;

(4bR,7R,8aS,9R)-3,8a-dihydroxy-7-(2-(4-hydroxypiperidin-1-yl)-2-oxoethyl)-11-methyl-8,8a,9,10-tetrahydro-5H-9,4b-(epiminoethano)phenanthren-6(7H)-one;

2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-isobutylacetamide;

N-benzyl-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide;

N-(cyclopropylmethyl)-2-((4bR,7R,8aS,9R)-3,8a-dihydroxy-11-methyl-6-oxo-6,7,8,8a,9,10-hexahydro-5H-9,4b-(epiminoethano)phenanthren-7-yl)acetamide;

2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-(2-hydroxyethyl)acetamide;

2-((4bR,7R,8aS,9R)-3,8a-dihydroxy-11-methyl-6-oxo-6,7,8,8a,9,10-hexahydro-5H-9,4b-(epiminoethano)phenanthren-7-yl)-N-(3-hydroxypropyl)acetamide;

2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)-N-(2-hydroxyethyl)acetamide;

2-((4bR,7R,8aS,9R)-11-(cyclopropylmethyl)-3,8a-dihydroxy-6-oxo-6,7,8,8a,9,10-hexahydro-5H-9,4b-(epiminoethano)phenanthren-7-yl)-N-(3-hydroxypropyl)acetamide;

(4bR,7R,8aS,9R)-3,8a-dihydroxy-11-methyl-7-(2-oxo-2-(piperazin-1-yl)ethyl)-8,8a,9,10-tetrahydro-5H-9,4b-(epiminoethano)phenanthren-6(7H)-one;

(4bR,7R,8aS,9R)-3,8a-dihydroxy-11-methyl-7-(2-(4-methylpiperazin-1-yl)-2-oxoethyl)-8,8a,9,10-tetrahydro-5H-9,4b-(epiminoethano)phenanthren-6(7H)-one;

(4bR,7R,8aS,9R)-7-(2-(4-benzylpiperazin-1-yl)-2-oxoethyl)-3,8a-dihydroxy-11-methyl-8,8a,9,10-tetrahydro-5H-9,4b-(epiminoethano)phenanthren-6(7H)-one;

(4bR,7R,8aS,9R)-3,8a-dihydroxy-11-methyl-7-(2-oxo-2-(4-phenylpiperazin-1-yl)ethyl)-8,8a,9,10-tetrahydro-5H-9,4b-(epiminoethano)phenanthren-6(7H)-one;

(4bR,7R,8aS,9R)-11-(cyclopropylmethyl)-3,8a-dihydroxy-7-(2-oxo-2-(piperazin-1-yl)ethyl)-8,8a,9,10-tetrahydro-5H-9,4b-(epiminoethano)phenanthren-6(7H)-one;

(4bR,7R,8aS,9R)-11-(cyclopropylmethyl)-3,8a-dihydroxy-7-(2-(4-methylpiperazin-1-yl)-2-oxoethyl)-8,8a,9,10-tetrahydro-5H-9,4b-(epiminoethano)phenanthren-6(7H)-one;

(4bR,7R,8aS,9R)-7-(2-(4-benzylpiperazin-1-yl)-2-oxoethyl)-11-(cyclopropylmethyl)-3,8a-dihydroxy-8,8a,9,10-tetrahydro-5H-9,4b-(epiminoethano)phenanthren-6(7H)-one;

(4bR,7R,8aS,9R)-11-(cyclopropylmethyl)-3,8a-dihydroxy-7-(2-oxo-2-(4-phenylpiperazin-1-yl)ethyl)-8,8a,9,10-tetrahydro-5H-9,4b-(epiminoethano)phenanthren-6(7H)-one;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)acetamide;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)propionamide;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)isobutyramide;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)pivalamide;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)-4-methylpentanamide;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)-5-methylhexanamide;

N-((4bR,7S,8aS,9R)-3,8a-dihydroxy-11-methyl-6-oxo-6,7,8,8a,9,10-hexahydro-5H-9,4b-(epiminoethano)phenanthren-7-yl)cyclohexanecarboxamide;

(4bS,7 S,8aR,9R)-11-(cyclopropylmethyl)-3-hydroxy-7-isopentyl-8,8a,9,10-tetrahydro-5H-9,4b-(epiminoethano)phenanthren-6(7H)-one;

(4bS,7S,8aR,9R)-7-(cyclopentylmethyl)-11-(cyclopropylmethyl)-3-hydroxy-8,8a,9,10-tetrahydro-5H-9,4b-(epiminoethano)phenanthren-6(7H)-one;

(4bR,7S,8 aS,9R)-3,8a-dihydroxy-7-isopentyl-11-methyl-8,8a,9,10-tetrahydro-5H-9,4b-(epiminoethano)phenanthren-6(7H)-one;

(4bS,7S,8aR,9R)-7-(cyclopentylmethyl)-3-hydroxy-11-methyl-8,8a,9,10-tetrahydro-5H-9,4b-(epiminoethano)phenanthren-6(7H)-one;

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)methanesulfonamide;

N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)piperidine-4-carboxamide; and N-((4bR,7S,8aS,9R)-11-(cyclopropylmethyl)-3,8a-dihydroxy-6-oxo-6,7,8,8a,9,10-hexahydro-5H-9,4b-(epiminoethano)phenanthren-7-yl)-2-(dimethylamino)acetamide or a pharmaceutically acceptable salt or solvate thereof.

16. A pharmaceutical composition comprising a compound of claim 1, or a pharmaceutically acceptable salt or solvate thereof, and one or more pharmaceutically acceptable carriers.

17. A method of treating pain in a patient, comprising administering an effective amount of a compound of claim 1, or a pharmaceutically acceptable salt or solvate thereof, to a patient in need of such treatment.

18. The method of claim 17, wherein said pain is acute pain, chronic pain, or surgical pain.

19. A method of modulating one or more opioid receptors in a patient, comprising administering to the patient an effective amount of a compound of claim 1, or a pharmaceutically acceptable salt or solvate thereof.

20. The method of claim 19, wherein the μ- or κ-opioid receptor is modulated, or both the μ- and κ-opioid receptors are modulated.

* * * * *